United States Patent
Cha et al.

(10) Patent No.: US 11,208,368 B2
(45) Date of Patent: *Dec. 28, 2021

(54) DOUBLE-SPIRO TYPE COMPOUND AND ORGANIC LIGHT-EMITTING DEVICE CONTAINING SAME

(71) Applicant: LG CHEM, LTD., Seoul (KR)

(72) Inventors: Yongbum Cha, Daejeon (KR); Jin Joo Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/519,939

(22) Filed: Jul. 23, 2019

(65) Prior Publication Data

US 2019/0345082 A1 Nov. 14, 2019

Related U.S. Application Data

(62) Division of application No. 15/545,577, filed as application No. PCT/KR2016/001559 on Feb. 16, 2016, now abandoned.

(30) Foreign Application Priority Data

Feb. 16, 2015 (KR) .................... 10-2015-0023506

(51) Int. Cl.
| | | |
|---|---|---|
| *C07C 13/72* | (2006.01) | |
| *C09K 11/06* | (2006.01) | |
| *H01L 51/50* | (2006.01) | |
| *C07D 239/24* | (2006.01) | |
| *C07D 251/12* | (2006.01) | |

(52) U.S. Cl.
CPC ............ *C07C 13/72* (2013.01); *C07D 239/24* (2013.01); *C07D 251/12* (2013.01); *C09K 11/06* (2013.01); *H01L 51/50* (2013.01); *C07C 2603/97* (2017.05)

(58) Field of Classification Search
None
See application file for complete search history.

(56) References Cited

U.S. PATENT DOCUMENTS

| | | | |
|---|---|---|---|
| 7,274,141 B2 | 9/2007 | Leo et al. | |
| 10,522,762 B2 * | 12/2019 | Huh | ........................ C09K 11/06 |
| 2004/0023060 A1 * | 2/2004 | Kim | ......................... C07C 13/72 |
| | | | 428/690 |
| 2016/0308129 A1 | 10/2016 | Stoessel et al. | |
| 2017/0025616 A1 | 1/2017 | Suzuki et al. | |
| 2018/0269402 A1 | 9/2018 | Huh et al. | |

FOREIGN PATENT DOCUMENTS

| | | |
|---|---|---|
| CN | 1338499 A | 3/2002 |
| EP | 3222695 A1 | 9/2017 |
| KR | 10-2002-0083614 A | 11/2002 |
| KR | 10-2011-0121147 A | 11/2011 |
| KR | 10-2014-0118849 A | 10/2014 |
| WO | 03/012890 A2 | 2/2003 |
| WO | 2015/086108 A1 | 6/2015 |
| WO | 2016080622 A1 | 5/2016 |

OTHER PUBLICATIONS

Machine English translation of Bae et al. (KR 10-2002-0083614). Dec. 13, 2018.

* cited by examiner

*Primary Examiner* — Jay Yang
*Assistant Examiner* — J. L. Yang
(74) *Attorney, Agent, or Firm* — Dentons US LLP

(57) ABSTRACT

The present specification relates to a double spiro structure compound, and an organic light emitting device comprising the same.

15 Claims, 1 Drawing Sheet

[Figure 1]
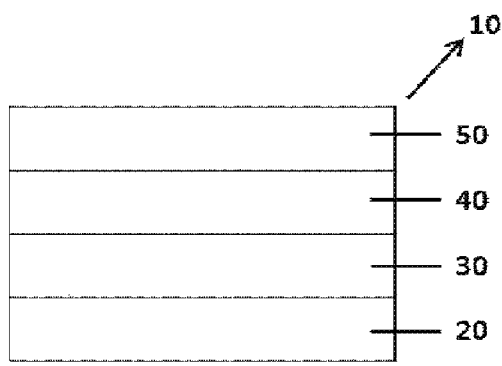
[Figure 2]
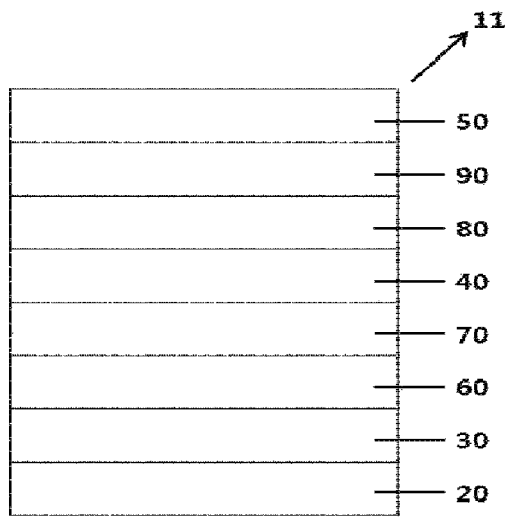

DOUBLE-SPIRO TYPE COMPOUND AND ORGANIC LIGHT-EMITTING DEVICE CONTAINING SAME

This application is a divisional of U.S. patent application Ser. No. 15/545,577, filed Jul. 21, 2017, which is the U.S. national stage of International Application No. PCT/KR2016/001559, filed Feb. 16, 2016, and claims the benefit of Korean Application No. 10-2015-0023506, filed Feb. 16, 2015, all of which are hereby incorporated by reference in their entirety for all purposes as if fully set forth herein.

TECHNICAL FIELD

This application claims priority to and the benefits of Korean Patent Application No. 10-2015-0023506, filed with the Korean Intellectual Property Office on Feb. 16, 2015, the entire contents of which are incorporated herein by reference.

The present specification relates to a double spiro structure compound and an organic light emitting device comprising the same.

BACKGROUND ART

An organic light emission phenomenon generally refers to a phenomenon converting electrical energy to light energy using an organic material. An organic light emitting device using an organic light emission phenomenon normally has a structure comprising an anode, a cathode, and an organic material layer therebetween. Herein, the organic material layer is often formed in a multilayer structure formed with different materials in order to increase efficiency and stability of the organic light emitting device, and for example, may be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

PRIOR ART DOCUMENTS

Patent Document

International Patent Application Laid-Open Publication No. 2003-012890.

DISCLOSURE

Technical Problem

The present specification provides a double spiro structure compound and an organic light emitting device comprising the same.

Technical Solution

One embodiment of the present specification provides a double spiro structure compound represented by the following Chemical Formula 1.

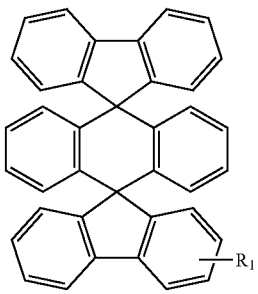

[Chemical Formula 1]

In Chemical Formula 1,
$R_1$ is represented by any one of the following Chemical Formula A to Chemical Formula C.

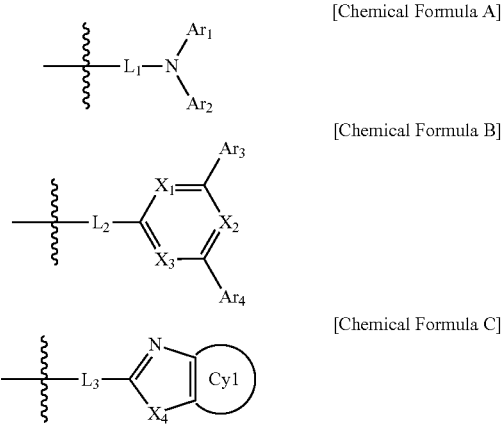

[Chemical Formula A]

[Chemical Formula B]

[Chemical Formula C]

In Chemical Formula A to Chemical Formula C,
$X_1$ to $X_3$ are the same as or different from each other, and each independently CH or N,
at least one of $X_1$ to $X_3$ is N,
$X_4$ is O, S or $NAr_5$,
$L_1$ to $L_3$ are the same as or different from each other, and each independently a direct bond; a substituted or unsubstituted monocyclic or multicyclic arylene group having 6 to 30 carbon atoms; or a substituted or unsubstituted heteroarylene group having 2 to 30 carbon atoms,
$Ar_1$ to $Ar_5$ are the same as or different from each other, and each independently selected from the group consisting of a substituted or unsubstituted arylamine group; a substituted or unsubstituted monocyclic or multicyclic aryl group having 6 to 30 carbon atoms; and a substituted or unsubstituted heteroaryl group having 2 to 30 carbon atoms, and
Cy1 is a substituted or unsubstituted monocyclic or multicyclic hydrocarbon ring having 3 to 30 carbon atoms; or a substituted or unsubstituted monocyclic or multicyclic heteroring having 2 to 30 carbon atoms.

Another embodiment of the present invention provides an organic light emitting device comprising an anode; a cathode provided opposite to the anode; and a light emitting layer and one or more organic material layers provided between the anode and the cathode, wherein the light emitting layer and one or more layers of the organic material layers comprise the double spiro structure compound represented by Chemical Formula 1.

Advantageous Effects

Compounds according to one embodiment of the present invention can be used as a material of an organic material layer of an organic light emitting device, and by using the compounds, efficiency enhancement, a low driving voltage and/or lifespan property enhancement can be accomplished in the organic light emitting device.

DESCRIPTION OF DRAWINGS

FIG. 1 is a diagram showing an organic light emitting device (10) according to one embodiment of the present specification.

FIG. 2 is a diagram showing an organic light emitting device (11) according to another embodiment of the present specification.

MODE FOR DISCLOSURE

Hereinafter, the present specification will be described in more detail.

The present specification provides a double spiro structure compound represented by Chemical Formula 1.

In the present specification, a description of a certain part "comprising" certain constituents means capable of further comprising other constituents, and does not exclude other constituents unless particularly stated on the contrary.

In the present specification, a description of one member being placed "on" another member includes not only a case of the one member adjoining the another member but a case of still another member being present between the two members.

In the present specification, an "adjacent" group may mean a substituent substituting an atom directly linking to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as "adjacent" groups.

Examples of the substituents are described below, however, the substituents are not limited thereto.

The term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

The term "substituted or unsubstituted" in the present specification means being substituted with one, two or more substituents selected from the group consisting of deuterium; a halogen group; a nitrile group; a nitro group; an imide group; an amide group; a carbonyl group; an ester group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; and a substituted or unsubstituted heteroring group, or being substituted with a substituent linking two or more substituents among the substituents illustrated above, or having no substituents. For example, "a substituent linking two or more substituents" may include a biphenyl group. In other words, a biphenyl group may be an aryl group, or interpreted as a substituent linking two phenyl groups.

In the present specification,

means a site bonding to other substituents or bonding sites.

In the present specification, the halogen group may include fluorine, chlorine, bromine or iodine.

In the present specification, the number of carbon atoms of the imide group is not particularly limited, but is preferably from 1 to 30. Specifically, compounds having structures such as below may be included, but the imide group is not limited thereto.

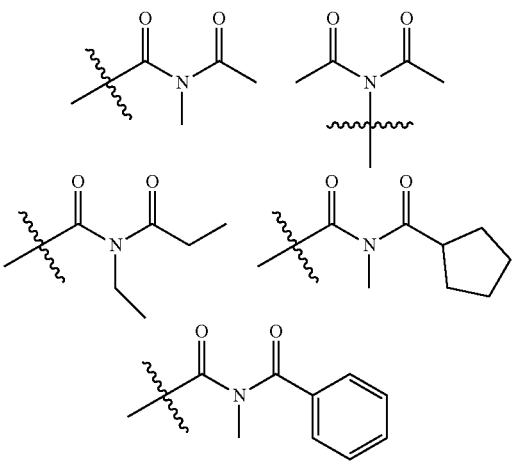

In the present specification, in the amide group, the nitrogen of the amide group may be substituted with a linear, branched or cyclic alkyl group having 1 to 30 carbon atoms or an aryl group having 6 to 30 carbon atoms. Specifically, compounds having the following structural formulae may be included, but the amide group is not limited thereto.

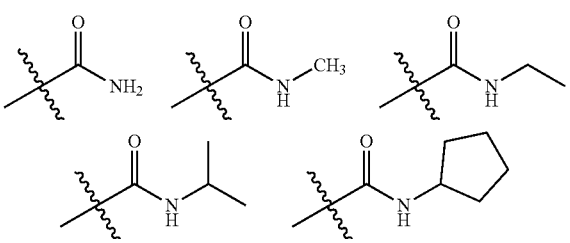

-continued

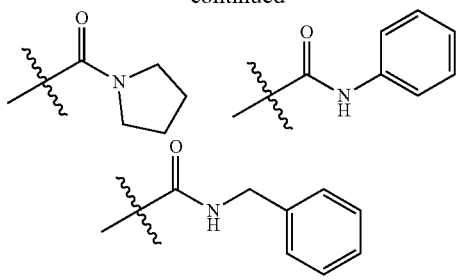

In the present specification, the number of carbon atoms of the carbonyl group is not particularly limited, but is preferably from 1 to 30. Specifically, compounds having structures such as below may be included, but the carbonyl group is not limited thereto.

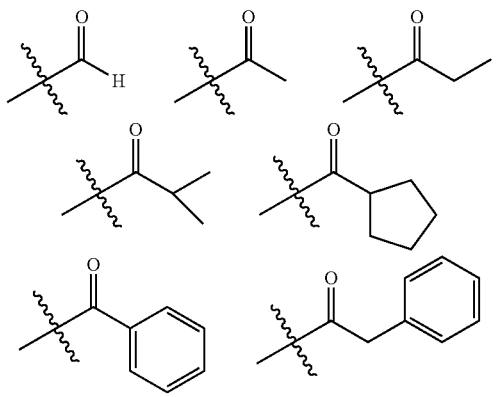

In the present specification, in the ester group, the oxygen of the ester group may be substituted with a linear, branched or cyclic alkyl group having 1 to 25 carbon atoms or an aryl group having 6 to 30 carbon atoms. Specifically, compounds having the following structural formulae may be included, but the ester group is not limited thereto.

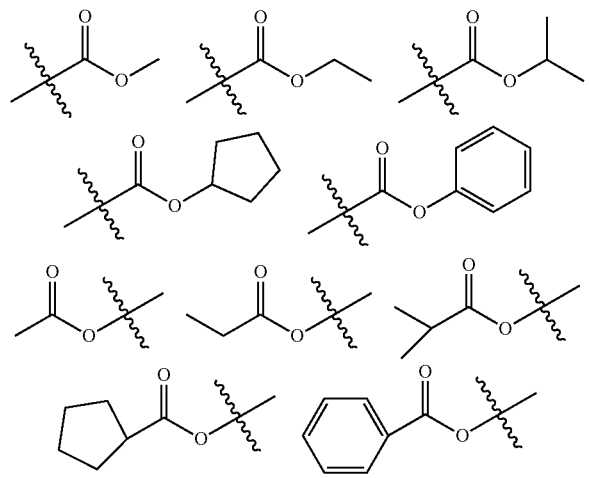

In the present specification, the alkyl group may be linear or branched, and the number of carbon atoms is not particularly limited, but is preferably from 1 to 30. Specific examples thereof may include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentyl-methyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl and the like, but are not limited thereto.

In the present specification, the cycloalkyl group is not particularly limited, but preferably has 3 to 30 carbon atoms, and specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkoxy group may be linear, branched or cyclic. The number of carbon atoms of the alkoxy group is not particularly limited, but is preferably from 1 to 30. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benxyloxy, p-methylbenxyloxy and the like, but are not limited thereto.

In the present specification, the amine group may be selected from the group consisting of —NH$_2$; an alkylamine group; an N-alkylarylamine group; an arylamine group; an N-arylheteroarylamine group; an N-alkylheteroarylamine group and a heteroarylamine group, and the number of carbon atoms is, although not particularly limited thereto, preferably 1 to 30. Specific examples of the amine group may include a methylamine group, a dimethylamine group, an ethylamine group, a diethylamine group, a phenylamine group, a naphthylamine group, a biphenylamine group, an anthracenylamine group, an N-9-methyl-anthracenylamine group, a diphenylamine group, an N-phenylnaphthylamine group, a ditolylamine group, an N-phenyltolylamine group, a triphenylamine group, an N-biphenylfluorenylamine group, an N-phenylfluorenylamine group, an N-phenylspirobifluorenylamine group, an N-biphenylspirobifluorenylamine group, an N-biphenyldibenzofuranylamine group, an N-phenylphenanthrenylamine group, an N-biphenylphenanthrenylamine group, an N-phenyldibenzofuranylamine group, an N-phenylbiphenylamine group, an N-phenylcarbazolylamine group, an N-biphenylcarbazolylamine group, an N-biphenyldibenzothiophenylamine group, an N-phenyldibenzothiophenylamine group, an N-biphenylnaphthylamine group, an N-biphenylterphenylamine group, an N-phenylterphenylamine group, an N-phenylnaphthylamine group, an N-quaterphenylfluorenylamine group, an N-terphenylfluorenylamine group, a difluorenylamine group, an N-phenylbenzocarbazolylamine group, an N-biphenylbenzocarbazolylamine group, an N-fluorenylcarbazolylamine group and the like, but are not limited thereto.

In the present specification, the N-alkylarylamine group means an amine group in which N of the amine group is substituted with an alkyl group and an aryl group.

In the present specification, the N-arylheteroarylamine group means an amine group in which N of the amine group is substituted with an aryl group and a heteroaryl group.

In the present specification, the N-alkylheteroarylamine group means an amine group in which N of the amine group is substituted with an alkyl group and a heteroarylamine group.

In the present specification, the alkyl group in the alkylamine group, the N-alkylarylamine group, the N-alkylheteroarylamine group, the alkylthioxy group and the alkylsulfoxy group is the same as the examples of the alkyl group described above. Specifically, the alkylthioxy group may include a methylthioxy group, an ethylthioxy group, a tert-butylthioxy group, a hexylthioxy group, an octylthioxy group and the like, and the alkylsulfoxy group may include a mesyl group, an ethylsulfoxy group, a propylsulfoxy group, a butylsulfoxy group and the like, however, the examples are not limited thereto.

In the present specification, the alkenyl group may be linear or branched, and although not particularly limited thereto, the number of carbon atoms is preferably from 2 to 30. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the boron group may be —BR$_{100}$R$_{101}$R$_{102}$, and herein, R$_{100}$, R$_{101}$ and R$_{102}$ are the same as or different from each other, and may be each independently selected from the group consisting of hydrogen; deuterium; a halogen group; a nitrile group; a substituted or unsubstituted monocyclic or multicyclic cycloalkyl group having 3 to 30 carbon atoms; a substituted or unsubstituted linear or branched alkyl group having 1 to 30 carbon atoms; a substituted or unsubstituted monocyclic or multicyclic aryl group having 6 to 30 carbon atoms; and a substituted or unsubstituted monocyclic or multicyclic heteroaryl group having 2 to 30 carbon atoms.

In the present specification, specific examples of the phosphine oxide group may include a diphenylphosphine oxide group, a dinaphthylphosphine oxide group, a dimethylphosphine oxide group and the like, but are not limited thereto.

When the aryl group is a monocyclic aryl group, the number of carbon atoms is not particularly limited, but is preferably from 6 to 30. Specific examples of the monocyclic aryl group may include a phenyl group, a biphenyl group, a terphenyl group, a quaterphenyl group and the like, but are not limited thereto.

When the aryl group is a multicyclic aryl group, the number of carbon atoms is not particularly limited, but is preferably from 10 to 30. Specific examples of the multicyclic aryl group may include a naphthyl group, an anthracenyl group, a phenanthryl group, a pyrenyl group, a perylenyl group, a crycenyl group, a fluorenyl group, a fluoranthenyl group and the like, but are not limited thereto.

In the present specification, the fluorenyl group may be substituted, and adjacent substituents may bond to each to form a ring.

When the fluorenyl group is substituted,

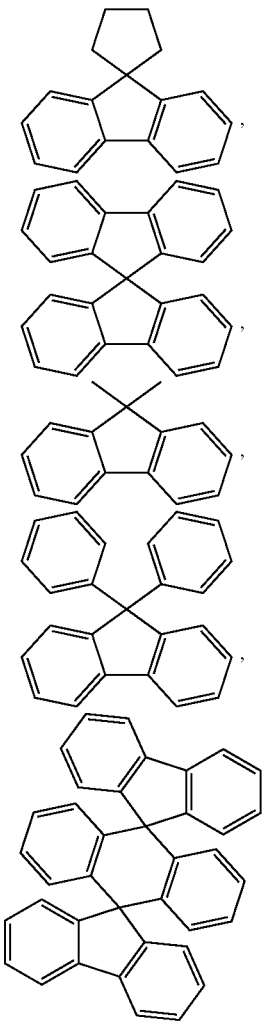

and the like may be included. However, the compound is not limited thereto.

In the present specification, the aryl group in the aryloxy group, the arylthioxy group, the arylsulfoxy group, the N-alkylarylamine group, the N-arylheteroarylamine group and the arylphosphine group may be same as the examples of the aryl group described above. Specific examples of the aryloxy group may include phenoxy, p-tolyloxy, m-tolyloxy, 3,5-dimethyl-phenoxy, 2,4,6-trimethylphenoxy, p-tert-butylphenoxy, 3-biphenyloxy, 4-biphenyloxy, 1-naphthyloxy, 2-naphthyloxy, 4-methyl-1-naphthyloxy, 5-methyl-2-naphthyloxy, 1-anthryloxy, 2-anthryloxy, 9-anthryloxy, 1-phenanthryloxy, 3-phenanthryloxy, 9-phenanthryloxy and the like, and specific examples of the arylthioxy group may include a phenylthioxy group, a 2-methylphenylthioxy group, a 4-tert-butylphenylthioxy group and the like, and specific examples of the arylsulfoxy group may include a benzenesulfoxy group, a p-toluenesulfoxy group and the like, however, the examples are not limited thereto.

In the present specification, examples of the arylamine group may include a substituted or unsubstituted monoarylamine group, a substituted or unsubstituted diarylamine group, or a substituted or unsubstituted triarylamine group. The aryl group in the arylamine group may be a monocyclic aryl group or a multicyclic aryl group. The arylamine group comprising two or more aryl groups may include monocyclic aryl groups, multicyclic aryl groups, or both a monocyclic aryl group and a multicyclic aryl group. For example, the aryl group in the arylamine group may be selected from the examples of the aryl group described above.

In the present specification, the heteroaryl group is a group comprising one or more atoms that are not carbon, that is, heteroatoms, and specifically, the heteroatom may include one or more atoms selected from the group consisting of O, N, Se, S and the like. The number of carbon atoms is not particularly limited, but is favorably from 2 to 30, and the heteroaryl group may be monocyclic or multicyclic. Examples of the heteroaryl group may include a thiophene group, a furanyl group, a pyrolyl group, an imidazolyl group, a thiazolyl group, an oxazolyl group, an oxadiazolyl group, a triazolyl group, a pyridyl group, a bipyridyl group, a pyrimidyl group, triazinyl group, a triazolyl group, an acridyl group, a pyridazinyl group, a pyrazinyl group, a qinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benxzimidazolyl group, a benzothiazolyl group, a benzocarbazolyl group, a benzothiophene group, a dibenzothiophene group, a benzofuranyl group, a phenanthrolinyl group, a thiazolyl group, an isoxazolyl group, an oxadiazolyl group, a thiadiazolyl group, a benzothiazolyl group, a phenothiazinyl group, a benzoquinazolinyl group, an indolofluorenyl group, an indolocarbazolyl group, a dibenzocarbazolyl group, a benzoquinolinyl group, a benzonaphthofuranyl group, a benzonaphthothiophene group, a dibenzofuranyl group, a phenoxazinyl group and the like, but are not limited thereto.

In the present specification, examples of the heteroarylamine group may include a substituted or unsubstituted monoheteroarylamine group, a substituted or unsubstituted diheteroarylamine group, or a substituted or unsubstituted triheteroarylamine group. The heteroarylamine group comprising two or more heteroaryl groups may include monocyclic heteroaryl groups, multicyclic heteroaryl groups, or both a monocyclic heteroaryl group and a multicyclic heteroaryl group. For example, the heteroaryl group in the heteroarylamine group may be selected from the examples of the heteroring group described above.

In the present specification, examples of the heteroaryl group in the N-arylheteroarylamine group and the N-alkylheteroarylamine group are the same as the examples of the heteroaryl group described above.

In the present specification, the heteroring group may be monocyclic or multicyclic, may be aromatic, aliphatic or a fused ring of aromatic and aliphatic, and may be selected from the examples of the heteroaryl group.

In the present specification, the arylene group means an aryl group having two bonding sites, that is, a divalent group. Descriptions on the aryl group made above may be applied except for those that are each a divalent group.

In the present specification, the heteroarylene group means a heteroaryl group having two bonding sites, that is, a divalent group. Descriptions on the heteroaryl group made above may be applied except for those that are each a divalent group.

In the present specification, the hydrocarbon ring may be aromatic, aliphatic or a fused ring of aromatic and aliphatic, and may be selected from the examples of the cycloalkyl group or the aryl group except for those are not monovalent.

In the present specification, the aromatic ring may be monocyclic or multicyclic, and may be selected from the examples of the aryl group except for those are not monovalent.

In the present specification, the heteroring is a group comprising one or more atoms that are not carbon, that is, heteroatoms, and specifically, the heteroatom may include one or more atoms selected from the group consisting of O, N, Se, S and the like. The heteroring may be monocyclic or multicyclic, may be aromatic, aliphatic or a fused ring of aromatic and aliphatic, and may be selected from the examples of the heteroaryl group except for those are not monovalent.

According to one embodiment of the present specification, the double spiro structure compound represented by Chemical Formula 1 may be represented by any one of the following Chemical Formulae 2 to 4.

[Chemical Formula 2]

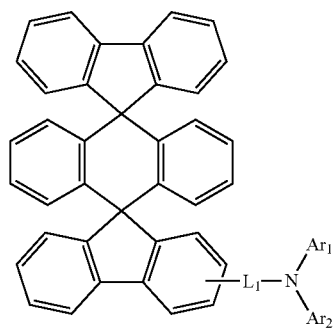

[Chemical Formula 3]

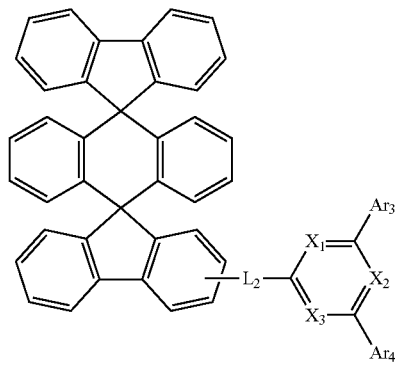

[Chemical Formula 4]

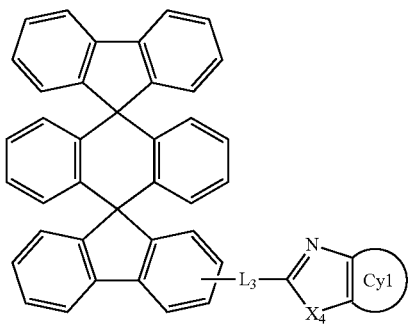

In Chemical Formulae 2 to 4, definitions of $X_1$ to $X_4$, $L_1$ to $L_3$, $Ar_1$ to $Ar_4$ and Cy1 are the same as in Chemical Formula 1.

According to one embodiment of the present specification, the double spiro structure compound represented by Chemical Formula 1 may be represented by any one of the following Chemical Formulae 1-1 to 1-3.

[Chemical Formula 1-1]

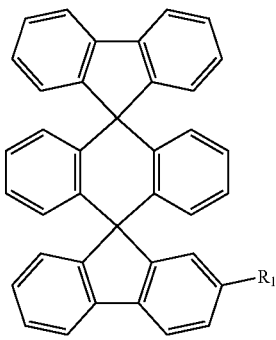

[Chemical Formula 1-2]

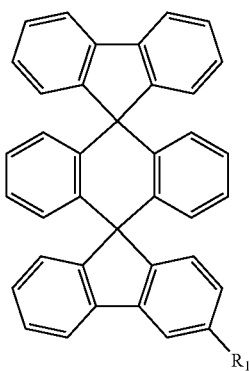

[Chemical Formula 1-3]

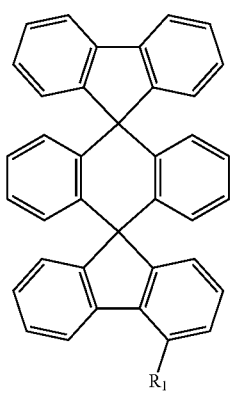

In Chemical Formula 1-1 to Chemical Formula 1-3, a definition of $R_1$ is the same as in Chemical Formula 1.

According to one embodiment of the present specification, the double spiro structure compound represented by Chemical Formula 1 may be represented by any one of the following Chemical Formulae 2-1 to 2-3.

[Chemical Formula 2-1]

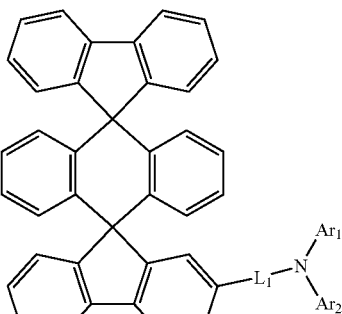

[Chemical Formula 2-2]

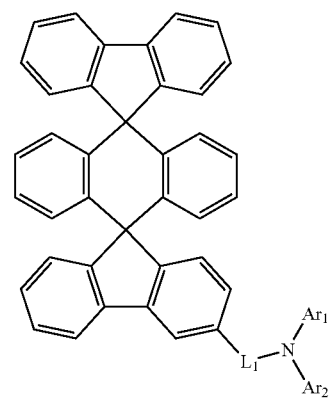

[Chemical Formmula 2-3]

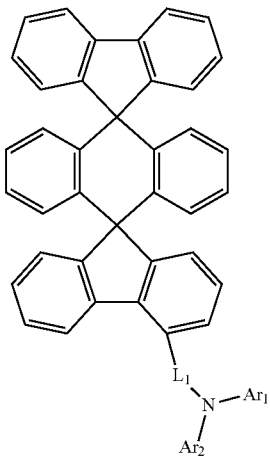

In Chemical Formula 2-1 to Chemical Formula 2-3, definitions of $L_1$, $Ar_1$ and $Ar_2$ are the same as in Chemical Formula 1.

According to one embodiment of the present specification, in Chemical Formula 1, $X_1$ to $X_3$ are the same as or different from each other, and each independently CH or N, and at least one of $X_1$ to $X_3$ is N.

According to another embodiment of the present specification, in Chemical Formula 1, $X_1$ to $X_3$ are the same as or different from each other, and each independently CH or N, and at least two of $X_1$ to $X_3$ are N.

According to another embodiment of the present specification, in Chemical Formula 1, $X_1$ to $X_3$ are N.

According to one embodiment of the present specification, the double spiro structure compound represented by Chemical Formula 1 may be represented by any one of the following Chemical Formulae 3-1 to 3-4.

[Chemical Formula 3-1]

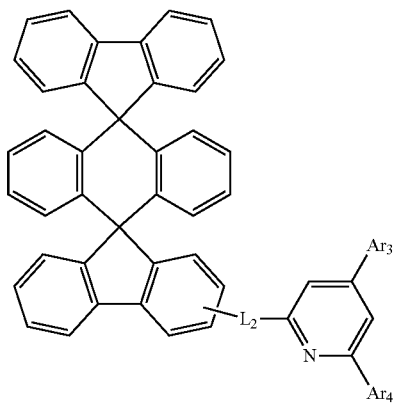

[Chemical Formula 3-2]

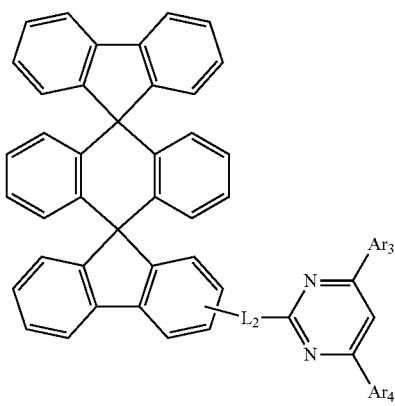

[Chemical Formula 3-3]

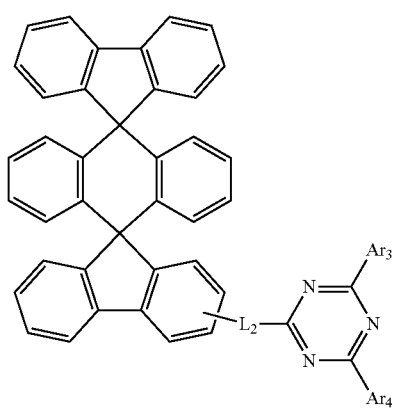

[Chemical Formula 3-4]

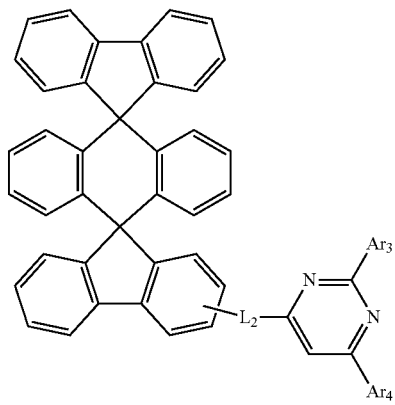

In Chemical Formulae 3-1 to 3-4, definitions of $L_2$, $Ar_3$ and $Ar_4$ are the same as in Chemical Formula 1.

According to one embodiment of the present specification, the double spiro structure compound represented by Chemical Formula 1 may be represented by any one of the following Chemical Formulae 3-5 to 3-16.

[Chemical Formula 3-5]

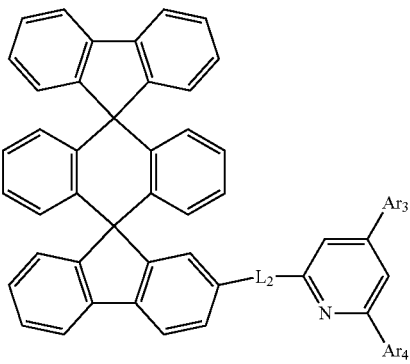

[Chemical Formula 3-6]

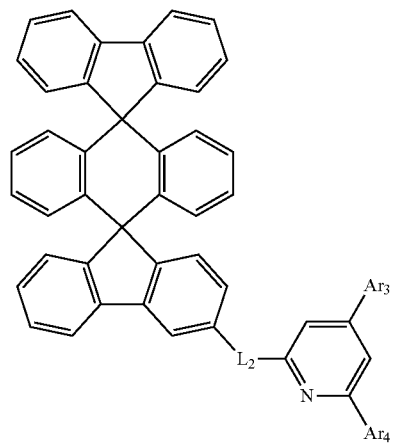

[Chemical Formula 3-7]
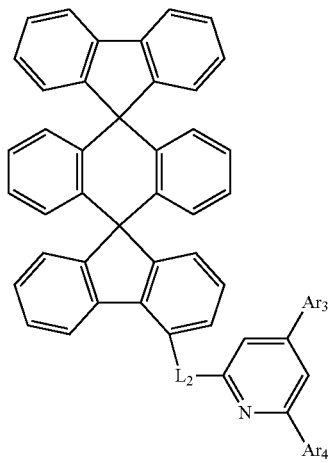
[Chemical Formula 3-10]
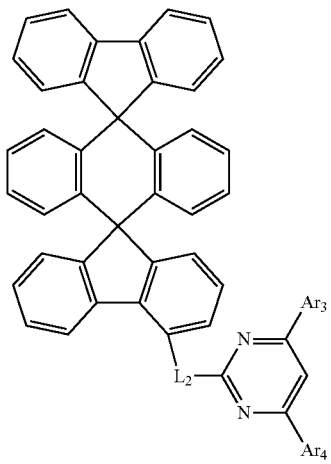
[Chemical Formula 3-8]
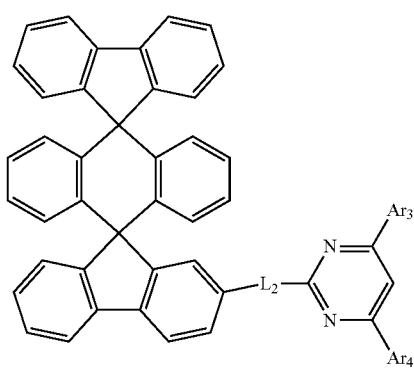
[Chemical Formula 3-11]
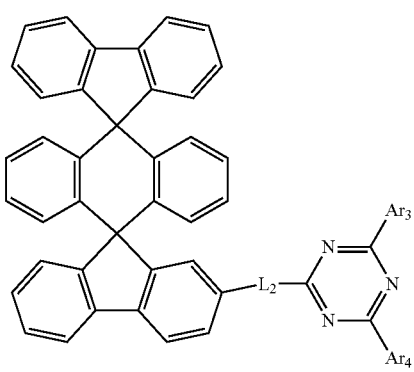
[Chemical Formula 3-9]
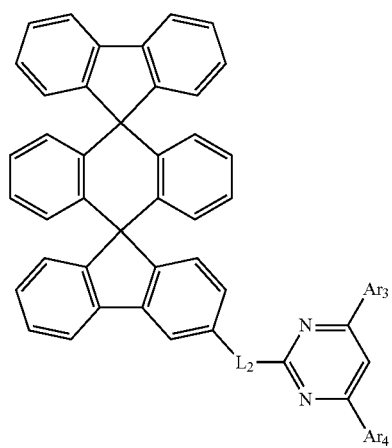
[Chemical Formula 3-12]
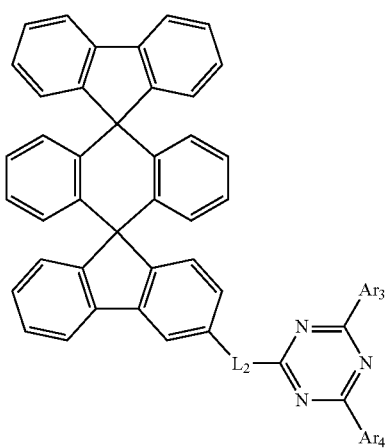

[Chemical Formula 3-13]

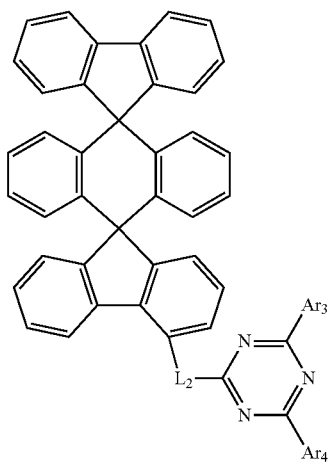

[Chemical Formula 3-14]

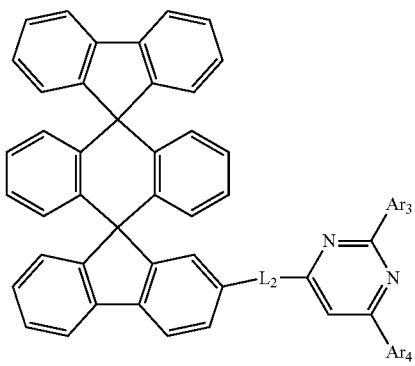

[Chemical Formula 3-15]

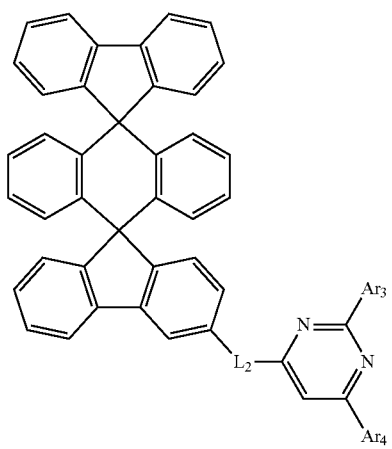

[Chemical Formula 16]

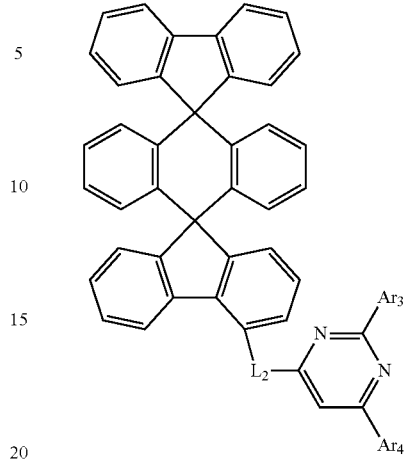

In Chemical Formulae 3-5 to 3-16, definitions of $L_2$, $Ar_3$ and $Ar_4$ are the same as in Chemical Formula 1.

According to one embodiment of the present specification, Chemical Formula 1 may be represented by any one of the following Chemical Formula 4-1 to Chemical Formula 4-3.

[Chemical Formula 4-1]

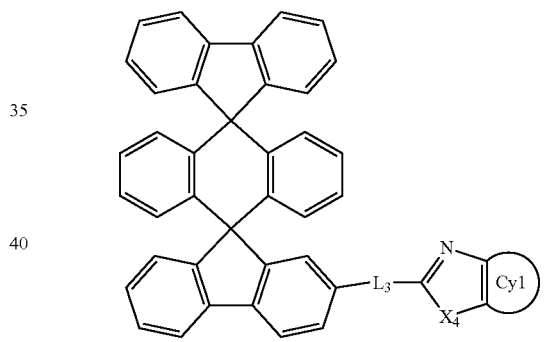

[Chemical Formula 4-2]

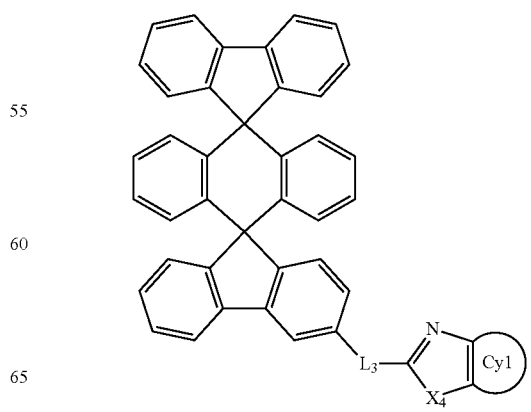

-continued

[Chemical Formula 4-3]

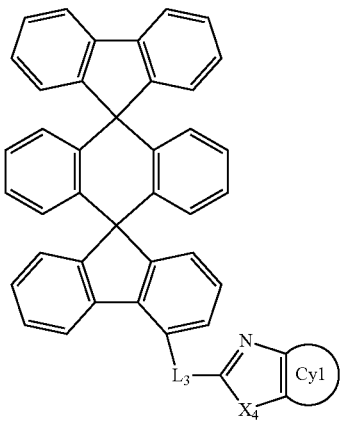

[Chemical Formula 4-5]

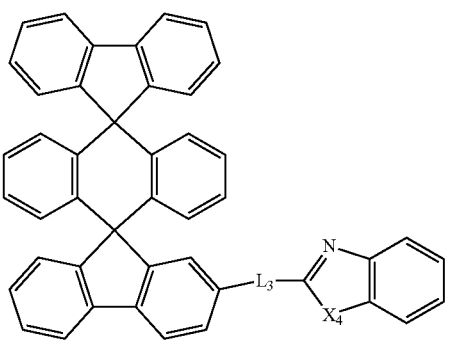

[Chemical Formula 4-6]

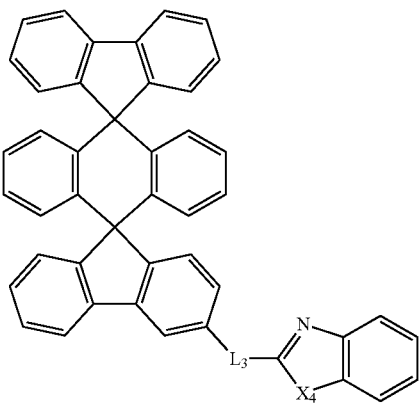

[Chemical Formula 4-7]

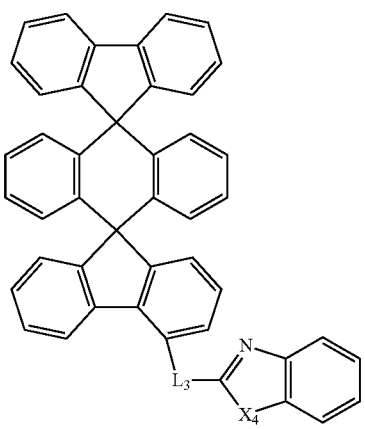

In Chemical Formula 4-1 to Chemical Formula 4-3, definitions of $X_4$, $L_3$ and Cy1 are the same as in Chemical Formula 1.

According to one embodiment of the present specification, in Chemical Formula 1, Cy1 is a substituted or unsubstituted monocyclic or multicyclic hydrocarbon ring having 3 to 30 carbon atoms.

According to one embodiment of the present specification, Cy1 is a substituted or unsubstituted monocyclic or multicyclic hydrocarbon ring having 3 to 20 carbon atoms.

According to one embodiment of the present specification, Cy1 is a substituted or unsubstituted monocyclic or multicyclic hydrocarbon ring having 3 to 10 carbon atoms.

According to one embodiment of the present specification, Cy1 is a substituted or unsubstituted benzene ring.

According to one embodiment of the present specification, Cy1 is a benzene ring.

According to one embodiment of the present specification, Chemical Formula 1 may be represented by the following Chemical Formula 4-4.

[Chemical Formula 4-4]

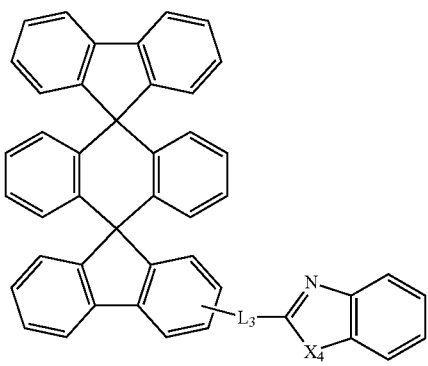

In Chemical Formula 4-4, definitions of $X_4$ and $L_3$ are the same as in Chemical Formula 1.

According to one embodiment of the present specification, the double spiro structure compound represented by Chemical Formula 1 may be represented by any one of the following Chemical Formulae 4-5 to 4-7.

In Chemical Formula 4-5 to Chemical Formula 4-7, definitions of $X_4$ and $L_3$ are the same as in Chemical Formula 1.

According to one embodiment of the present specification, in Chemical Formula 1, $L_1$ to $L_3$ are the same as or different from each other, and each independently a direct bond; or a substituted or unsubstituted monocyclic or multicyclic arylene group having 6 to 20 carbon atoms.

According to one embodiment of the present specification, $L_1$ to $L_3$ are the same as or different from each other, and each independently a direct bond; or a substituted or unsubstituted monocyclic or multicyclic arylene group having 6 to 15 carbon atoms.

According to one embodiment of the present specification, $L_1$ to $L_3$ are the same as or different from each other, and each independently a direct bond; a substituted or unsubstituted phenylene group; or a substituted or unsubstituted biphenylylene group.

According to one embodiment of the present specification, $L_1$ to $L_3$ are the same as or different from each other, and each independently a direct bond; a phenylene group; or a biphenylylene group.

According to one embodiment of the present specification, in Chemical Formula 1, $Ar_1$ to $Ar_5$ are the same as or different from each other, and each independently selected from the group consisting of a substituted or unsubstituted arylamine group; a substituted or unsubstituted monocyclic or multicyclic aryl group having 6 to 25 carbon atoms; and a substituted or unsubstituted heteroaryl group having 2 to 25 carbon atoms.

According to one embodiment of the present specification, $Ar_1$ to $Ar_5$ are the same as or different from each other, and each independently selected from the group consisting of a substituted or unsubstituted phenyl group; a substituted or unsubstituted biphenylyl group; a substituted or unsubstituted naphthyl group; a substituted or unsubstituted terphenyl group; a substituted or unsubstituted quaterphenyl group; a substituted or unsubstituted fluorenyl group; a substituted or unsubstituted phenanthrenyl group; a substituted or unsubstituted terphenylenyl group; a substituted or unsubstituted dibenzothiophene group; and a substituted or unsubstituted dibenzofuran group.

According to one embodiment of the present specification, $Ar_1$ to $Ar_5$ are the same as or different from each other, and each independently selected from the group consisting of a phenyl group; a biphenylyl group; a naphthyl group; a terphenyl group; a quaterphenyl group; a fluorenyl group; a phenanthrenyl group; a terphenylenyl group; a dibenzothiophene group; and a dibenzofuran group, and $Ar_1$ to $Ar_5$ may be unsubstituted or substituted with one or more selected from the group consisting of deuterium; a fluorine group; a nitrile group; a methyl group; a phenyl group; a biphenyl group; a naphthyl group; a fluorenyl group; a phenanthrenyl group; a dibenzothiophene group; a dibenzofuran group; a carbazolyl group; a benzocarbazolyl group; a diphenylamine group; a dibiphenylamine group; an N-phenylbiphenylamine group; an N-phenylfluorenylamine group; and an N-biphenylfluorenylamine group.

According to one embodiment of the present specification, $Ar_1$ to $Ar_5$ are the same as or different from each other, and may be each independently selected as any one among the following structural formulae.

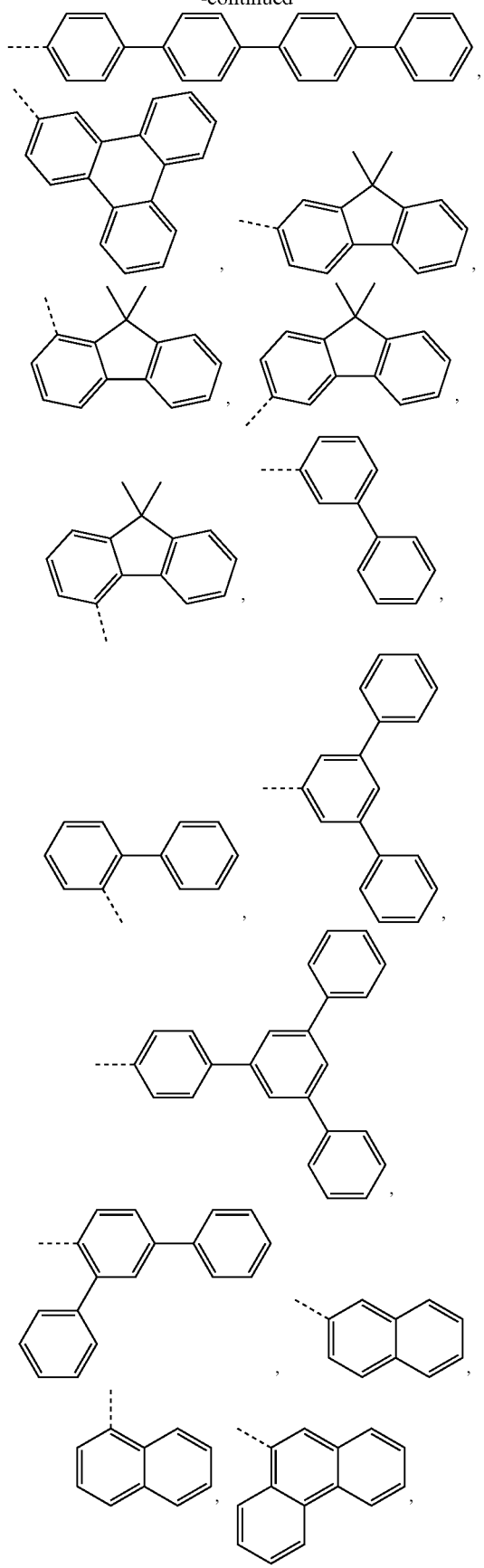

-continued
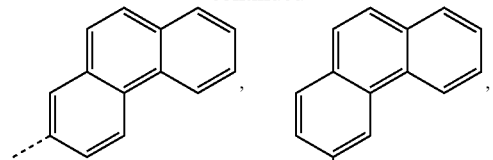
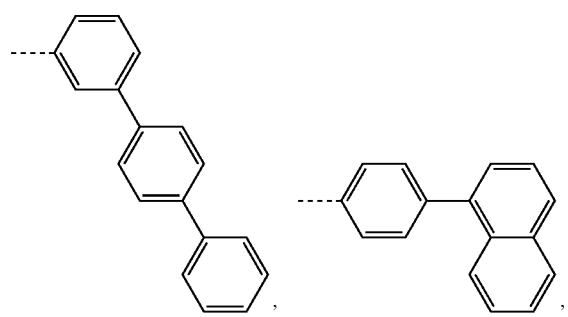
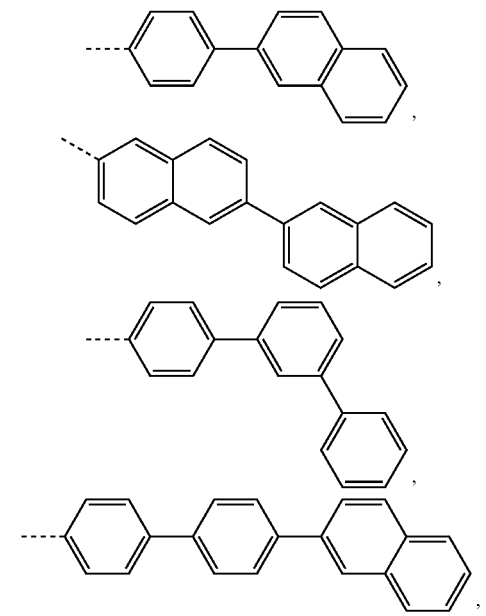
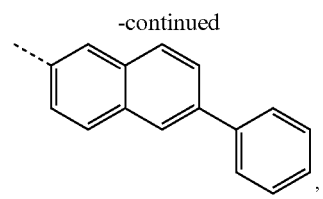
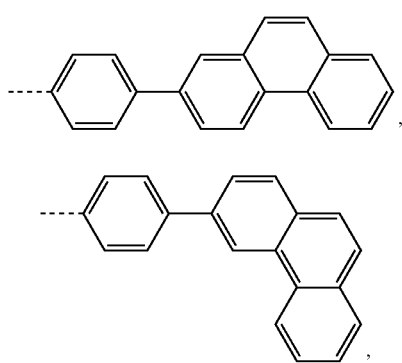
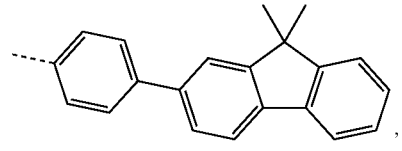
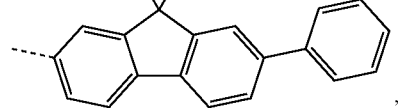
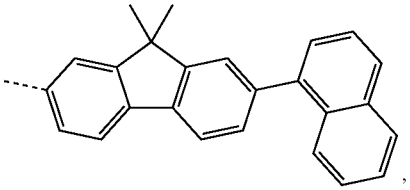
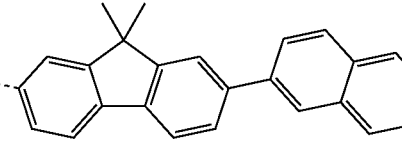
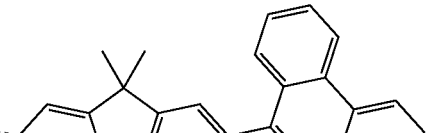
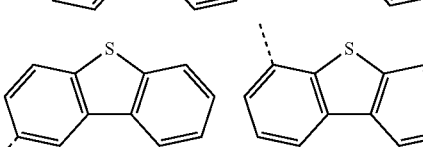
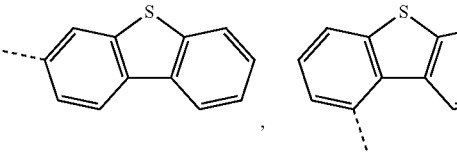

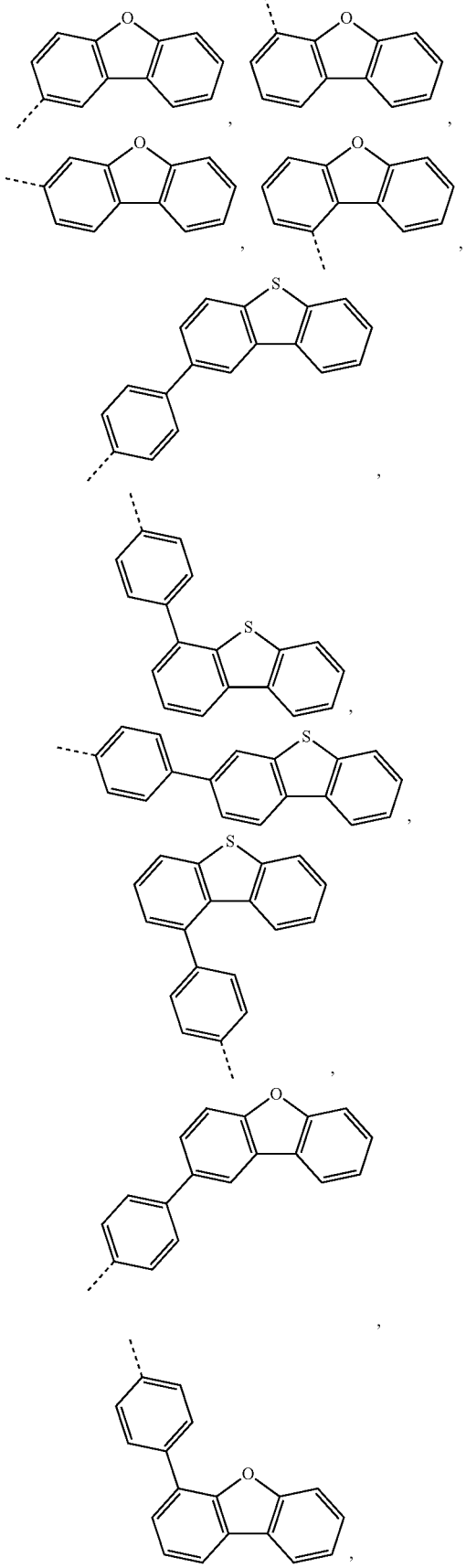
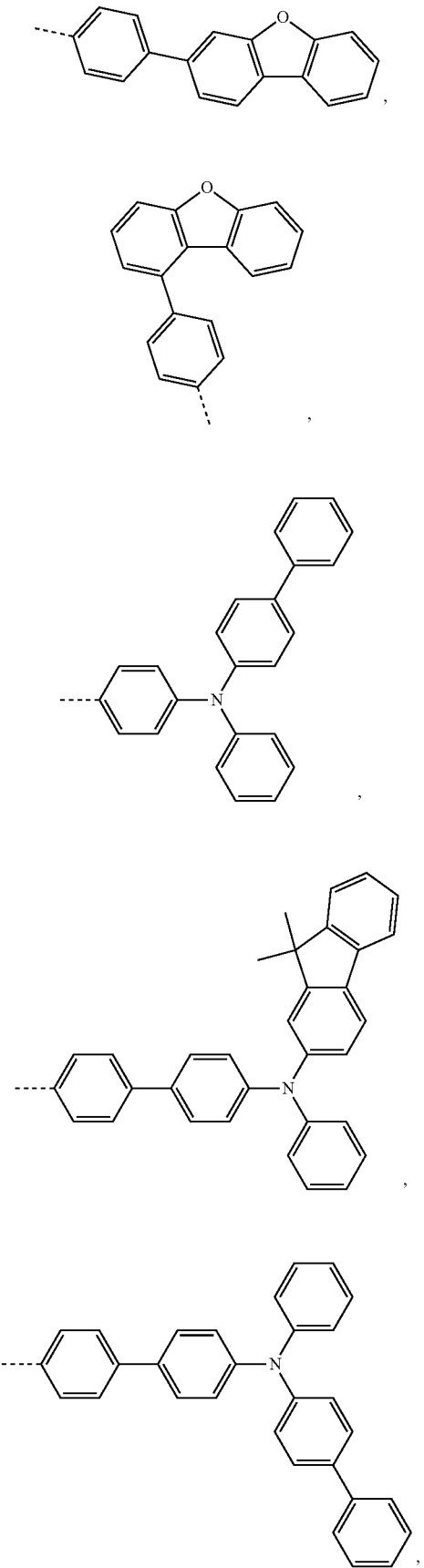

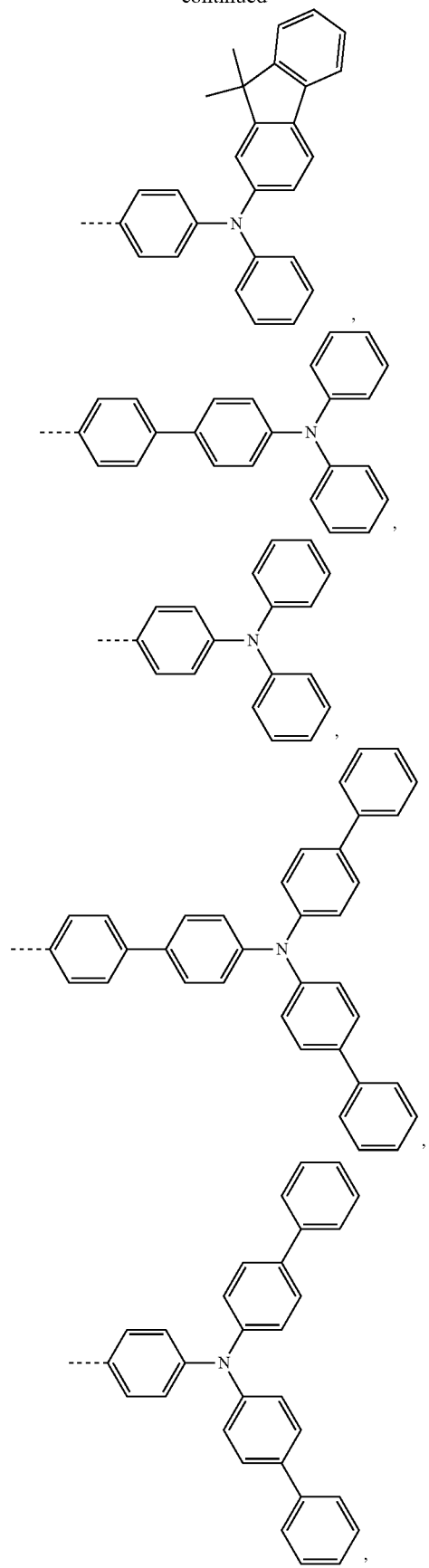
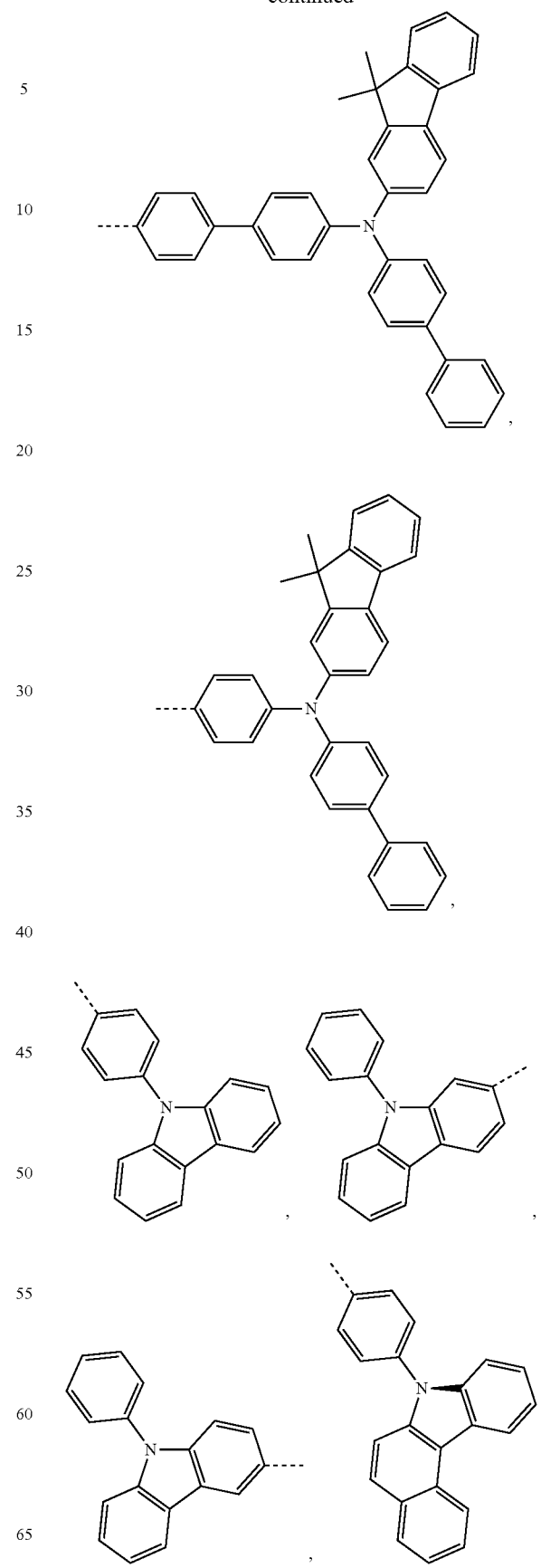

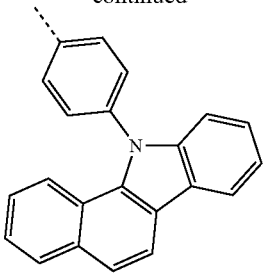

According to one embodiment of the present specification, --- means a site linking to other substituents.

According to one embodiment of the present specification, in Chemical Formula 1, $Ar_1$ and $Ar_2$ are the same as or different from each other, and each independently selected from the group consisting of a substituted or unsubstituted phenyl group; a substituted or unsubstituted biphenylyl group; a substituted or unsubstituted naphthyl group; a substituted or unsubstituted terphenyl group; a substituted or unsubstituted quaterphenyl group; a substituted or unsubstituted fluorenyl group; a substituted or unsubstituted phenanthrenyl group; a substituted or unsubstituted terphenylenyl group; a substituted or unsubstituted dibenzothiophene group; and a substituted or unsubstituted dibenzofuran group.

According to one embodiment of the present specification, $Ar_1$ and $Ar_2$ are the same as or different from each other, and each independently selected from the group consisting of a phenyl group; a biphenylyl group; a naphthyl group; a terphenyl group; a quaterphenyl group; a fluorenyl group; a phenanthrenyl group; a terphenylenyl group; a dibenzothiophene group; and a dibenzofuran group, and $Ar_1$ and $Ar_2$ may be unsubstituted or substituted with one or more selected from the group consisting of deuterium; a fluorine group; a nitrile group; a methyl group; a phenyl group; a biphenyl group; a naphthyl group; a fluorenyl group; a dibenzothiophene group; a dibenzofuranyl group; a carbazolyl group; a benzocarbazolyl group; a diphenylamine group; a dibiphenylamine group; an N-phenylbiphenylamine group; an N-phenylfluorenylamine group; and an N-biphenylfluorenylamine group.

According to one embodiment of the present specification, $Ar_1$ and Ar2 are the same as or different from each other, and may be each independently selected as any one among the following structural formulae.

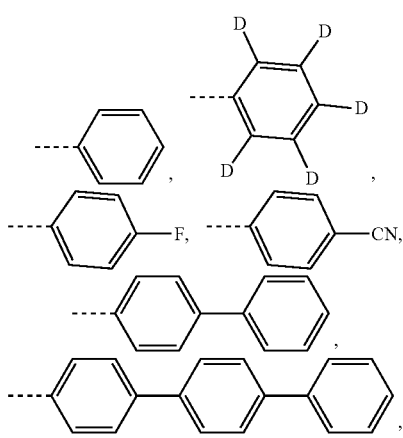

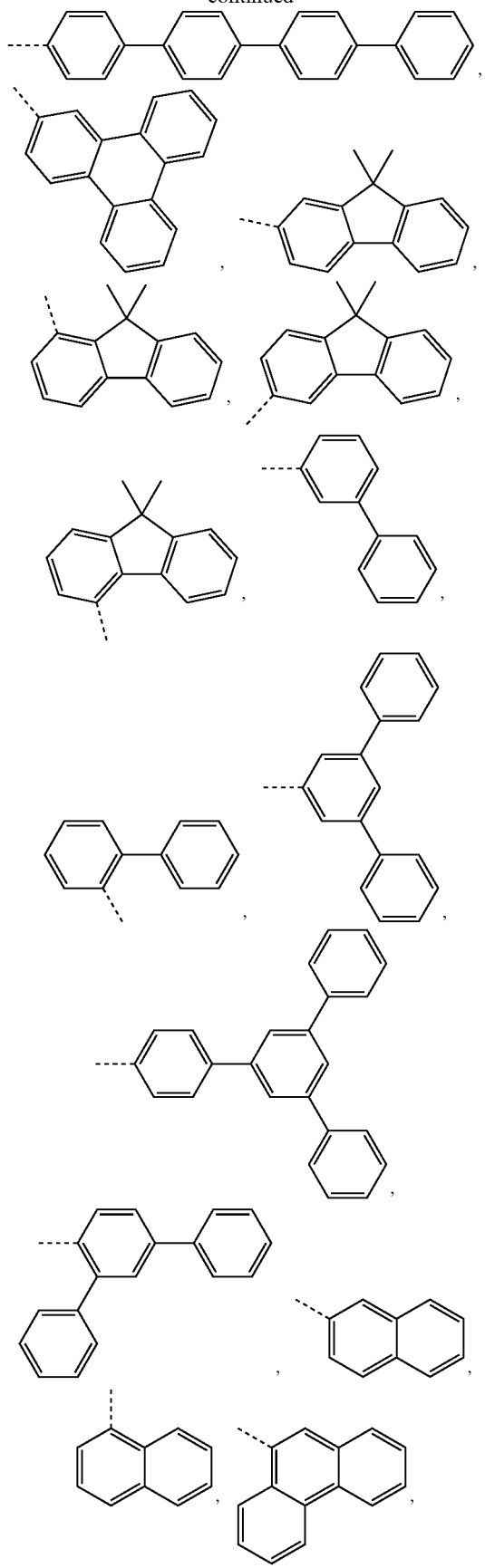

31
-continued
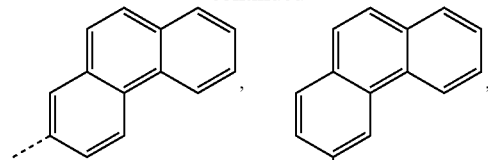
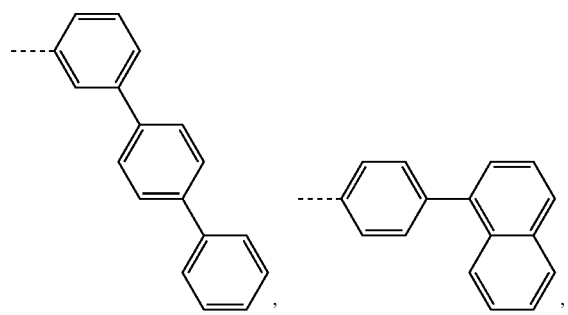
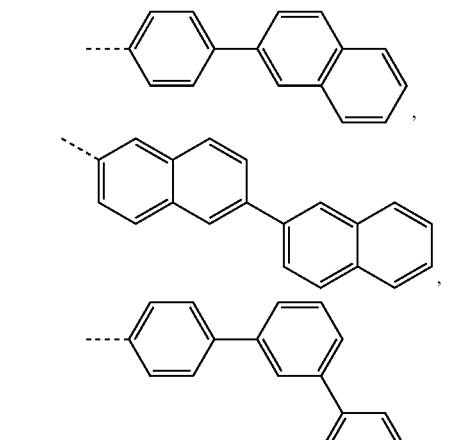
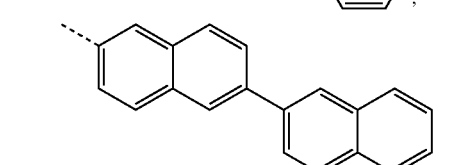
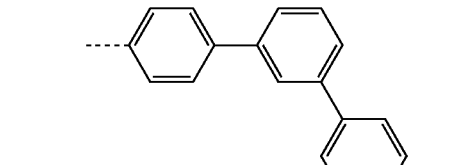
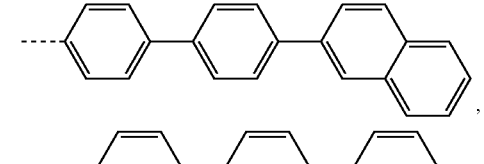
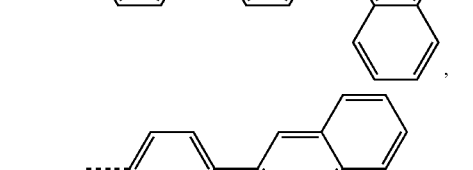
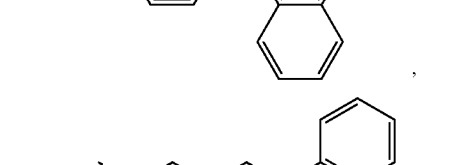
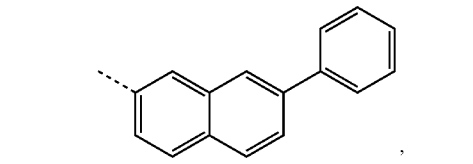
32
-continued
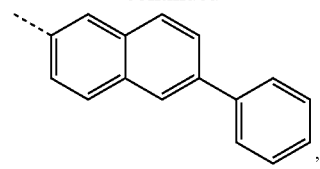
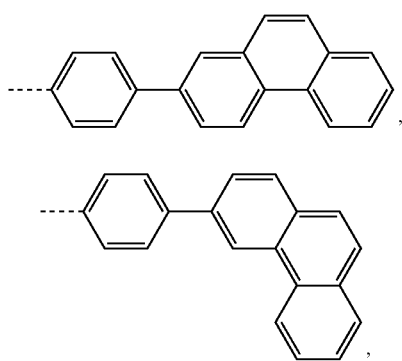
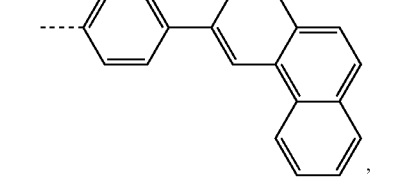
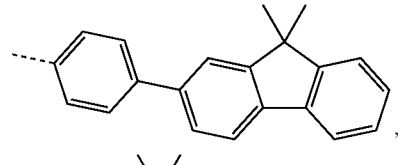
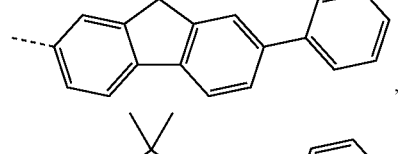
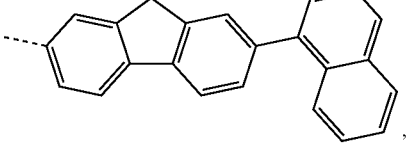
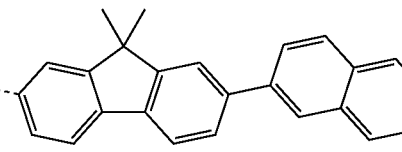
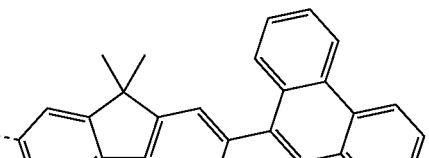
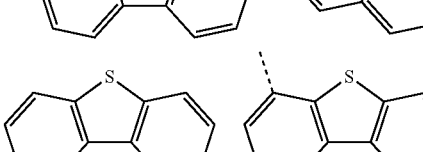
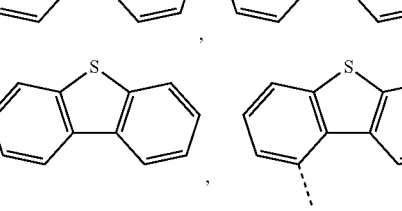
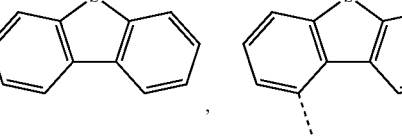
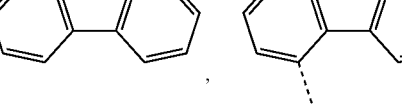

-continued

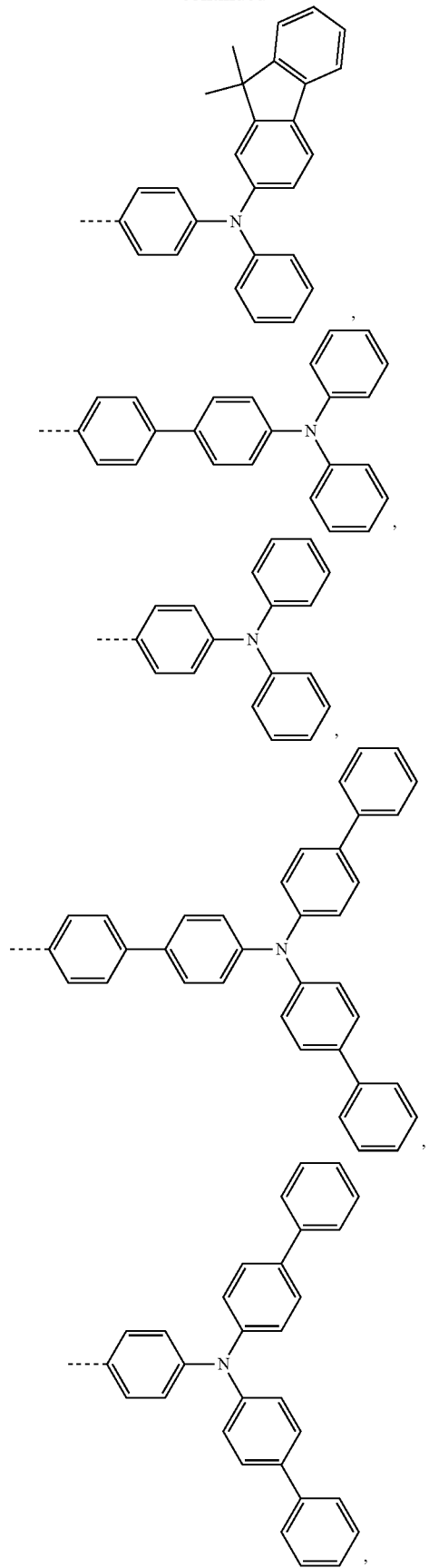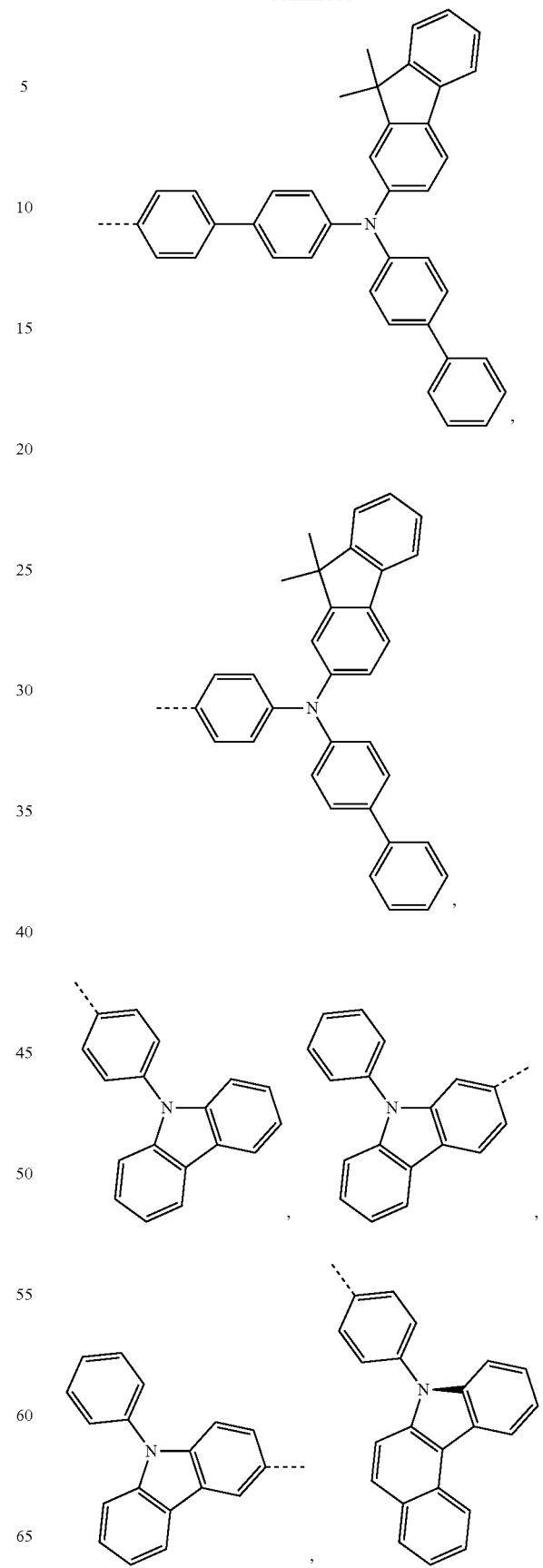

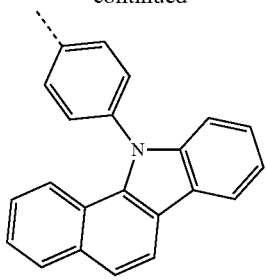

According to one embodiment of the present specification, in Chemical Formula 1, $Ar_3$ and $Ar_4$ are the same as or different from each other, and each independently selected from the group consisting of a substituted or unsubstituted phenyl group; a substituted or unsubstituted biphenylyl group; a substituted or unsubstituted naphthyl group; a substituted or unsubstituted terphenyl group; a substituted or unsubstituted fluorenyl group; and a substituted or unsubstituted phenanthrenyl group.

According to one embodiment of the present specification, in Chemical Formula 1, $Ar_3$ and $Ar_4$ are the same as or different from each other, and each independently selected from the group consisting of a phenyl group; a biphenylyl group; a naphthyl group; a terphenyl group; a fluorenyl group; and a phenanthrenyl group, and $Ar_3$ and $Ar_4$ may be unsubstituted or substituted with one or more selected from the group consisting of a methyl group; a phenyl group; a biphenyl group; a naphthyl group; and a fluorenyl group.

According to one embodiment of the present specification, $Ar_3$ and $Ar_4$ are the same as or different from each other, and may be each independently selected as any one among the following structural formulae.

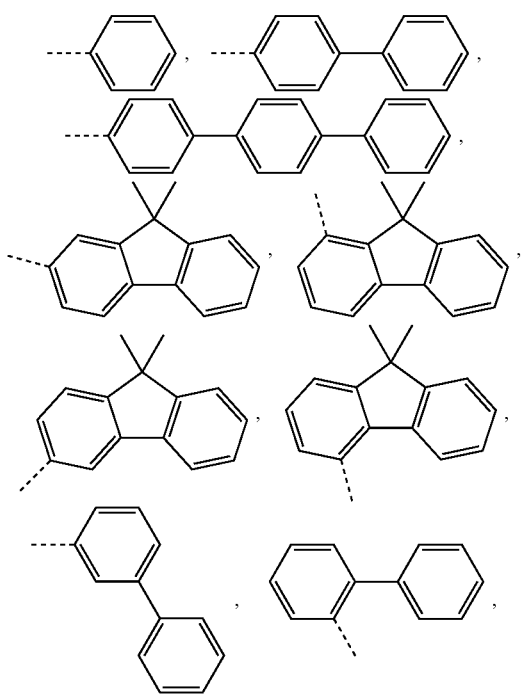

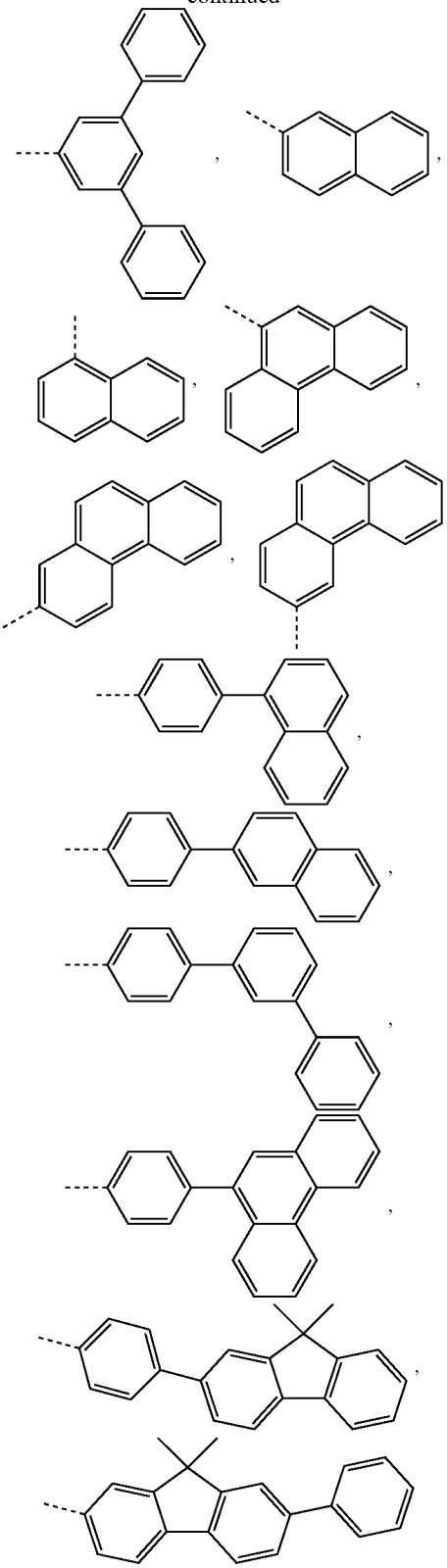

According to one embodiment of the present specification, in Chemical Formula 1, $Ar_5$ is selected from the group consisting of a substituted or unsubstituted phenyl group; a substituted or unsubstituted biphenylyl group; a substituted or unsubstituted naphthyl group; a substituted or unsubstituted terphenyl group; a substituted or unsubstituted fluorenyl group; a substituted or unsubstituted phenanthrenyl group; a substituted or unsubstituted dibenzothiophene group; and a substituted or unsubstituted dibenzofuran group.

According to one embodiment of the present specification, in Chemical Formula 1, $Ar_5$ is selected from the group consisting of a phenyl group; a biphenylyl group; a naphthyl group; a terphenyl group; a fluorenyl group; a phenanthrenyl group; a dibenzothiophene group; and a dibenzofuran group, and $Ar_5$ may be unsubstituted or substituted with one or more selected from the group consisting of a methyl group; a phenyl group; a biphenyl group; a naphthyl group; a phenanthrenyl group; and a fluorenyl group.

According to one embodiment of the present specification, $Ar_5$ may be selected as any one among the following structural formulae.

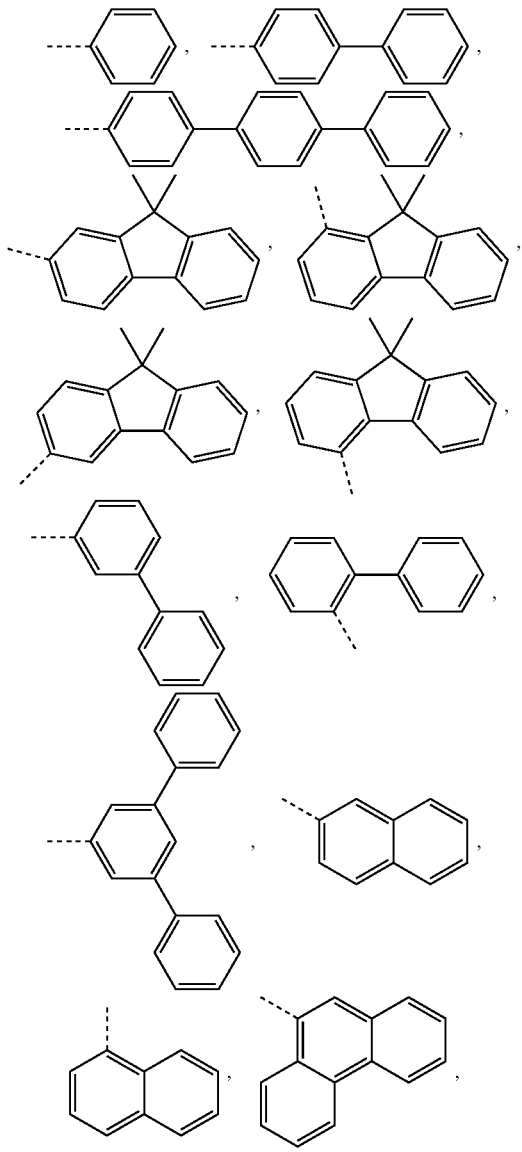

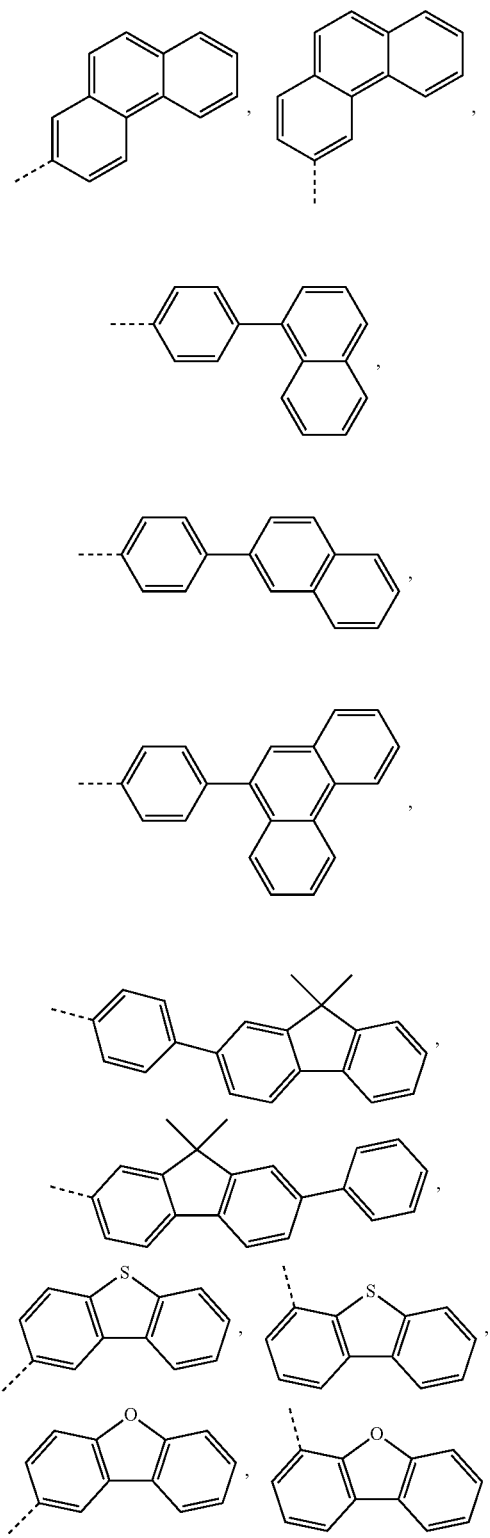

According to one embodiment of the present specification, the double spiro structure compound represented by Chemical Formula 1 is represented by the following Chemical Formula 2, and in the following Chemical Formula 2, $L_1$, $Ar_1$ and $Ar_2$ are any one selected from among 2-1-1 to 2-1-334 of the following Table 1.

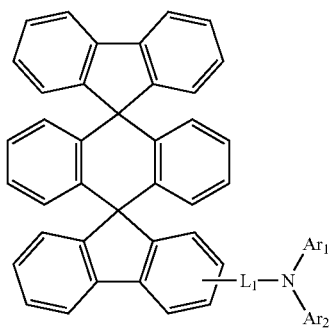

[Chemical Formula 2]

5

10

TABLE 1

| | ---L₁--- | ---Ar₁ | ---Ar₂ |
|---|---|---|---|
| 2-1-1 | Direct bond | phenyl | phenyl |
| 2-1-2 | Direct bond | phenyl | naphthalen-1-yl |
| 2-1-3 | Direct bond | phenyl | naphthalen-2-yl |
| 2-1-4 | Direct bond | 4-(naphthalen-1-yl)phenyl | 9,9-dimethylfluoren-2-yl |
| 2-1-5 | Direct bond | 4-(naphthalen-2-yl)phenyl | 9,9-dimethylfluoren-2-yl |
| 2-1-6 | Direct bond | phenyl | 9,9-dimethylfluoren-2-yl |
| 2-1-7 | Direct bond | biphenyl-4-yl | 9,9-dimethylfluoren-2-yl |
| 2-1-8 | Direct bond | 4-(naphthalen-1-yl)phenyl | biphenyl-4-yl |

TABLE 1-continued
| | ---L$_1$--- | ---Ar$_1$ | ---Ar$_2$ |
|---|---|---|---|
| 2-1-9 | Direct bond | 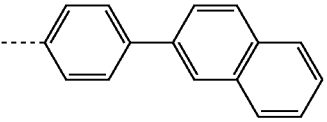 | 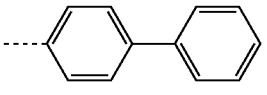 |
| 2-1-10 | Direct bond | 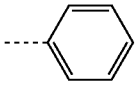 | 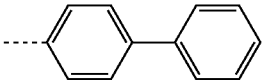 |
| 2-1-11 | Direct bond | 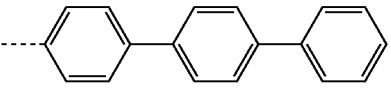 | 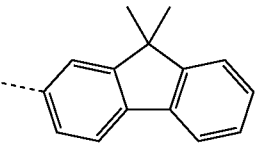 |
| 2-1-12 | Direct bond | 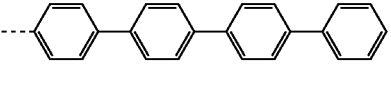 | 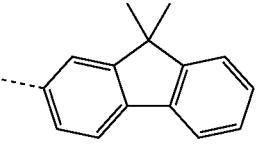 |
| 2-1-13 | Direct bond | 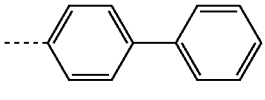 | 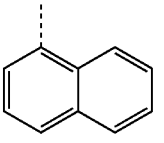 |
| 2-1-14 | Direct bond | 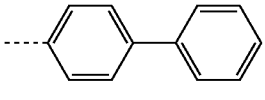 | 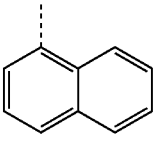 |
| 2-1-15 | Direct bond | 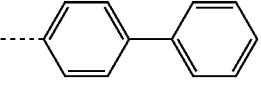 | 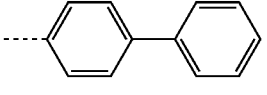 |
| 2-1-16 | Direct bond | 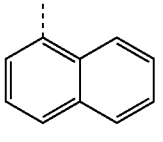 | 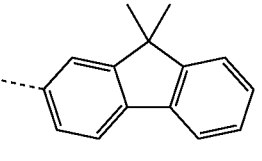 |
| 2-1-17 | Direct bond | 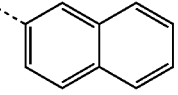 | 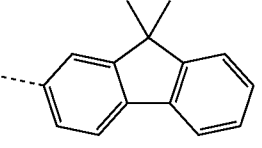 |
| 2-1-18 | Direct bond | 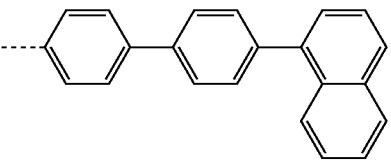 | 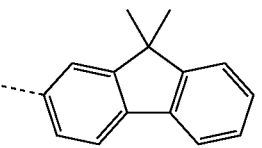 |

TABLE 1-continued
| | ---L$_1$--- | ---Ar$_1$ | ---Ar$_2$ |
|---|---|---|---|
| 2-1-19 | Direct bond | 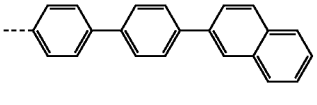 | 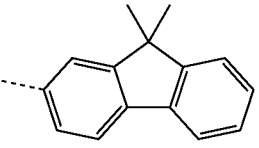 |
| 2-1-20 | Direct bond | 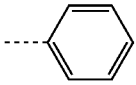 | 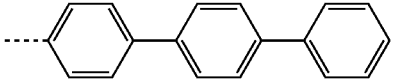 |
| 2-1-21 | Direct bond | 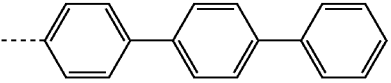 | 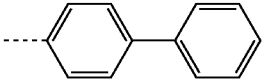 |
| 2-1-22 | Direct bond | 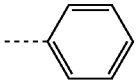 | 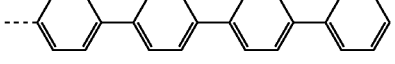 |
| 2-1-23 | Direct bond | 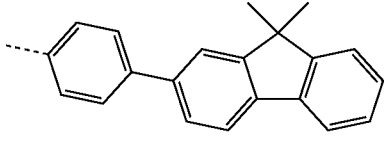 | 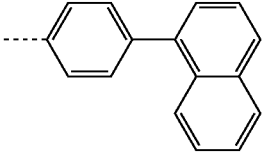 |
| 2-1-24 | Direct bond | 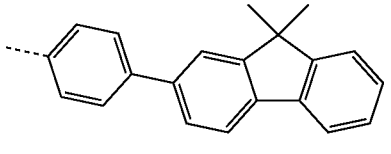 | 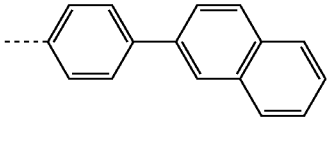 |
| 2-1-25 | Direct bond | 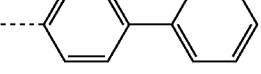 | 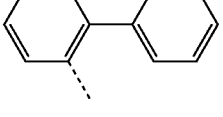 |
| 2-1-26 | Direct bond | 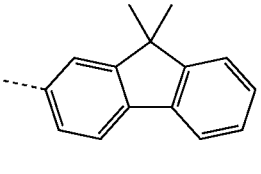 | 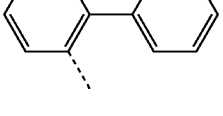 |
| 2-1-27 | Direct bond | 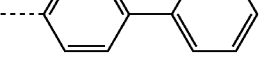 | 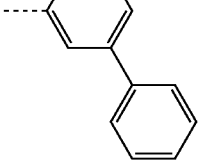 |
| 2-1-28 | Direct bond | 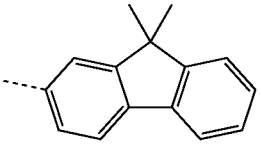 | 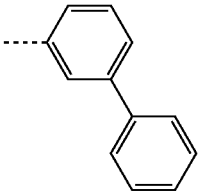 |

TABLE 1-continued
| | ---L₁--- | ---Ar₁ | ---Ar₂ |
|---|---|---|---|
| 2-1-29 | Direct bond | 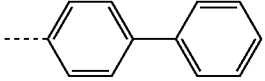 | 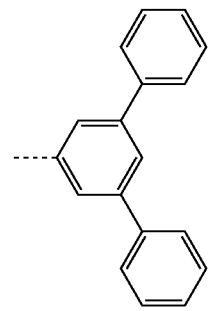 |
| 2-1-30 | Direct bond | 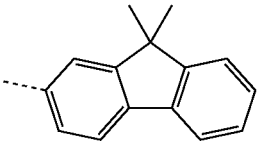 | 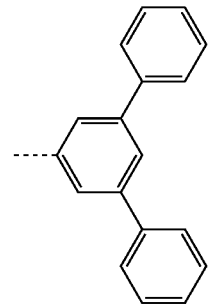 |
| 2-1-31 | Direct bond | 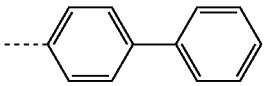 | 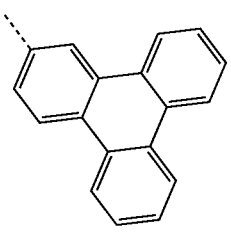 |
| 2-1-32 | Direct bond | 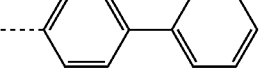 | 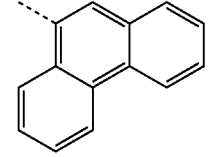 |
| 2-1-33 | Direct bond | 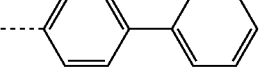 | 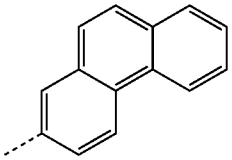 |
| 2-1-34 | Direct bond | 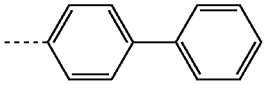 | 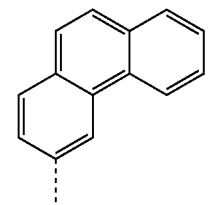 |
| 2-1-35 | Direct bond | 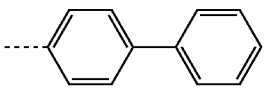 |  |
| 2-1-36 | Direct bond | 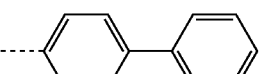 |  |

TABLE 1-continued
| | ---L₁--- | ---Ar₁ | ---Ar₂ |
|---|---|---|---|
| 2-1-37 | Direct bond | 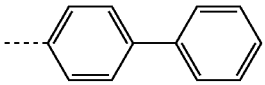 | 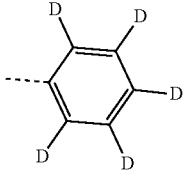 |
| 2-1-38 | Direct bond | 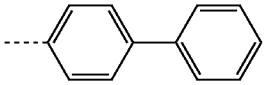 | 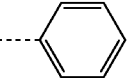 |
| 2-1-39 | Direct bond | 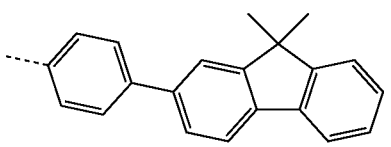 | 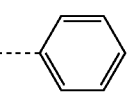 |
| 2-1-40 | Direct bond | 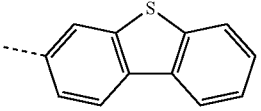 | 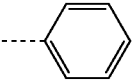 |
| 2-1-41 | Direct bond | 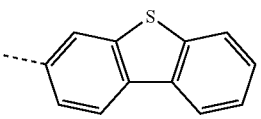 | 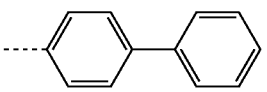 |
| 2-1-42 | Direct bond | 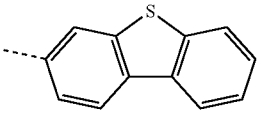 | 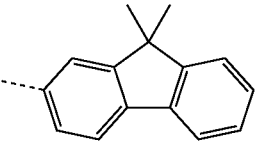 |
| 2-1-43 | Direct bond | 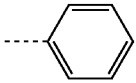 | 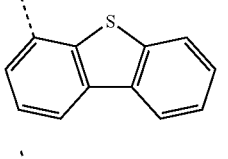 |
| 2-1-44 | Direct bond | 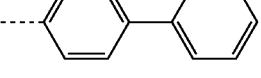 | 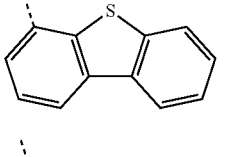 |
| 2-1-45 | Direct bond | 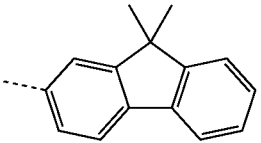 | 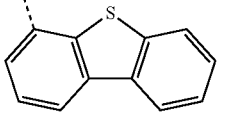 |
| 2-1-46 | Direct bond | 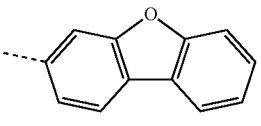 | 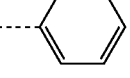 |
| 2-1-47 | Direct bond | 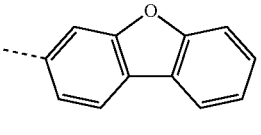 | 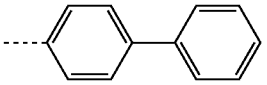 |

TABLE 1-continued

| | ---L₁--- | ---Ar₁ | ---Ar₂ |
|---|---|---|---|
| 2-1-48 | Direct bond | dibenzofuran | 9,9-dimethylfluorene |
| 2-1-49 | Direct bond | phenyl | dibenzofuran |
| 2-1-50 | Direct bond | biphenyl | dibenzofuran |
| 2-1-51 | Direct bond | 9,9-dimethylfluorene | dibenzofuran |
| 2-1-52 | Direct bond | 9,9-dimethylfluorene | 9-phenylcarbazole (via phenyl) |
| 2-1-53 | Direct bond | 9,9-dimethylfluorene | 9-phenylcarbazole |
| 2-1-54 | Direct bond | 9,9-dimethylfluorene | 9-phenylcarbazole |

TABLE 1-continued
| | ---L₁--- | ---Ar₁ | ---Ar₂ |
|---|---|---|---|
| 2-1-55 | Direct bond | 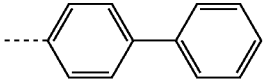 | 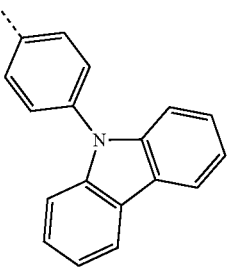 |
| 2-1-56 | Direct bond | 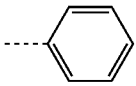 | 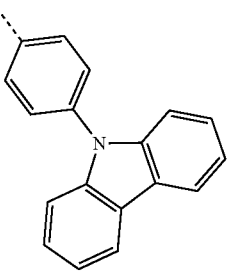 |
| 2-1-57 | Direct bond | 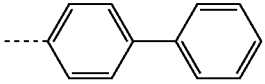 | 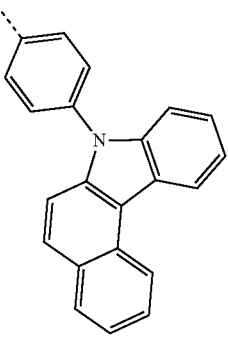 |
| 2-1-58 | Direct bond | 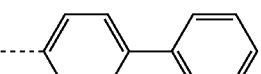 | 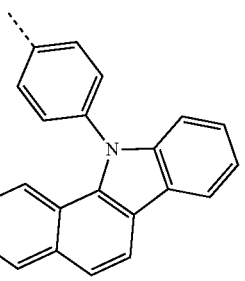 |
| 2-1-59 | Direct bond | 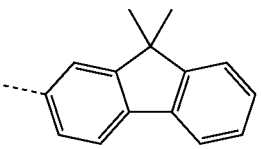 | 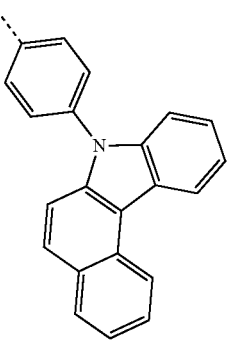 |

TABLE 1-continued

| | ---L₁--- | ---Ar₁--- | ---Ar₂--- |
|---|---|---|---|
| 2-1-60 | Direct bond | 9,9-dimethylfluorenyl | phenyl-benzo[a]carbazolyl |
| 2-1-61 | Direct bond | biphenyl-3-yl | phenyl-carbazolyl |
| 2-1-62 | Direct bond | phenyl | phenyl-benzo[a]carbazolyl |
| 2-1-63 | Direct bond | phenyl | phenyl-benzo[c]carbazolyl |
| 2-1-64 | phenylene | phenyl | phenyl |
| 2-1-65 | phenylene | phenyl | biphenyl |
| 2-1-66 | phenylene | phenyl | terphenyl |
| 2-1-67 | phenylene | biphenyl | biphenyl |

TABLE 1-continued
| | ---L$_1$--- | ---Ar$_1$ | ---Ar$_2$ |
|---|---|---|---|
| 2-1-68 |  | 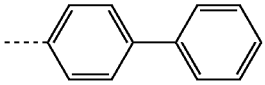 | 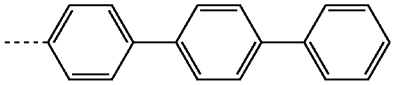 |
| 2-1-69 |  | 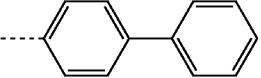 | 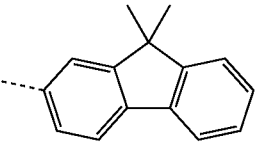 |
| 2-1-70 |  | 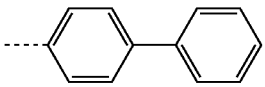 | 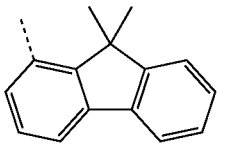 |
| 2-1-71 |  | 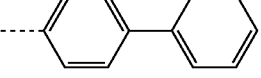 | 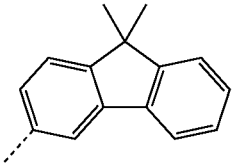 |
| 2-1-72 |  | 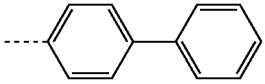 | 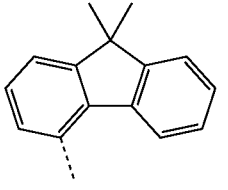 |
| 2-1-73 | 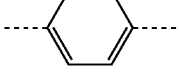 | 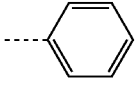 | 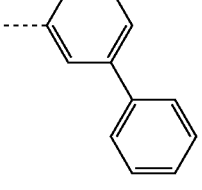 |
| 2-1-74 | 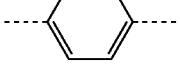 | 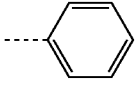 | 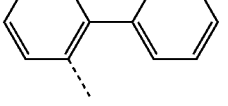 |
| 2-1-75 | 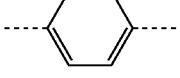 | 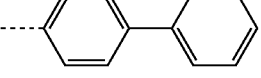 | 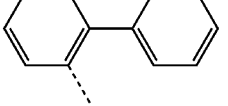 |
| 2-1-76 |  | 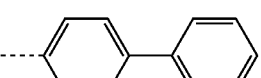 | 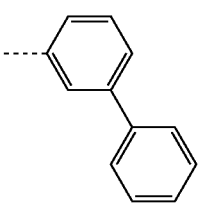 |

TABLE 1-continued
| | ---L$_1$--- | ---Ar$_1$--- | ---Ar$_2$ |
|---|---|---|---|
| 2-1-77 |  | 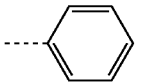 | 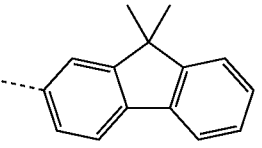 |
| 2-1-78 |  | 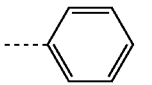 | 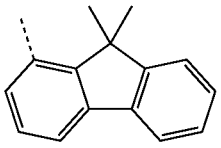 |
| 2-1-79 |  | 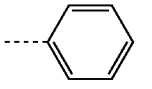 | 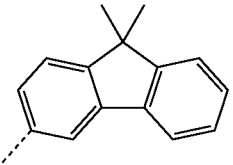 |
| 2-1-80 |  | 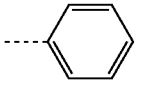 | 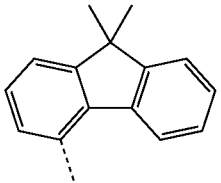 |
| 2-1-81 |  | 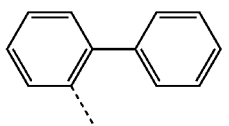 | 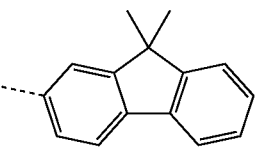 |
| 2-1-82 |  | 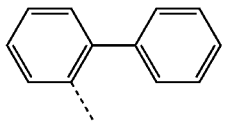 | 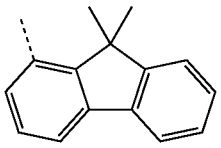 |
| 2-1-83 |  | 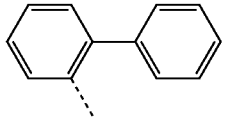 | 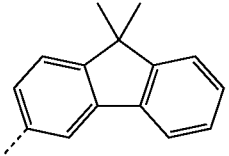 |
| 2-1-84 |  | 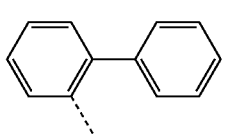 | 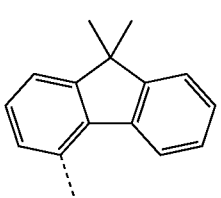 |

TABLE 1-continued
| | ---L$_1$--- | ---Ar$_1$--- | ---Ar$_2$ |
|---|---|---|---|
| 2-1-85 |  | 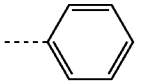 | 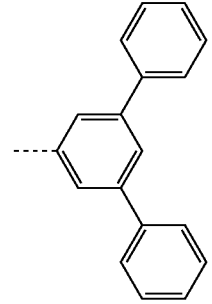 |
| 2-1-86 |  | 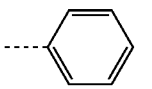 | 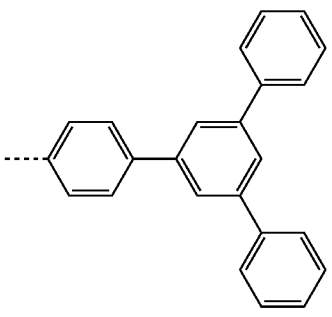 |
| 2-1-87 |  | 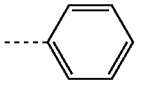 | 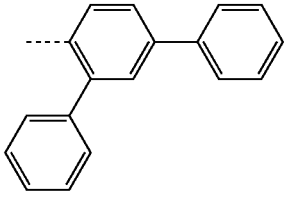 |
| 2-1-88 |  | 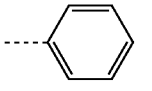 | 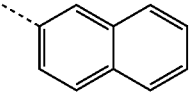 |
| 2-1-89 |  | 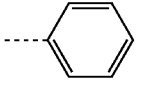 | 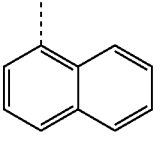 |
| 2-1-90 | 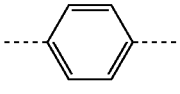 | 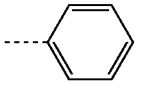 | 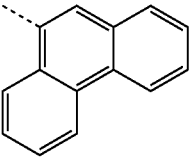 |
| 2-1-91 |  | 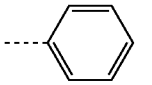 | 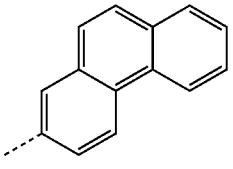 |

TABLE 1-continued
| | ---L$_1$--- | ---Ar$_1$--- | ---Ar$_2$--- |
|---|---|---|---|
| 2-1-92 |  | 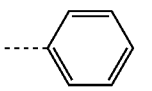 | 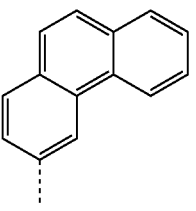 |
| 2-1-93 |  | 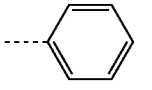 | 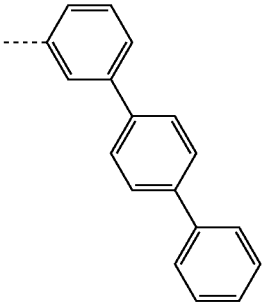 |
| 2-1-94 |  | 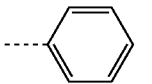 | 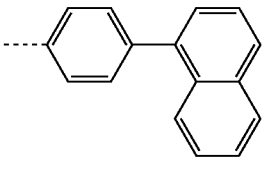 |
| 2-1-95 | 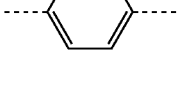 | 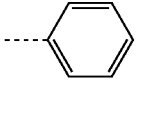 | 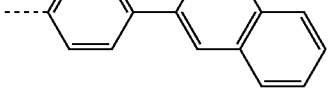 |
| 2-1-96 |  | 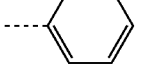 | 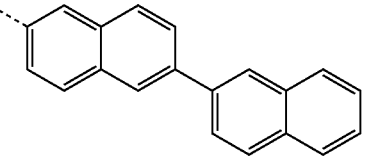 |
| 2-1-97 | 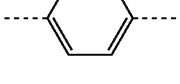 | 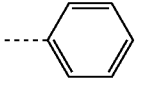 | 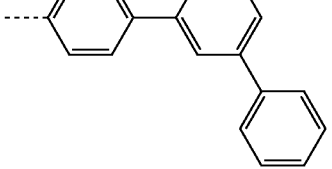 |
| 2-1-98 |  | 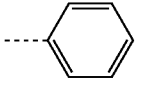 | 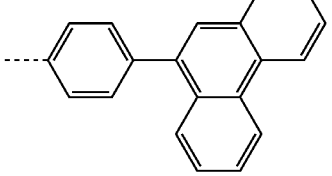 |
| 2-1-99 |  | 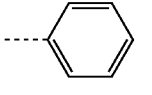 | 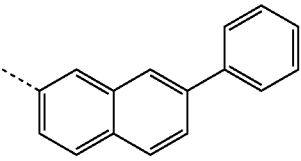 |

TABLE 1-continued
| | ---L$_1$--- | ---Ar$_1$--- | ---Ar$_2$ |
|---|---|---|---|
| 2-1-100 |  | 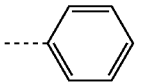 | 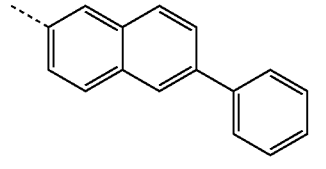 |
| 2-1-101 |  | 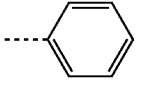 | 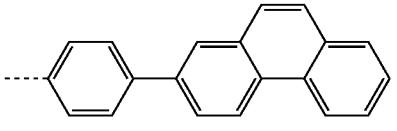 |
| 2-1-102 |  | 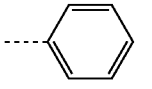 | 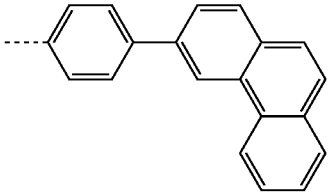 |
| 2-1-103 |  | 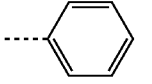 | 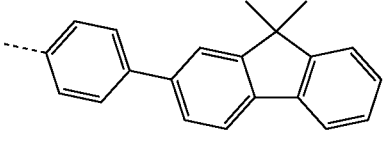 |
| 2-1-104 | 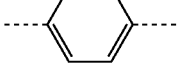 | 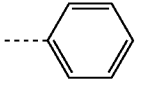 | 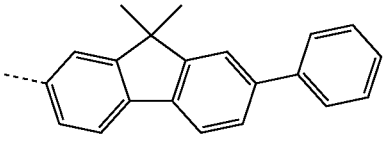 |
| 2-1-105 | 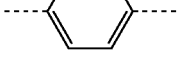 | 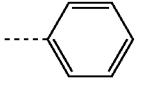 | 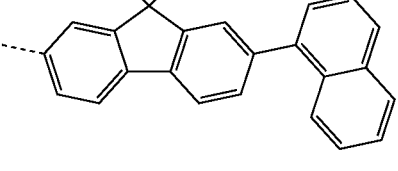 |
| 2-1-106 |  | 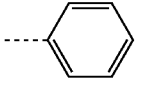 | 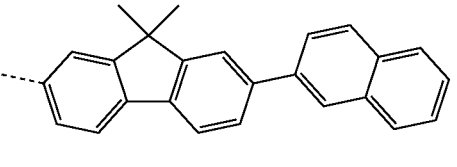 |
| 2-1-107 | 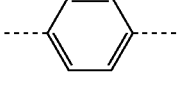 | 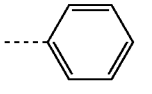 | 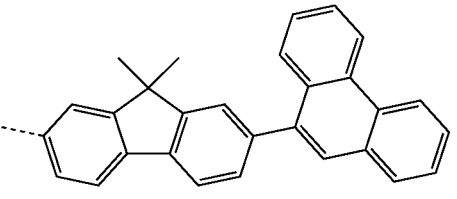 |

TABLE 1-continued
| | ---L₁--- | ---Ar₁ | ---Ar₂ |
|---|---|---|---|
| 2-1-108 | 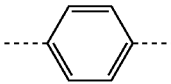 | 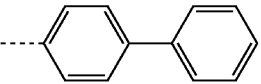 | 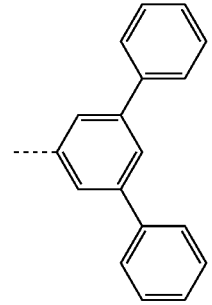 |
| 2-1-109 | 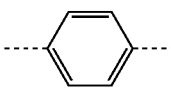 | 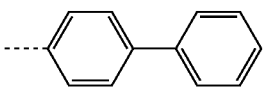 | 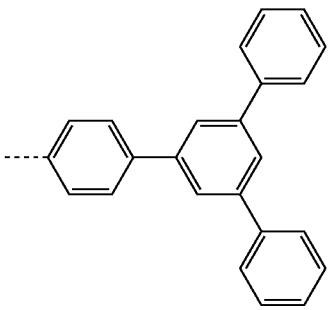 |
| 2-1-110 | 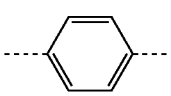 | 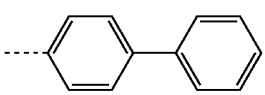 | 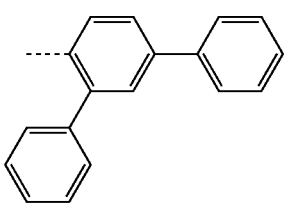 |
| 2-1-111 | 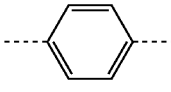 | 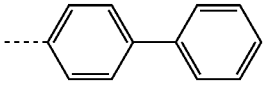 | 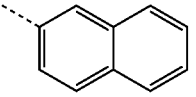 |
| 2-1-112 | 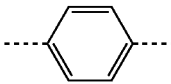 | 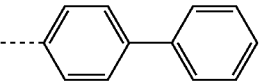 | 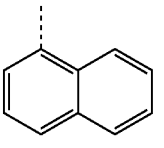 |
| 2-1-113 | 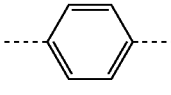 | 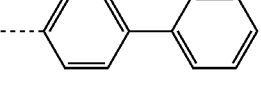 | 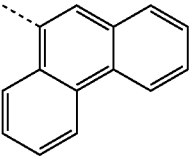 |
| 2-1-114 | 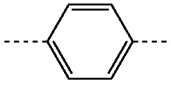 | 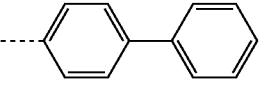 | 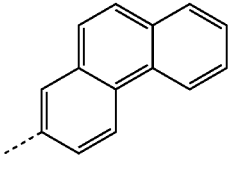 |

TABLE 1-continued
| | ---L$_1$--- | ---Ar$_1$--- | ---Ar$_2$--- |
|---|---|---|---|
| 2-1-115 |  | 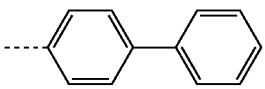 | 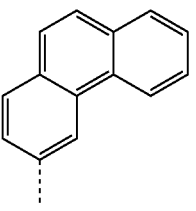 |
| 2-1-116 |  | 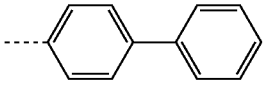 | 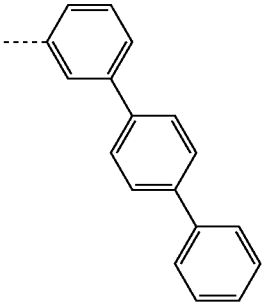 |
| 2-1-117 |  | 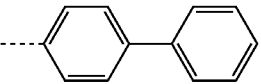 | 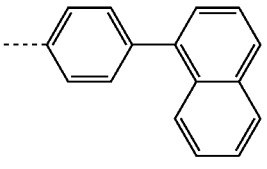 |
| 2-1-118 | 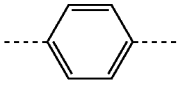 | 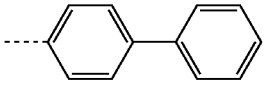 | 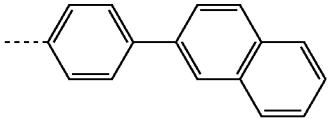 |
| 2-1-119 |  | 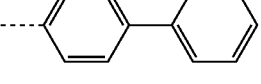 | 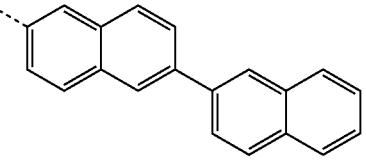 |
| 2-1-120 |  | 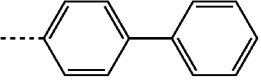 | 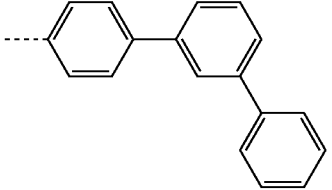 |
| 2-1-121 |  | 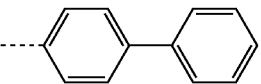 | 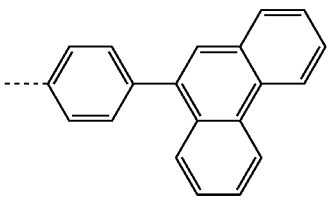 |
| 2-1-122 |  | 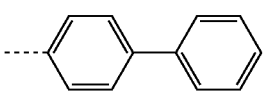 | 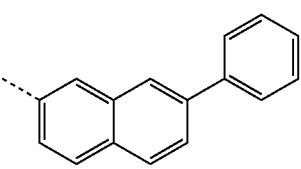 |

TABLE 1-continued
| | ---L$_1$--- | ---Ar$_1$--- | ---Ar$_2$ |
|---|---|---|---|
| 2-1-123 |  | 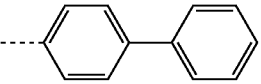 | 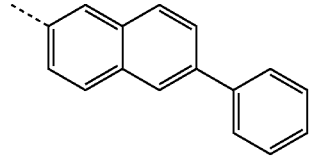 |
| 2-1-124 |  | 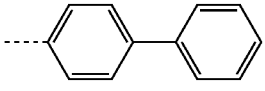 | 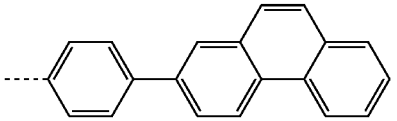 |
| 2-1-125 |  | 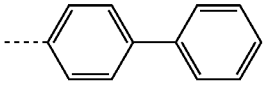 | 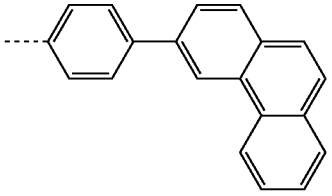 |
| 2-1-126 |  | 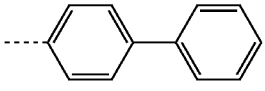 | 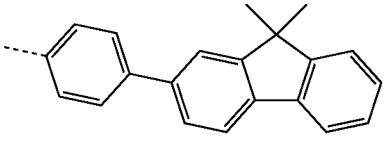 |
| 2-1-127 | 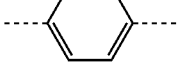 | 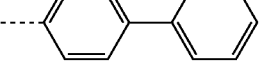 | 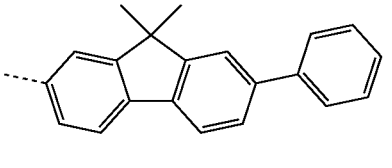 |
| 2-1-128 | 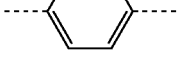 | 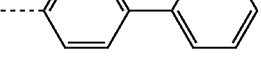 | 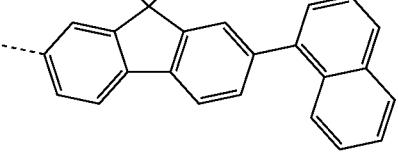 |
| 2-1-129 |  | 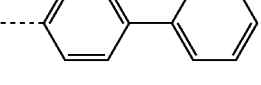 | 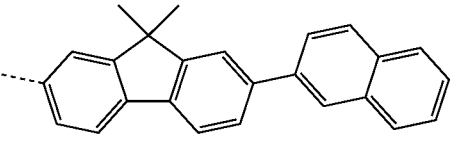 |
| 2-1-130 | 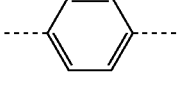 | 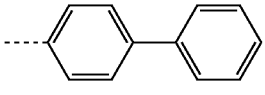 | 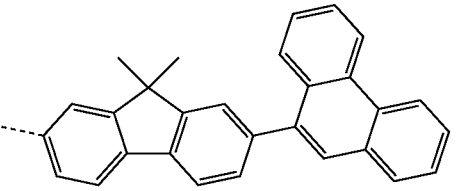 |

TABLE 1-continued
| | ---L₁--- | ---Ar₁--- | ---Ar₂--- |
|---|---|---|---|
| 2-1-131 |  | 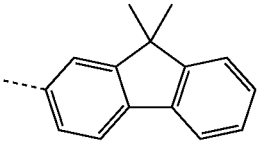 | 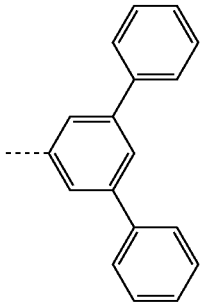 |
| 2-1-132 |  | 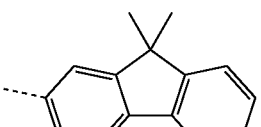 | 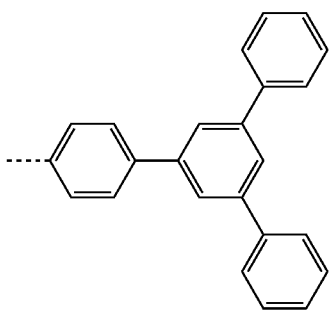 |
| 2-1-133 |  | 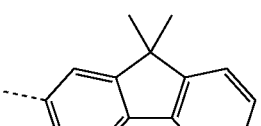 | 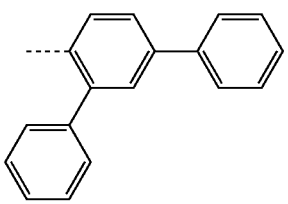 |
| 2-1-134 |  | 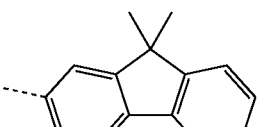 | 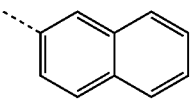 |
| 2-1-135 |  | 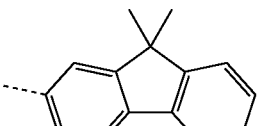 | 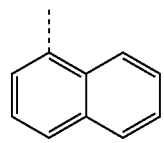 |
| 2-1-136 |  | 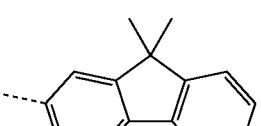 | 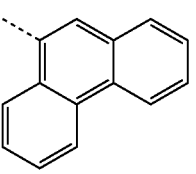 |
| 2-1-137 |  | 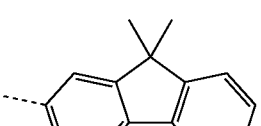 | 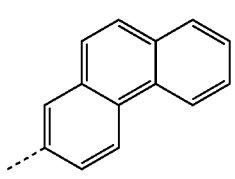 |

TABLE 1-continued
| | ---L$_1$--- | ---Ar$_1$--- | ---Ar$_2$--- |
|---|---|---|---|
| 2-1-138 | 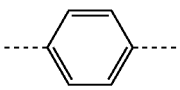 | 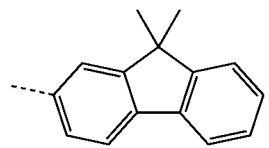 | 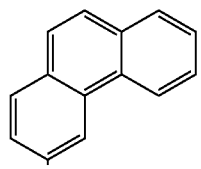 |
| 2-1-139 | 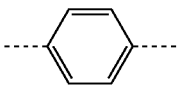 | 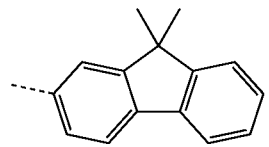 | 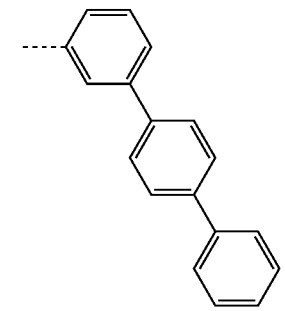 |
| 2-1-140 | 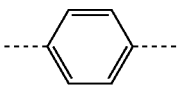 | 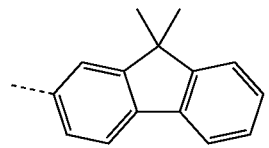 | 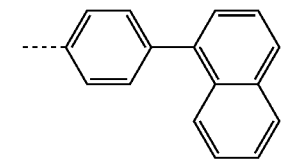 |
| 2-1-141 | 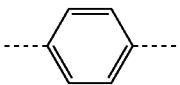 | 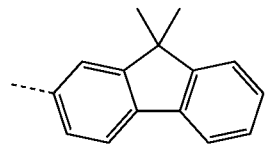 | 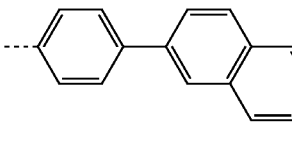 |
| 2-1-142 | 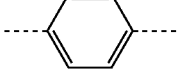 | 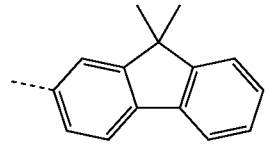 | 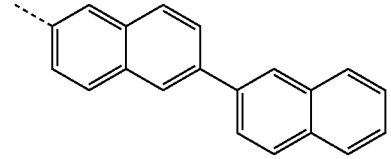 |
| 2-1-143 | 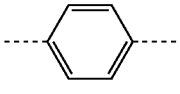 | 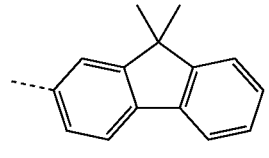 | 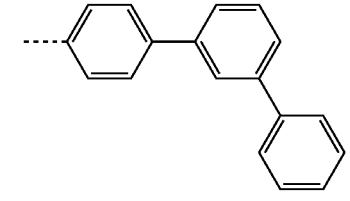 |
| 2-1-144 | 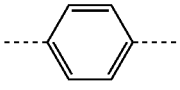 | 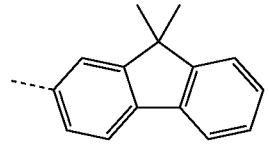 | 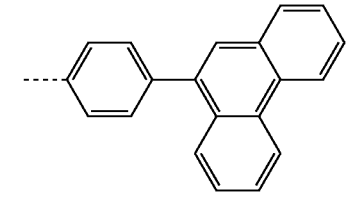 |
| 2-1-145 | 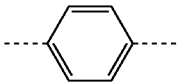 | 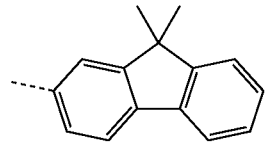 | 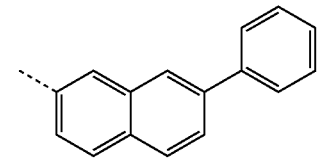 |

TABLE 1-continued
| | ---L$_1$--- | ---Ar$_1$ | ---Ar$_2$ |
|---|---|---|---|
| 2-1-146 |  | 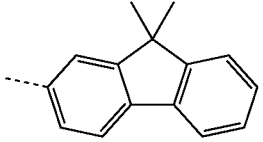 | 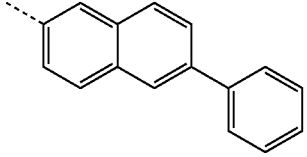 |
| 2-1-147 |  |  | 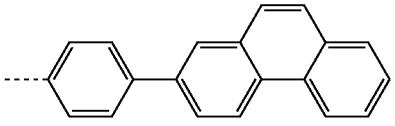 |
| 2-1-148 |  | 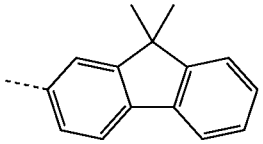 | 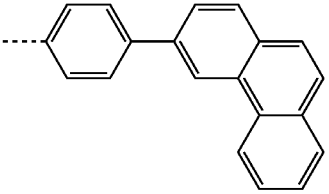 |
| 2-1-149 |  |  | 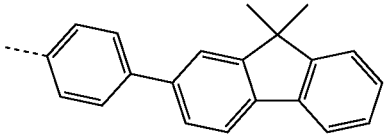 |
| 2-1-150 |  | 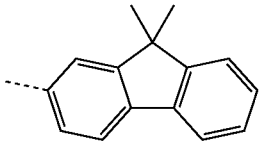 | 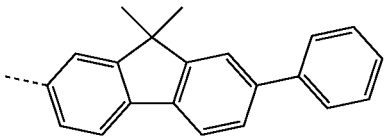 |
| 2-1-151 |  | 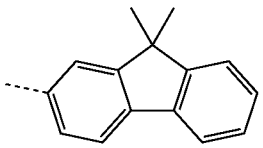 | 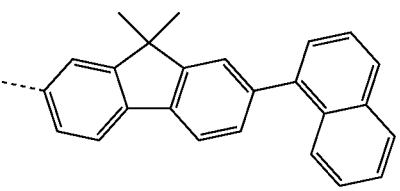 |
| 2-1-152 |  | 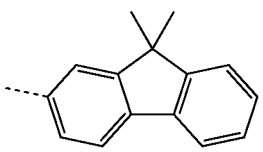 | 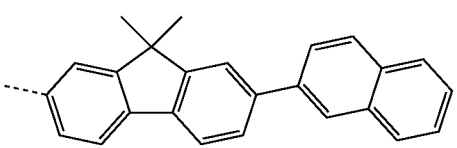 |
| 2-1-153 |  | 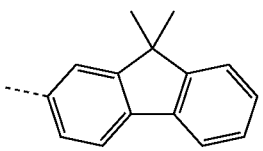 | 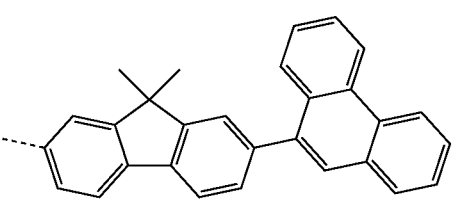 |

TABLE 1-continued
| | ---L$_1$--- | ---Ar$_1$ | ---Ar$_2$ |
|---|---|---|---|
| 2-1-154 |  | 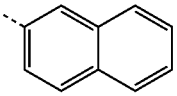 | 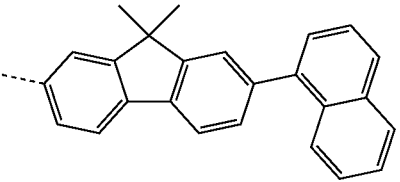 |
| 2-1-155 |  | 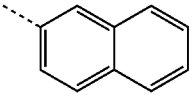 | 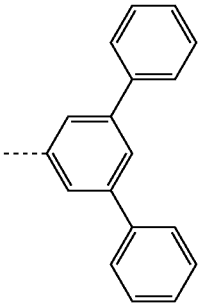 |
| 2-1-156 |  | 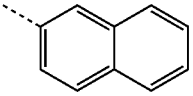 | 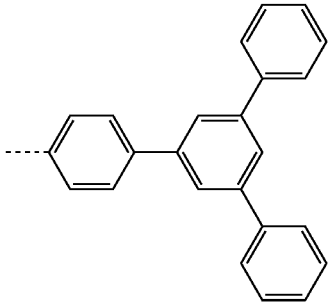 |
| 2-1-157 |  | 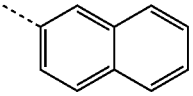 | 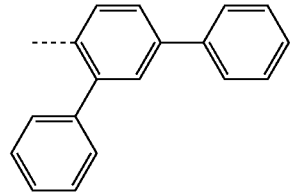 |
| 2-1-158 |  | 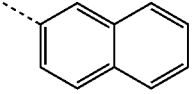 | 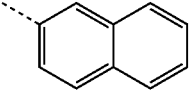 |
| 2-1-159 |  | 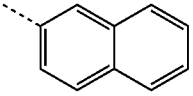 | 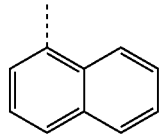 |
| 2-1-160 |  | 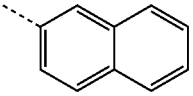 | 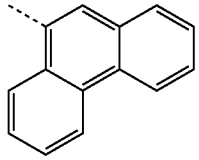 |

TABLE 1-continued

| | ---L₁--- | ---Ar₁ | ---Ar₂ |
|---|---|---|---|
| 2-1-161 | phenylene | 2-naphthyl | phenanthrenyl |
| 2-1-162 | phenylene | 2-naphthyl | phenanthrenyl |
| 2-1-163 | phenylene | 2-naphthyl | m-biphenyl-phenyl |
| 2-1-164 | phenylene | 2-naphthyl | phenyl-naphthyl |
| 2-1-165 | phenylene | 2-naphthyl | phenyl-naphthyl |
| 2-1-166 | phenylene | 2-naphthyl | binaphthyl |
| 2-1-167 | phenylene | 2-naphthyl | terphenyl |
| 2-1-168 | phenylene | 2-naphthyl | phenyl-phenanthrenyl |

TABLE 1-continued
| | ---L$_1$--- | ---Ar$_1$ | ---Ar$_2$ |
|---|---|---|---|
| 2-1-169 |  | 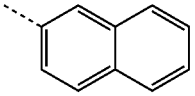 | 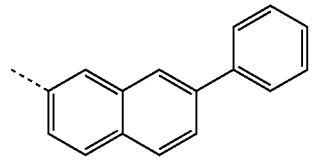 |
| 2-1-170 |  | 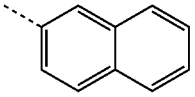 | 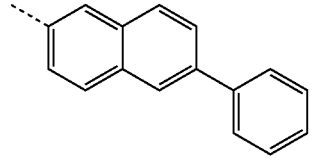 |
| 2-1-171 | 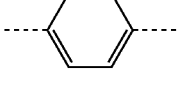 | 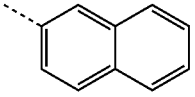 | 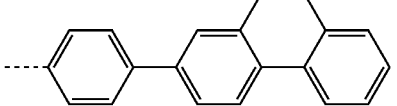 |
| 2-1-172 |  | 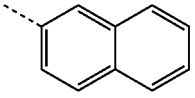 | 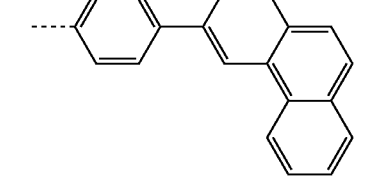 |
| 2-1-173 | 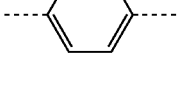 | 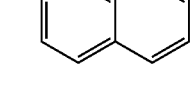 | 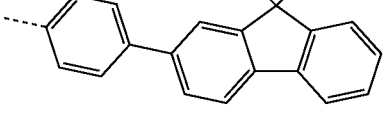 |
| 2-1-174 | 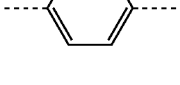 | 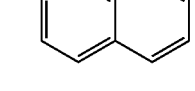 | 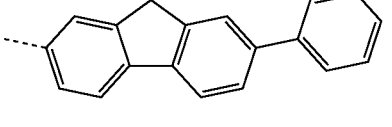 |
| 2-1-175 | 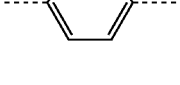 | 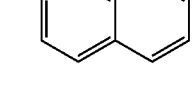 | 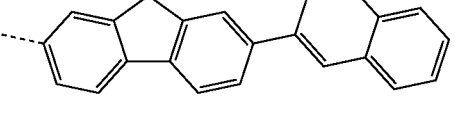 |
| 2-1-176 | 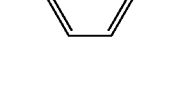 | 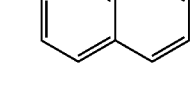 | 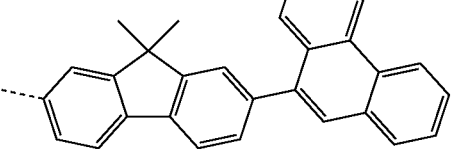 |
| 2-1-177 |  | 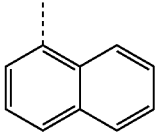 | 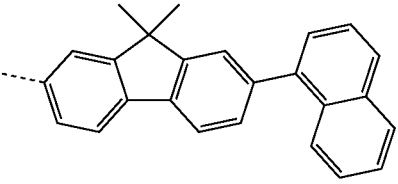 |

TABLE 1-continued
| | ---L₁--- | ---Ar₁ | ---Ar₂ |
|---|---|---|---|
| 2-1-178 |  | 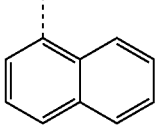 | 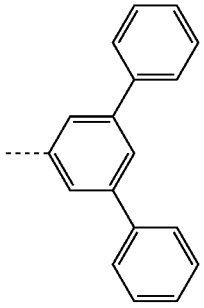 |
| 2-1-179 |  | 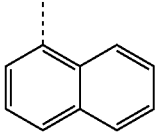 | 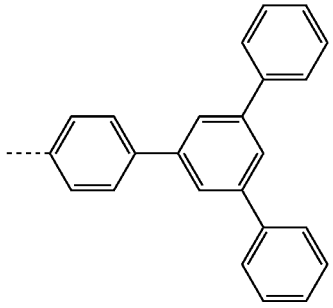 |
| 2-1-180 |  | 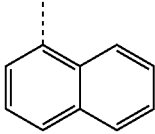 | 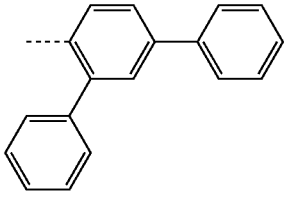 |
| 2-1-181 |  | 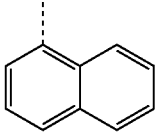 | 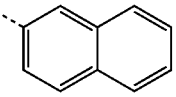 |
| 2-1-182 |  | 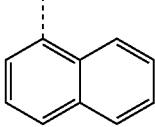 | 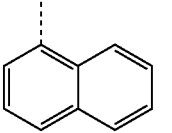 |
| 2-1-183 | 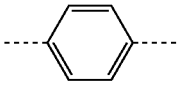 | 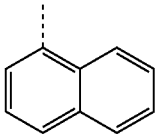 | 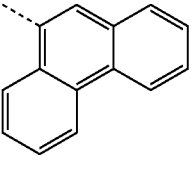 |
| 2-1-184 |  | 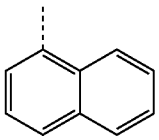 | 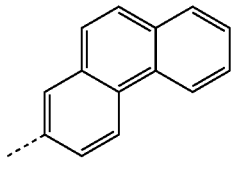 |

TABLE 1-continued
| | ---L$_1$--- | ---Ar$_1$--- | ---Ar$_2$--- |
|---|---|---|---|
| 2-1-185 | 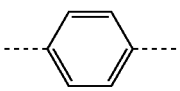 | 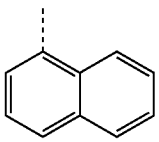 | 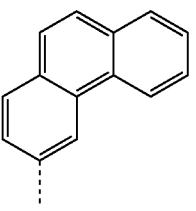 |
| 2-1-186 | 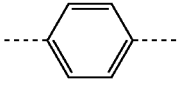 | 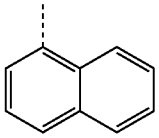 | 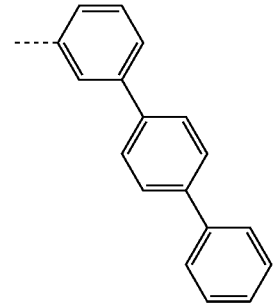 |
| 2-1-187 | 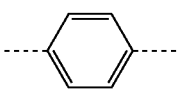 | 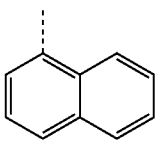 | 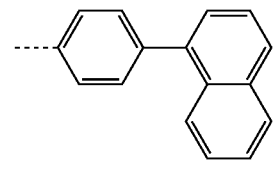 |
| 2-1-188 | 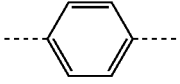 | 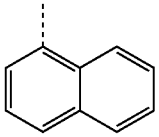 | 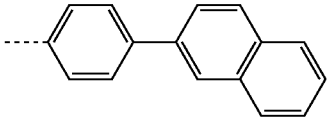 |
| 2-1-189 | 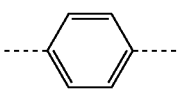 | 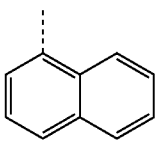 | 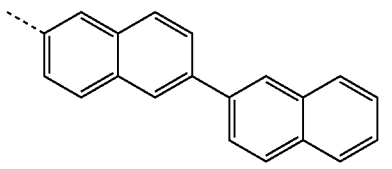 |
| 2-1-190 | 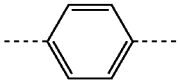 | 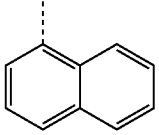 | 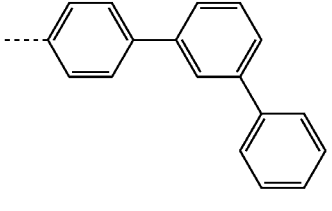 |
| 2-1-191 | 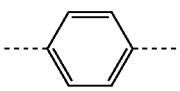 | 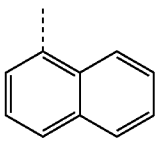 | 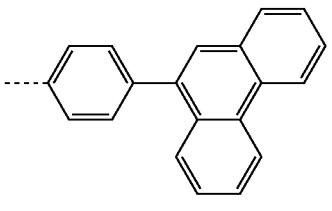 |
| 2-1-192 | 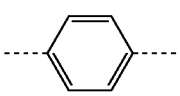 | 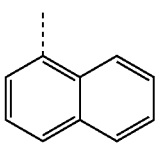 | 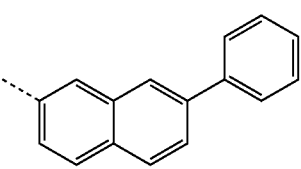 |

TABLE 1-continued
| | ---L$_1$--- | ---Ar$_1$--- | ---Ar$_2$--- |
|---|---|---|---|
| 2-1-193 | 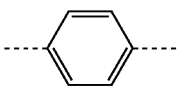 | 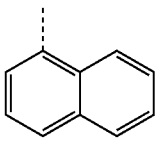 | 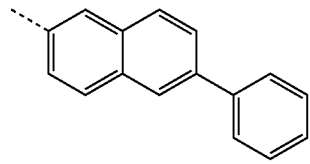 |
| 2-1-194 | 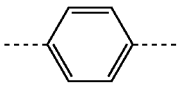 | 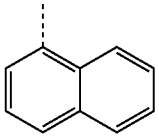 | 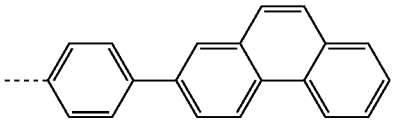 |
| 2-1-195 | 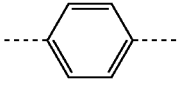 | 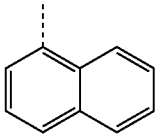 | 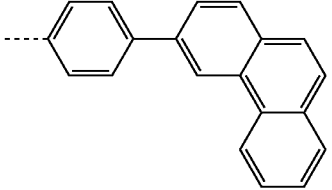 |
| 2-1-196 | 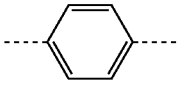 | 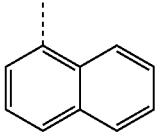 | 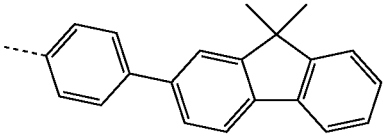 |
| 2-1-197 | 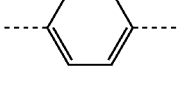 | 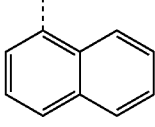 | 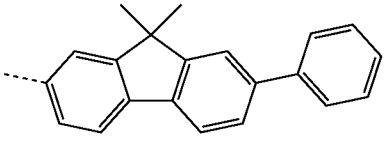 |
| 2-1-198 | 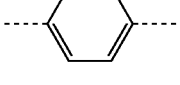 | 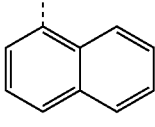 | 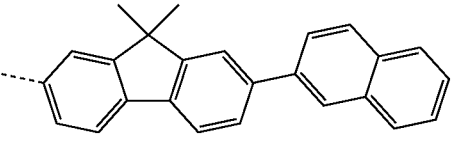 |
| 2-1-199 | 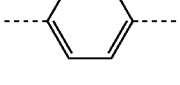 | 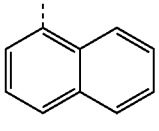 | 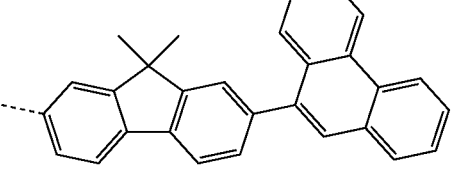 |
| 2-1-200 | 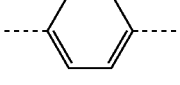 | 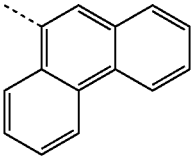 | 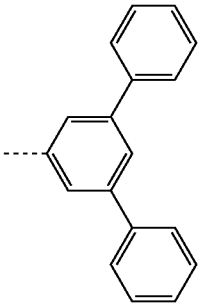 |

TABLE 1-continued
| | ---L$_1$--- | ---Ar$_1$--- | ---Ar$_2$--- |
|---|---|---|---|
| 2-1-201 | 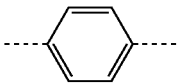 | 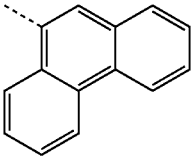 | 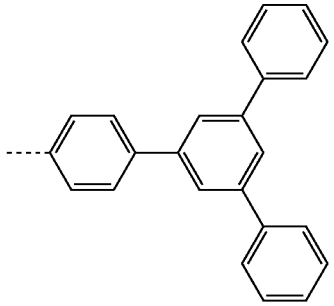 |
| 2-1-202 |  | 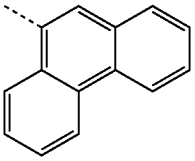 | 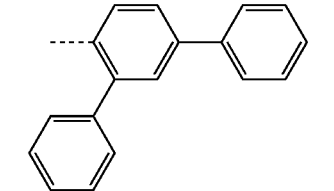 |
| 2-1-203 | 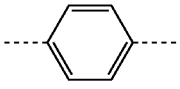 | 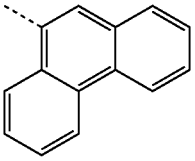 | 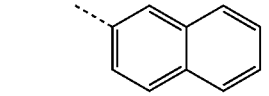 |
| 2-1-204 | 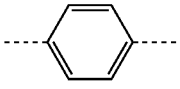 | 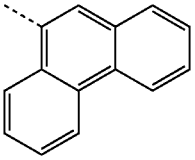 | 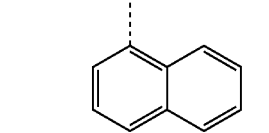 |
| 2-1-205 | 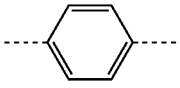 | 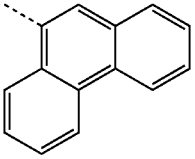 | 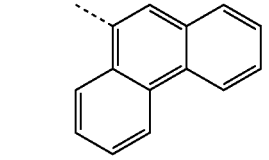 |
| 2-1-206 | 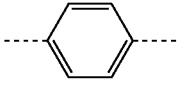 | 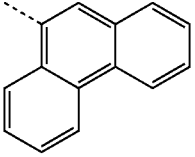 | 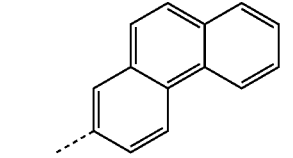 |
| 2-1-207 | 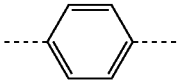 | 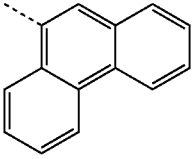 | 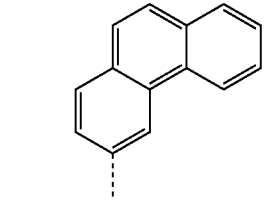 |

TABLE 1-continued
| | ---L$_1$--- | ---Ar$_1$ | ---Ar$_2$ |
|---|---|---|---|
| 2-1-208 |  | 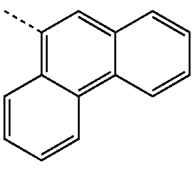 | 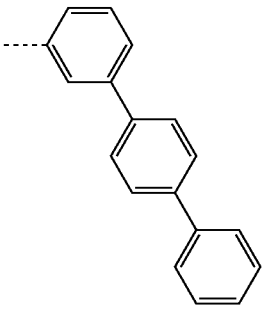 |
| 2-1-209 |  | 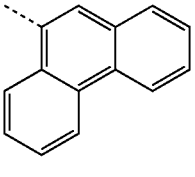 | 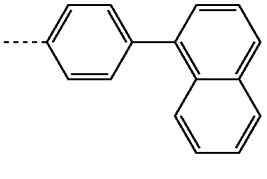 |
| 2-1-210 |  | 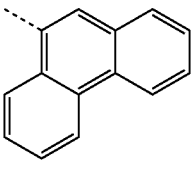 | 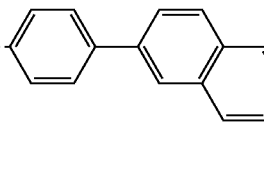 |
| 2-1-211 |  | 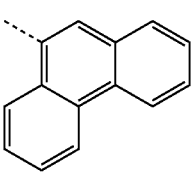 | 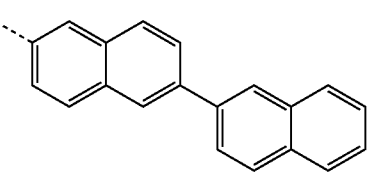 |
| 2-1-212 | 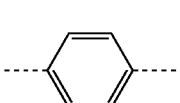 | 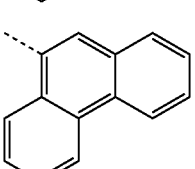 | 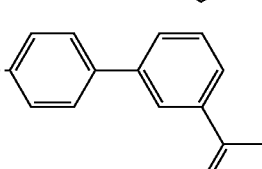 |
| 2-1-213 |  | 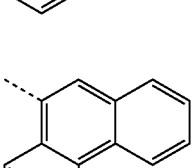 | 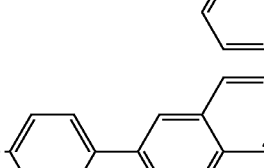 |
| 2-1-214 |  | 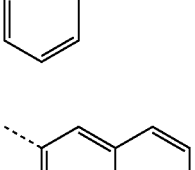 | 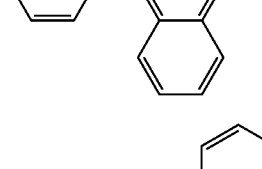 |
| 2-1-215 | 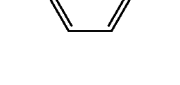 | 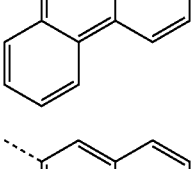 | 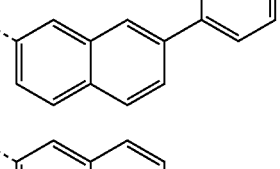 |

TABLE 1-continued
| | ---L$_1$--- | ---Ar$_1$ | ---Ar$_2$ |
|---|---|---|---|
| 2-1-216 |  | 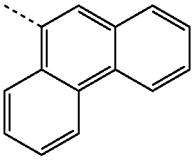 | 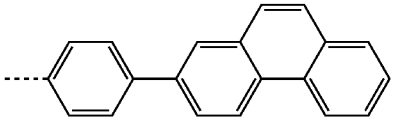 |
| 2-1-217 | 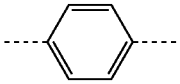 | 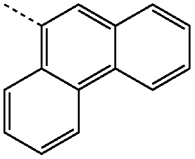 | 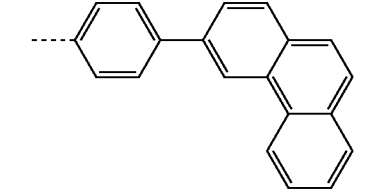 |
| 2-1-218 | 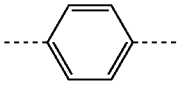 | 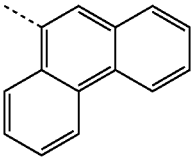 | 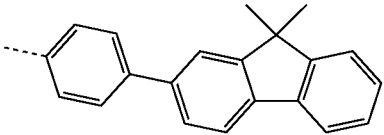 |
| 2-1-219 | 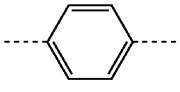 | 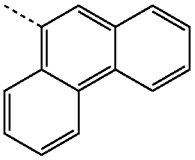 | 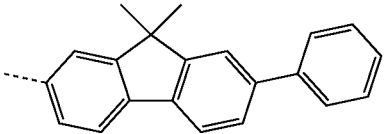 |
| 2-1-220 | 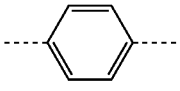 | 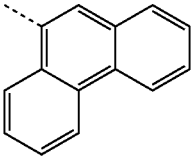 | 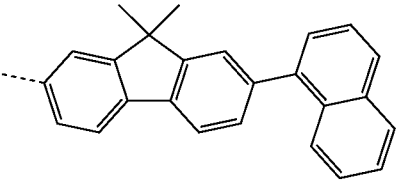 |
| 2-1-221 | 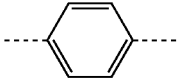 | 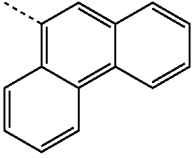 | 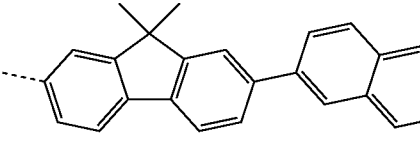 |
| 2-1-222 | 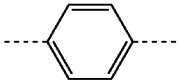 | 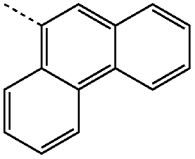 | 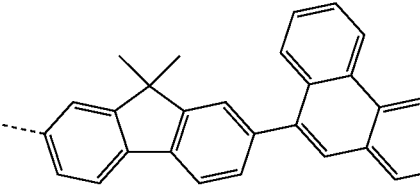 |
| 2-1-223 | 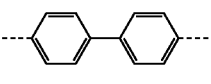 | 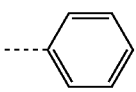 | 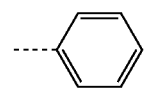 |
| 2-1-224 | 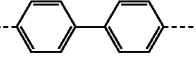 | 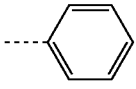 | 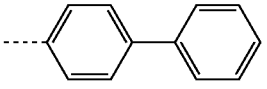 |

TABLE 1-continued

| | ---L₁--- | ---Ar₁ | ---Ar₂ |
|---|---|---|---|
| 2-1-225 | biphenyl-4,4'-diyl | phenyl | 2-biphenyl |
| 2-1-226 | biphenyl-4,4'-diyl | phenyl | 9,9-dimethylfluoren-2-yl |
| 2-1-227 | biphenyl-4,4'-diyl | phenyl | phenanthren-9-yl |
| 2-1-228 | biphenyl-4,4'-diyl | phenyl | phenanthren-2-yl |
| 2-1-229 | biphenyl-4,4'-diyl | phenyl | phenanthren-3-yl |
| 2-1-230 | biphenyl-4,4'-diyl | phenyl | naphthalen-1-yl |
| 2-1-231 | biphenyl-4,4'-diyl | phenyl | naphthalen-2-yl |
| 2-1-232 | biphenyl-4,4'-diyl | 4-biphenyl | 2-biphenyl |
| 2-1-233 | biphenyl-4,4'-diyl | 4-biphenyl | 9,9-dimethylfluoren-2-yl |
| 2-1-234 | biphenyl-4,4'-diyl | 4-biphenyl | phenanthren-9-yl |

TABLE 1-continued
| | ---L$_1$--- | ---Ar$_1$ | ---Ar$_2$ |
|---|---|---|---|
| 2-1-235 | 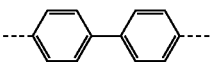 | 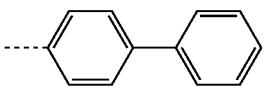 | 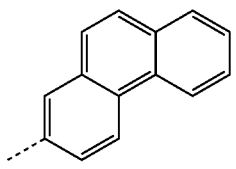 |
| 2-1-236 | 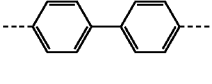 | 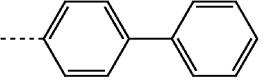 | 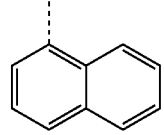 |
| 2-1-237 | 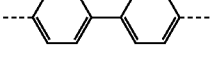 | 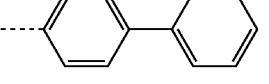 | 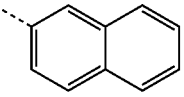 |
| 2-1-238 | 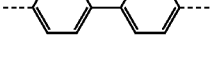 | 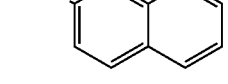 | 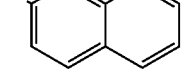 |
| 2-1-239 | 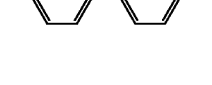 | 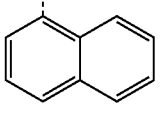 | 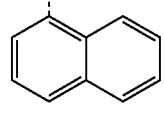 |
| 2-1-240 |  | 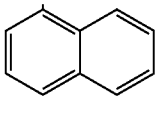 | 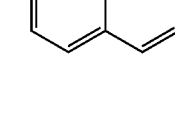 |
| 2-1-241 | 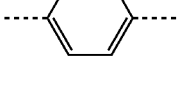 | 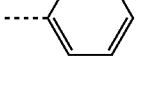 | 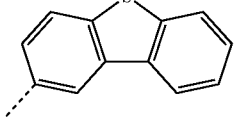 |
| 2-1-242 | 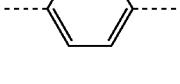 | 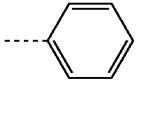 | 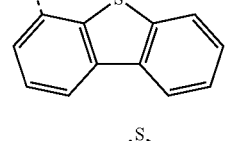 |
| 2-1-243 | 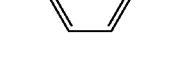 | 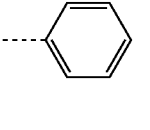 | 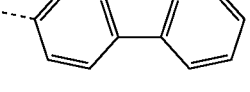 |
| 2-1-244 | 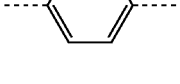 | 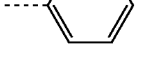 | 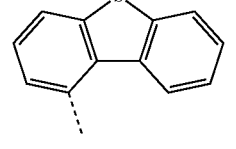 |
| 2-1-245 | 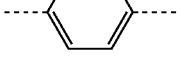 | 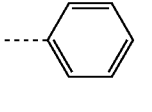 | 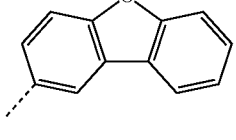 |

TABLE 1-continued
| | ---L$_1$--- | ---Ar$_1$--- | ---Ar$_2$ |
|---|---|---|---|
| 2-1-246 |  | 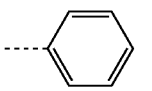 | 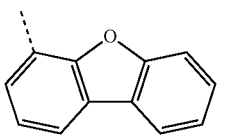 |
| 2-1-247 |  | 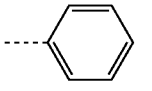 | 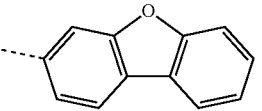 |
| 2-1-248 |  | 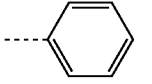 | 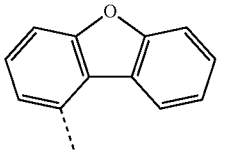 |
| 2-1-249 |  | 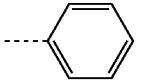 | 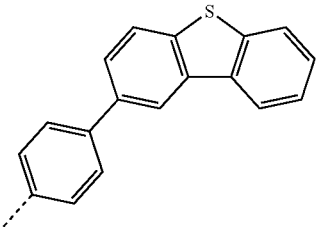 |
| 2-1-250 |  | 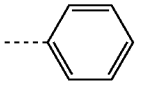 | 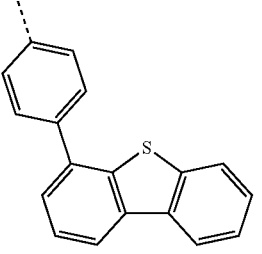 |
| 2-1-251 |  | 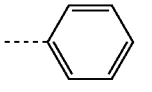 | 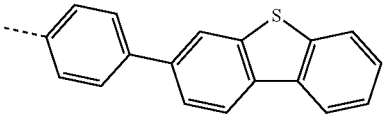 |
| 2-1-252 |  | 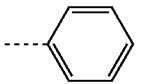 | 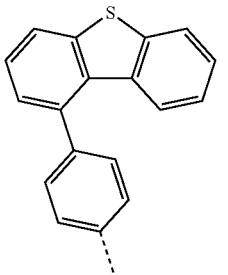 |

TABLE 1-continued
| | ---L$_1$--- | ---Ar$_1$--- | ---Ar$_2$--- |
|---|---|---|---|
| 2-1-253 |  | 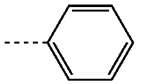 | 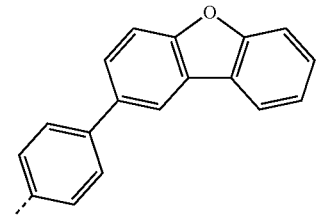 |
| 2-1-254 |  | 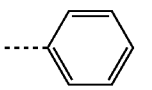 | 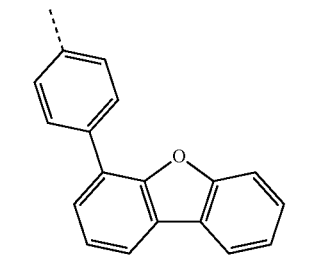 |
| 2-1-255 |  | 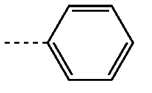 | 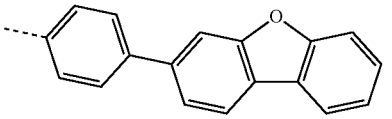 |
| 2-1-256 |  | 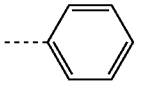 | 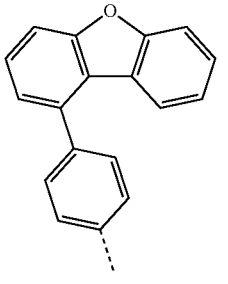 |
| 2-1-257 | 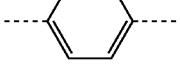 | 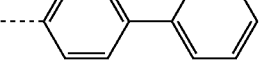 | 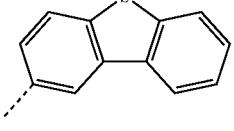 |
| 2-1-258 | 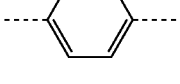 | 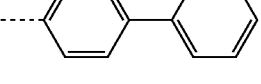 | 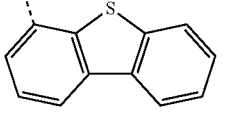 |
| 2-1-259 | 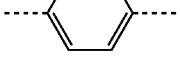 | 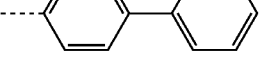 | 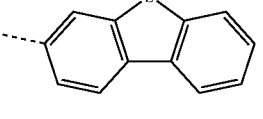 |
| 2-1-260 |  | 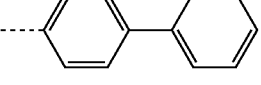 | 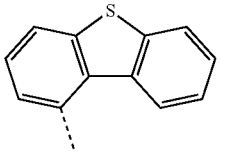 |

TABLE 1-continued

| | ---L₁--- | ---Ar₁ | ---Ar₂ |
|---|---|---|---|
| 2-1-261 | phenylene | biphenyl | dibenzofuran-2-yl |
| 2-1-262 | phenylene | biphenyl | dibenzofuran-4-yl |
| 2-1-263 | phenylene | biphenyl | dibenzofuran-3-yl |
| 2-1-264 | phenylene | biphenyl | dibenzofuran-1-yl |
| 2-1-265 | phenylene | biphenyl | 4-(dibenzothiophen-2-yl)phenyl |
| 2-1-266 | phenylene | biphenyl | 4-(dibenzothiophen-4-yl)phenyl |
| 2-1-267 | phenylene | biphenyl | 4-(dibenzothiophen-3-yl)phenyl |
| 2-1-268 | phenylene | biphenyl | 4-(dibenzothiophen-1-yl)phenyl |

TABLE 1-continued
| | ---L₁--- | ---Ar₁ | ---Ar₂ |
|---|---|---|---|
| 2-1-269 |  | 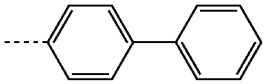 | 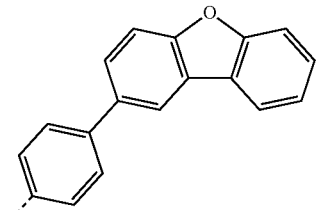 |
| 2-1-270 |  | 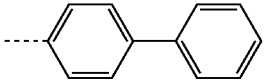 | 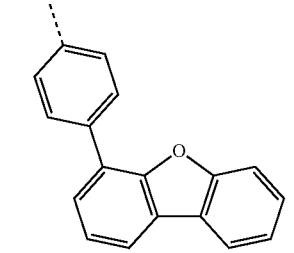 |
| 2-1-271 |  | 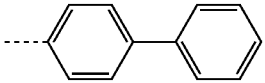 | 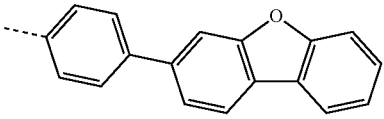 |
| 2-1-272 |  | 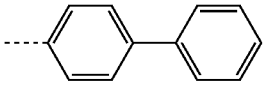 | 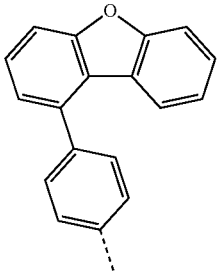 |
| 2-1-273 |  | 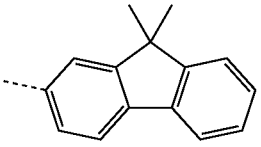 | 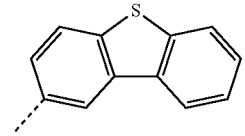 |
| 2-1-274 |  | 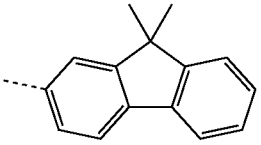 | 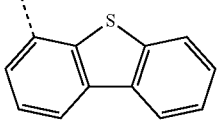 |
| 2-1-275 |  | 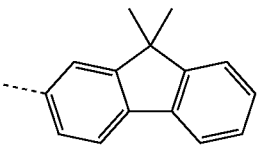 | 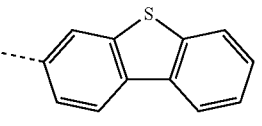 |
| 2-1-276 |  | 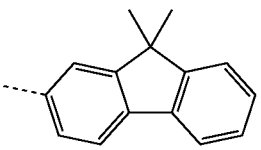 | 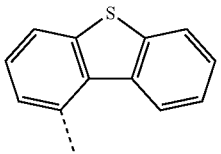 |

TABLE 1-continued
| | ---L$_1$--- | ---Ar$_1$ | ---Ar$_2$ |
|---|---|---|---|
| 2-1-277 |  | 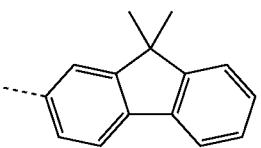 | 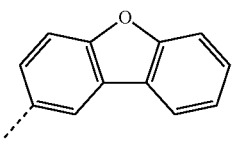 |
| 2-1-278 |  | 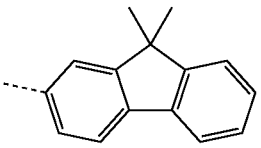 | 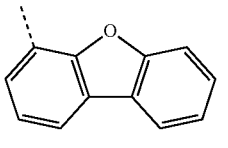 |
| 2-1-279 |  | 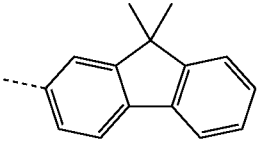 | 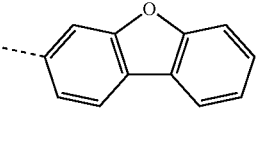 |
| 2-1-280 |  | 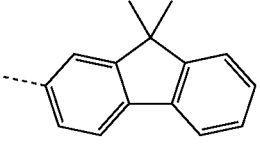 | 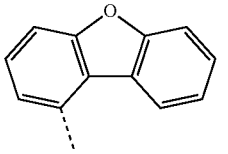 |
| 2-1-281 |  | 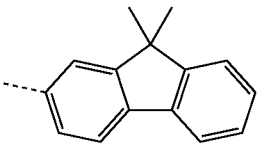 | 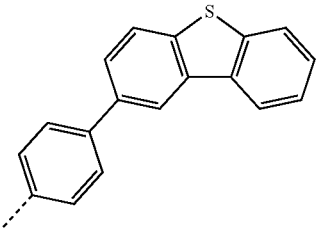 |
| 2-1-282 |  | 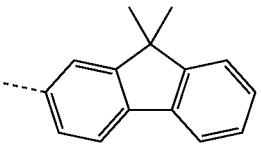 | 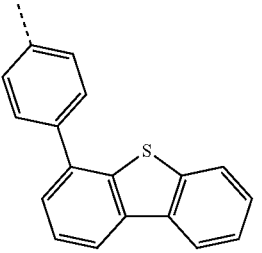 |
| 2-1-283 |  | 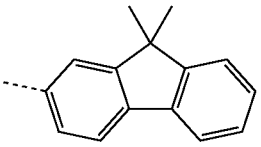 | 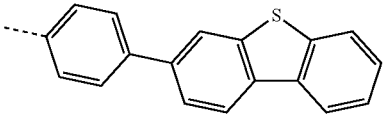 |
| 2-1-284 |  | 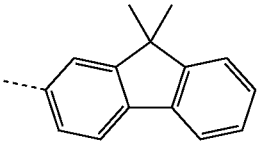 | 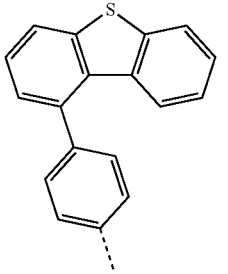 |

TABLE 1-continued
| | ---L$_1$--- | ---Ar$_1$--- | ---Ar$_2$--- |
|---|---|---|---|
| 2-1-285 | 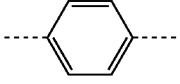 | 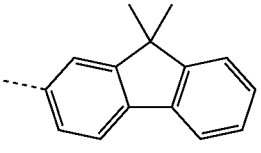 | 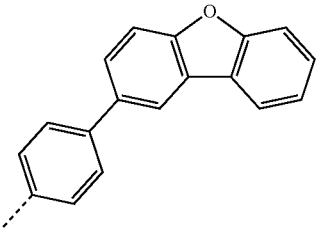 |
| 2-1-286 | 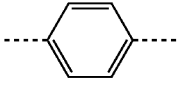 | 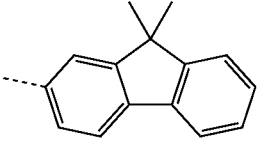 | 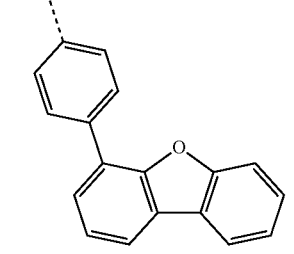 |
| 2-1-287 | 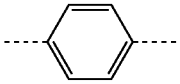 | 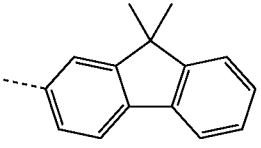 | 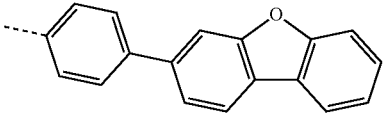 |
| 2-1-288 | 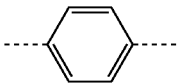 | 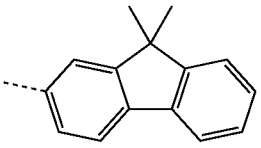 | 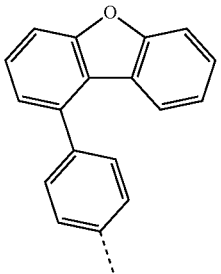 |
| 2-1-289 | 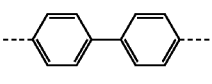 | 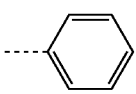 | 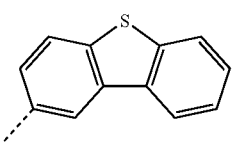 |
| 2-1-290 | 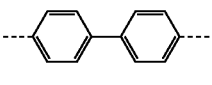 | 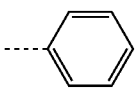 | 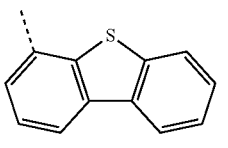 |
| 2-1-291 | 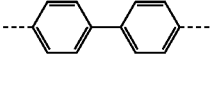 | 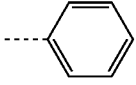 | 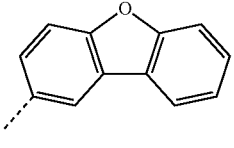 |
| 2-1-292 | 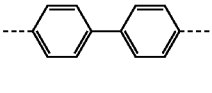 | 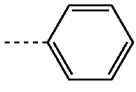 | 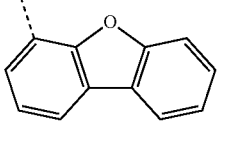 |

TABLE 1-continued

| | —L₁— | —Ar₁— | —Ar₂— |
|---|---|---|---|
| 2-1-293 | biphenyl-4,4'-diyl | phenyl | 2-(4-phenyl)dibenzothiophene |
| 2-1-294 | biphenyl-4,4'-diyl | phenyl | 4-(4-phenyl)dibenzothiophene |
| 2-1-295 | biphenyl-4,4'-diyl | phenyl | 2-(4-phenyl)dibenzofuran |
| 2-1-296 | biphenyl-4,4'-diyl | phenyl | 4-(4-phenyl)dibenzofuran |
| 2-1-297 | biphenyl-4,4'-diyl | biphenyl | 2-dibenzothiophene |
| 2-1-298 | biphenyl-4,4'-diyl | biphenyl | 4-dibenzothiophene |
| 2-1-299 | biphenyl-4,4'-diyl | biphenyl | 2-dibenzofuran |
| 2-1-300 | biphenyl-4,4'-diyl | biphenyl | 4-dibenzofuran |

TABLE 1-continued
| | ---L$_1$--- | ---Ar$_1$--- | ---Ar$_2$--- |
|---|---|---|---|
| 2-1-301 |  | 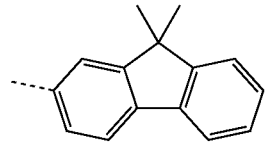 | 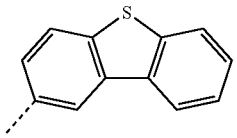 |
| 2-1-302 |  | 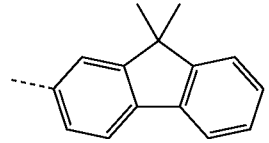 | 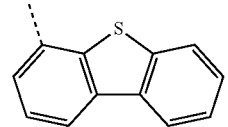 |
| 2-1-303 | 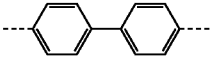 | 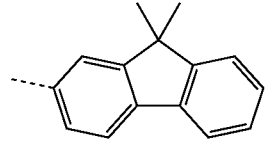 | 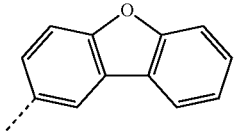 |
| 2-1-304 | 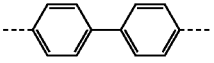 | 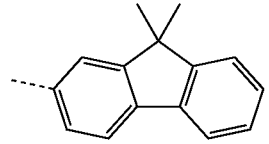 | 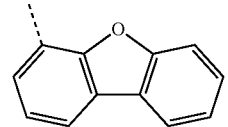 |
| 2-1-305 | 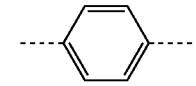 | 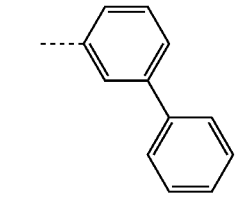 | 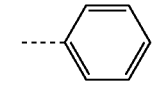 |
| 2-1-306 | 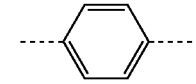 | 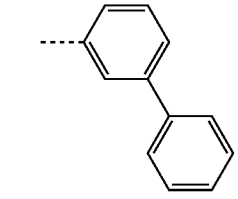 | 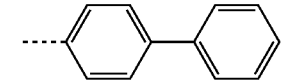 |
| 2-1-307 | 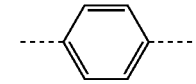 | 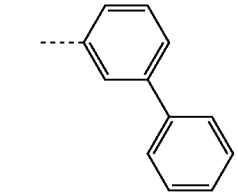 | 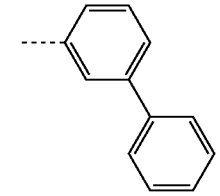 |
| 2-1-308 | 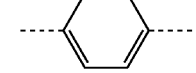 | 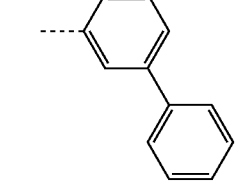 | 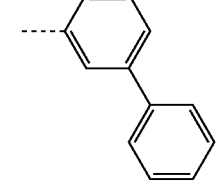 |

TABLE 1-continued
| | ---L$_1$--- | ---Ar$_1$--- | ---Ar$_2$--- |
|---|---|---|---|
| 2-1-309 | 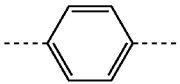 | 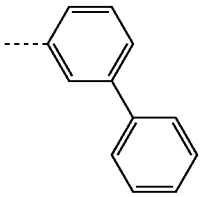 | 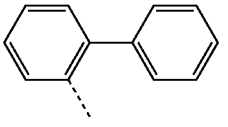 |
| 2-1-310 | 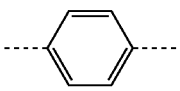 | 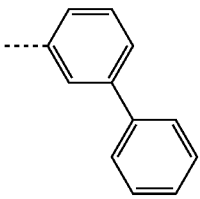 | 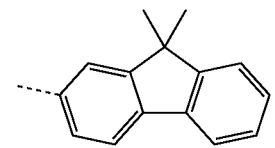 |
| 2-1-311 | 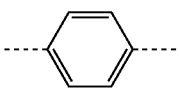 | 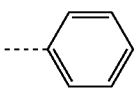 | 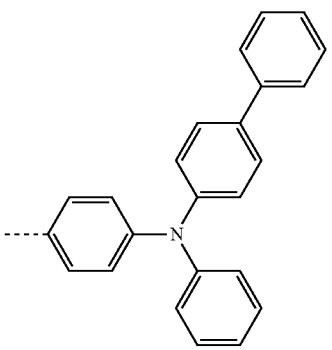 |
| 2-1-312 | 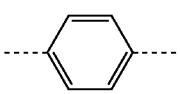 | 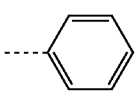 | 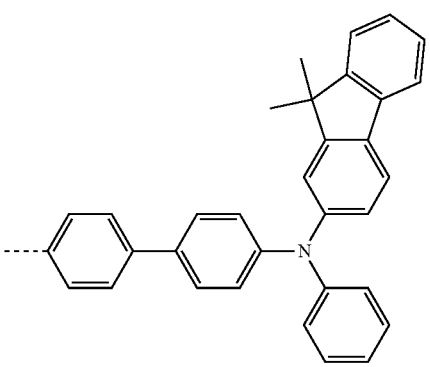 |
| 2-1-313 |  | 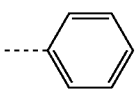 | 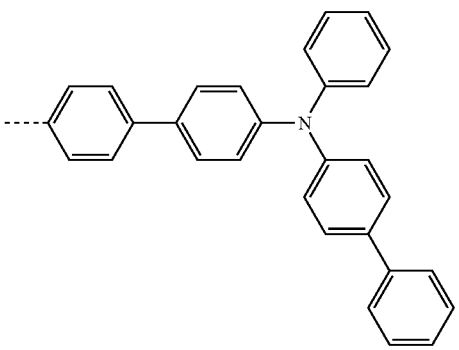 |

TABLE 1-continued
| | ---L₁--- | ---Ar₁ | ---Ar₂ |
|---|---|---|---|
| 2-1-314 | 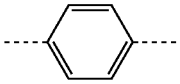 | 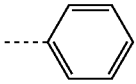 | 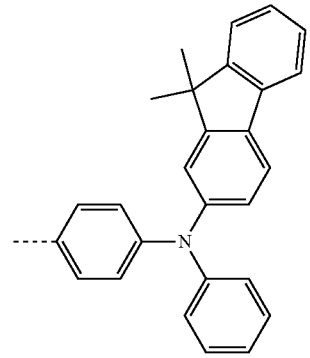 |
| 2-1-315 | 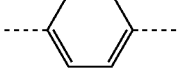 | 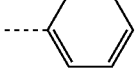 | 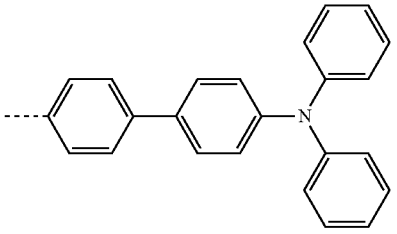 |
| 2-1-316 | 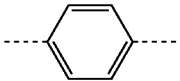 | 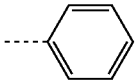 | 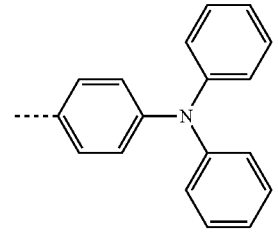 |
| 2-1-317 | 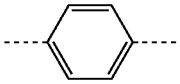 | 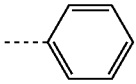 | 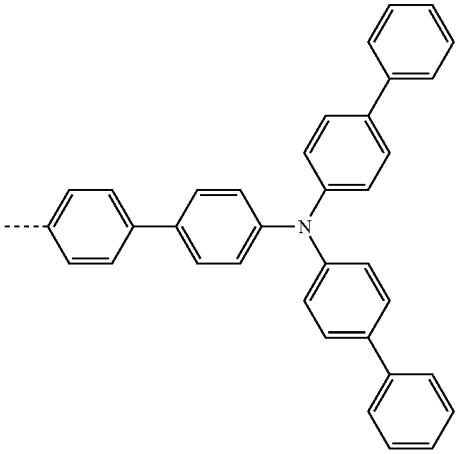 |

TABLE 1-continued

| | ---L₁--- | ---Ar₁ | ---Ar₂ |
|---|---|---|---|
| 2-1-318 | phenylene | phenyl | N,N-(biphenyl)(phenyl)-phenylamine |
| 2-1-319 | phenylene | phenyl | N-(9,9-dimethylfluoren-2-yl)-N-(biphenyl)-biphenylamine |
| 2-1-320 | phenylene | phenyl | N-(9,9-dimethylfluoren-2-yl)-N-phenyl-biphenylamine |

TABLE 1-continued

| | ---L₁--- | ---Ar₁--- | ---Ar₂--- |
|---|---|---|---|
| 2-1-321 | phenylene | biphenyl | N,N-diphenyl-N-biphenyl amine substituent |
| 2-1-322 | phenylene | biphenyl | N-(9,9-dimethylfluoren-2-yl)-N-phenyl biphenyl amine |
| 2-1-323 | phenylene | biphenyl | N,N-bis(biphenyl)amine substituent on biphenyl |
| 2-1-324 | phenylene | biphenyl | N-(9,9-dimethylfluoren-2-yl)-N-phenyl phenylamine |

TABLE 1-continued
| | ---L$_1$--- | ---Ar$_1$ | ---Ar$_2$ |
|---|---|---|---|
| 2-1-325 |  | 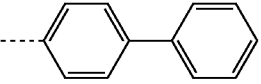 | 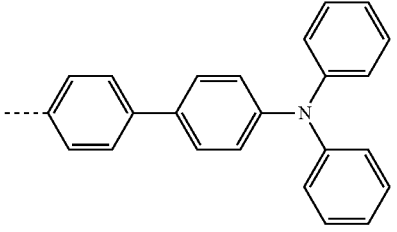 |
| 2-1-326 |  | 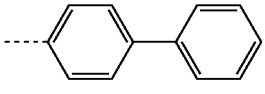 | 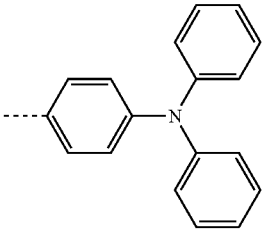 |
| 2-1-327 | 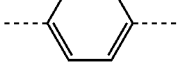 | 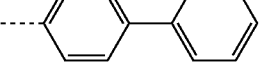 | 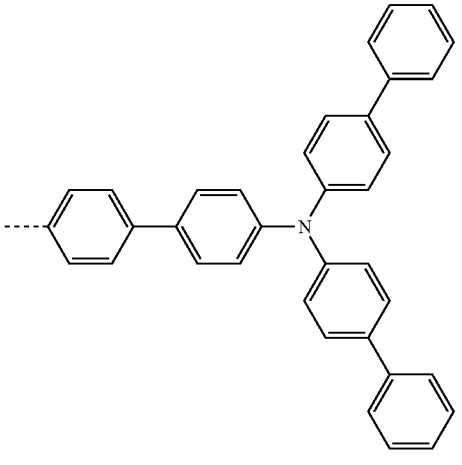 |
| 2-1-328 |  | 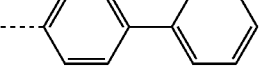 | 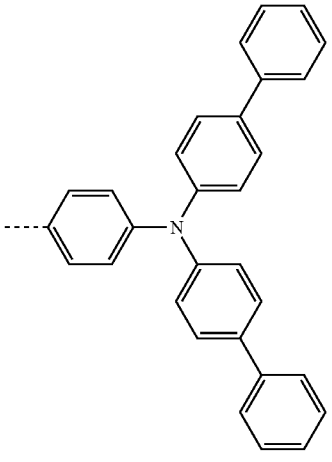 |

TABLE 1-continued

| | ---L₁--- | ---Ar₁--- | ---Ar₂--- |
|---|---|---|---|
| 2-1-329 | | | |
| 2-1-330 | | | |
| 2-1-331 | | | |
| 2-1-332 | | | |

TABLE 1-continued

| | ---L₁--- | ---Ar₁ | ---Ar₂ |
|---|---|---|---|
| 2-1-333 | biphenyl-diyl | biphenyl | 4-(diphenylamino)phenyl |
| 2-1-334 | biphenyl-diyl | biphenyl | 4-(N-phenyl-N-(9,9-dimethylfluoren-2-yl)amino)phenyl |

According to one embodiment of the present specification, the double spiro structure compound represented by Chemical Formula 1 is represented by any one of the following Chemical Formulae 2-1 to 2-3, and in the following Chemical Formulae 2-1 to 2-3, $L_1$, $Ar_1$ and $Ar_2$ may be selected from Table 1. For example, in the following Chemical Formula 2-1, $L_1$, when $Ar_1$ and $Ar_2$ correspond to 2-1-10 in Table 1, it may be expressed as Compound 2-1-10 (2-1), and when corresponding to 2-1-20, it may be expressed as Compound 2-1-20 (2-1).

In addition, in the following Chemical Formula 2-2, when $L_1$, $Ar_1$ and $Ar_2$ correspond to 2-1-10 in Table 1, it may be expressed as Compound 2-1-10 (2-2), and when corresponding to 2-1-20, it may be expressed as Compound 2-1-20 (2-2).

Furthermore, in the following Chemical Formula 2-3, when $L_1$, $Ar_1$ and $Ar_2$ correspond to 2-1-10 in Table 1, it may be expressed as Compound 2-1-10 (2-3), and when corresponding to 2-1-20, it may be expressed as Compound 2-1-20 (2-3).

[Chemical Formula 2-1]

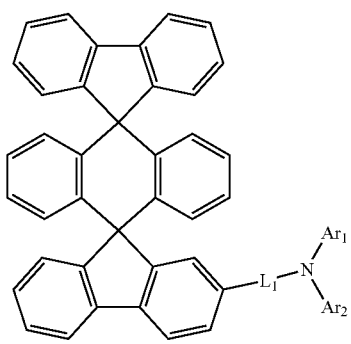

[Chemical Formula 2-2]

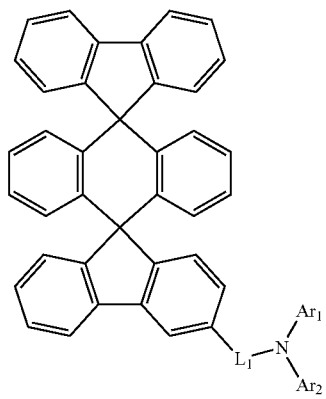

[Chemical Formmula 2-3]

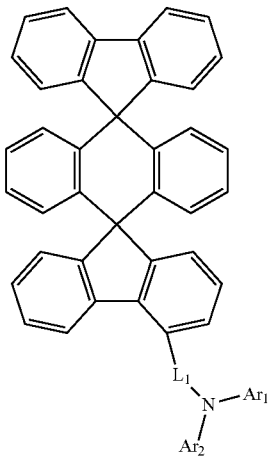

According to one embodiment of the present specification, the double spiro structure compound represented by Chemical Formula 1 is represented by the following Chemical Formula 3-1, and in the following Chemical Formula 3-1, L₂, Ar₃ and Ar₄ are any one selected from among 3-1-1 to 3-1-104 of the following Table 2.

[Chemical Formula 3-1]

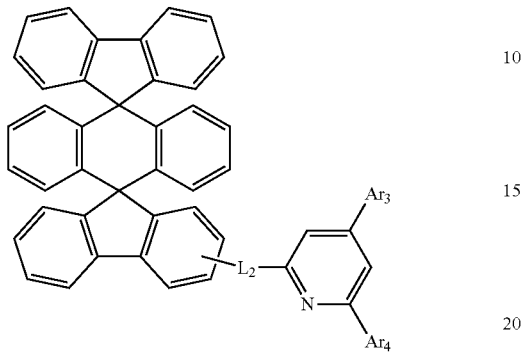

TABLE 2

| | ----L₂--- | ----Ar₃ | ----Ar₄ |
|---|---|---|---|
| 3-1-1 | Direct Bond | phenyl | phenyl |
| 3-1-2 | Direct Bond | biphenyl | phenyl |
| 3-1-3 | Direct Bond | biphenyl | 1-naphthyl |
| 3-1-4 | Direct Bond | biphenyl | 2-naphthyl |
| 3-1-5 | Direct Bond | biphenyl | phenanthrenyl |
| 3-1-6 | Direct Bond | 9,9-dimethylfluorenyl | phenyl |
| 3-1-7 | Direct Bond | 1-naphthyl | 1-naphthyl |

TABLE 2-continued
| | ----L₂---- | ----Ar₃---- | ----Ar₄---- |
|---|---|---|---|
| 3-1-8 | Direct Bond | 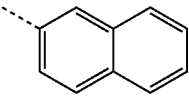 | 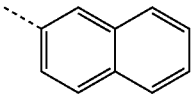 |
| 3-1-9 | Direct Bond | 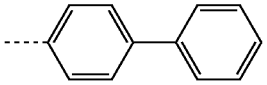 | 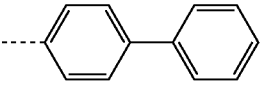 |
| 3-1-10 | Direct Bond | 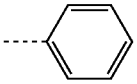 | 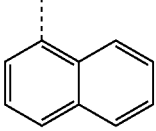 |
| 3-1-11 | Direct Bond | 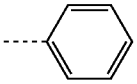 | 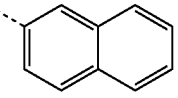 |
| 3-1-12 | 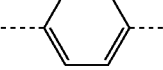 | 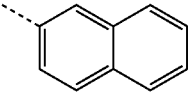 | 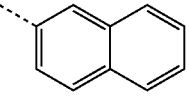 |
| 3-1-13 | 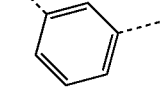 | 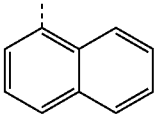 | 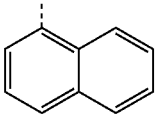 |
| 3-1-14 | 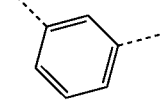 | 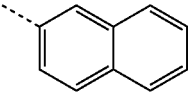 | 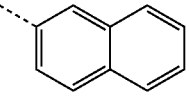 |
| 3-1-15 |  | 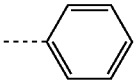 | 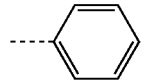 |
| 3-1-16 |  | 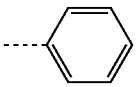 | 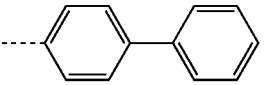 |
| 3-1-17 | 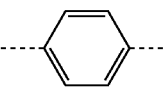 | 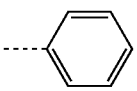 | 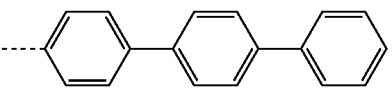 |
| 3-1-18 |  | 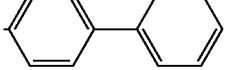 | 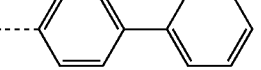 |
| 3-1-19 |  | 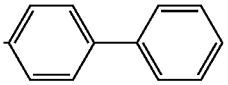 | 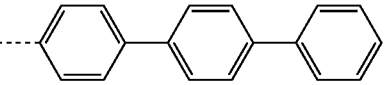 |
| 3-1-20 |  | 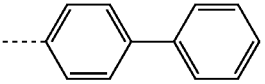 | 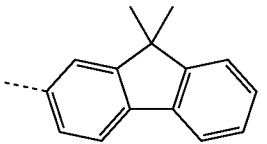 |

TABLE 2-continued
| | ----L₂---- | ----Ar₃ | ----Ar₄ |
|---|---|---|---|
| 3-1-21 | 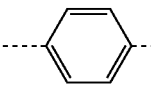 | 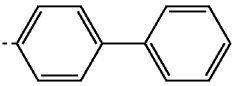 | 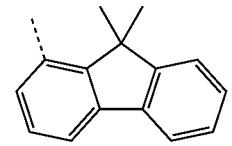 |
| 3-1-22 | 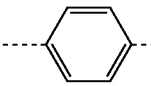 | 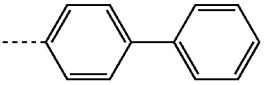 | 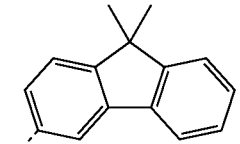 |
| 3-1-23 | 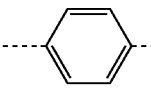 | 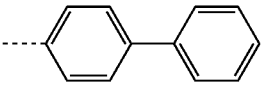 | 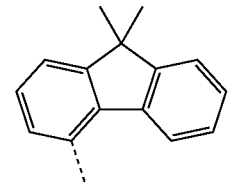 |
| 3-1-24 | 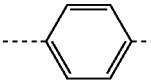 | 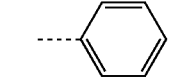 | 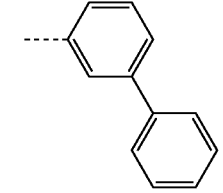 |
| 3-1-25 | 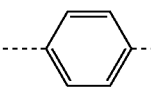 | 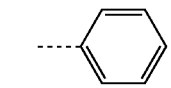 | 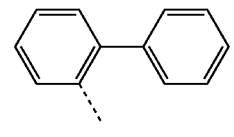 |
| 3-1-26 | 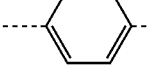 | 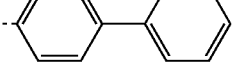 | 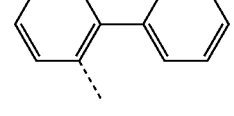 |
| 3-1-27 | 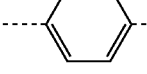 | 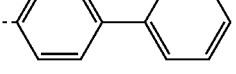 | 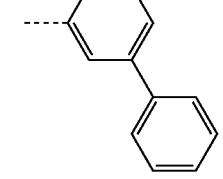 |
| 3-1-28 | 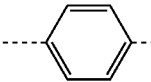 | 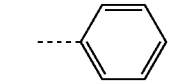 | 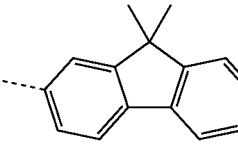 |
| 3-1-29 | 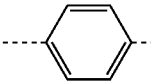 | 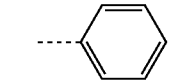 | 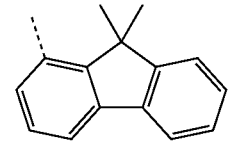 |

TABLE 2-continued
| | ----L₂---- | ----Ar₃---- | ----Ar₄---- |
|---|---|---|---|
| 3-1-30 | 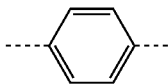 | 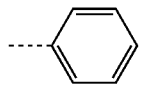 | 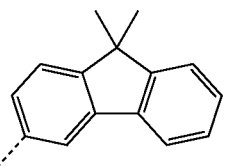 |
| 3-1-31 | 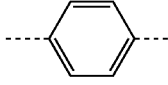 | 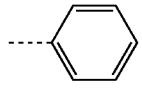 | 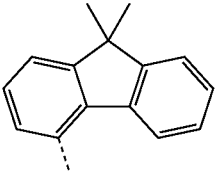 |
| 3-1-32 | 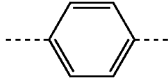 | 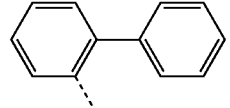 | 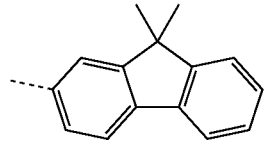 |
| 3-1-33 | 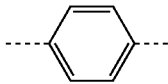 | 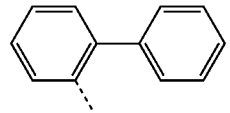 | 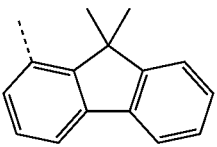 |
| 3-1-34 |  | 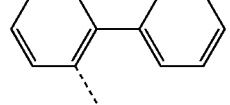 | 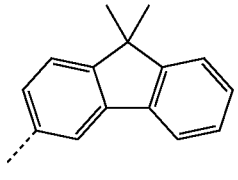 |
| 3-1-35 | 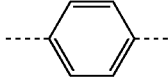 | 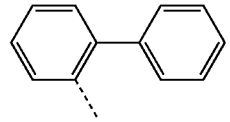 | 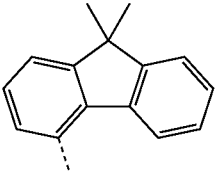 |
| 3-1-36 | 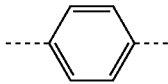 | 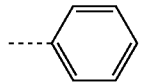 | 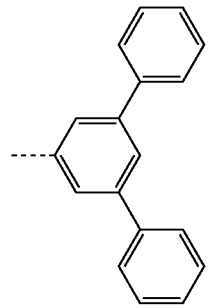 |
| 3-1-37 | 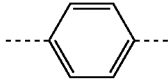 | 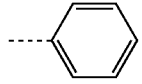 | 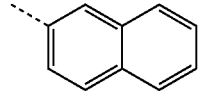 |

TABLE 2-continued
| | ----L₂--- | ----Ar₃ | ----Ar₄ |
|---|---|---|---|
| 3-1-38 | 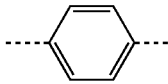 | 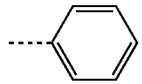 | 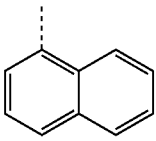 |
| 3-1-39 | 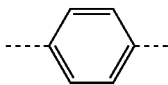 | 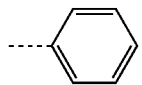 | 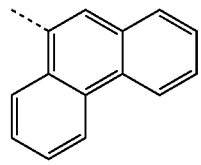 |
| 3-1-40 | 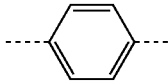 | 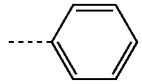 | 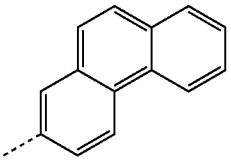 |
| 3-1-41 | 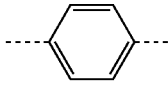 | 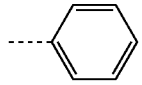 | 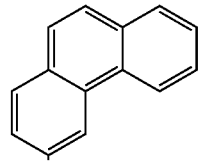 |
| 3-1-42 | 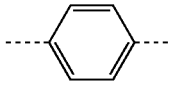 | 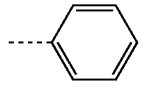 | 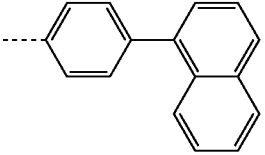 |
| 3-1-43 | 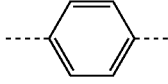 | 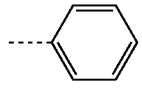 | 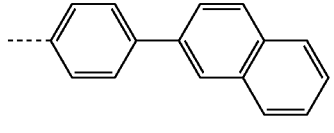 |
| 3-1-44 | 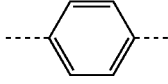 | 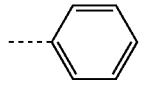 | 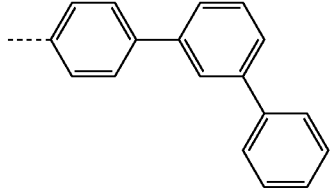 |
| 3-1-45 | 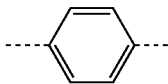 | 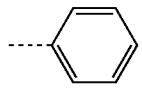 | 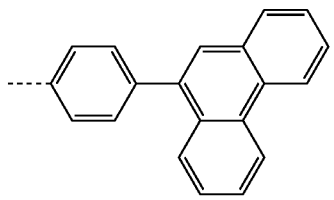 |
| 3-1-46 | 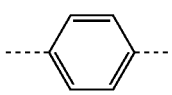 | 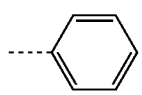 | 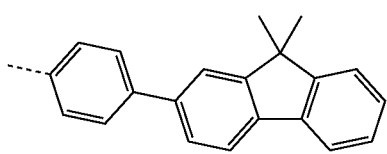 |

TABLE 2-continued
| | ----L₂---- | ----Ar₃---- | ----Ar₄---- |
|---|---|---|---|
| 3-1-47 |  | 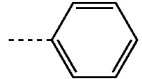 | 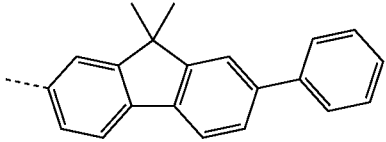 |
| 3-1-48 |  | 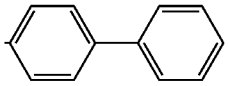 | 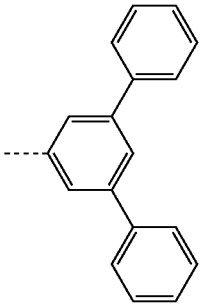 |
| 3-1-49 |  | 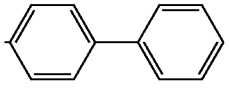 | 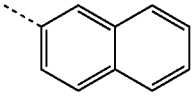 |
| 3-1-50 |  | 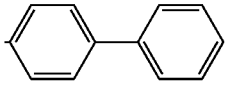 | 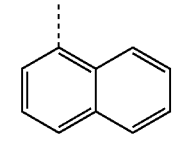 |
| 3-1-51 |  | 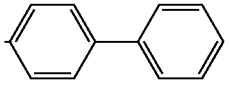 | 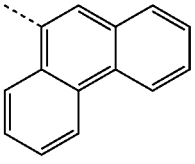 |
| 3-1-52 |  | 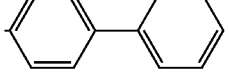 | 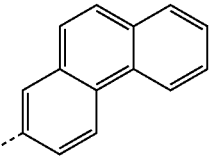 |
| 3-1-53 |  | 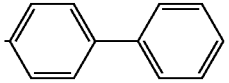 | 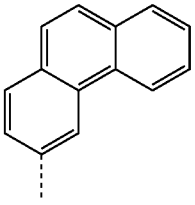 |
| 3-1-54 |  | 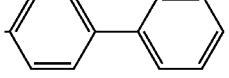 | 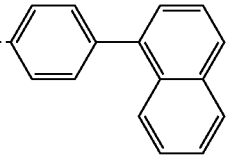 |

TABLE 2-continued

| | ----L₂---- | ----Ar₃ | ----Ar₄ |
|---|---|---|---|
| 3-1-55 | phenylene | biphenyl | phenyl-naphthyl |
| 3-1-56 | phenylene | biphenyl | m-terphenyl |
| 3-1-57 | phenylene | biphenyl | phenyl-anthracenyl |
| 3-1-58 | phenylene | biphenyl | phenyl-(9,9-dimethylfluorenyl) |
| 3-1-59 | phenylene | biphenyl | 7-phenyl-9,9-dimethylfluorenyl |
| 3-1-60 | m-phenylene | phenyl | phenyl |
| 3-1-61 | m-phenylene | phenyl | biphenyl |
| 3-1-62 | m-phenylene | phenyl | p-terphenyl |
| 3-1-63 | m-phenylene | biphenyl | biphenyl |
| 3-1-64 | m-phenylene | biphenyl | p-terphenyl |

TABLE 2-continued

| | ----L₂---- | ----Ar₃---- | ----Ar₄---- |
|---|---|---|---|
| 3-1-65 | phenylene | biphenyl | 9,9-dimethylfluorene (2-position) |
| 3-1-66 | phenylene | biphenyl | 9,9-dimethylfluorene (1-position) |
| 3-1-67 | phenylene | biphenyl | 9,9-dimethylfluorene (3-position) |
| 3-1-68 | phenylene | biphenyl | 9,9-dimethylfluorene (4-position) |
| 3-1-69 | phenylene | phenyl | biphenyl (3-position) |
| 3-1-70 | phenylene | phenyl | biphenyl (2-position) |
| 3-1-71 | phenylene | biphenyl | biphenyl (2-position) |
| 3-1-72 | phenylene | biphenyl | biphenyl (3-position) |
| 3-1-73 | phenylene | phenyl | 9,9-dimethylfluorene (2-position) |

TABLE 2-continued

| | ----L₂--- | ----Ar₃ | ----Ar₄ |
|---|---|---|---|
| 3-1-74 | | | |
| 3-1-75 | | | |
| 3-1-76 | | | |
| 3-1-77 | | | |
| 3-1-78 | | | |
| 3-1-79 | | | |
| 3-1-80 | | | |
| 3-1-81 | | | |

TABLE 2-continued

| | ----L₂---- | ----Ar₃---- | ----Ar₄ |
|---|---|---|---|
| 3-1-82 | | | |
| 3-1-83 | | | |
| 3-1-84 | | | |
| 3-1-85 | | | |
| 3-1-86 | | | |
| 3-1-87 | | | |
| 3-1-88 | | | |
| 3-1-89 | | | |
| 3-1-90 | | | |

TABLE 2-continued
| | ----L₂---- | ----Ar₃---- | ----Ar₄---- |
|---|---|---|---|
| 3-1-91 | 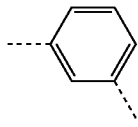 | 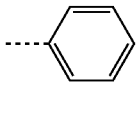 | 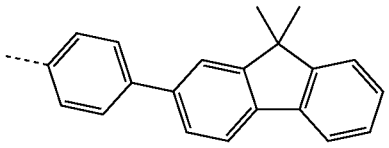 |
| 3-1-92 | 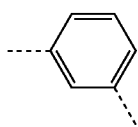 | 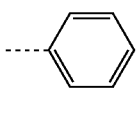 | 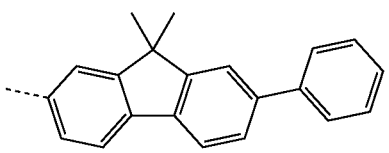 |
| 3-1-93 | 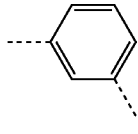 | 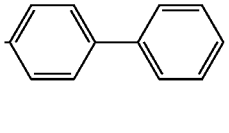 | 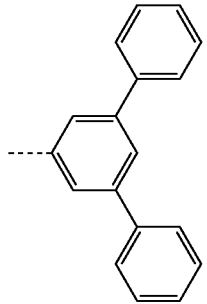 |
| 3-1-94 | 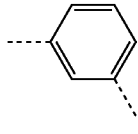 | 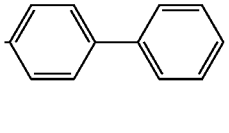 | 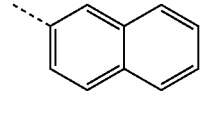 |
| 3-1-95 | 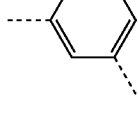 | 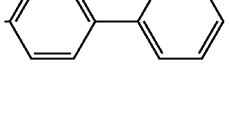 | 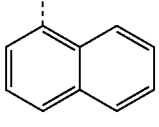 |
| 3-1-96 | 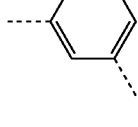 | 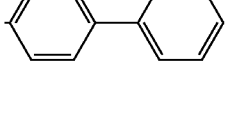 | 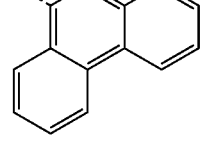 |
| 3-1-97 | 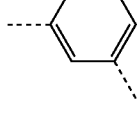 | 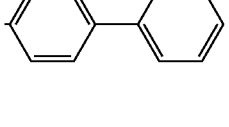 | 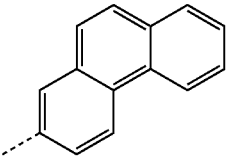 |
| 3-1-98 | 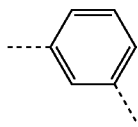 | 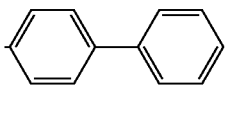 | 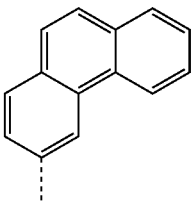 |

TABLE 2-continued

| ----L₂---- | ----Ar₃---- | ----Ar₄---- |
|---|---|---|
| 3-1-99 | | |
| 3-1-100 | | |
| 3-1-101 | | |
| 3-1-102 | | |
| 3-1-103 | | |
| 3-1-104 | | |

According to one embodiment of the present specification, the double spiro structure compound represented by Chemical Formula 1 is represented by any one of the following Chemical Formulae 3-5 to 3-7, and in the following Chemical Formulae 3-5 to 3-7, $L_2$, $Ar_3$ and $Ar_4$ may be selected from Table 2. For example, in the following Chemical Formula 3-5, when $L_2$, $Ar_3$ and $Ar_4$ correspond to 3-1-10 in Table 2, it may be expressed as Compound 3-1-10 (3-5), and when corresponding to 3-1-20, it may be expressed as Compound 3-1-20 (3-5).

In addition, in the following Chemical Formula 3-6, when $L_2$, $Ar_3$ and $Ar_4$ correspond to 3-1-10 in Table 2, it may be expressed as Compound 3-1-10 (3-6), and when corresponding to 3-1-20, it may be expressed as Compound 3-1-20 (3-6).

Furthermore, in the following Chemical Formula 3-7, when $L_2$, $Ar_3$ and $Ar_4$ correspond to 3-1-10 in Table 2, it may be expressed as Compound 3-1-10 (3-7), and when corresponding to 3-1-20, it may be expressed as Compound 3-1-20 (3-7).

[Chemical Formula 3-5]

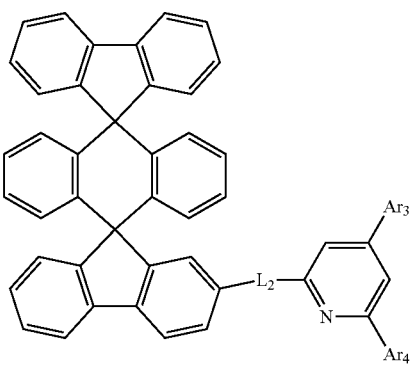

-continued

[Chemical Formula 3-6]

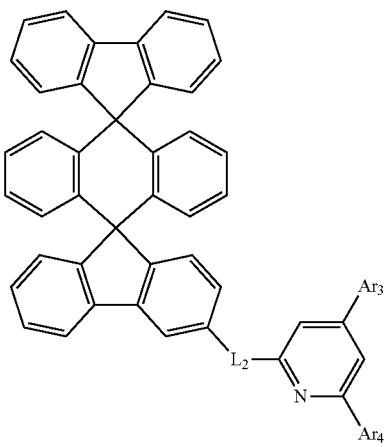

[Chemical Formula 3-7]

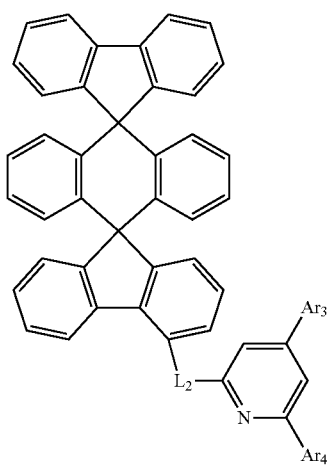

According to one embodiment of the present specification, the double spiro structure compound represented by Chemical Formula 1 is represented by the following Chemical Formula 3-2, and in the following Chemical Formula 3-2, $L_2$, $Ar_3$ and $Ar_4$ are any one selected from among 3-2-1 to 3-2-104 of the following Table 3.

[Chemical Formula 3-2]

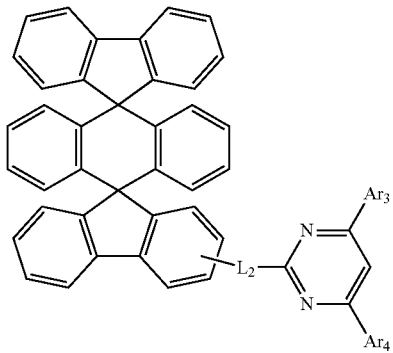

TABLE 3

| | ----$L_2$---- | ----$Ar_3$ | ----$Ar_4$ |
|---|---|---|---|
| 3-2-1 | Direct bond | phenyl | phenyl |
| 3-2-2 | Direct bond | biphenyl | phenyl |
| 3-2-3 | Direct bond | biphenyl | 1-naphthyl |
| 3-2-4 | Direct bond | biphenyl | 2-naphthyl |

TABLE 3-continued
| | ----L₂--- | ----Ar₃ | ----Ar₄ |
|---|---|---|---|
| 3-2-5 | Direct bond | 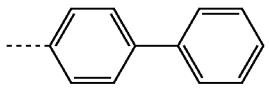 | 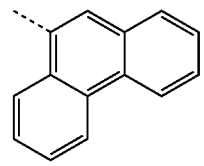 |
| 3-2-6 | Direct bond | 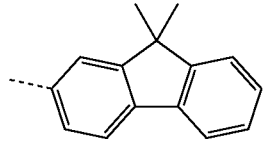 | 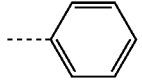 |
| 3-2-7 | Direct bond | 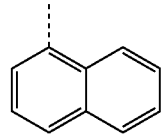 | 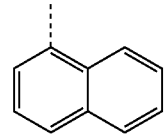 |
| 3-2-8 | Direct bond | 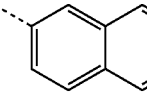 | 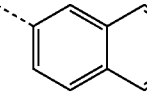 |
| 3-2-9 | Direct bond | 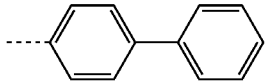 | 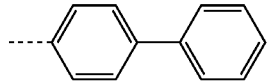 |
| 3-2-10 | Direct bond | 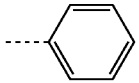 | 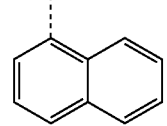 |
| 3-2-11 | Direct bond | 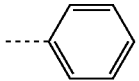 | 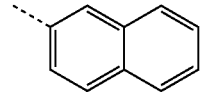 |
| 3-2-12 | 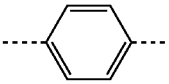 | 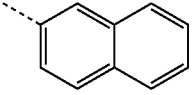 | 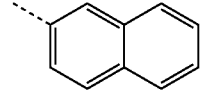 |
| 3-2-13 | 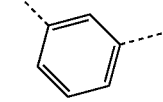 | 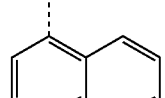 | 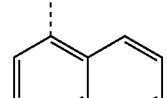 |
| 3-2-14 | 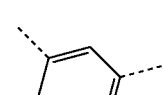 | 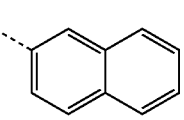 | 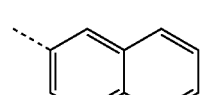 |
| 3-2-15 | 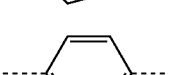 | 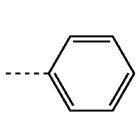 | 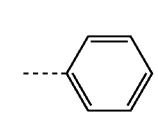 |
| 3-2-16 | 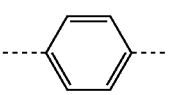 | 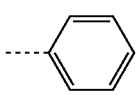 | 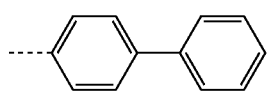 |

TABLE 3-continued
| | ----L₂---- | ----Ar₃---- | ----Ar₄---- |
|---|---|---|---|
| 3-2-17 | 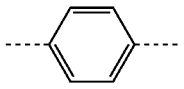 | 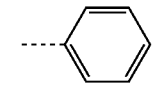 | 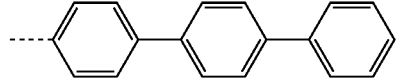 |
| 3-2-18 | 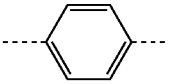 | 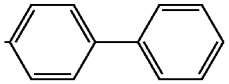 | 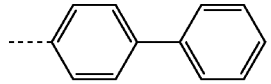 |
| 3-2-19 | 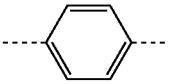 | 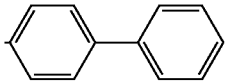 | 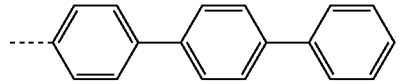 |
| 3-2-20 | 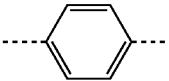 |  | 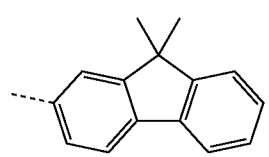 |
| 3-2-21 | 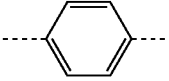 | 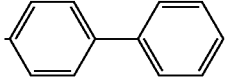 | 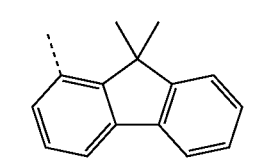 |
| 3-2-22 | 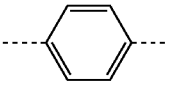 | 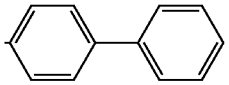 | 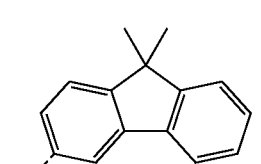 |
| 3-2-23 | 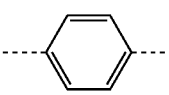 | 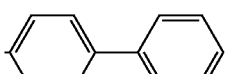 | 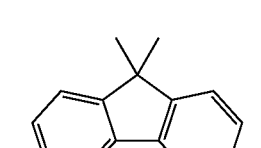 |
| 3-2-24 | 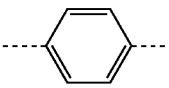 | 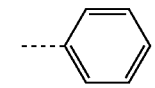 | 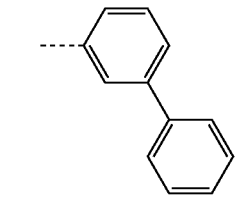 |
| 3-2-25 | 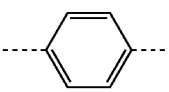 | 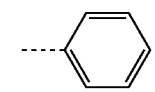 | 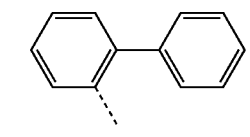 |
| 3-2-26 | 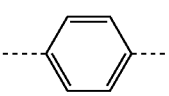 | 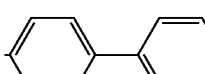 | 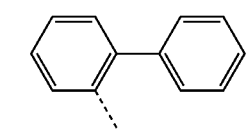 |

TABLE 3-continued

| | ----L₂---- | ----Ar₃ | ----Ar₄ |
|---|---|---|---|
| 3-2-27 | phenylene | biphenyl | biphenyl |
| 3-2-28 | phenylene | phenyl | 9,9-dimethylfluoren-2-yl |
| 3-2-29 | phenylene | phenyl | 9,9-dimethylfluoren-1-yl |
| 3-2-30 | phenylene | phenyl | 9,9-dimethylfluoren-3-yl |
| 3-2-31 | phenylene | phenyl | 9,9-dimethylfluoren-4-yl |
| 3-2-32 | phenylene | biphenyl | 9,9-dimethylfluoren-2-yl |
| 3-2-33 | phenylene | biphenyl | 9,9-dimethylfluoren-1-yl |
| 3-2-34 | phenylene | biphenyl | 9,9-dimethylfluoren-3-yl |
| 3-2-35 | phenylene | biphenyl | 9,9-dimethylfluoren-4-yl |

TABLE 3-continued
| | ----L₂---- | ----Ar₃ | ----Ar₄ |
|---|---|---|---|
| 3-2-36 | 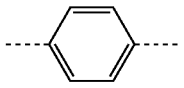 | 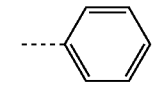 | 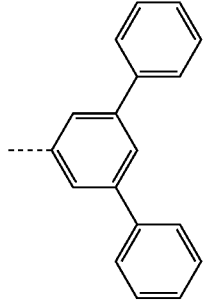 |
| 3-2-37 | 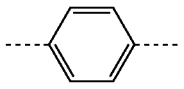 | 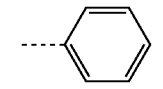 | 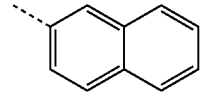 |
| 3-2-38 | 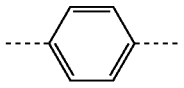 | 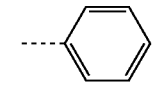 | 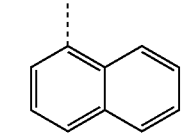 |
| 3-2-39 | 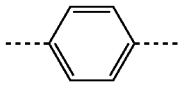 | 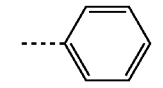 | 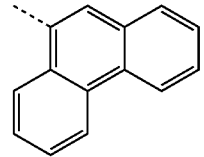 |
| 3-2-40 | 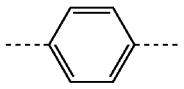 | 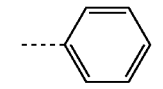 | 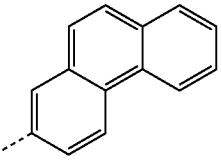 |
| 3-2-41 | 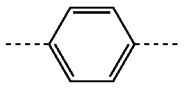 | 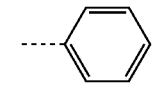 | 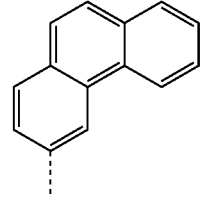 |
| 3-2-42 | 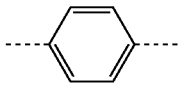 | 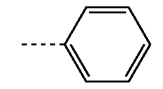 | 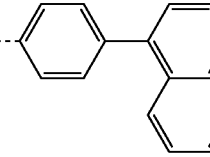 |
| 3-2-43 | 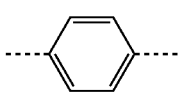 | 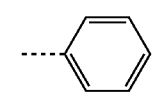 | 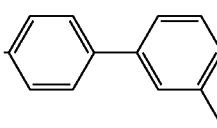 |

| | ----L₂---- | ----Ar₃---- | ----Ar₄---- |
|---|---|---|---|
| 3-2-44 | 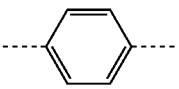 | 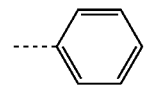 | 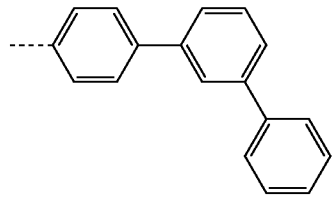 |
| 3-2-45 | 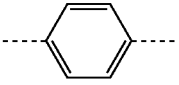 | 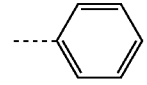 | 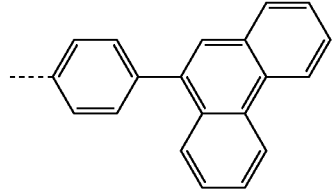 |
| 3-2-46 | 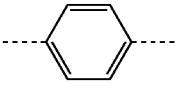 | 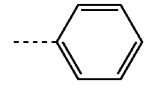 | 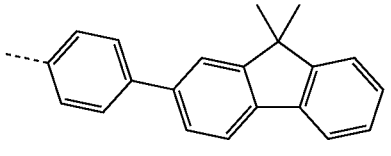 |
| 3-2-47 | 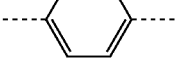 | 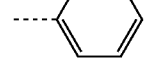 | 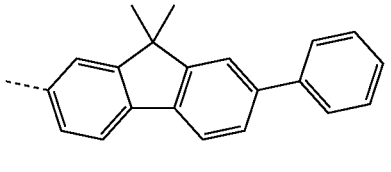 |
| 3-2-48 | 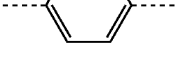 | 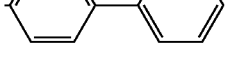 | 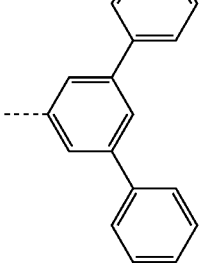 |
| 3-2-49 | 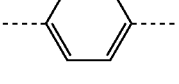 | 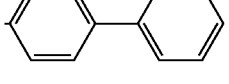 | 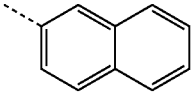 |
| 3-2-50 | 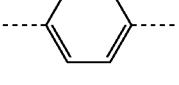 | 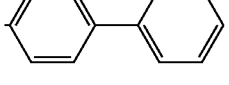 | 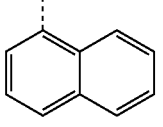 |
| 3-2-51 | 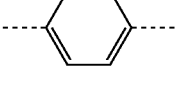 | 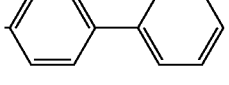 | 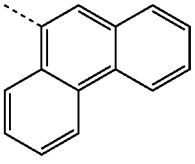 |

TABLE 3-continued

| | ----L₂---- | ----Ar₃---- | ----Ar₄---- |
|---|---|---|---|
| 3-2-52 | phenylene | biphenyl | phenanthrene |
| 3-2-53 | phenylene | biphenyl | phenanthrene |
| 3-2-54 | phenylene | biphenyl | phenyl-naphthalene (1-linked) |
| 3-2-55 | phenylene | biphenyl | phenyl-naphthalene (2-linked) |
| 3-2-56 | phenylene | biphenyl | m-terphenyl |
| 3-2-57 | phenylene | biphenyl | phenyl-anthracene |
| 3-2-58 | phenylene | biphenyl | 9,9-dimethylfluorenyl-phenyl |
| 3-2-59 | phenylene | biphenyl | 9,9-dimethyl-phenylfluorenyl |
| 3-2-60 | phenylene | phenyl | phenyl |

TABLE 3-continued

| | ----L₂--- | ----Ar₃ | ----Ar₄ |
|---|---|---|---|
| 3-2-61 | phenylene | phenyl | biphenyl |
| 3-2-62 | phenylene | phenyl | terphenyl |
| 3-2-63 | phenylene | biphenyl | biphenyl |
| 3-2-64 | phenylene | biphenyl | terphenyl |
| 3-2-65 | phenylene | biphenyl | 9,9-dimethylfluoren-2-yl |
| 3-2-66 | phenylene | biphenyl | 9,9-dimethylfluoren-1-yl |
| 3-2-67 | phenylene | biphenyl | 9,9-dimethylfluoren-3-yl |
| 3-2-68 | phenylene | biphenyl | 9,9-dimethylfluoren-4-yl |
| 3-2-69 | phenylene | phenyl | biphenyl (meta) |
| 3-2-70 | phenylene | phenyl | biphenyl (ortho) |

TABLE 3-continued
| | ----L₂---- | ----Ar₃ | ----Ar₄ |
|---|---|---|---|
| 3-2-71 | 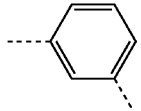 | 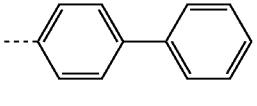 | 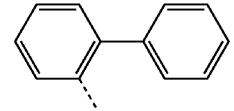 |
| 3-2-72 | 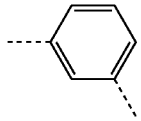 | 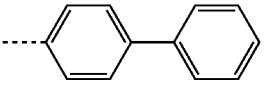 | 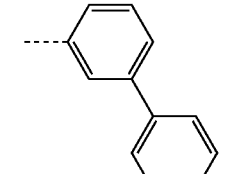 |
| 3-2-73 | 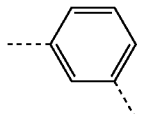 | 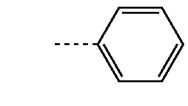 | 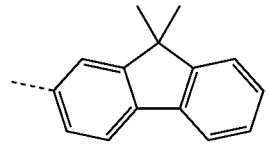 |
| 3-2-74 | 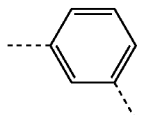 | 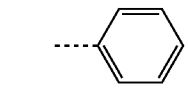 | 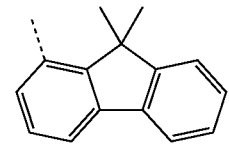 |
| 3-2-75 | 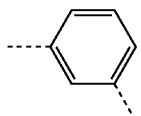 | 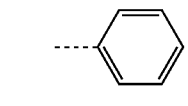 | 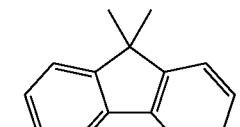 |
| 3-2-76 | 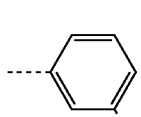 | 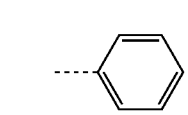 | 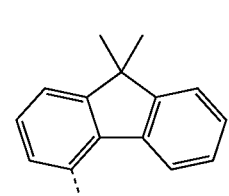 |
| 3-2-77 | 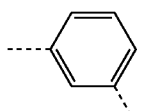 | 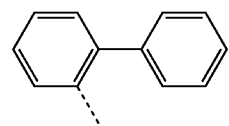 | 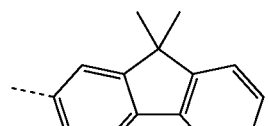 |
| 3-2-78 | 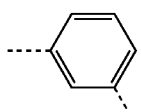 | 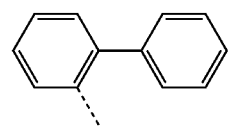 | 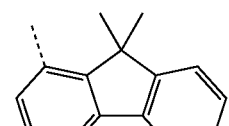 |
| 3-2-79 | 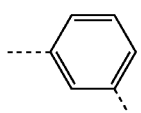 | 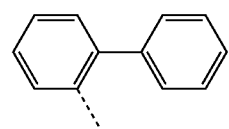 | 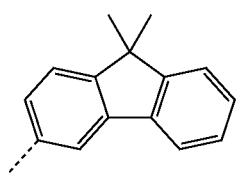 |

TABLE 3-continued
| | ----L$_2$---- | ----Ar$_3$---- | ----Ar$_4$---- |
|---|---|---|---|
| 3-2-80 | 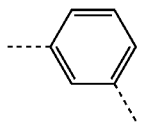 | 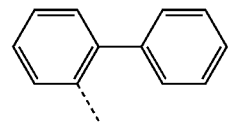 | 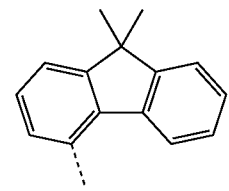 |
| 3-2-81 | 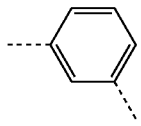 | 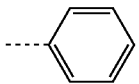 | 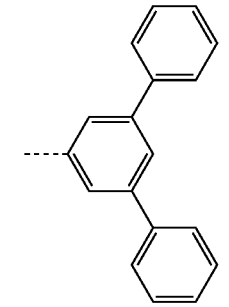 |
| 3-2-82 | 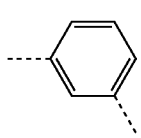 | 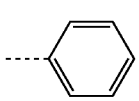 | 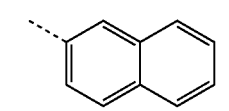 |
| 3-2-83 | 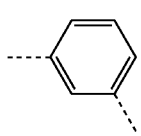 | 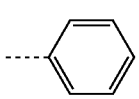 | 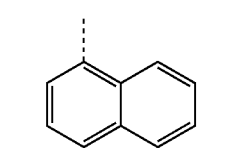 |
| 3-2-84 | 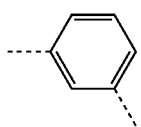 | 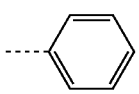 | 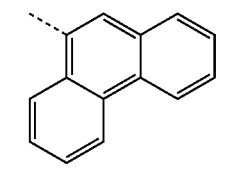 |
| 3-2-85 | 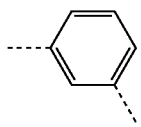 | 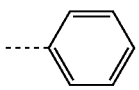 | 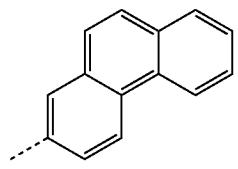 |
| 3-2-86 | 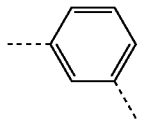 | 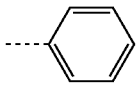 | 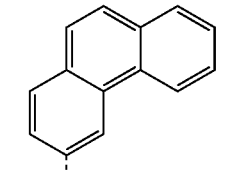 |
| 3-2-87 | 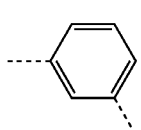 | 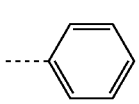 | 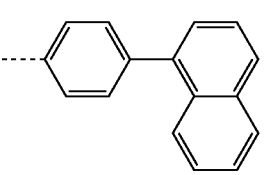 |

TABLE 3-continued

| | ----L₂---- | ----Ar₃ | ----Ar₄ |
|---|---|---|---|
| 3-2-88 | phenylene | phenyl | 4-(2-naphthyl)phenyl |
| 3-2-89 | phenylene | phenyl | 3'-phenyl-biphenyl-4-yl |
| 3-2-90 | phenylene | phenyl | 4-(9-phenanthrenyl)phenyl |
| 3-2-91 | phenylene | phenyl | 4-(9,9-dimethylfluoren-2-yl)phenyl |
| 3-2-92 | phenylene | phenyl | 7-phenyl-9,9-dimethylfluoren-2-yl |
| 3-2-93 | phenylene | biphenyl | 3,5-diphenylphenyl |
| 3-2-94 | phenylene | biphenyl | 2-naphthyl |
| 3-2-95 | phenylene | biphenyl | 1-naphthyl |

TABLE 3-continued

| | ----L₂--- | ----Ar₃ | ----Ar₄ |
|---|---|---|---|
| 3-2-96 | phenyl | biphenyl | phenanthrenyl |
| 3-2-97 | phenyl | biphenyl | phenanthrenyl |
| 3-2-98 | phenyl | biphenyl | phenanthrenyl |
| 3-2-99 | phenyl | biphenyl | phenyl-naphthyl |
| 3-2-100 | phenyl | biphenyl | phenyl-naphthyl |
| 3-2-101 | phenyl | biphenyl | terphenyl |
| 3-2-102 | phenyl | biphenyl | phenyl-phenanthrenyl |
| 3-2-103 | phenyl | biphenyl | phenyl-9,9-dimethylfluorenyl |

TABLE 3-continued

| ----L₂--- | ----Ar₃ | ----Ar₄ |
|---|---|---|
| 3-2-104 | 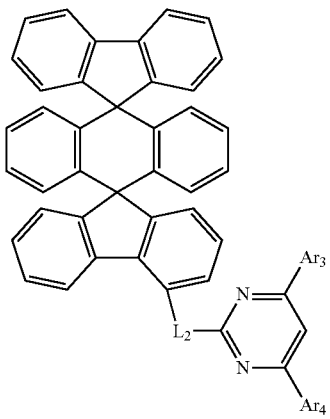 | |

According to one embodiment of the present specification, the double spiro structure compound represented by Chemical Formula 1 is represented by any one of the following Chemical Formulae 3-8 to 3-10, and in the following Chemical Formulae 3-8 to 3-10, $L_2$, $Ar_3$ and $Ar_4$ may be selected from Table 3. For example, in the following Chemical Formula 3-8, when $L_2$, $Ar_3$ and $Ar_4$ correspond to 3-2-10 in Table 3, t may be expressed as Compound 3-2-10 (3-8), and when corresponding to 3-2-20, it may be expressed as Compound 3-2-20 (3-8).

In addition, in the following Chemical Formula 3-9, when $L_2$, $Ar_3$ and $Ar_4$ correspond to 3-2-10 in Table 3, it may be expressed as Compound 3-2-10 (3-9), and when corresponding to 3-2-20, it may be expressed as Compound 3-2-20 (3-9).

Furthermore, in the following Chemical Formula 3-10, when $L_2$, $Ar_3$ and $Ar_4$ correspond to 3-2-10 in Table 3, it may be expressed as Compound 3-2-10 (3-10), and when corresponding to 3-2-20, it may be expressed as Compound 3-2-20 (3-10).

[Chemical Formula 3-8]

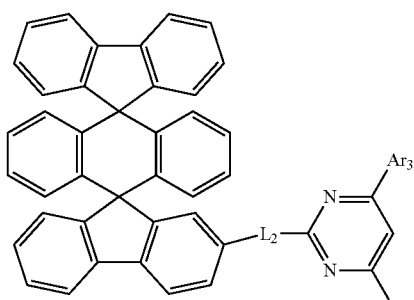

[Chemical Formula 3-9]

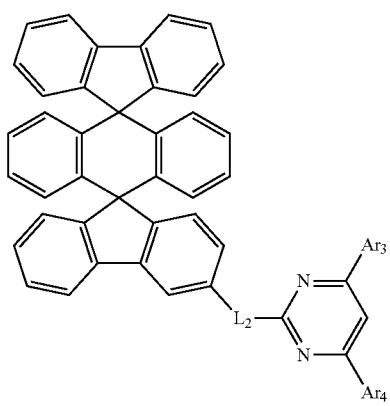

[Chemical Formula 3-10]

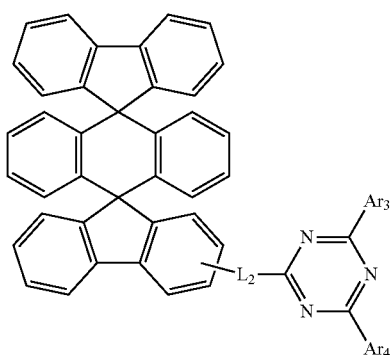

According to one embodiment of the present specification, the double spiro structure compound represented by Chemical Formula 1 is represented by the following Chemical Formula 3-3, and in the following Chemical Formula 3-3, $L_2$, $Ar_3$ and $Ar_4$ are any one selected from among 3-3-1 to 3-3-104 of the following Table 4.

[Chemical Formula 3-3]

TABLE 4
| | ----L₂---- | ----Ar₃ | ----Ar₄ |
|---|---|---|---|
| 3-1-1 | Direct bond | 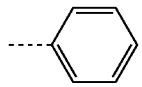 | 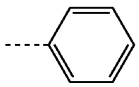 |
| 3-3-2 | Direct bond | 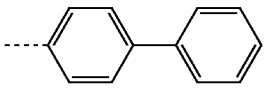 | 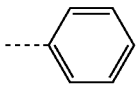 |
| 3-3-3 | Direct bond | 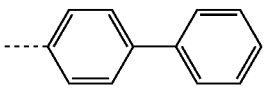 | 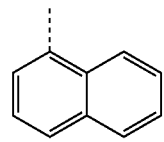 |
| 3-3-4 | Direct bond | 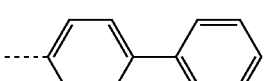 | 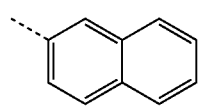 |
| 3-3-5 | Direct bond | 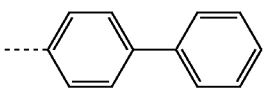 | 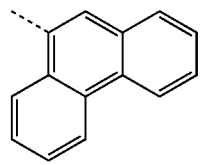 |
| 3-3-6 | Direct bond | 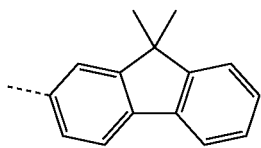 | 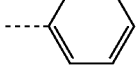 |
| 3-3-7 | Direct bond | 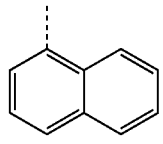 | 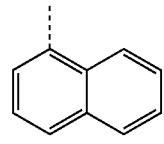 |
| 3-3-8 | Direct bond | 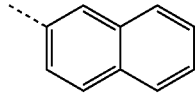 | 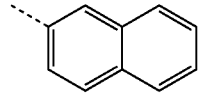 |
| 3-3-9 | Direct bond | 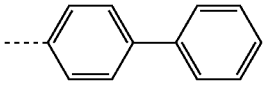 | 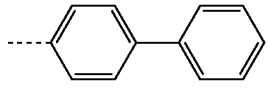 |
| 3-3-10 | Direct bond | 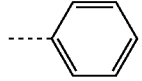 | 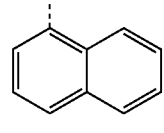 |
| 3-3-11 | Direct bond | 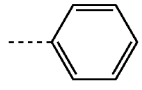 | 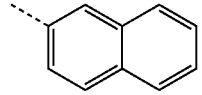 |
| 3-3-12 |  | 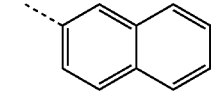 | 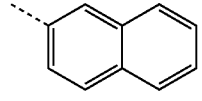 |

TABLE 4-continued
| | ----L$_2$---- | ----Ar$_3$---- | ----Ar$_4$---- |
|---|---|---|---|
| 3-3-13 | 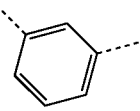 | 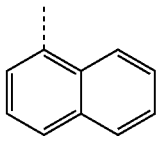 | 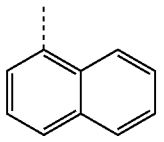 |
| 3-3-14 | 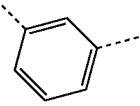 | 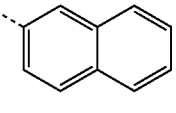 | 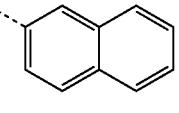 |
| 3-3-15 |  | 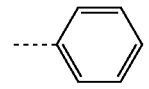 | 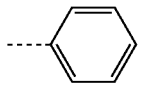 |
| 3-3-16 | 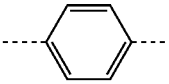 | 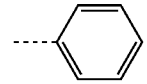 | 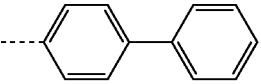 |
| 3-3-17 | 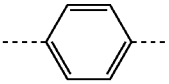 | 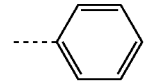 | 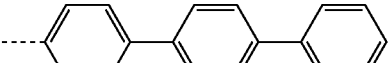 |
| 3-3-18 | 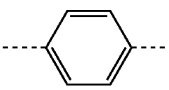 | 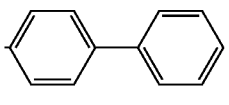 | 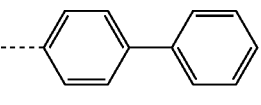 |
| 3-3-19 | 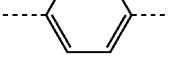 | 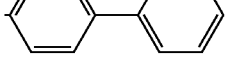 | 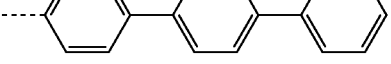 |
| 3-3-20 | 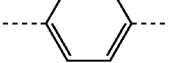 | 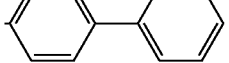 | 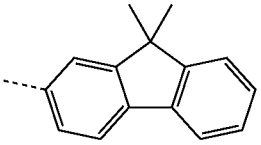 |
| 3-3-21 | 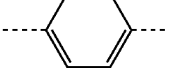 | 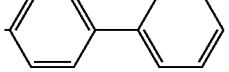 | 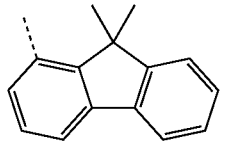 |
| 3-3-22 | 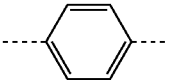 | 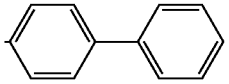 | 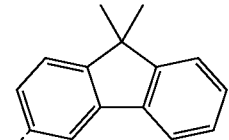 |
| 3-3-23 | 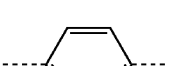 | 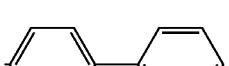 | 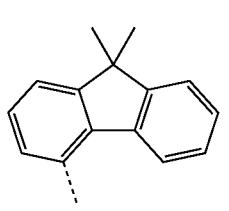 |

TABLE 4-continued
| | ----L₂--- | ----Ar₃ | ----Ar₄ |
|---|---|---|---|
| 3-3-24 | 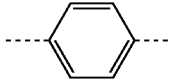 | 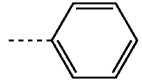 | 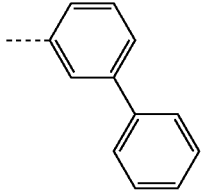 |
| 3-3-25 | 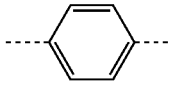 | 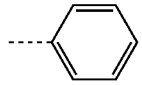 | 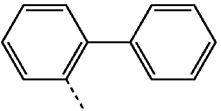 |
| 3-3-26 | 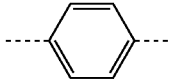 | 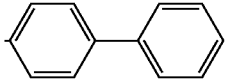 | 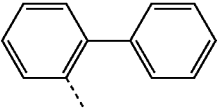 |
| 3-3-27 | 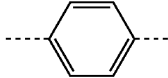 | 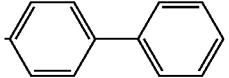 | 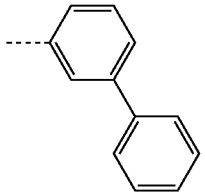 |
| 3-3-28 | 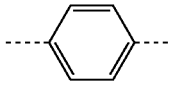 | 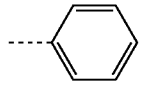 | 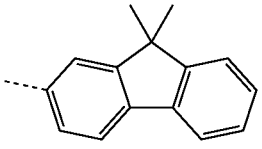 |
| 3-3-29 | 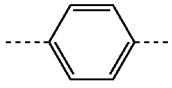 | 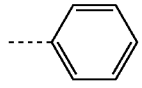 | 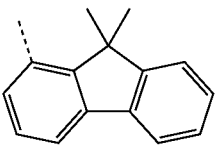 |
| 3-3-30 | 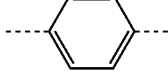 | 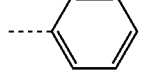 | 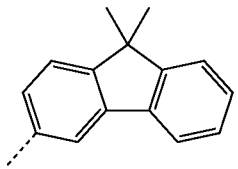 |
| 3-3-31 | 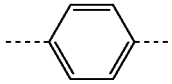 | 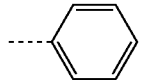 | 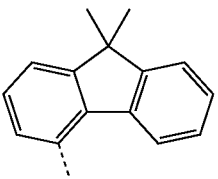 |
| 3-3-32 | 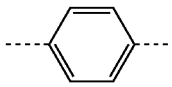 | 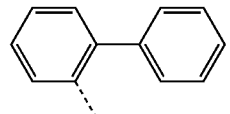 | 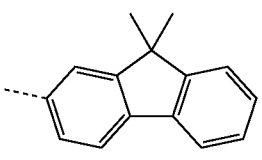 |

TABLE 4-continued
| | ----L$_2$---- | ----Ar$_3$---- | ----Ar$_4$---- |
|---|---|---|---|
| 3-3-33 | 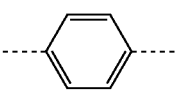 | 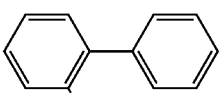 | 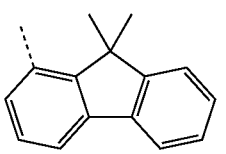 |
| 3-3-34 | 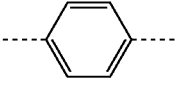 | 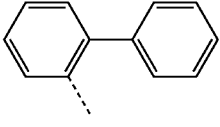 | 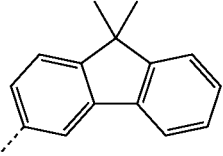 |
| 3-3-35 | 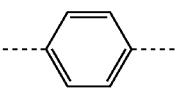 | 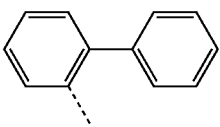 | 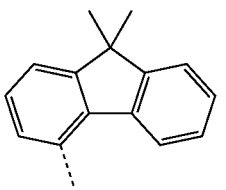 |
| 3-3-36 | 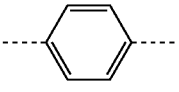 | 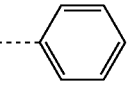 | 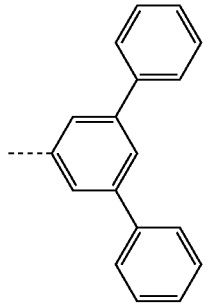 |
| 3-3-37 | 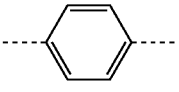 | 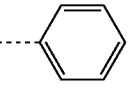 | 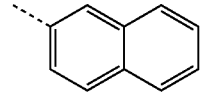 |
| 3-3-38 | 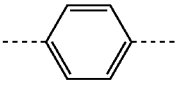 | 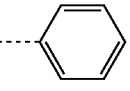 | 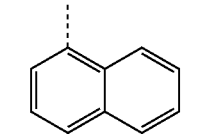 |
| 3-3-39 | 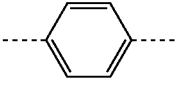 | 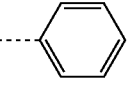 | 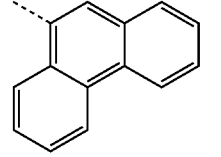 |
| 3-3-40 | 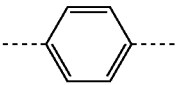 | 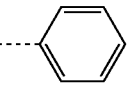 | 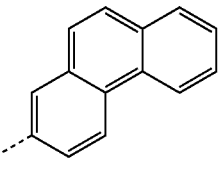 |

TABLE 4-continued
| | ----L₂---- | ----Ar₃ | ----Ar₄ |
|---|---|---|---|
| 3-3-41 | 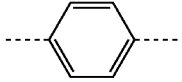 | 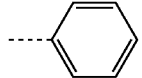 | 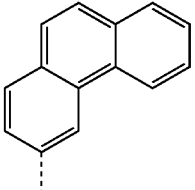 |
| 3-3-42 | 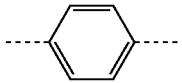 | 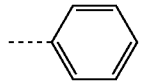 | 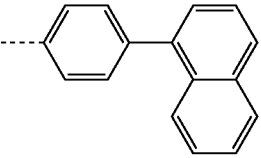 |
| 3-3-43 | 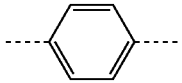 | 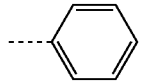 | 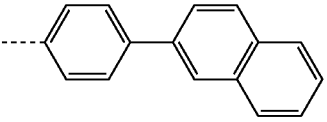 |
| 3-3-44 | 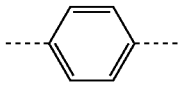 | 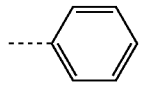 | 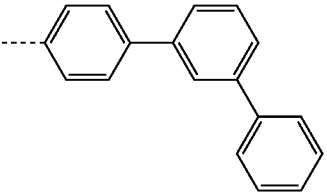 |
| 3-3-45 | 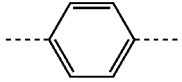 | 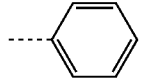 | 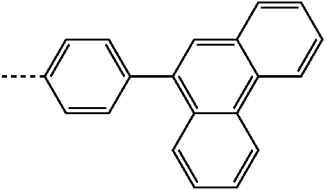 |
| 3-3-46 | 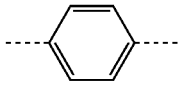 | 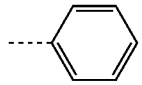 | 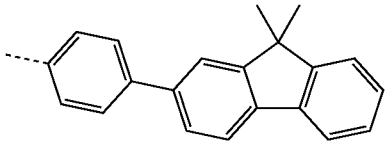 |
| 3-3-47 | 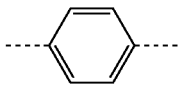 | 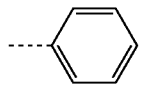 | 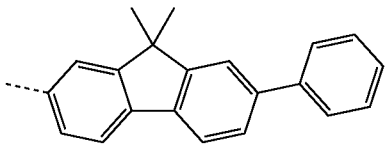 |
| 3-3-48 | 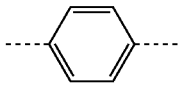 | 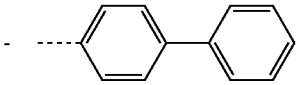 | 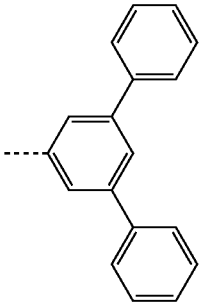 |

TABLE 4-continued

| | ----L₂---- | ----Ar₃ | ----Ar₄ |
|---|---|---|---|
| 3-3-49 | | | |
| 3-3-50 | | | |
| 3-3-51 | | | |
| 3-3-52 | | | |
| 3-3-53 | | | |
| 3-3-54 | | | |
| 3-3-55 | | | |
| 3-3-56 | | | |
| 3-3-57 | | | |

TABLE 4-continued
| | ----L₂---- | ----Ar₃---- | ----Ar₄---- |
|---|---|---|---|
| 3-3-58 | 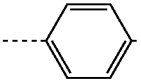 | 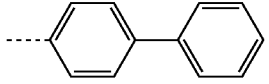 | 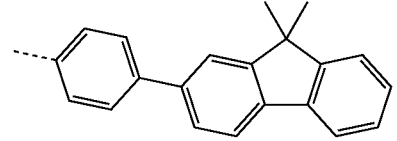 |
| 3-3-59 | 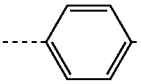 | 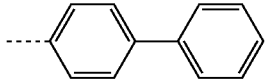 | 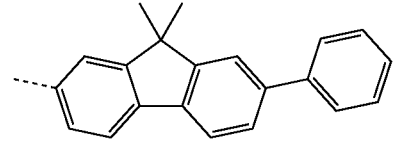 |
| 3-3-60 | 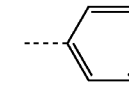 | 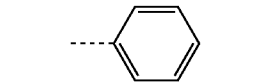 | 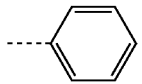 |
| 3-3-61 | 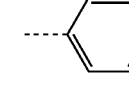 | 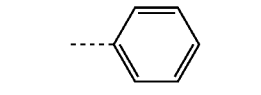 | 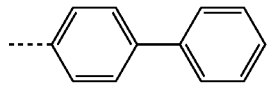 |
| 3-3-62 | 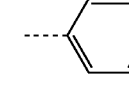 | 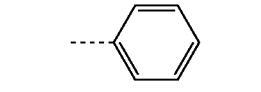 | 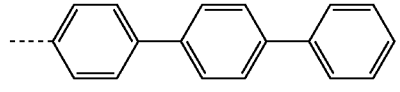 |
| 3-3-63 | 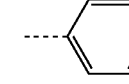 | 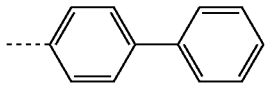 | 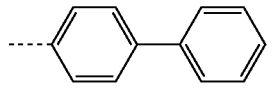 |
| 3-3-64 | 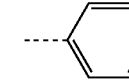 | 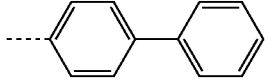 | 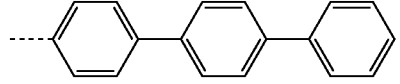 |
| 3-3-65 | 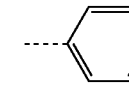 | 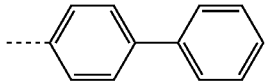 | 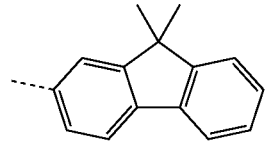 |
| 3-3-66 | 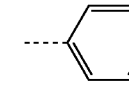 | 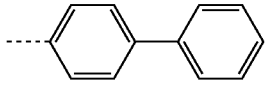 | 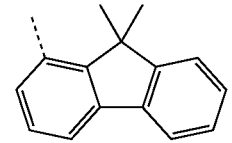 |
| 3-3-67 | 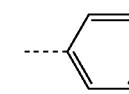 | 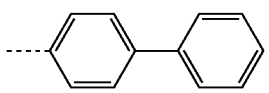 | 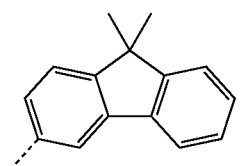 |

TABLE 4-continued

| | ----L₂---- | ----Ar₃---- | ----Ar₄---- |
|---|---|---|---|
| 3-3-68 | phenylene | biphenyl | 9,9-dimethylfluorene (4-position) |
| 3-3-69 | phenylene | phenyl | biphenyl (meta) |
| 3-3-70 | phenylene | phenyl | biphenyl (ortho) |
| 3-3-71 | phenylene | biphenyl | biphenyl (ortho) |
| 3-3-72 | phenylene | biphenyl | biphenyl (meta) |
| 3-3-73 | phenylene | phenyl | 9,9-dimethylfluorene (2-position) |
| 3-3-74 | phenylene | phenyl | 9,9-dimethylfluorene (1-position) |
| 3-3-75 | phenylene | phenyl | 9,9-dimethylfluorene (3-position) |
| 3-3-76 | phenylene | phenyl | 9,9-dimethylfluorene (4-position) |

TABLE 4-continued

| | ----L$_2$---- | ----Ar$_3$---- | ----Ar$_4$---- |
|---|---|---|---|
| 3-3-77 | phenylene | 2-biphenyl | 9,9-dimethylfluoren-2-yl |
| 3-3-78 | phenylene | 2-biphenyl | 9,9-dimethylfluoren-1-yl |
| 3-3-79 | phenylene | 2-biphenyl | 9,9-dimethylfluoren-3-yl |
| 3-3-80 | phenylene | 2-biphenyl | 9,9-dimethylfluoren-4-yl |
| 3-3-81 | phenylene | phenyl | 3,5-diphenylphenyl |
| 3-3-82 | phenylene | phenyl | naphthalen-2-yl |
| 3-3-83 | phenylene | phenyl | naphthalen-1-yl |
| 3-3-84 | phenylene | phenyl | phenanthren-9-yl |

TABLE 4-continued

| | ----L₂---- | ----Ar₃ | ----Ar₄ |
|---|---|---|---|
| 3-3-85 | phenylene | phenyl | phenanthrenyl |
| 3-3-86 | phenylene | phenyl | phenanthrenyl |
| 3-3-87 | phenylene | phenyl | 4-(1-naphthyl)phenyl |
| 3-3-88 | phenylene | phenyl | 4-(2-naphthyl)phenyl |
| 3-3-89 | phenylene | phenyl | 4-(3-biphenyl)phenyl |
| 3-3-90 | phenylene | phenyl | 4-(9-phenanthrenyl)phenyl |
| 3-3-91 | phenylene | phenyl | 4-(9,9-dimethylfluoren-2-yl)phenyl |
| 3-3-92 | phenylene | phenyl | 7-phenyl-9,9-dimethylfluoren-2-yl |

TABLE 4-continued

| | ----L$_2$---- | ----Ar$_3$---- | ----Ar$_4$---- |
|---|---|---|---|
| 3-3-93 | phenylene (meta) | biphenyl | 3,5-diphenylphenyl |
| 3-3-94 | phenylene (meta) | biphenyl | 2-naphthyl |
| 3-3-95 | phenylene (meta) | biphenyl | 1-naphthyl |
| 3-3-96 | phenylene (meta) | biphenyl | 9-phenanthryl |
| 3-3-97 | phenylene (meta) | biphenyl | 2-phenanthryl |
| 3-3-98 | phenylene (meta) | biphenyl | 3-phenanthryl |
| 3-3-99 | phenylene (meta) | biphenyl | 4-(1-naphthyl)phenyl |
| 3-3-100 | phenylene (meta) | biphenyl | 4-(2-naphthyl)phenyl |

TABLE 4-continued

| | ----L$_2$--- | ----Ar$_3$ | ----Ar$_4$ |
|---|---|---|---|
| 3-3-101 | | | |
| 3-2-102 | | | |
| 3-3-103 | | | |
| 3-3-104 | | | |

According to one embodiment of the present specification, the double spiro structure compound represented by Chemical Formula 1 is represented by any one of the following Chemical Formulae 3-11 to 3-13, and in the following Chemical Formulae 3-11 to 3-13, L$_2$, Ar$_3$ and Ar$_4$ may be selected from Table 4. For example, in the following Chemical Formula 3-11, L$_2$, when Ar$_3$ and Ar$_4$ correspond to 3-3-10 in Table 4, it may be expressed as Compound 3-3-10 (3-11), and when corresponding to 3-3-20, it may be expressed as Compound 3-3-20 (3-11).

In addition, in the following Chemical Formula 3-12, when L$_2$, Ar$_3$ and Ar$_4$ correspond to 3-3-10 in Table 4, it may be expressed as Compound 3-3-10 (3-12), and when corresponding to 3-3-20, it may be expressed as Compound 3-3-20 (3-12).

Furthermore, in the following Chemical Formula 3-13, when L$_2$, Ar$_3$ and Ar$_4$ correspond to 3-3-10 in Table 4, it may be expressed as Compound 3-3-10 (3-13), and when corresponding to 3-3-20, it may be expressed as Compound 3-3-20 (3-13).

[Chemical Formula 3-11]

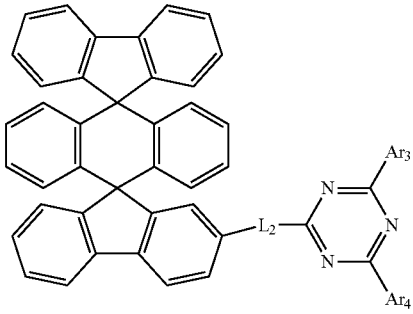

[Chemical Formula 3-12]

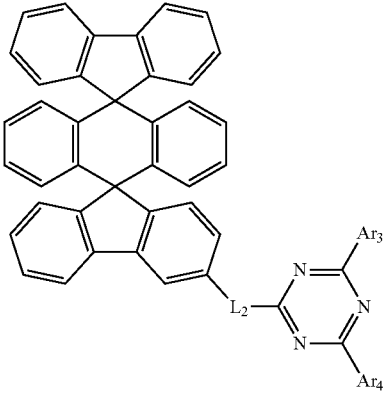

[Chemical Formula 3-13]

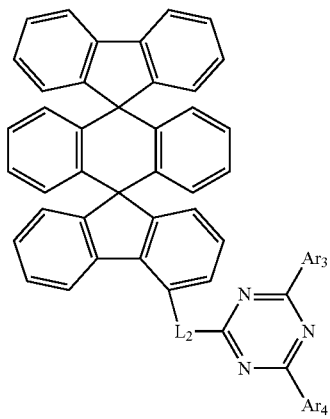

According to one embodiment of the present specification, the double spiro structure compound represented by Chemical Formula 1 is represented by the following Chemical Formula 3-4, and in the following Chemical Formula 3-4, $L_2$, $Ar_3$ and $Ar_4$ are any one selected from among 3-4-1 to 3-4-104 of the following Table 5.

[Chemical Formula 3-4]

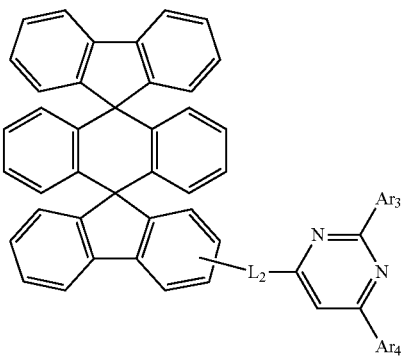

TABLE 5

| | ---$L_2$--- | ---$Ar_3$--- | ---$Ar_4$--- |
|---|---|---|---|
| 3-4-1 | Direct bond | phenyl | phenyl |
| 3-4-2 | Direct bond | biphenyl | phenyl |
| 3-4-3 | Direct bond | biphenyl | naphthyl |
| 3-4-4 | Direct bond | biphenyl | naphthyl |
| 3-4-5 | Direct bond | biphenyl | phenanthrenyl |
| 3-4-6 | Direct bond | 9,9-dimethylfluorenyl | phenyl |
| 3-4-7 | Direct bond | naphthyl | naphthyl |

TABLE 5-continued
| | ---L$_2$--- | ---Ar$_3$ | ---Ar$_4$ |
|---|---|---|---|
| 3-4-8 | Direct bond | 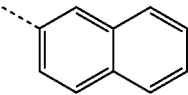 | 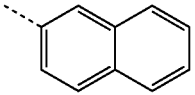 |
| 3-4-9 | Direct bond | 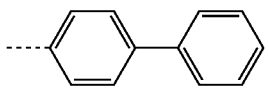 | 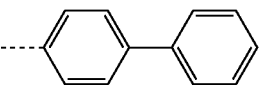 |
| 3-4-10 | Direct bond | 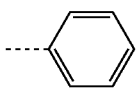 | 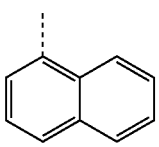 |
| 3-4-11 | Direct bond | 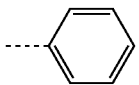 | 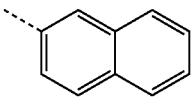 |
| 3-4-12 | 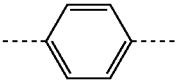 | 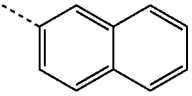 | 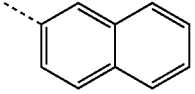 |
| 3-4-13 | 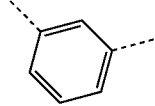 | 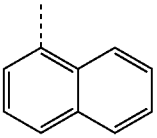 | 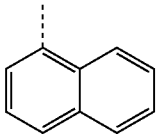 |
| 3-4-14 | 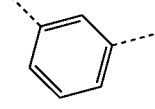 | 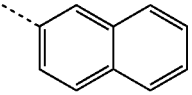 | 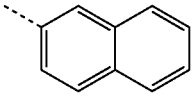 |
| 3-4-15 |  | 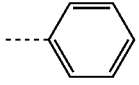 | 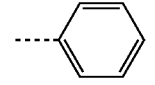 |
| 3-4-16 | 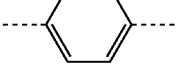 | 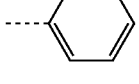 | 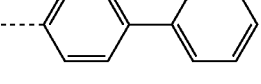 |
| 3-4-17 | 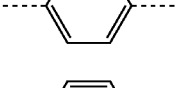 | 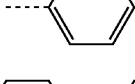 | 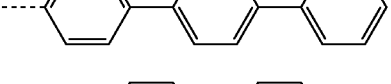 |
| 3-4-18 | 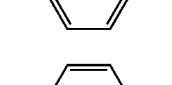 |  | 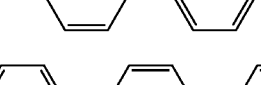 |
| 3-4-19 | 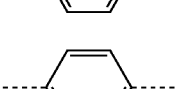 |  |  |
| 3-4-20 |  |  | 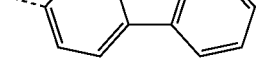 |

TABLE 5-continued
| | ---L₂--- | ---Ar₃ | ---Ar₄ |
|---|---|---|---|
| 3-4-21 | 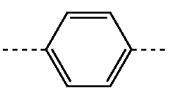 | 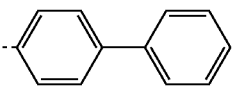 | 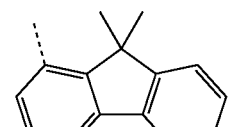 |
| 3-4-22 | 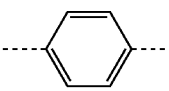 | 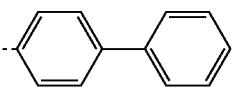 | 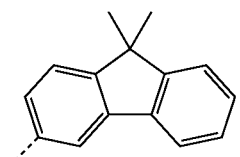 |
| 3-4-23 | 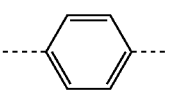 | 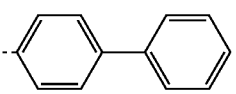 | 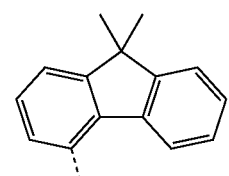 |
| 3-4-24 | 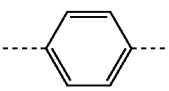 | 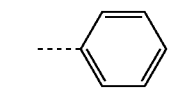 | 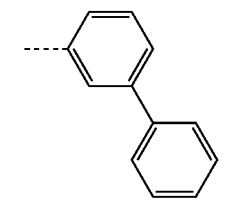 |
| 3-4-25 | 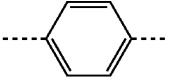 | 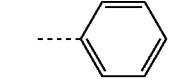 | 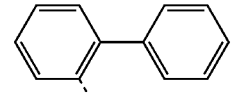 |
| 3-4-26 | 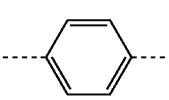 | 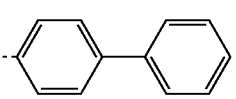 | 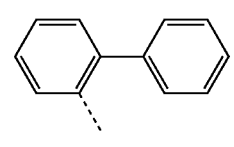 |
| 3-4-27 | 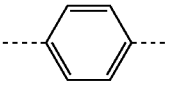 | 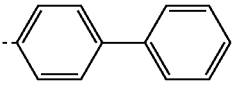 | 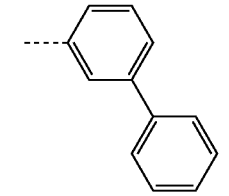 |
| 3-4-28 | 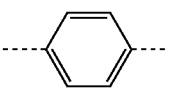 | 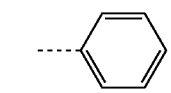 | 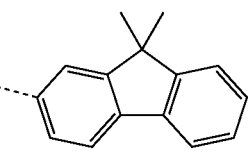 |
| 3-4-29 | 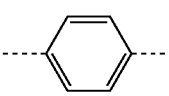 | 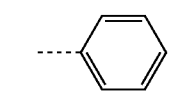 | 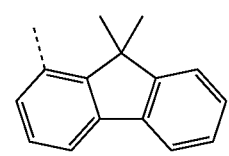 |

TABLE 5-continued
| | ---L₂--- | ---Ar₃ | ---Ar₄ |
|---|---|---|---|
| 3-4-30 | 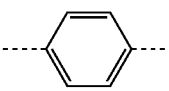 | 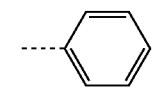 | 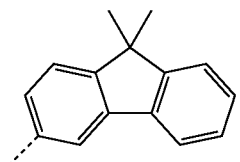 |
| 3-4-31 | 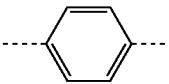 | 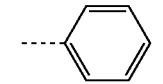 | 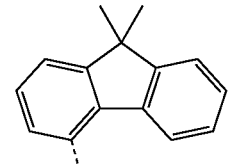 |
| 3-4-32 | 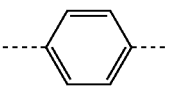 | 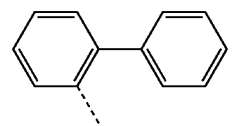 | 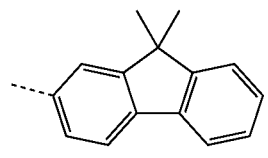 |
| 3-4-33 | 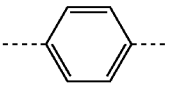 | 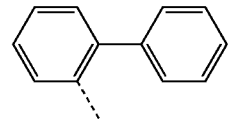 | 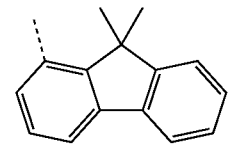 |
| 3-4-34 | 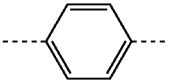 | 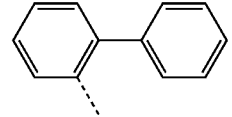 | 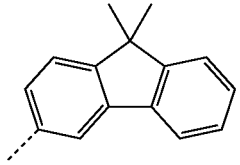 |
| 3-4-35 | 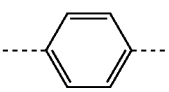 | 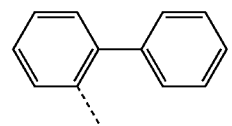 | 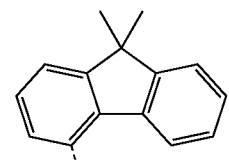 |
| 3-4-36 | 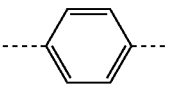 | 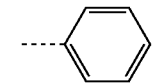 | 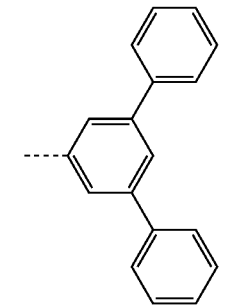 |
| 3-4-37 | 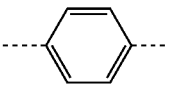 | 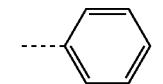 | 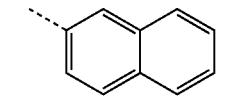 |

TABLE 5-continued
| | ---L$_2$--- | ---Ar$_3$ | ---Ar$_4$ |
|---|---|---|---|
| 3-4-38 | 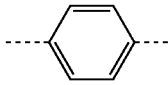 | 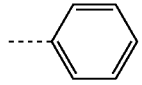 | 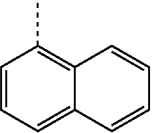 |
| 3-4-39 | 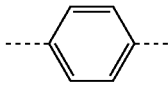 | 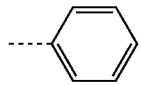 | 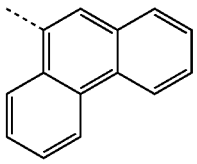 |
| 3-4-40 | 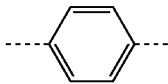 | 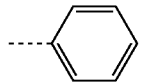 | 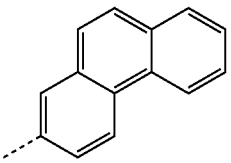 |
| 3-4-41 | 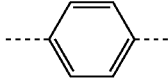 | 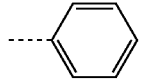 | 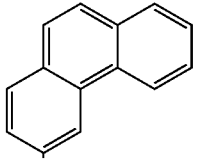 |
| 3-4-42 | 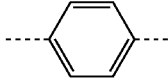 | 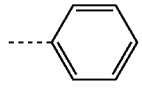 | 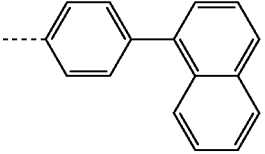 |
| 3-4-43 | 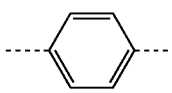 | 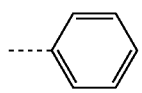 | 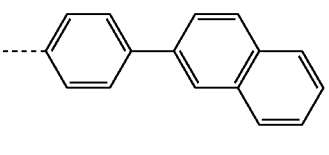 |
| 3-4-44 | 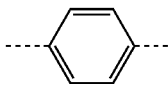 | 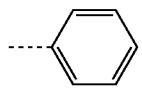 | 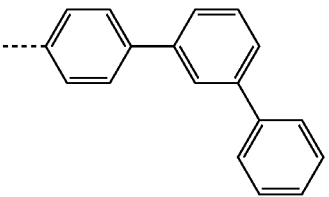 |
| 3-4-45 | 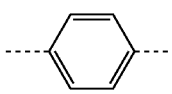 | 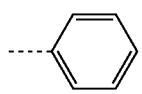 | 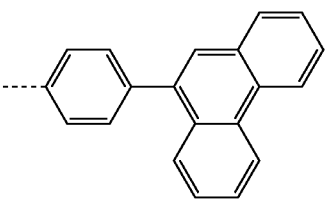 |
| 3-4-46 | 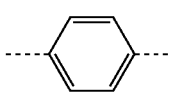 | 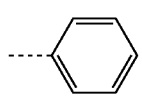 | 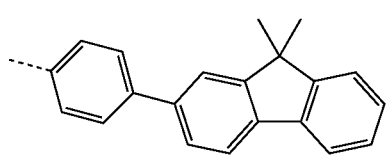 |

TABLE 5-continued
| | ---L$_2$--- | ---Ar$_3$--- | ---Ar$_4$ |
|---|---|---|---|
| 3-4-47 |  | 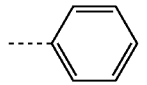 | 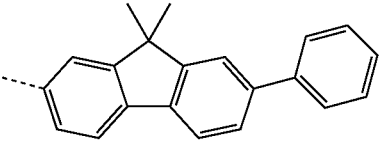 |
| 3-4-48 |  | 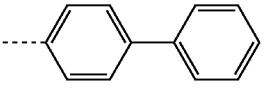 | 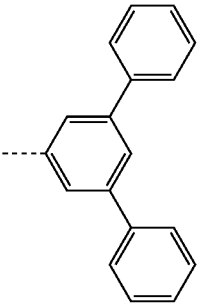 |
| 3-4-49 | 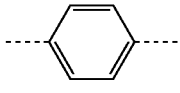 | 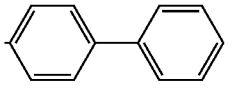 | 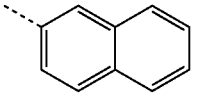 |
| 3-4-50 | 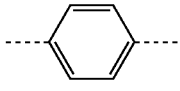 | 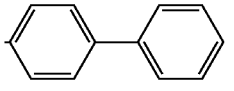 | 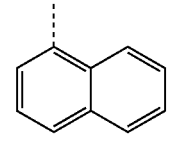 |
| 3-4-51 | 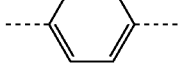 | 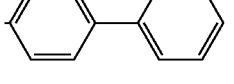 | 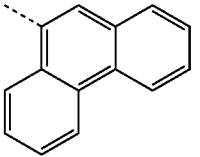 |
| 3-4-52 |  | 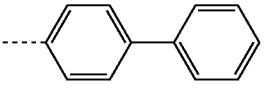 | 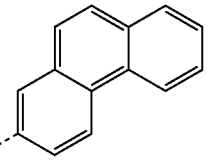 |
| 3-4-53 |  | 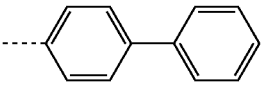 | 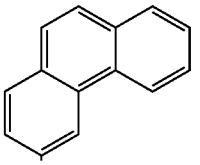 |
| 3-4-54 |  | 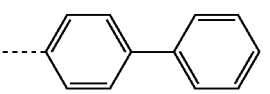 | 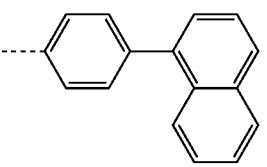 |
| 3-4-55 |  | 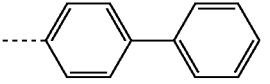 | 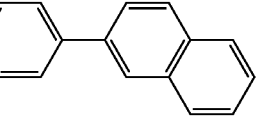 |

TABLE 5-continued

| | ---L₂--- | ---Ar₃ | ---Ar₄ |
|---|---|---|---|
| 3-4-56 | | | |
| 3-4-57 | | | |
| 3-4-58 | | | |
| 3-4-59 | | | |
| 3-4-60 | | | |
| 3-4-61 | | | |
| 3-4-62 | | | |
| 3-4-63 | | | |
| 3-4-64 | | | |
| 3-4-65 | | | |

TABLE 5-continued

| | ---L₂--- | ---Ar₃ | ---Ar₄ |
|---|---|---|---|
| 3-4-66 | (m-phenylene) | (4-biphenyl) | (9,9-dimethylfluoren-1-yl) |
| 3-4-67 | (m-phenylene) | (4-biphenyl) | (9,9-dimethylfluoren-3-yl) |
| 3-4-68 | (m-phenylene) | (4-biphenyl) | (9,9-dimethylfluoren-4-yl) |
| 3-4-69 | (m-phenylene) | (phenyl) | (biphenyl-3-yl) |
| 3-4-70 | (m-phenylene) | (phenyl) | (biphenyl-2-yl) |
| 3-4-71 | (m-phenylene) | (4-biphenyl) | (biphenyl-2-yl) |
| 3-4-72 | (m-phenylene) | (4-biphenyl) | (biphenyl-3-yl) |
| 3-4-73 | (m-phenylene) | (phenyl) | (9,9-dimethylfluoren-2-yl) |
| 3-4-74 | (m-phenylene) | (phenyl) | (9,9-dimethylfluoren-1-yl) |

TABLE 5-continued

| | ---L$_2$--- | ---Ar$_3$--- | ---Ar$_4$--- |
|---|---|---|---|
| 3-4-75 | | | |
| 3-4-76 | | | |
| 3-4-77 | | | |
| 3-4-78 | | | |
| 3-4-79 | | | |
| 3-4-80 | | | |
| 3-4-81 | | | |
| 3-4-82 | | | |

TABLE 5-continued

| | ---L₂--- | ---Ar₃ | ---Ar₄ |
|---|---|---|---|
| 3-4-83 | | | |
| 3-4-84 | | | |
| 3-4-85 | | | |
| 3-4-86 | | | |
| 3-4-87 | | | |
| 3-4-88 | | | |
| 3-4-89 | | | |
| 3-4-90 | | | |
| 3-4-91 | | | |

TABLE 5-continued

| | ---L₂--- | ---Ar₃ | ---Ar₄ |
|---|---|---|---|
| 3-4-92 | | | |
| 3-4-93 | | | |
| 3-4-94 | | | |
| 3-4-95 | | | |
| 3-4-96 | | | |
| 3-4-97 | | | |
| 3-4-98 | | | |
| 3-4-99 | | | |

TABLE 5-continued

| | ---L$_2$--- | ---Ar$_3$ | ---Ar$_4$ |
|---|---|---|---|
| 3-4-100 | | | |
| 3-4-101 | | | |
| 3-4-102 | | | |
| 3-4-103 | | | |
| 3-4-104 | | | |

According to one embodiment of the present specification, the double spiro structure compound represented by Chemical Formula 1 is represented by any one of the following Chemical Formulae 3-14 to 3-16, and in the following Chemical Formulae 3-14 to 3-16, L$_2$, Ar$_3$ and Ar$_4$ may be selected from Table 5. For example, in the following Chemical Formula 3-14, when L$_2$, Ar$_3$ and Ar$_4$ correspond to 3-4-10 in Table 5, it may be expressed as Compound 3-4-10 (3-14), and when corresponding to 3-4-20, it may be expressed as Compound 3-4-20 (3-14).

In addition, in the following Chemical Formula 3-15, when L$_2$, Ar$_3$ and Ar$_4$ correspond to 3-4-10 in Table 5, it may be expressed as Compound 3-4-10 (3-15), and when corresponding to 3-4-20, it may be expressed as Compound 3-4-20 (3-15).

Furthermore, in the following Chemical Formula 3-16, when L$_2$, Ar$_3$ and Ar$_4$ correspond to 3-4-10 in Table 5, it may be expressed as Compound 3-4-10 (3-16), and when corresponding to 3-4-20, it may be expressed as Compound 3-4-20 (3-16).

[Chemical Formula 3-14]

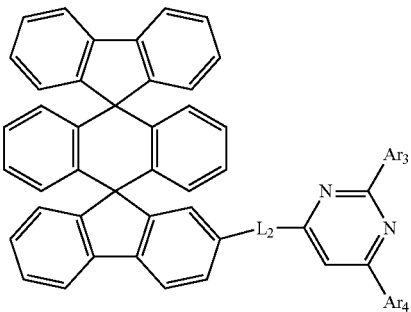

-continued

[Chemical Formula 3-15]

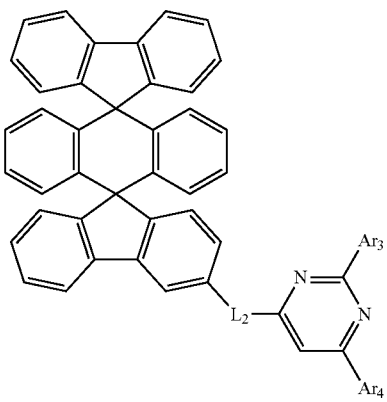

[Chemical Formula 3-16]

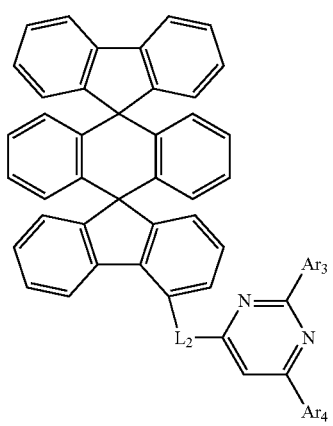

According to one embodiment of the present specification, the double spiro structure compound represented by Chemical Formula 1 is represented by the following Chemical Formula 4-4, and in the following Chemical Formula 4-4, $L_3$ and $X_4$ are any one selected from among 4-4-1 to 4-4-22 of the following Table 6.

[Chemical Formula 4-4]

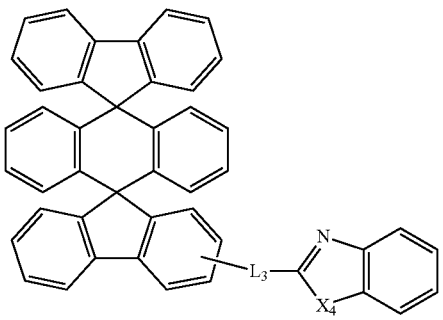

TABLE 6

| | $X_4$ | ----$L_3$---- | ----$Ar_5$---- |
|---|---|---|---|
| 4-4-1 | O | ----⌬---- | |
| 4-4-2 | S | ----⌬---- | |
| 4-4-3 | $NAr_5$ | ----⌬---- | ----⌬ |
| 4-4-4 | $NAr_5$ | ----⌬---- | ----⌬-⌬ |
| 4-4-5 | $NAr_5$ | ----⌬---- | ----⌬-⌬-⌬ |

TABLE 6-continued
| | X₄ | ----L₃---- | ----Ar₅ |
|---|---|---|---|
| 4-4-6 | NAr₅ |  | 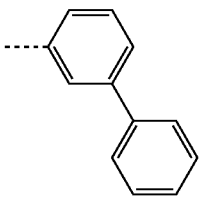 |
| 4-4-7 | NAr₅ |  | 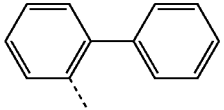 |
| 4-4-8 | NAr₅ |  | 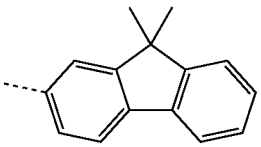 |
| 4-4-9 | NAr₅ |  | 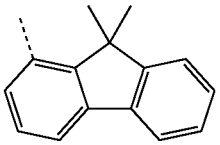 |
| 4-4-10 | NAr₅ |  | 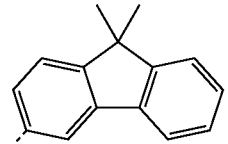 |
| 4-4-11 | NAr₅ |  | 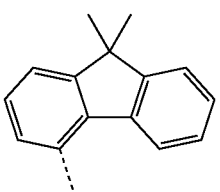 |
| 4-4-12 | NAr₅ |  | 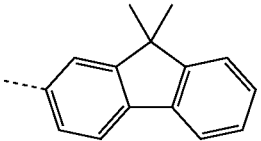 |
| 4-4-13 | NAr₅ |  | 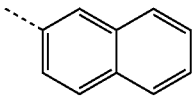 |
| 4-4-14 | NAr₅ |  | 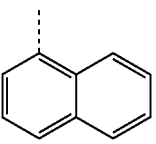 |

TABLE 6-continued

| | $X_4$ | ----$L_3$---- | ----$Ar_5$ |
|---|---|---|---|
| 4-4-15 | $NAr_5$ | phenylene | phenanthrenyl |
| 4-4-16 | $NAr_5$ | phenylene | phenanthrenyl |
| 4-4-17 | $NAr_5$ | phenylene | phenyl-naphthalenyl |
| 4-4-18 | $NAr_5$ | phenylene | phenyl-naphthalenyl |
| 4-4-19 | $NAr_5$ | phenylene | phenyl-anthracenyl |
| 4-4-20 | $NAr_5$ | phenylene | m-terphenyl |
| 4-4-21 | $NAr_5$ | phenylene | 9,9-dimethylfluorenyl-phenyl |
| 4-4-22 | $NAr_5$ | phenylene | phenyl-9,9-dimethylfluorenyl |

According to one embodiment of the present specification, the double spiro structure compound represented by Chemical Formula 1 is represented by any one of the following Chemical Formulae 4-5 to 4-7, and in the following Chemical Formulae 4-5 to 4-7, $L_3$ and $X_4$ may be selected from Table 6. For example, in the following Chemical Formula 4-5, when L$_3$ and X$_4$ correspond to 4-4-10 in Table 6, it may be expressed as Compound 4-4-10 (4-5), and when corresponding to 4-4-20, it may be expressed as Compound 4-4-20 (4-5).

In addition, in the following Chemical Formula 4-6, when L$_3$ and X$_4$ correspond to 4-4-10 in Table 6, it may be expressed as Compound 4-4-10 (4-6), and when corresponding to 4-4-20, it may be expressed as Compound 4-4-20 (4-6).

Furthermore, in the following Chemical Formula 4-7, when L$_3$ and X$_4$ correspond to 4-4-10 in Table 6, it may be expressed as Compound 4-4-10 (4-7), and when corresponding to 4-4-20, it may be expressed as Compound 4-4-20 (4-7).

[Chemical Formula 4-5]

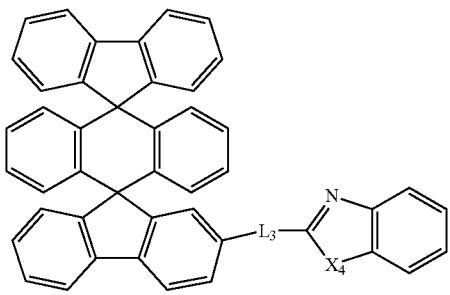

[Chemical Formula 4-6]

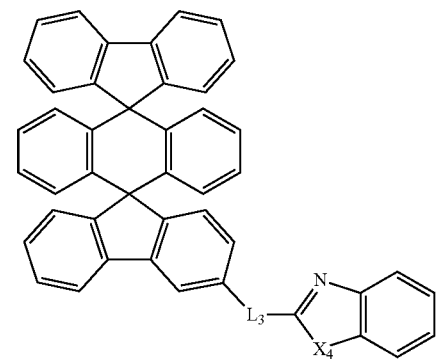

[Chemical Formula 4-7]

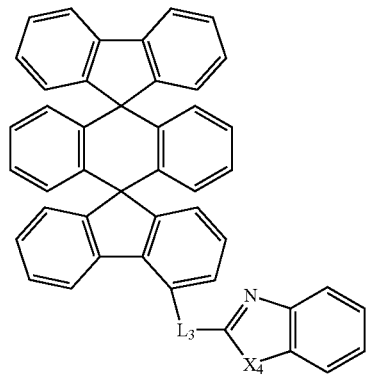

One embodiment of the present specification provides an organic light emitting device comprising an anode; a cathode provided opposite to the anode; and a light emitting layer and one or more organic material layers provided between the anode and the cathode, wherein the light emitting layer or one or more layers of the organic material layers comprise the double spiro structure compound represented by Chemical Formula 1.

The organic material layer of the organic light emitting device of the present specification may be formed in a single layer structure, but may be formed in a multilayer structure in which two or more organic material layers are laminated. For example, the organic light emitting device of the present invention may have a structure comprising a hole injection layer, a hole transfer layer, an electron blocking layer, a hole blocking layer, an electron transfer layer, an electron injection layer and the like as the organic material layer.

However, the structure of the organic light emitting device is not limited thereto, and may comprise less numbers of organic material layers.

For example, the structure of the organic light emitting device of the present invention may be as shown in FIG. 1 and FIG. 2, but is not limited thereto.

FIG. 1 illustrates a structure of an organic light emitting device (10) in which an anode (30), a light emitting layer (40) and a cathode (50) are consecutively laminated on a substrate (20). FIG. 1 is an illustrative structure of the organic light emitting device according to one embodiment of the present specification, and other organic material layers may be further included therein.

FIG. 2 illustrates a structure of an organic light emitting device in which an anode (30), a hole injection layer (60), a hole transfer layer (70), a light emitting layer (40), an electron transfer layer (80), an electron injection layer (90) and a cathode (50) are consecutively laminated on a substrate (20). FIG. 2 is an illustrative structure of the organic light emitting device according to one embodiment of the present specification, and other organic material layers may be further included therein.

According to one embodiment of the present specification, the organic material layer comprises a hole injection layer or a hole transfer layer, and the hole injection layer or the hole transfer layer comprises the double spiro structure compound represented by Chemical Formula 1.

According to another embodiment of the present specification, the organic material layer comprises an electron blocking layer, and the electron blocking layer comprises the double spiro structure compound represented by Chemical Formula 1.

According to another embodiment of the present specification, the light emitting layer comprises the double spiro structure compound represented by Chemical Formula 1.

According to one embodiment of the present specification, the organic material layer comprises an electron transfer layer or an electron injection layer, wherein the electron transfer layer or the electron injection layer comprises the double spiro structure compound represented by Chemical Formula 1.

According to one embodiment of the present specification, the organic material layer comprises an electron transfer layer, an electron injection layer, or a layer carrying out electron transfer and electron injection at the same time, and the electron transfer layer, the electron injection layer, or the layer carrying out electron transfer and electron injection at the same time comprises the double spiro structure compound represented by Chemical Formula 1.

According to one embodiment of the present specification, the organic light emitting device comprises one or more organic material layers provided between the anode and the light emitting layer, wherein the organic material layer comprises a double spiro structure compound represented by the following Chemical Formula 2.

[Chemical Formula 2]

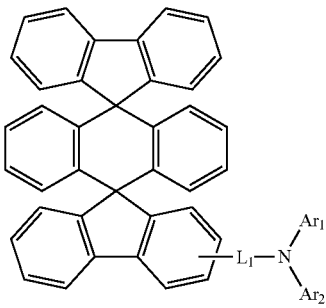

In Chemical Formula 2,

L$_1$ is a direct bond; a substituted or unsubstituted monocyclic or multicyclic arylene group having 6 to 30 carbon atoms; or a substituted or unsubstituted heteroarylene group having 2 to 30 carbon atoms, and Ar$_1$ and Ar$_2$ are the same as or different from each other, and each independently selected from the group consisting of hydrogen; a substituted or unsubstituted arylamine group; a substituted or unsubstituted monocyclic or multicyclic aryl group having 6 to 30 carbon atoms; and a substituted or unsubstituted heteroaryl group having 2 to 30 carbon atoms.

According to one embodiment of the present specification, the double spiro structure compound represented by Chemical Formula 2 may be represented by any one of Chemical Formulae 2-1 to 2-3 described above.

According to one embodiment of the present specification, the organic light emitting device comprises one or more organic material layers provided between the cathode and the light emitting layer, and the light emitting layer and one or more layers of the organic material layers comprise a double spiro structure compound represented by the following Chemical Formula 3.

[Chemical Formula 3]

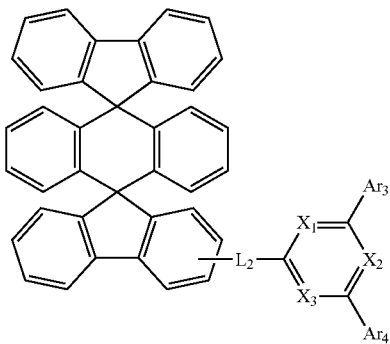

In Chemical Formula 3,

X$_1$ to X$_3$ are the same as or different from each other, and each independently CH or N, at least one of X$_1$ to X$_3$ is N, L$_2$ is a direct bond; a substituted or unsubstituted monocyclic or multicyclic arylene group having 6 to 30 carbon atoms; or a substituted or unsubstituted monocyclic or multicyclic heteroarylene group having 2 to 30 carbon atoms, and Ar$_3$ and Ar$_4$ are the same as or different from each other, and each independently selected from the group consisting of hydrogen; a substituted or unsubstituted arylamine group; a substituted or unsubstituted monocyclic or multicyclic aryl group having 6 to 30 carbon atoms; and a substituted or unsubstituted heteroaryl group having 2 to 30 carbon atoms.

According to one embodiment of the present specification, the double spiro structure compound represented by Chemical Formula 3 may be represented by any one of Chemical Formulae 3-1 to 3-9 described above.

According to one embodiment of the present specification, the organic light emitting device comprises one or more organic material layers provided between the cathode and the light emitting layer, wherein the organic material layer comprises a double spiro structure compound represented by the following Chemical Formula 4.

[Chemical Formula 4]

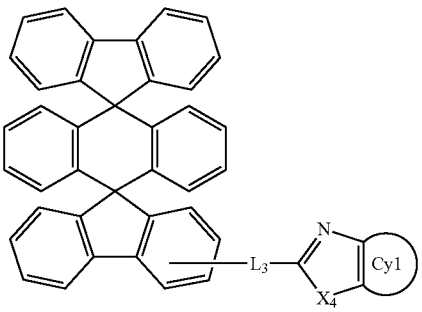

In Chemical Formula 4,

X$_4$ is O, S or NAr$_5$,

L$_3$ is a direct bond; a substituted or unsubstituted monocyclic or multicyclic arylene group having 6 to 30 carbon atoms; or a substituted or unsubstituted monocyclic or multicyclic heteroarylene group having 2 to 30 carbon atoms, Ar$_5$ is selected from the group consisting of hydrogen; a substituted or unsubstituted arylamine group; a substituted or unsubstituted monocyclic or multicyclic aryl group having 6 to 30 carbon atoms; and a substituted or unsubstituted heteroaryl group having 2 to 30 carbon atoms, and Cy1 is a substituted or unsubstituted monocyclic or multicyclic hydrocarbon ring having 3 to 30 carbon atoms; or a substituted or unsubstituted monocyclic or multicyclic heteroring having 2 to 30 carbon atoms.

According to one embodiment of the present specification, the double spiro structure compound represented by Chemical Formula 4 may be represented by any one of Chemical Formulae 4-1 to 4-3 described above.

The organic light emitting device of the present specification may be manufactured using materials and methods known in the art, except that one or more layers of organic material layers comprise the double spiro structure compound of the present specification, that is, the double spiro structure compound represented by Chemical Formula 1.

When the organic light emitting device comprises a plurality of organic material layers, the organic material layers may be formed with the same material or with different materials.

For example, the organic light emitting device of the present specification may be manufactured by consecutively laminating an anode, an organic material layer and a cathode on a substrate. Herein, the organic light emitting device may be manufactured by forming the anode on the substrate by depositing a metal, a metal oxide having conductivity, or alloys thereof using a physical vapor deposition (PVD) method such as a sputtering method or an e-beam evaporation method, forming the organic material layer comprising a hole injection layer, a hole transfer layer, a light emitting layer and an electron transfer layer thereon, then depositing a material capable of being used as the cathode thereon. In addition to such a method, the organic light emitting device may be manufactured by consecutively depositing a cathode material, an organic material layer, and an anode material. Furthermore, when manufacturing the organic light emitting device, the double Spiro structure compound represented by Chemical Formula 1 may be formed as the organic material layer using a solution coating method as well as a vacuum deposition method. Herein, the solution coating method means spin coating, dip coating, doctor blading, ink jet printing, screen printing, a spray method, roll coating and the like, but is not limited thereto.

As the anode material, a material having large work function is normally preferable so that hole injection to the organic material layer is smooth. Specific examples of the anode material capable of being used in the present invention include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylen-1,2-dioxy)thiophene] (PEDOT), polypyrrole and polyaniline, and the like, but are not limited thereto.

As the cathode material, a material having small work function is normally preferable so that electron injection to the organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al, $LiO_2$/Al or Mg/Ag, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition, has an excellent thin film forming ability. The highest occupied molecular orbital (HOMO) of the hole injection material is preferably in between the work function of an anode material and the HOMO of surrounding organic material layers. Specific examples of the hole injection material include a metal porphyrin, oligothiophene, an arylamine-based organic material, a hexanitrile hexazatriphenylene-based organic material, a quinacridone-based organic material, a perylene-based organic material, anthraquinone, and a polyaniline- and a polythiophene-based conductive polymer, and the like, but are not limited thereto.

The hole transfer layer is a layer that receives holes from a hole injection layer and transfers the holes to a light emitting layer, and as the hole transfer material, a material capable of receiving holes from an anode or a hole injection layer, moving the holes to a light emitting layer, and having high mobility for the holes, is suitable. Specific examples thereof include an arylamine-based organic material, a conductive polymer, a block copolymer having conjugated parts and non-conjugated parts together, and the like, but are not limited thereto.

A light emitting material of the light emitting layer is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include a 8-hydroxy-quinoline aluminum complex ($Alq_3$); a carbazole-based compound; a dimerized styryl compound; BAlq; a 10-hydroxybenzo quinoline-metal compound; a benzoxazole-, a benzthiazole- and a benzimidazole-based compound; a poly (p-phenylenevinylene) (PPV)-based polymer; a spiro compound; polyfluorene, rubrene, and the like, but are not limited thereto.

The light emitting layer may comprise a host material and a dopant material. The host material includes a fused aromatic ring derivative, a heteroring-containing compound or the like. Specifically, the fused aromatic ring derivative includes an anthracene derivative, a pyrene derivative, a naphthalene derivative, a pentacene derivative, a phenanthrene compound, a fluoranthene compound and the like, and the heteroring-containing compound includes a carbazole derivative, a dibenzofuran derivative, a ladder-type furan compound, a pyrimidine derivative and the like, but the material is not limited thereto.

The dopant material includes an aromatic amine derivative, a styrylamine compound, a boron complex, a fluoranthene compound, a metal complex and the like. Specifically, the aromatic amine derivative is a fused aromatic ring derivative having a substituted or unsubstituted arylamino group and includes arylamino group-including pyrene, anthracene, crycene, peryflanthene and the like, and the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamino group are substituted or unsubstituted. Specifically, styrylamine, styryldiamine, styryltriamine, styryltetramine or the like is included, but the styrylamine compound is not limited thereto. In addition, the metal complex includes an iridium complex, a platinum complex or the like, but is not limited thereto.

The electron transfer layer is a layer that receives electrons from an electron injection layer and transfers the electrons to a light emitting layer, and as the electron transfer material, a material capable of favorably receiving electrons from a cathode, moving the electrons to a light emitting layer, and having high mobility for the electrons, is suitable. Specific examples thereof include an Al complex of 8-hydroxyquinoline; a complex including $Alq_3$; an organic radical compound; a hydroxyflavon-metal complex and the like, but are not limited thereto. The electron transfer layer may be used together with any desired cathode material as used according to existing technologies. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, a metal complex compound, a nitrogen-containing 5-membered ring derivative, and the like, but are not limited thereto.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato) gallium, bis(10-hydroxybenzo[h]quinolinato)berylium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium and the like, but is not limited thereto.

The organic light emitting device according to the present specification may be a top-emission type, a bottom-emission type or a dual-emission type depending on the materials used.

According to one embodiment of the present specification, the double spiro structure compound represented by Chemical Formula 1 may be included in an organic solar cell or an organic transistor in addition to an organic light emitting device.

Hereinafter, the present specification will be specifically described with reference to synthesis examples, preparation examples and examples. However, synthesis examples, preparation examples and examples according to the present specification may be modified to various other forms, and the scope of the present specification is not interpreted to be limited to synthesis examples, preparation examples and examples described below. The synthesis examples, the preparation examples and the examples of the present specification are provided in order to more completely describe the present specification to those having average knowledge in the art.

The double spiro structure compound represented by Chemical Formula 1 according to the present specification may be prepared through a multi-step chemical reaction. The preparation of the compounds is described by the following synthesis examples and preparation examples.

The double spiro structure compound represented by Chemical Formula 1 may be prepared to compounds corresponding to Chemical Formula 2, Chemical Formula 3 and Chemical Formula 4 using methods and orders as in the following Reaction Formula 1-1, Reaction Formula 1-2 and Reaction Formula 1-3, respectively, and although not limited to such reactions, reaction formulae are simply described in order to illuminate the present invention.

Synthesis Example

<Reaction Formula 1-1>
Preparation of Chemical Formula 2

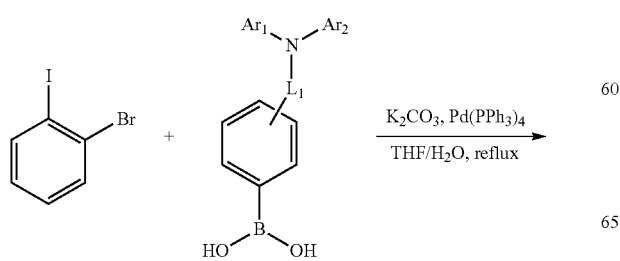

-continued

<Reaction Formula 1-2>
Preparation of Chemical Formula 3

243
-continued
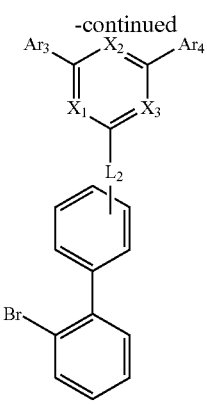
+
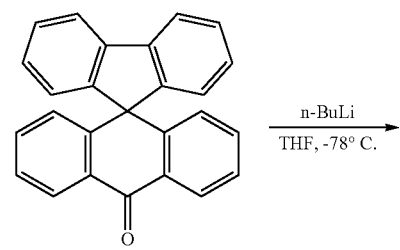
↓ n-BuLi
THF, -78° C.
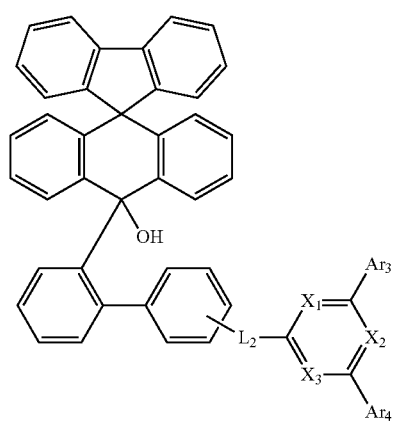
↓ HCl(conc.)
H₂SO₄
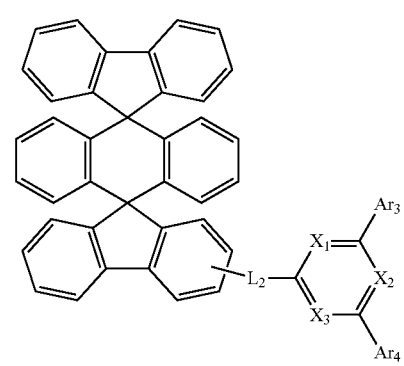
Chemical Formula 3
244
<Reaction Formula 1-3>
Preparation of Chemical Formula 4
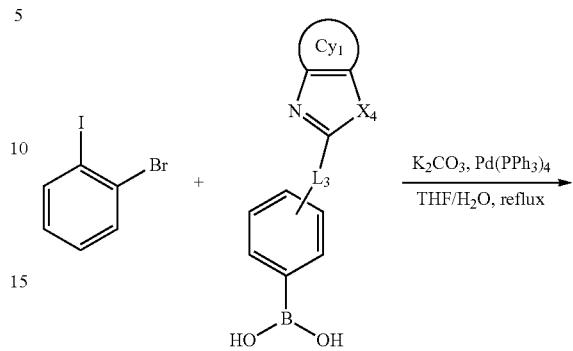
$K_2CO_3$, $Pd(PPh_3)_4$
THF/$H_2O$, reflux
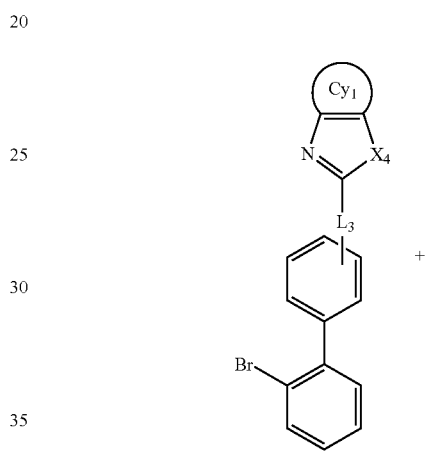
+
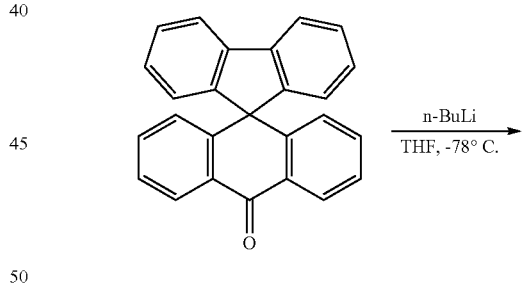
↓ n-BuLi
THF, -78° C.
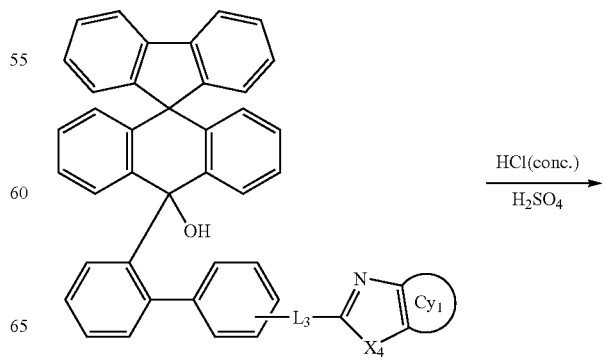
HCl(conc.)
$H_2SO_4$ -continued

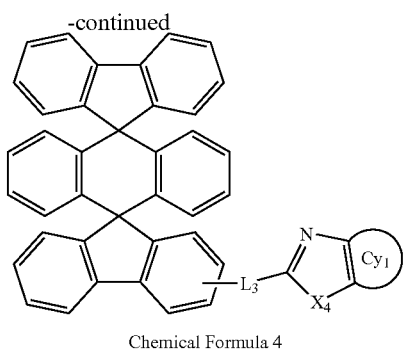

Chemical Formula 4

In Reaction Formulae 1-1 to 1-3, compounds represented by Chemical Formulae 2 to 4 may be diversely prepared through varying $L_1$ to $L_3$, $Ar_1$ to Ar4, $Cy_1$, and $X_1$ to $X_4$.

Preparation Example 1-1

Preparation of Compound 1-A

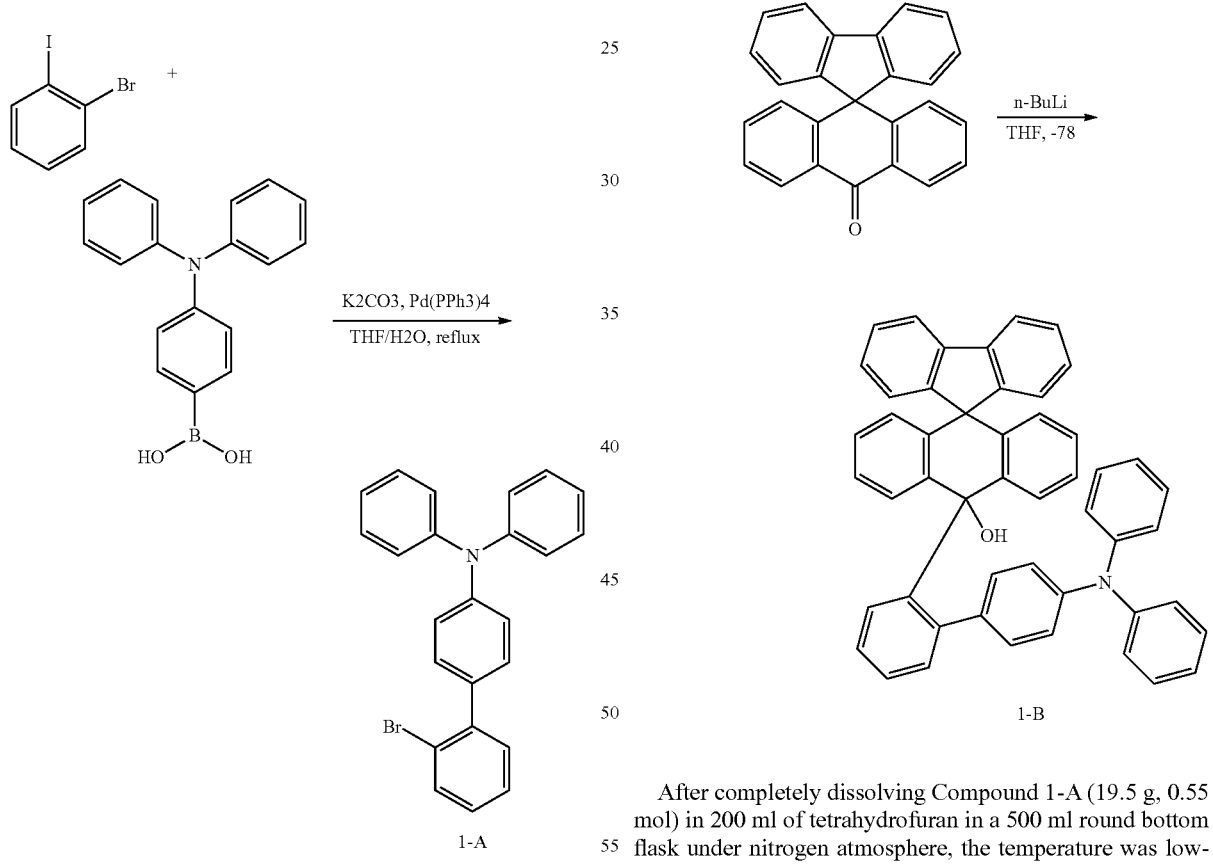

After completely dissolving 1-bromo-2-iodobenzene (15 g, 0.53 mol) and (4-(diphenylamino)phenyl)boronic acid (18.37 g, 0.64 mol) in 240 ml of tetrahydrofuran in a 500 ml round bottom flask under nitrogen atmosphere, a 2 M aqueous potassium carbonate solution (120 ml) and then tetrakis-(triphenylphosphine)palladium (1.22 g, 1.06 mmol) were added thereto, and then the result was heated and stirred for 2 hours. After lowering the temperature to room temperature, the water layer was removed, and the result was dried with anhydrous magnesium sulfate, vacuum concentrated, and then recrystallized with 300 ml of ethanol to prepare Compound 1-A (19.52 g, yield: 92%).

MS[M+H]$^+$=401

Preparation of Compound 1-B

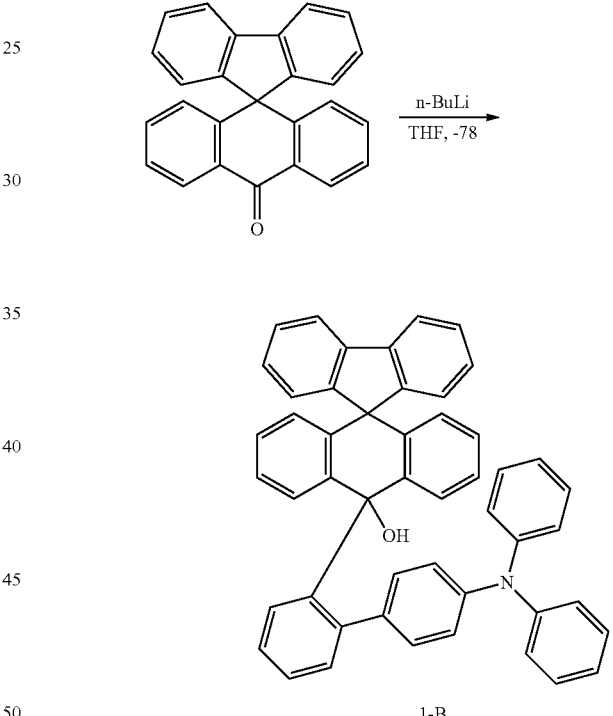

After completely dissolving Compound 1-A (19.5 g, 0.55 mol) in 200 ml of tetrahydrofuran in a 500 ml round bottom flask under nitrogen atmosphere, the temperature was lowered to −78° C., then 34 ml of n-BuLi was added thereto, the result was stirred for 30 minutes, and 10H-spiro[anthracene-9,9'-fluoren]-10-one (16.78 g, 0.55 mol) was slowly added thereto. The temperature was raised to room temperature after 3 hours had passed, and 200 ml of water was added thereto to terminate the reaction. The water layer was removed, and the result was dried with anhydrous magnesium sulfate, vacuum concentrated and recrystallized with 300 ml of ethanol to prepare Compound 1-B (28.65 g, yield: 88%).

MS[M+H]$^+$=666

Preparation of the following Compound 2-1-1 (2-1)

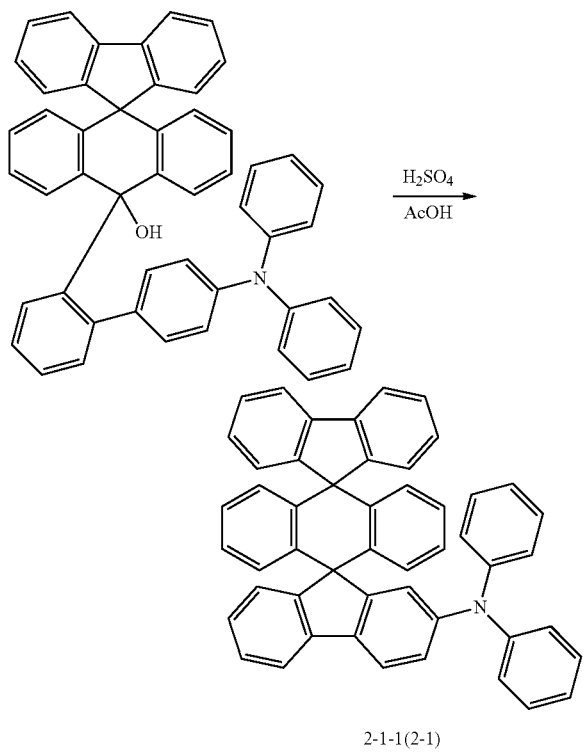

2-1-1(2-1)

After adding Compound 1-B (28.65 g, 0.43 mol) to 200 ml of acetic acid in a 500 ml round bottom flask under nitrogen atmosphere, 0.6 ml of HCl was slowly added thereto, and the result was heated and stirred for 2 hours. The temperature was lowered to room temperature, and the precipitated solid was filtered and washed with water. The filter cake was collected and dissolved in 1 L of chloroform. Water was added thereto and the water layer was separated. The result was recrystallized with 300 ml of ethanol to prepare Compound 2-1-1 (2-1) (25.78 g, yield: 89%).

MS[M+H]$^+$=648

Preparation Example 1-2

Preparation of Compound 2-1-6 (2-1)

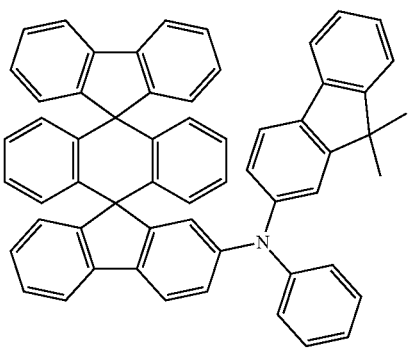 [SMILES: CC1(C)c2ccccc2-c2ccc(N(c3ccccc3)c3ccc4c(c3)C3(c5ccccc5-4)c4ccccc4C4(c5ccccc5-c5ccccc54)c4ccccc43)cc21]

Compound 2-1-6 (2-1) was prepared in the same manner as in Preparation Example 1-1 preparing Compound 2-1-1 (2-1) except that phenylfluoreneaminophenyl boronic acid was used instead of (4-(diphenylamino)phenyl)boronic acid.

MS[M+H]$^+$=764

Preparation Example 1-3

Preparation of Compound 2-1-7 (2-1)

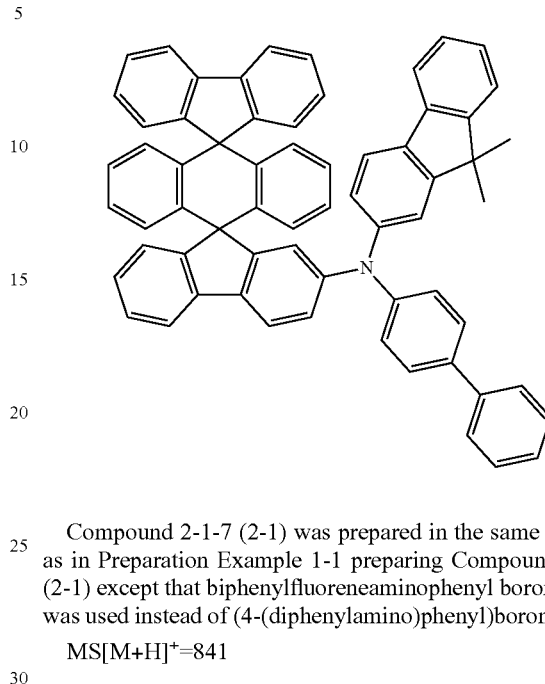

Compound 2-1-7 (2-1) was prepared in the same manner as in Preparation Example 1-1 preparing Compound 2-1-1 (2-1) except that biphenylfluoreneaminophenyl boronic acid was used instead of (4-(diphenylamino)phenyl)boronic acid.

MS[M+H]$^+$=841

Preparation Example 1-4

Preparation of Compound 2-1-10 (2-1)

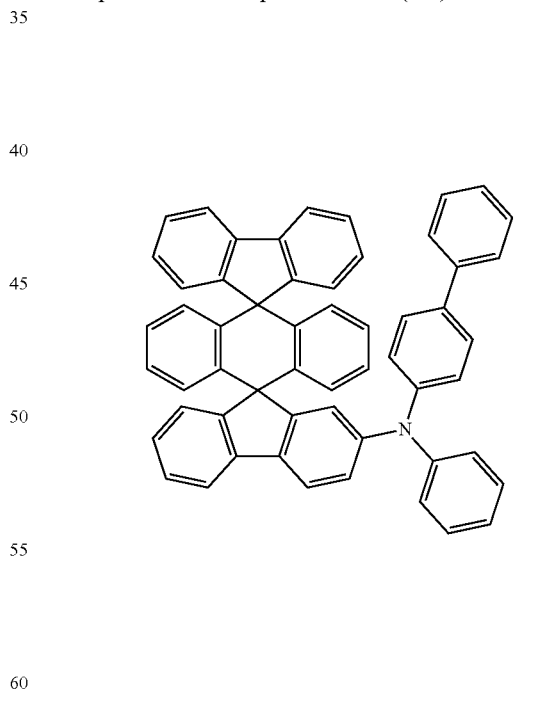

Compound 2-1-10 (2-1) was prepared in the same manner as in Preparation Example 1-1 preparing Compound 2-1-1 (2-1) except that 1,1'-biphenylphenylaminophenyl boronic acid was used instead of (4-(diphenylamino)phenyl)boronic acid.

MS[M+H]$^+$=724

Preparation Example 1-5

Preparation of Compound 2-1-15 (2-1)

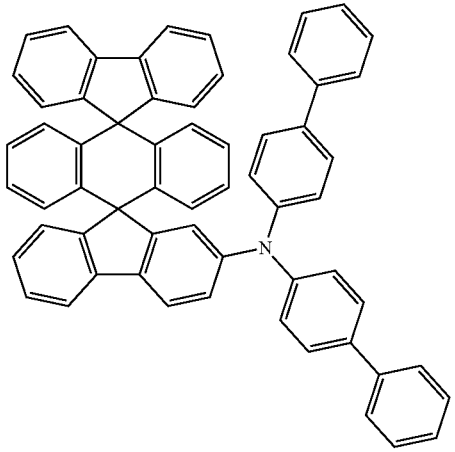 [SMILES: c1ccc(-c2ccc(N(c3ccc(-c4ccccc4)cc3)c3ccc4c(c3)C3(c5ccccc5-4)c4ccccc4C4(c5ccccc5-c5ccccc54)c4ccccc43)cc2)cc1]

Compound 2-1-15 (2-1) was prepared in the same manner as in Preparation Example 1-1 preparing Compound 2-1-1 (2-1) except that bisbiphenylaminophenyl boronic acid was used instead of (4-(diphenylamino)phenyl)boronic acid.

MS[M+H]$^+$=801

Preparation Example 1-6

Preparation of Compound 2-1-20 (2-1)

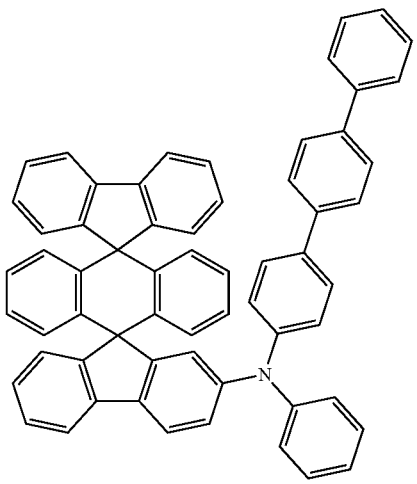 [SMILES: c1ccc(-c2ccc(-c3ccc(N(c4ccccc4)c4ccc5c(c4)C4(c6ccccc6-5)c5ccccc5C5(c6ccccc6-c6ccccc65)c5ccccc54)cc3)cc2)cc1]

Compound 2-1-20 (2-1) was prepared in the same manner as in Preparation Example 1-1 preparing Compound 2-1-1 (2-1) except that terphenylphenylaminophenyl boronic acid was used instead of (4-(diphenylamino)phenyl)boronic acid.

MS[M+H]$^+$=801

Preparation Example 1-7

Preparation of Compound 2-1-25 (2-1)

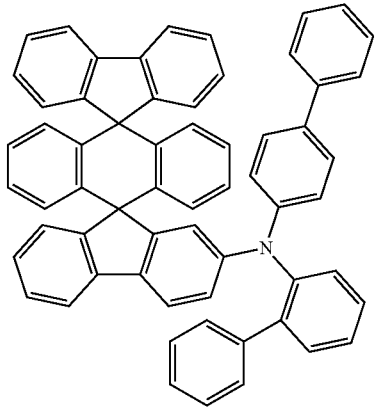 [SMILES: c1ccc(-c2ccc(N(c3ccc4c(c3)C3(c5ccccc5-4)c4ccccc4C4(c5ccccc5-c5ccccc54)c4ccccc43)c3ccccc3-c3ccccc3)cc2)cc1]

Compound 2-1-25 (2-1) was prepared in the same manner as in Preparation Example 1-1 preparing Compound 2-1-1 (2-1) except that orthobiphenylphenylaminophenyl boronic acid was used instead of (4-(diphenylamino)phenyl)boronic acid.

MS[M+H]$^+$=801

Preparation Example 1-8

Preparation of Compound 2-1-26 (2-1)

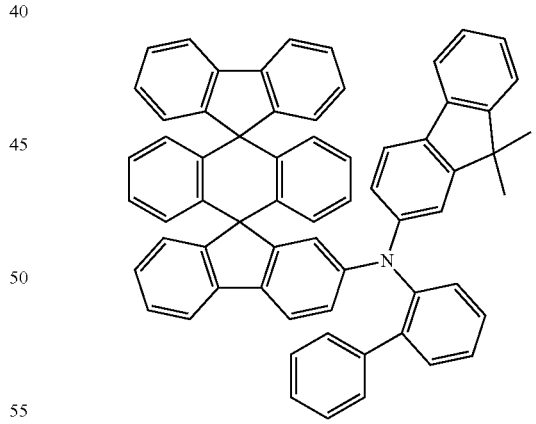

Compound 2-1-26 (2-1) was prepared in the same manner as in Preparation Example 1-1 preparing Compound 2-1-1 (2-1) except that orthobiphenylfluoreneaminophenyl boronic acid was used instead of (4-(diphenylamino)phenyl) boronic acid.

MS[M+H]$^+$=841

Preparation Example 1-9

Preparation of Compound 2-1-40 (2-1)

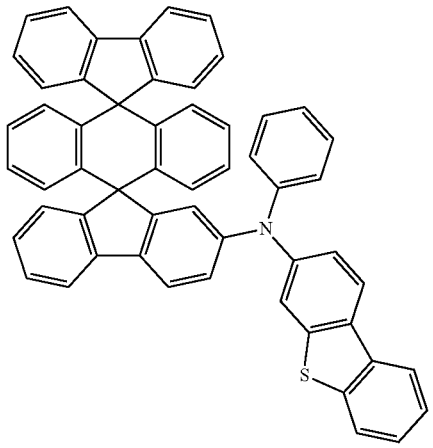 [SMILES: c1ccc(N(c2ccc3c(c2)C2(c4ccccc4-3)c3ccccc3C3(c4ccccc4-c4ccccc43)c3ccccc32)c2ccc3c(c2)oc2ccccc23)cc1]

Compound 2-1-40 (2-1) was prepared in the same manner as in Preparation Example 1-1 preparing Compound 2-1-1 (2-1) except that 2-dibenzothiophenephenylaminophenyl boronic acid was used instead of (4-(diphenylamino)phenyl) boronic acid.

MS[M+H]$^+$=754

Preparation Example 1-10

Preparation of Compound 2-1-41 (2-1)

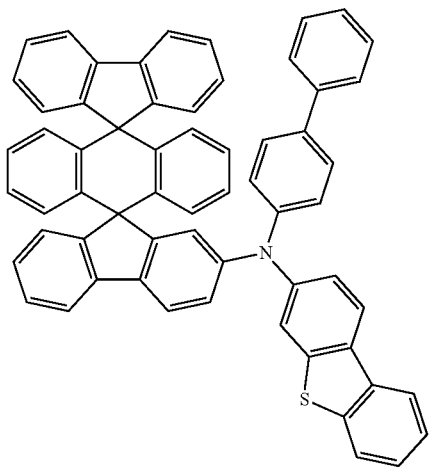

Compound 2-1-41 (2-1) was prepared in the same manner as in Preparation Example 1-1 preparing Compound 2-1-1 (2-1) except that 2-dibenzothiophenebiphenylaminophenyl boronic acid was used instead of (4-(diphenylamino)phenyl) boronic acid.

MS[M+H]$^+$=831

Preparation Example 1-11

Preparation of Compound 2-1-42 (2-1)

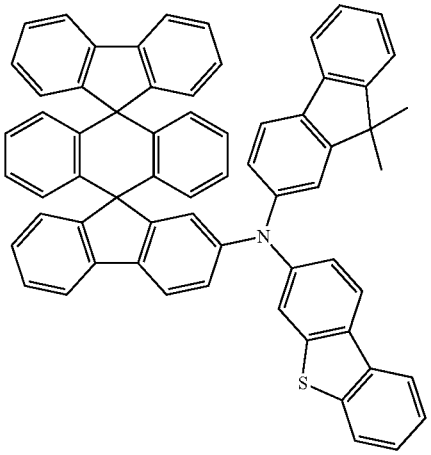

Compound 2-1-42 (2-1) was prepared in the same manner as in Preparation Example 1-1 preparing Compound 2-1-1 (2-1) except that 2-dibenzothiophenefluoreneaminophenyl boronic acid was used instead of (4-(diphenylamino)phenyl) boronic acid.

MS[M+H]$^+$=871

Preparation Example 1-12

Preparation of Compound 2-1-46 (2-1)

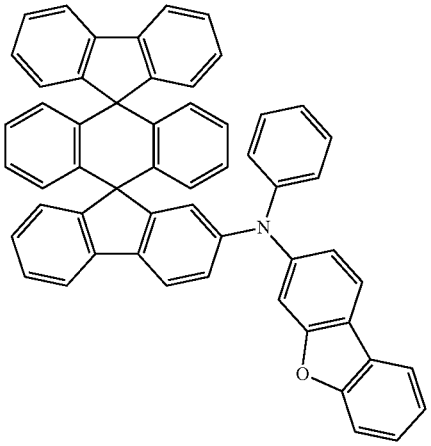

Compound 2-1-46 (2-1) was prepared in the same manner as in Preparation Example 1-1 preparing Compound 2-1-1 (2-1) except that 2-dibenzofuranphenylaminophenyl boronic acid was used instead of (4-(diphenylamino)phenyl) boronic acid.

MS[M+H]$^+$=738

Preparation Example 1-13

Preparation of Compound 2-1-47 (2-1)

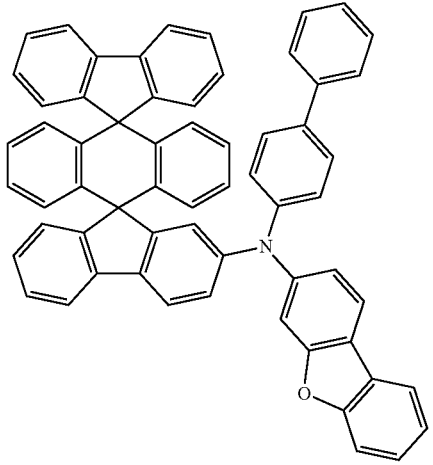 [SMILES: c1ccc(-c2ccc(N(c3ccc4c(c3)C3(c5ccccc5-4)c4ccccc4C4(c5ccccc5-c5ccccc54)c4ccccc43)c3ccc4c(c3)oc3ccccc34)cc2)cc1]

Compound 2-1-47 (2-1) was prepared in the same manner as in Preparation Example 1-1 preparing Compound 2-1-1 (2-1) except that 2-dibenzofuranbiphenylaminophenyl boronic acid was used instead of (4-(diphenylamino)phenyl) boronic acid.

MS[M+H]$^+$=815

Preparation Example 1-14

Preparation of Compound 2-1-48 (2-1)

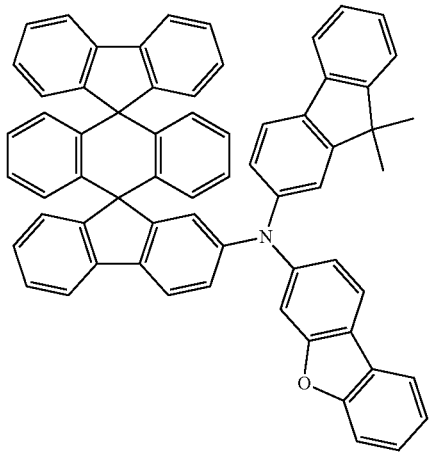 [SMILES: CC1(C)c2ccccc2-c2ccc(N(c3ccc4c(c3)C3(c5ccccc5-4)c4ccccc4C4(c5ccccc5-c5ccccc54)c4ccccc43)c3ccc4c(c3)oc3ccccc34)cc21]

Compound 2-1-48 (2-1) was prepared in the same manner as in Preparation Example 1-1 preparing Compound 2-1-1 (2-1) except that 2-dibenzofuranfluoreneaminophenyl boronic acid was used instead of (4-(diphenylamino)phenyl) boronic acid.

MS[M+H]$^+$=855

Preparation Example 1-15

Preparation of Compound 2-1-52 (2-1)

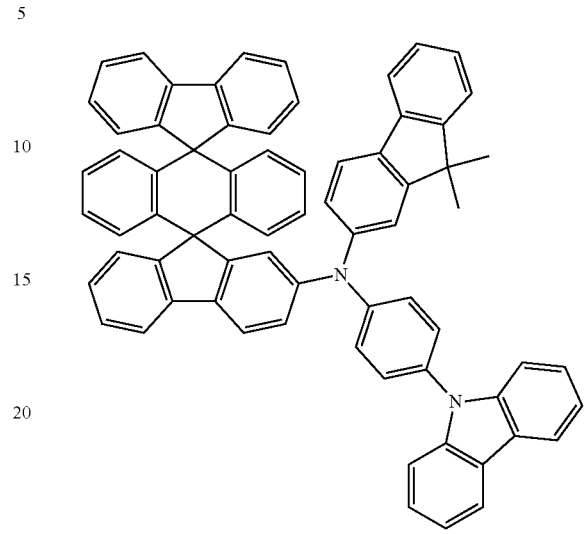

Compound 2-1-52 (2-1) was prepared in the same manner as in Preparation Example 1-1 preparing Compound 2-1-1 (2-1) except that N-(4-(9H-carbazol-9-yl)phenyl)-9,9'-dimethyl-9H-fluoren-2-aminophenyl boronic acid was used instead of (4-(diphenylamino)phenyl)boronic acid.

MS[M+H]$^+$=930

Preparation Example 1-16

Preparation of Compound 2-1-54 (2-1)

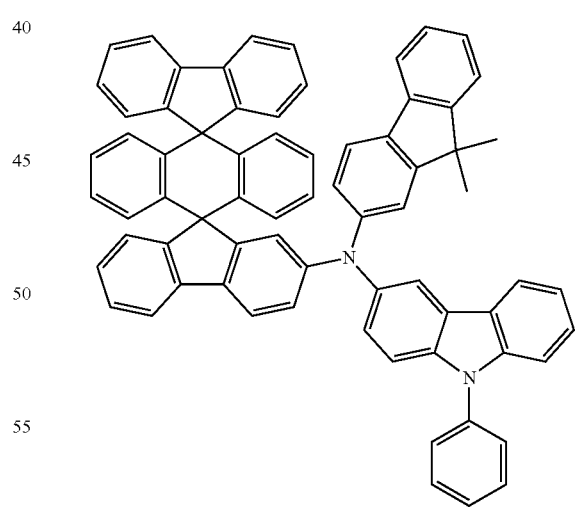

Compound 2-1-54 (2-1) was prepared in the same manner as in Preparation Example 1-1 preparing Compound 2-1-1 (2-1) except that N-(9,9'-dimethyl-9H-fluoren-2-yl)-9-phenyl-9H-carbazol-3-1-Amino)phenyl)boronic acid was used instead of (4-(diphenylamino)phenyl)boronic acid.

MS[M+H]+=930

Preparation Example 1-17

Preparation of Compound 2-1-64 (2-1)

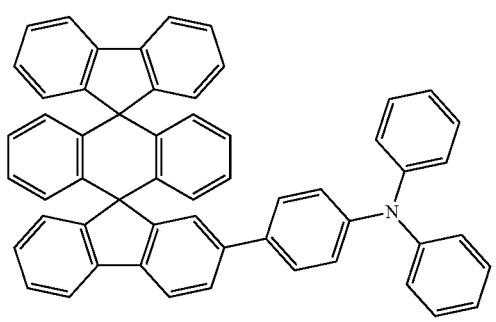 [SMILES: c1ccc(N(c2ccccc2)c2ccc(-c3ccc4c(c3)C3(c5ccccc5-4)c4ccccc4C4(c5ccccc5-c5ccccc54)c4ccccc43)cc2)cc1]

Compound 2-1-64 (2-1) was prepared in the same manner as in Preparation Example 1-1 preparing Compound 2-1-1 (2-1) except that (4'-(diphenylamino)-[1,1'-biphenyl]-4-yl)boronic acid was used instead of (4-(diphenylamino)phenyl)boronic acid.

MS[M+H]$^+$=724

Preparation Example 1-18

Preparation of Compound 2-1-65 (2-1)

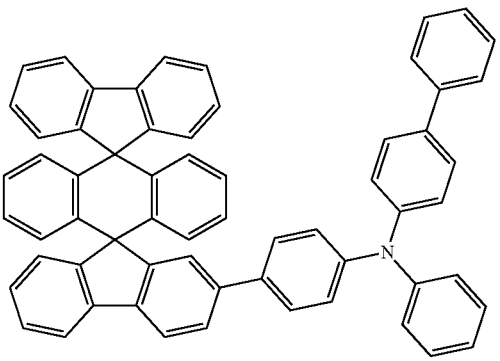 [SMILES: c1ccc(-c2ccc(N(c3ccccc3)c3ccc(-c4ccc5c(c4)C4(c6ccccc6-5)c5ccccc5C5(c6ccccc6-c6ccccc65)c5ccccc54)cc3)cc2)cc1]

Compound 2-1-65 (2-1) was prepared in the same manner as in Preparation Example 1-1 preparing Compound 2-1-1 (2-1) except that (4'-([1,1'-biphenyl]-4-yl(phenyl)amino)-[1,1'-biphenyl]-4-yl)boronic acid was used instead of (4-(diphenylamino)phenyl)boronic acid.

MS[M+H]$^+$=801

Preparation Example 1-19

Preparation of Compound 2-1-66 (2-1)

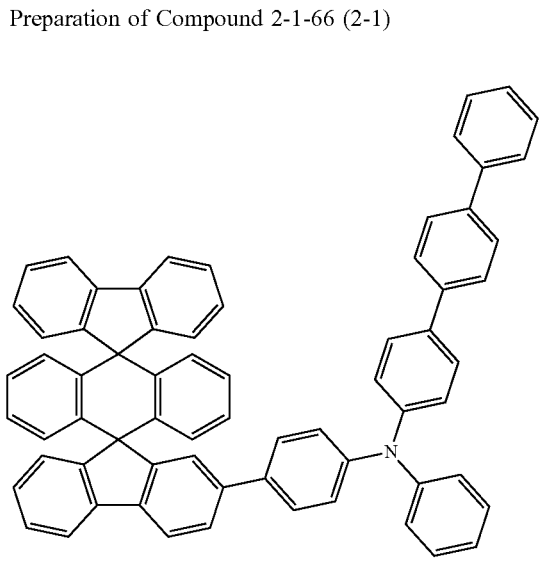

Compound 2-1-66 (2-1) was prepared in the same manner as in Preparation Example 1-1 preparing Compound 2-1-1 (2-1) except that (4'-([1,1':4',1''-terphenyl]-4-yl(phenyl)amino)-[1,1'-biphenyl]-4-yl)boronic acid was used instead of (4-(diphenylamino)phenyl)boronic acid.

MS[M+H]$^+$=877

Preparation Example 1-20

Preparation of Compound 2-1-67 (2-1)

Compound 2-1-67 (2-1) was prepared in the same manner as in Preparation Example 1-1 preparing Compound 2-1-1 (2-1) except that (4'-(di([1,1'-biphenyl]-4-yl)amino)-[1,1'-biphenyl]-4-yl)boronic acid was used instead of (4-(diphenylamino)phenyl)boronic acid.

MS[M+H]$^+$=877

Preparation Example 1-21

Preparation of Compound 2-1-69 (2-1)

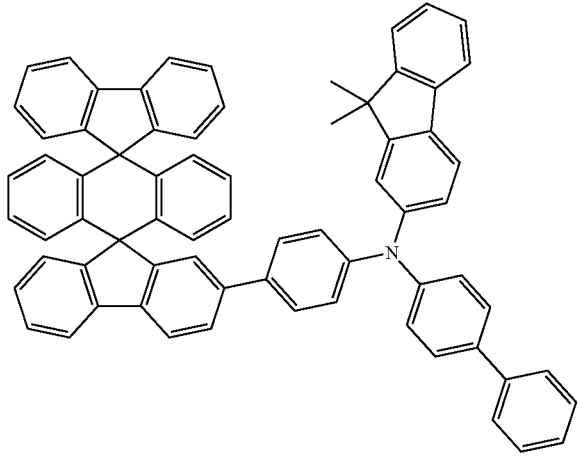 [SMILES: CC1(C)c2ccccc2-c2ccc(N(c3ccc(-c4ccccc4)cc3)c3ccc(-c4ccc5c(c4)C4(c6ccccc6-5)c5ccccc5C5(c6ccccc6-c6ccccc65)c5ccccc54)cc3)cc21]

Compound 2-1-69 (2-1) was prepared in the same manner as in Preparation Example 1-1 preparing Compound 2-1-1 (2-1) except that (4'-([1,1'-biphenyl]-4-yl(9,9-dimethyl-9H-fluoren-2-yl)amino)-[1,1'-biphenyl]-4-yl)boronic acid was used instead of (4-(diphenylamino)phenyl)boronic acid.

MS[M+H]$^+$=917

Preparation Example 1-22

Preparation of Compound 2-1-75 (2-1)

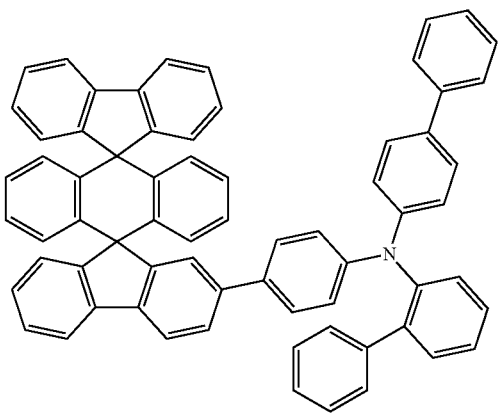 [SMILES: c1ccc(-c2ccc(N(c3ccc(-c4ccc5c(c4)C4(c6ccccc6-5)c5ccccc5C5(c6ccccc6-c6ccccc65)c5ccccc54)cc3)c3ccccc3-c3ccccc3)cc2)cc1]

Compound 2-1-75 (2-1) was prepared in the same manner as in Preparation Example 1-1 preparing Compound 2-1-1 (2-1) except that (4'-([1,1'-biphenyl]-2-yl([1,1'-biphenyl]-4-yl)amino)-[1,1'-biphenyl]-4-yl)boronic acid was used instead of (4-(diphenylamino)phenyl)boronic acid.

MS[M+H]$^+$=877

Preparation Example 1-23

Preparation of Compound 2-1-77 (2-1)

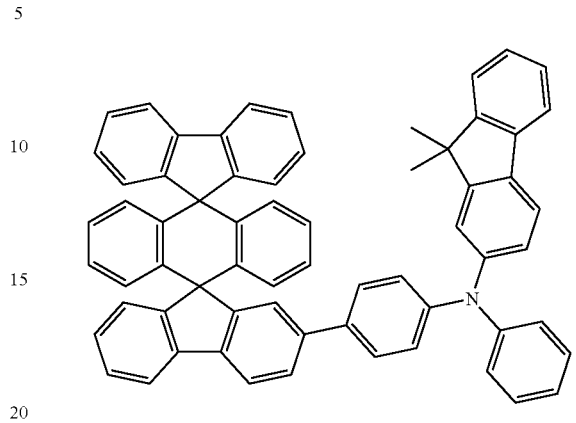

Compound 2-1-77 (2-1) was prepared in the same manner as in Preparation Example 1-1 preparing Compound 2-1-1 (2-1) except that (4'-((9,9-dimethyl-9H-fluoren-2-yl)(phenyl)amino)-[1,1'-biphenyl]-4-yl)boronic acid was used instead of (4-(diphenylamino)phenyl)boronic acid.

MS[M+H]$^+$=841

Preparation Example 1-24

Preparation of Compound 2-1-81 (2-1)

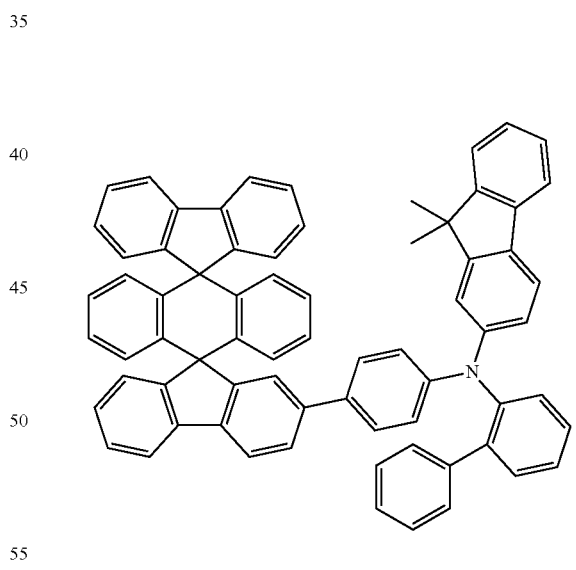

Compound 2-1-81 (2-1) was prepared in the same manner as in Preparation Example 1-1 preparing Compound 2-1-1 (2-1) except that (4'-([1,1'-biphenyl]-2-yl(9,9-dimethyl-9H-fluoren-2-yl)amino)-[1,1'-biphenyl]-4-yl)boronic acid was used instead of (4-(diphenylamino)phenyl)boronic acid.

MS[M+H]$^+$=917

Preparation Example 1-25

Preparation of Compound 2-1-241 (2-1)

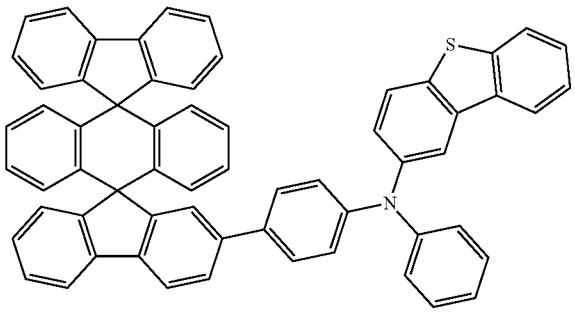 [SMILES: c1ccc(N(c2ccc(-c3ccc4c(c3)C3(c5ccccc5-4)c4ccccc4C4(c5ccccc5-c5ccccc54)c4ccccc43)cc2)c2ccc3sc4ccccc4c3c2)cc1]

Compound 2-1-241 (2-1) was prepared in the same manner as in Preparation Example 1-1 preparing Compound 2-1-1 (2-1) except that (4'-(dibenzo[b,d]thiophen-2-yl(phenyl)amino)-[1,1'-biphenyl]-4-yl)boronic acid was used instead of (4-(diphenylamino)phenyl)boronic acid.
MS[M+H]$^+$=831

Preparation Example 1-26

Preparation of Compound 2-1-242 (2-1)

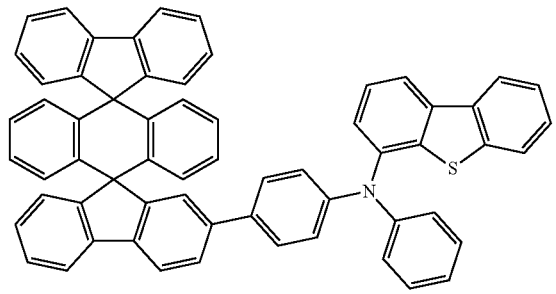 [SMILES: c1ccc(N(c2ccc(-c3ccc4c(c3)C3(c5ccccc5-4)c4ccccc4C4(c5ccccc5-c5ccccc54)c4ccccc43)cc2)c2cccc3c2sc2ccccc23)cc1]

Compound 2-1-242 (2-1) was prepared in the same manner as in Preparation Example 1-1 preparing Compound 2-1-1 (2-1) except that (4'-(dibenzo[b,d]thiophen-4-yl(phenyl)amino)-[1,1'-biphenyl]-4-yl)boronic acid was used instead of (4-(diphenylamino)phenyl)boronic acid.
MS[M+H]$^+$=831

Preparation Example 1-27

Preparation of Compound 2-1-246 (2-1)

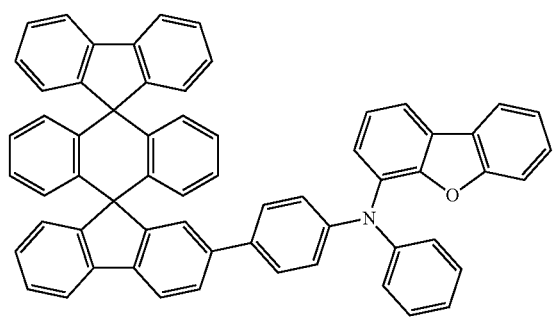 [SMILES: c1ccc(N(c2ccc(-c3ccc4c(c3)C3(c5ccccc5-4)c4ccccc4C4(c5ccccc5-c5ccccc54)c4ccccc43)cc2)c2cccc3c2oc2ccccc23)cc1]

Compound 2-1-246 (2-1) was prepared in the same manner as in Preparation Example 1-1 preparing Compound 2-1-1 (2-1) except that (4'-(dibenzo[b,d]furan-4-yl(phenyl)amino)-[1,1'-biphenyl]-4-yl)boronic acid was used instead of (4-(diphenylamino)phenyl)boronic acid.
MS[M+H]$^+$=815

Preparation Example 1-28

Preparation of Compound 2-1-315 (2-1)

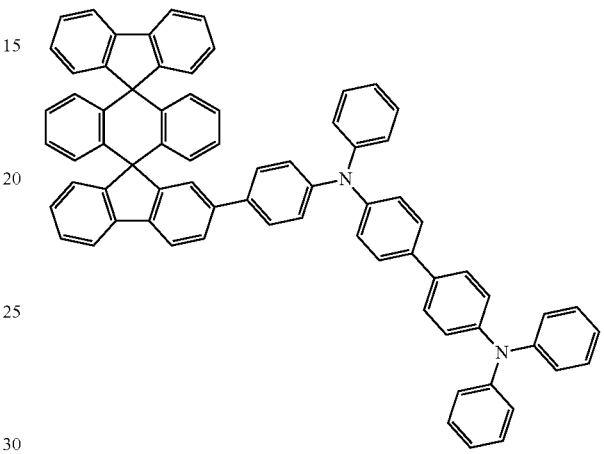

Compound 2-1-315 (2-1) was prepared in the same manner as in Preparation Example 1-1 preparing Compound 2-1-1 (2-1) except that (4'-((4'-(diphenylamino)-[1,1'-biphenyl]-4-yl)(phenyl)amino)-[1,1'-biphenyl]-4-yl)boronic acid was used instead of (4-(diphenylamino)phenyl)boronic acid.
MS[M+H]$^+$=968

Preparation Example 1-29

Preparation of Compound 2-1-316 (2-1)

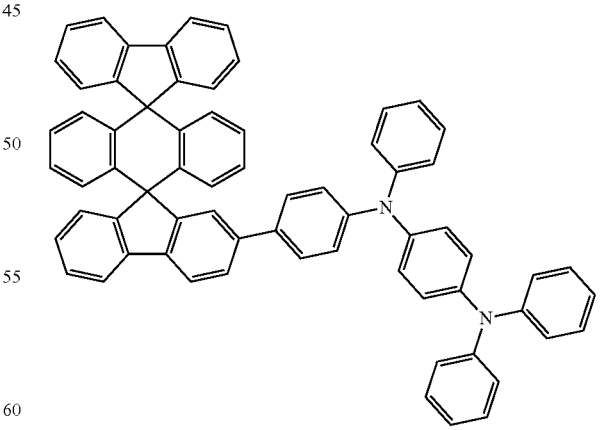

Compound 2-1-316 (2-1) was prepared in the same manner as in Preparation Example 1-1 preparing Compound 2-1-1 (2-1) except that (4'-((4-(diphenylamino)phenyl)(phenyl)amino)-[1,1'-biphenyl]-4-yl)boronic acid was used instead of (4-(diphenylamino)phenyl)boronic acid.

MS[M+H]⁺=892

Preparation Example 1-30

Preparation of Compound 2-1-311 (2-1)

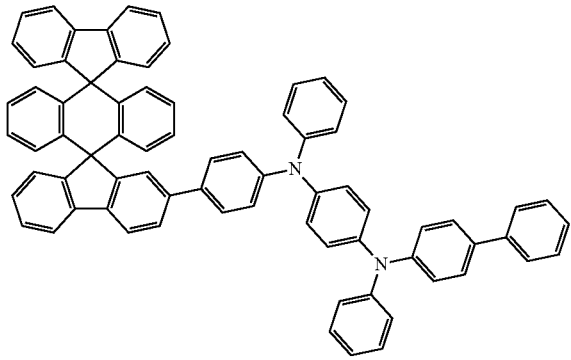 [SMILES: c1ccc(-c2ccc(N(c3ccccc3)c3ccc(N(c4ccccc4)c4ccc(-c5ccc6c(c5)C5(c7ccccc7-6)c6ccccc6C6(c7ccccc7-c7ccccc76)c6ccccc65)cc4)cc3)cc2)cc1]

Compound 2-1-311 (2-1) was prepared in the same manner as in Preparation Example 1-1 preparing Compound 2-1-1 (2-1) except that (4'-((4-([1,1'-biphenyl]-4-yl(phenyl)amino)phenyl)(phenyl)amino)-[1,1'-biphenyl]-4-yl)boronic acid was used instead of (4-(diphenylamino)phenyl)boronic acid.

MS[M+H]⁺=968

Preparation Example 1-31

Preparation of Compound 2-1-318 (2-1)

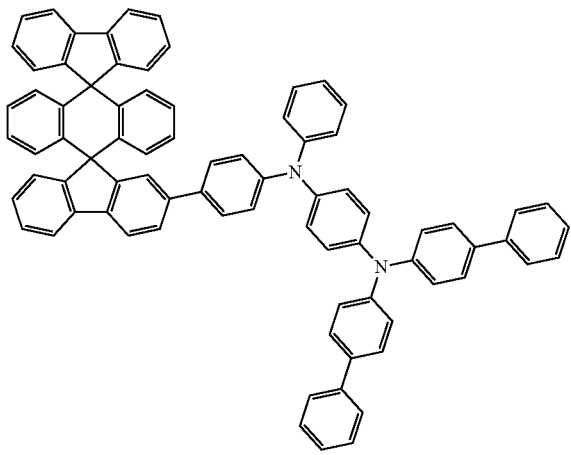 [SMILES: c1ccc(-c2ccc(N(c3ccc(-c4ccccc4)cc3)c3ccc(N(c4ccccc4)c4ccc(-c5ccc6c(c5)C5(c7ccccc7-6)c6ccccc6C6(c7ccccc7-c7ccccc76)c6ccccc65)cc4)cc3)cc2)cc1]

Compound 2-1-318 (2-1) was prepared in the same manner as in Preparation Example 1-1 preparing Compound 2-1-1 (2-1) except that (4'-((4-(di([1,1'-biphenyl]-4-yl)amino)phenyl)(phenyl)amino)-[1,1'-biphenyl]-4-yl)boronic acid was used instead of (4-(diphenylamino)phenyl)boronic acid.

MS[M+H]⁺=1044

Preparation Example 1-32

Preparation of Compound 2-1-320 (2-1)

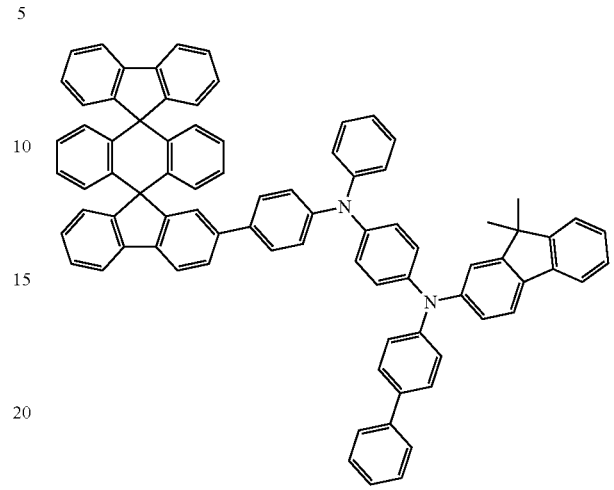

Compound 2-1-320 (2-1) was prepared in the same manner as in Preparation Example 1-1 preparing Compound 2-1-1 (2-1) except that (4'-((4-([1,1'-biphenyl]-4-yl(9,9-dimethyl-9H-fluoren-2-yl)amino)phenyl)(phenyl)amino)-[1,1'-biphenyl]-4-yl)boronic acid was used instead of (4-(diphenylamino)phenyl)boronic acid.

MS[M+H]⁺=1084

Preparation Example 2-1-1

Preparation of Compound 2-A

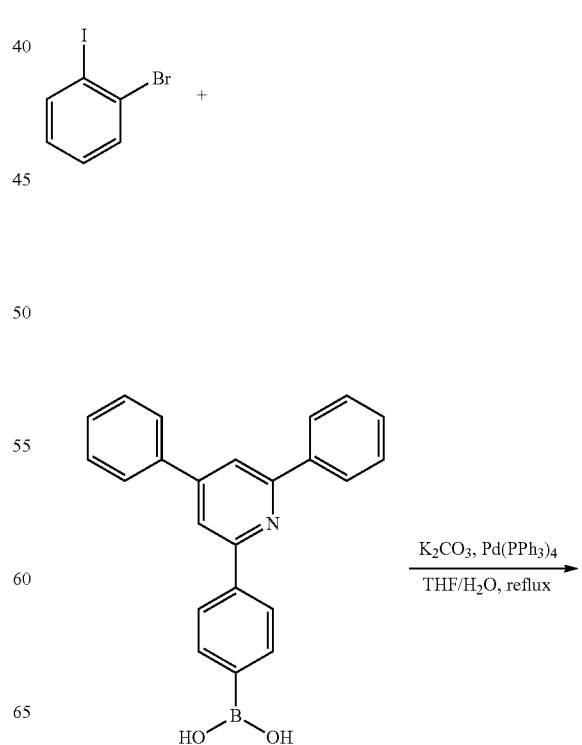

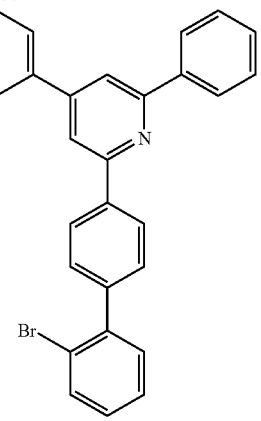

2-A

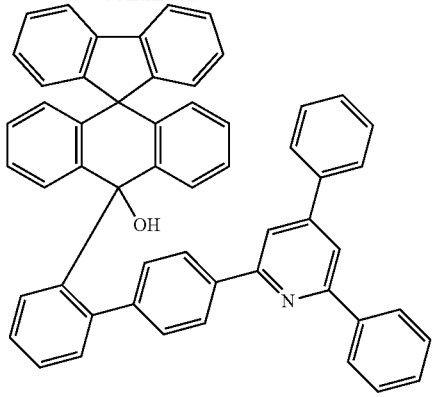

2-B

After completely dissolving 1-bromo-2-iodobenzene (15 g, 0.53 mol) and (4-(4,6-diphenylpyridin-2-yl)phenyl)boronic acid (19.35 g, 0.64 mol) in 240 ml of tetrahydrofuran in a 500 ml round bottom flask under nitrogen atmosphere, a 2 M aqueous potassium carbonate solution (120 ml) and then tetrakis-(triphenylphosphine)palladium (1.22 g, 1.06 mmol) were added thereto, and then the result was heated and stirred for 2 hours. After lowering the temperature to room temperature, the water layer was removed, and the result was dried with anhydrous magnesium sulfate, vacuum concentrated, and then recrystallized with 300 ml of ethanol to prepare Compound 2-A (18.41 g, yield: 88%).

MS[M+H]$^+$=463

Preparation of Compound 2-B

After completely dissolving Compound 2-A (18.41 g, 0.55 mol) in 200 ml of tetrahydrofuran in a 500 ml round bottom flask under nitrogen atmosphere, the temperature was lowered to −78° C., then 34 ml of n-BuLi was added thereto, the result was stirred for 30 minutes, and 10H-spiro[anthracene-9,9'-fluoren]-10-one (16.78 g, 0.55 mol) was slowly added thereto. The temperature was raised to room temperature after 3 hours had passed, and 200 ml of water was added thereto to terminate the reaction. The water layer was removed, and the result was dried with anhydrous magnesium sulfate, vacuum concentrated and recrystallized with 300 ml of ethanol to prepare Compound 2-B (26.65 g, yield: 85%).

MS[M+H]$^+$=728

Preparation of Compound 3-1-1 (3-5)

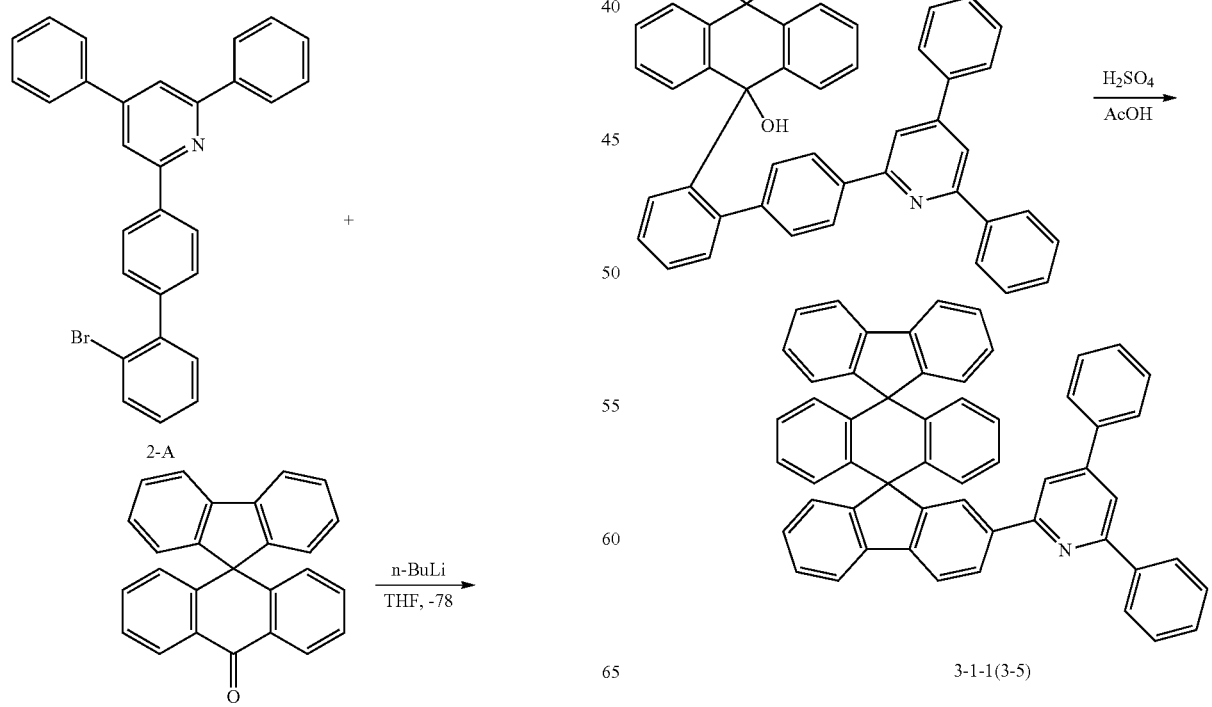

3-1-1(3-5)

After adding Compound 2-B (28.65 g, 0.43 mol) to 200 ml of acetic acid in a 500 ml round bottom flask under nitrogen atmosphere, 0.7 ml of HCl was slowly added thereto, and the result was heated and stirred for 2 hours. The temperature was lowered to room temperature, and the precipitated solid was filtered and washed with water. The filter cake was collected and dissolved in 1 L of chloroform. Water was added thereto and the water layer was separated. The result was recrystallized with 300 ml of ethanol to prepare Compound 3-1-1 (3-5) (23.12 g, yield: 84%).

MS[M+H]$^+$=710

Preparation Example 2-1-2

Preparation of Compound 3-1-2 (3-5)

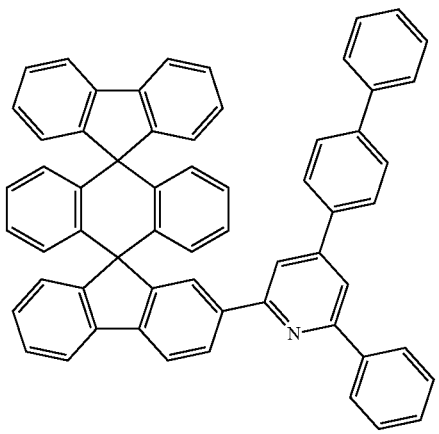 [SMILES: c1ccc(-c2ccc(-c3cc(-c4ccccc4)nc(-c4ccc5c(c4)C4(c6ccccc6-5)c5ccccc5C5(c6ccccc6-c6ccccc65)c5ccccc54)c3)cc2)cc1]

Compound 3-1-2 (3-5) was prepared in the same manner as in Preparation Example 2-1-1 preparing Compound 3-1-1 (3-5) except that (4-(4-([1,1'-biphenyl]-4-yl)-6-phenylpyridin-2-yl)phenyl)boronic acid was used instead of (4-(4,6-diphenylpyridin-2-yl)phenyl)boronic acid.

MS[M+H]$^+$=786

Preparation Example 2-1-3

Preparation of Compound 3-1-6 (3-5)

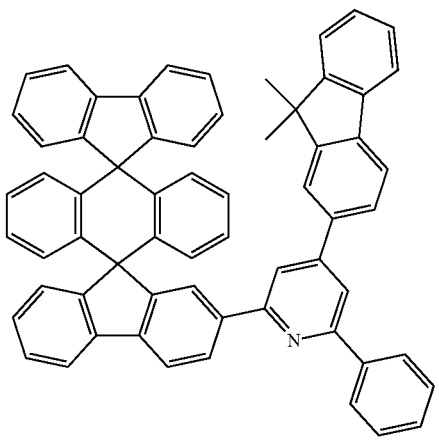 [SMILES: CC1(C)c2ccccc2-c2ccc(-c3cc(-c4ccccc4)nc(-c4ccc5c(c4)C4(c6ccccc6-5)c5ccccc5C5(c6ccccc6-c6ccccc65)c5ccccc54)c3)cc21]

Compound 3-1-6 (3-5) was prepared in the same manner as in Preparation Example 2-1-1 preparing Compound 3-1-1 (3-5) except that (4-4-(9,9-dimethyl-9H-fluoren-2-yl)-6-phenylpyridin-2-yl)phenyl)boronic acid was used instead of (4-(4, 6-diphenylpyridin-2-yl)phenyl)boronic acid.

MS[M+H]$^+$=827

Preparation Example 2-1-4

Preparation of Compound 3-1-9 (3-5)

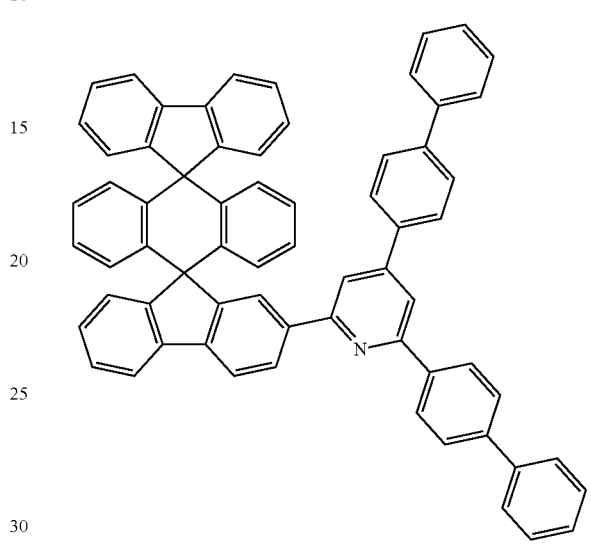

Compound 3-1-9 (3-5) was prepared in the same manner as in Preparation Example 2-1-1 preparing Compound 3-1-1 (3-5) except that (4-(4,6-di([1,1'-biphenyl]-4-yl)pyridin-2-yl)phenyl)boronic acid was used instead of (4-(4,6-diphenylpyridin-2-yl)phenyl)boronic acid.

MS[M+H]$^+$=863

Preparation Example 2-1-5

Preparation of Compound 3-1-15 (3-5)

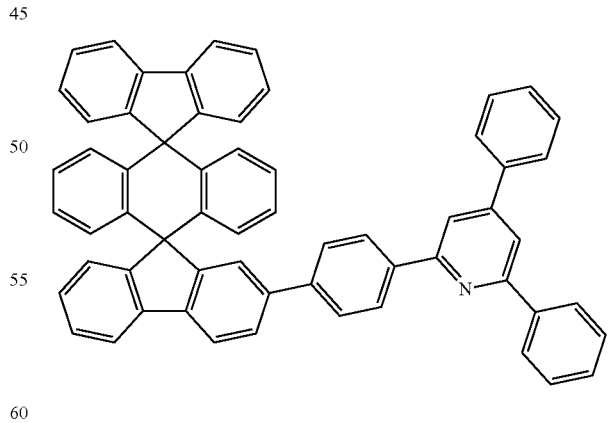

Compound 3-1-15 (3-5) was prepared in the same manner as in Preparation Example 2-1-1 preparing Compound 3-1-1 (3-5) except that (4'-(4,6-diphenylpyridin-2-yl)-[1,1'-biphenyl]-4-yl)boronic acid was used instead of (4-(4,6-diphenylpyridin-2-yl)phenyl)boronic acid.

MS[M+H]$^+$=786

Preparation Example 2-1-6

Preparation of Compound 3-1-16 (3-5)

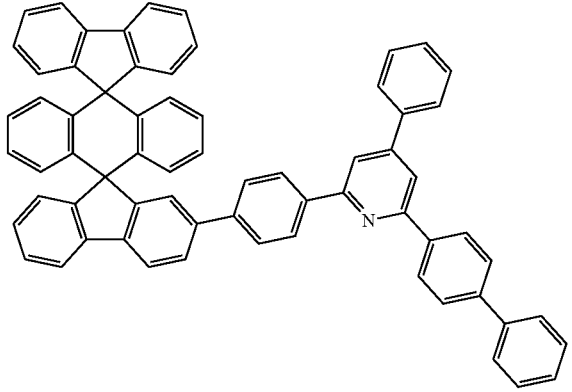

Compound 3-1-16 (3-5) was prepared in the same manner as in Preparation Example 2-1-1 preparing Compound 3-1-1 (3-5) except that (4'-(6-([1,1'-biphenyl]-4-yl)-4-phenylpyridin-2-yl)-[1,1'-biphenyl]-4-yl)boronic acid was used instead of (4-(4,6-diphenylpyridin-2-yl)phenyl)boronic acid.

Preparation Example 2-1-7

Preparation of Compound 3-1-18 (3-5)

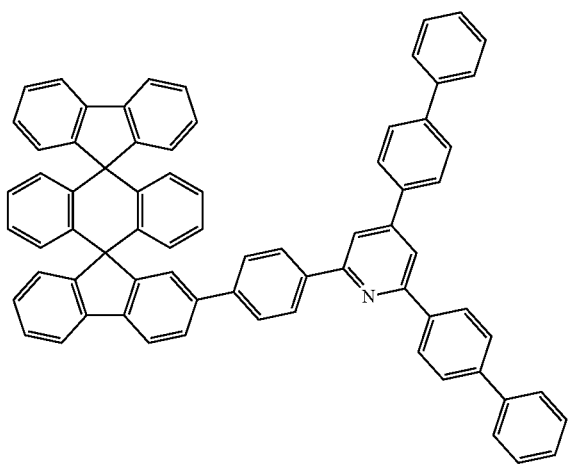

Compound 3-1-18 (3-5) was prepared in the same manner as in Preparation Example 2-1-1 preparing Compound 3-1-1 (3-5) except that (4'-(4,6-di([1,1'-biphenyl]-4-yl)pyridin-2-yl)-[1,1'-biphenyl]-4-yl)boronic acid was used instead of (4-(4,6-diphenylpyridin-2-yl)phenyl)boronic acid.

MS[M+H]$^+$=939

Preparation Example 2-1-8

Preparation of Compound 3-1-20 (3-5)

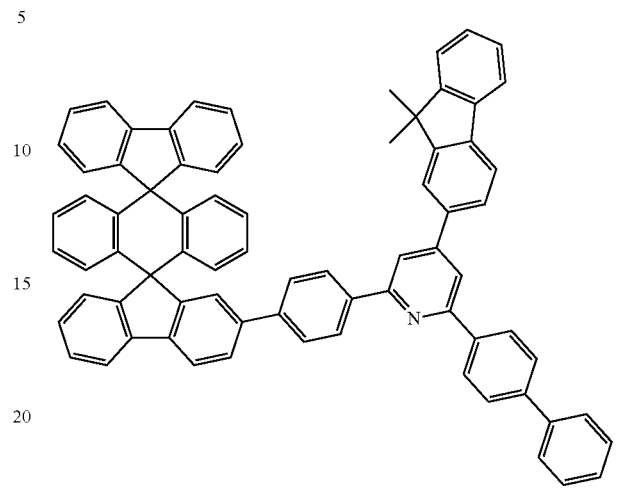

Compound 3-1-20 (3-5) was prepared in the same manner as in Preparation Example 2-1-1 preparing Compound 3-1-1 (3-5) except that (4'-(6-([1,1'-biphenyl]-4-yl)-4-(9,9-dimethyl-9H-fluoren-2-yl)pyridin-2-yl)-[1,1'-biphenyl]-4-yl) boronic acid was used instead of (4-(4,6-diphenylpyridin-2-yl)phenyl)boronic acid.

MS[M+H]$^+$=979

Preparation Examples 2-2-1 to 2-2-8

The following Compounds 3-2-1 (3-8), 3-2-2 (3-8), 3-2-6 (3-8), 3-2-9 (3-8), 3-2-15 (3-8), 3-2-16 (3-8), 3-2-18 (3-8) and 3-2-20 (3-8) were prepared in the same manner as in Preparation Example 2-1-1 except that 4-(4,6-diphenylpyrimidin-2-yl)phenylboronic acid, (4-(4-([1,1'-biphenyl]-4-yl)-6-phenylpyrimidin-2-yl)phenyl)boronic acid, (4-(4-(9,9-dimethyl-9H-fluoren-2-yl)-6-phenylpyrimidin-2-yl)phenyl) boronic acid, (4-(4,6-di([1,1'-biphenyl]-4-yl)pyrimidin-2-yl) phenyl)boronic acid, (4'-(4,6-diphenylpyrimidin-2-yl)-[1,1'-biphenyl]-4-acid, (4'-(6-([1,1'-biphenyl]-4-yl)-4-phenylpyrimidin-2-yl)-[1,1'-biphenyl]-4-yl)boronic acid, (4'-(4,6-di([1,1'-biphenyl]-4-yl)pyrimidin-2-yl)-[1,1'-biphenyl]-4-yl)boronic acid, or (4'-(6-([1,1'-biphenyl]-4-yl)-4-(9, 9-dimethyl-9H-fluoren-2-yl)pyrimidin-2-yl)-[1,1'-biphenyl]-4-yl)boronic acid were used instead of (4-(4,6-diphenylpyridin-2-yl)phenyl)boronic acid.

3-2-1(3-8)

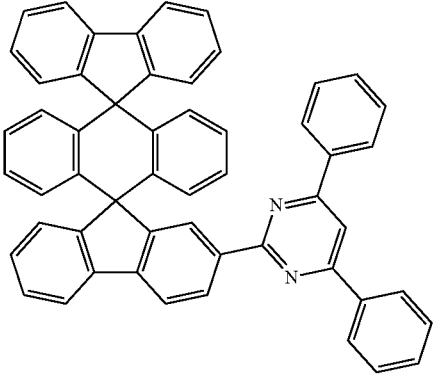

3-2-2(3-8)
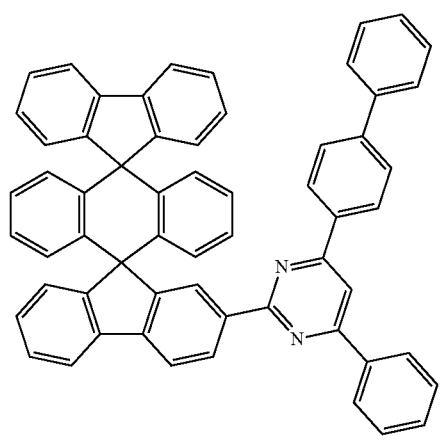
3-2-15(3-8)
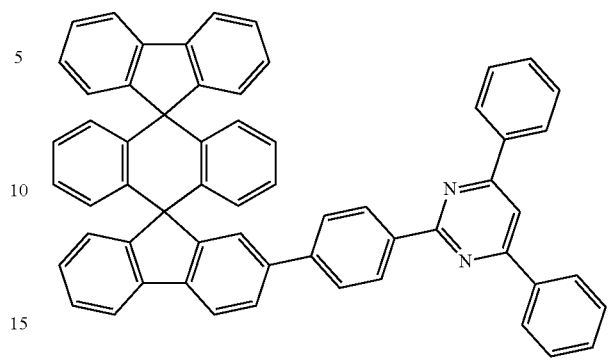
3-2-6(3-8)
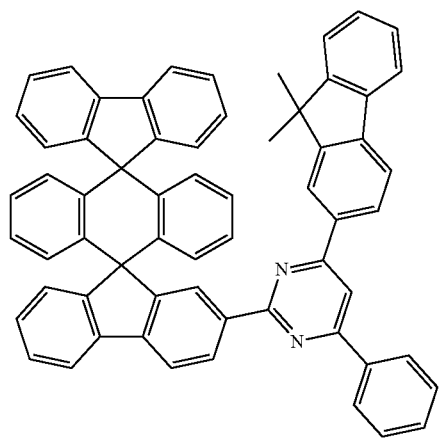
3-2-16(3-8)
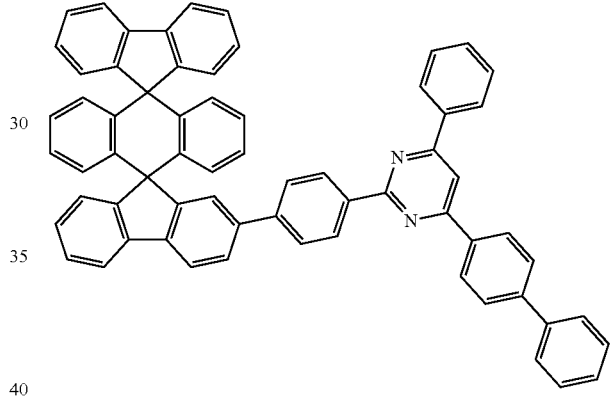
3-2-9(3-8)
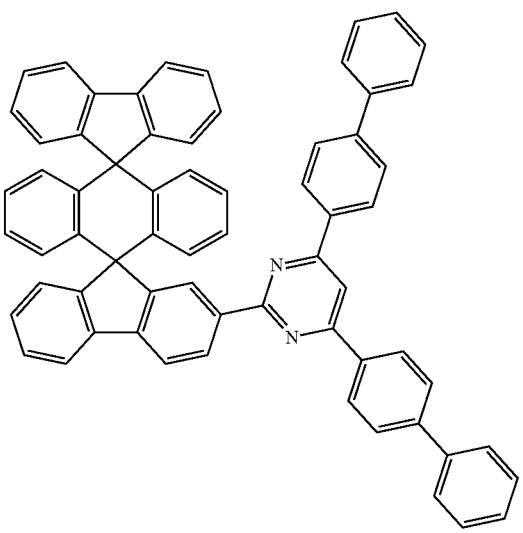 [SMILES: c1ccc(-c2ccc(-c3cc(-c4ccc(-c5ccccc5)cc4)nc(-c4ccc5c(c4)C4(c6ccccc6-5)c5ccccc5C5(c6ccccc6-c6ccccc65)c5ccccc54)c3)cc2)cc1]
3-2-18(3-8)
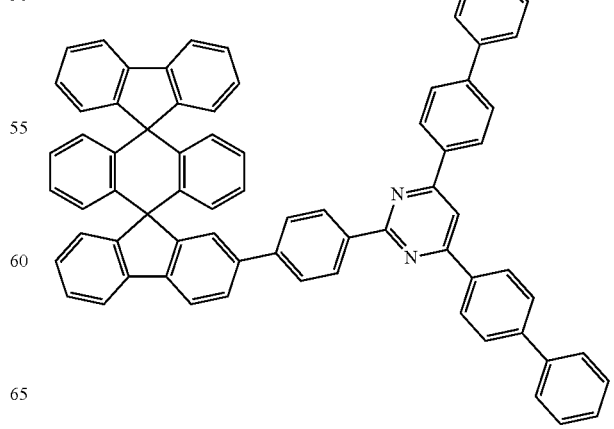

3-2-20(3-8)

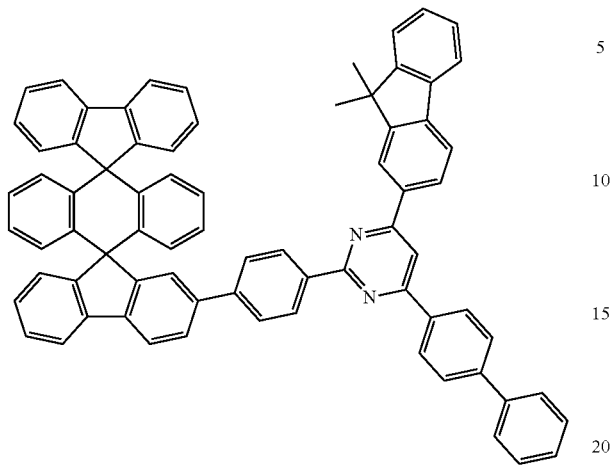

3-3-2(3-11)

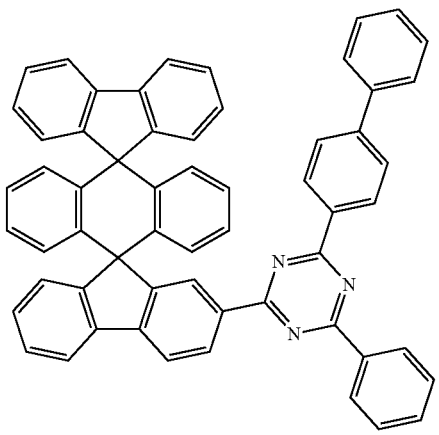

Preparation Examples 2-3-1 to 2-3-8

The following Compounds 3-3-1 (3-11), 3-3-2 (3-11), 3-3-6 (3-11), 3-3-9 (3-11), 3-3-15 (3-11), 3-3-16 (3-11), 3-3-18 (3-11) and 3-3-20 (3-11) were prepared in the same manner as in Preparation Example 2-1-1 except that 4-(4,6-diphenyl-1,3,5-triazin-2-yl)phenylboronic acid, (4-(4-([1,1'-biphenyl]-4-yl)-6-phenyl-1,3,5-triazin-2-yl)phenyl)boronic acid, (4-(4-(9,9-dimethyl-9H-fluoren-2-yl)-6-phenyl-1,3,5-triazin-2-yl)phenyl)boronic acid, (4-(4,6-di([1,1'-biphenyl]-4-yl)-1,3,5-triazin-2-yl)phenyl)boronic acid, (4'-(4,6-diphenyl-1,3,5-triazin-2-yl)-[1,1'-biphenyl]-4-yl)boronic acid, (4'-(6-([1,1'-biphenyl]-4-yl)-4-phenyl-1,3,5-triazin-2-yl)-[1,1'-biphenyl]-4-yl)boronic acid, (4'-(4,6-di([1,1'-biphenyl]-4-yl)-1,3,5-triazin-2-yl)-[1,1'-biphenyl]-4-yl)boronic acid, or (4'-(6-([1,1'-biphenyl]-4-yl)-4-(9,9-dimethyl-9H-fluoren-2-yl)-1,3,5-triazin-2-yl)-[1,1'-biphenyl]-4-yl)boronic acid were used instead of (4-(4,6-diphenylpyridin-2-yl)phenyl)boronic acid.

3-3-6(3-11)

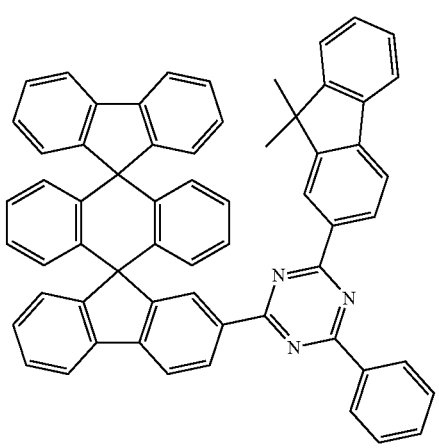

3-3-1(3-11)

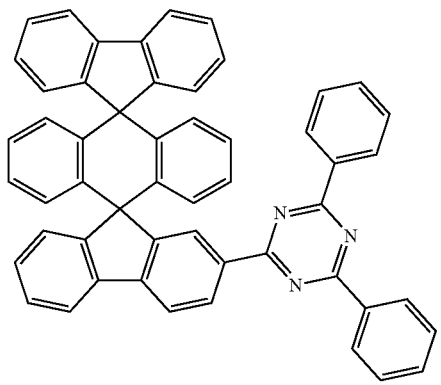

(3-3-9(3-11))

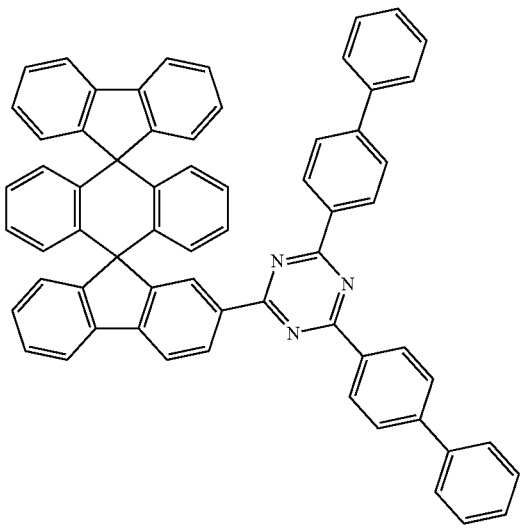

3-2-15(3-11)

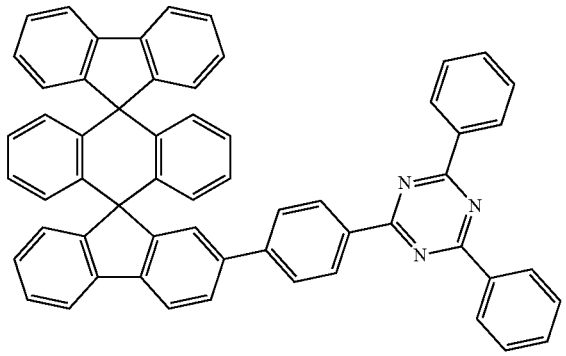 [SMILES: c1ccc(-c2cc(-c3ccccc3)nc(-c3ccc(-c4ccc5c(c4)C4(c6ccccc6-5)c5ccccc5C5(c6ccccc6-c6ccccc65)c5ccccc54)cc3)c2)cc1]

3-2-20(3-11)

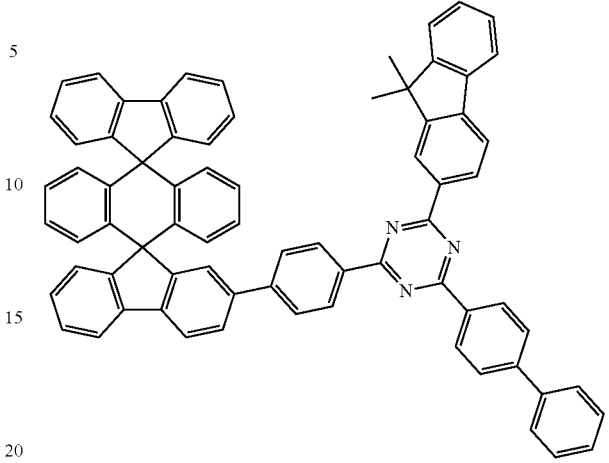

3-2-16(3-11)

3-2-18(3-11)

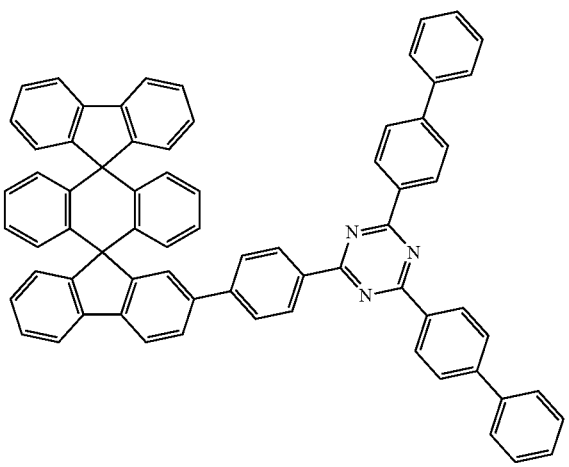 [SMILES: c1ccc(-c2ccc(-c3cc(-c4ccc(-c5ccccc5)cc4)nc(-c4ccc(-c5ccc6c(c5)C5(c7ccccc7-6)c6ccccc6C6(c7ccccc7-c7ccccc76)c6ccccc65)cc4)c3)cc2)cc1]

Preparation Examples 2-4-1 to 2-4-8

The following Compounds 3-4-1 (3-14), 3-4-2 (3-14), 3-4-6 (3-14), 3-4-9 (3-14), 3-4-15 (3-14), 3-4-16 (3-14), 3-4-18 (3-14) and 3-4-20 (3-14) were prepared in the same manner as in Preparation Example 2-1-1 except that 4-(2,6-diphenylpyrimidin-4-yl)phenylboronic acid, (4-(2-([1,1'-biphenyl]-4-yl)-6-phenylpyrimidin-2-yl)phenyl)boronic acid, (4-(2-(9,9-dimethyl-9H-fluoren-2-yl)-6-phenylpyrimidin-2-yl)phenyl)boronic acid, (4-(2,6-di([1,1'-biphenyl]-4-yl)pyrimidin-2-yl)phenyl)boronic acid, (4'-(2,6-diphenylpyrimidin-2-yl)-[1,1'-biphenyl]-4-yl)boronic acid, (4'-(6-([1,1'-biphenyl]-4-yl)-2-phenylpyrimidin-2-yl)-[1,1'-biphenyl]-4-yl)boronic acid, (4'-(2,6-di([1,1'-biphenyl]-4-yl)pyrimidin-2-yl)-[1,1'-biphenyl]-4-yl)boronic acid, or (4'-(6-([1,1'-biphenyl]-4-yl)-2-(9,9-dimethyl-9H-fluoren-2-yl)pyrimidin-2-yl)-[1,1'-biphenyl]-4-yl)boronic acid were used instead of (4-(4,6-diphenylpyridin-2-yl)phenyl)boronic acid.

3-4-1(3-14)

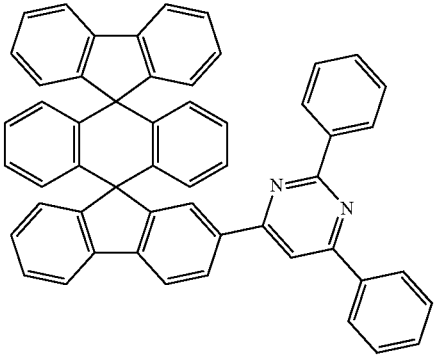

3-4-2(3-14)
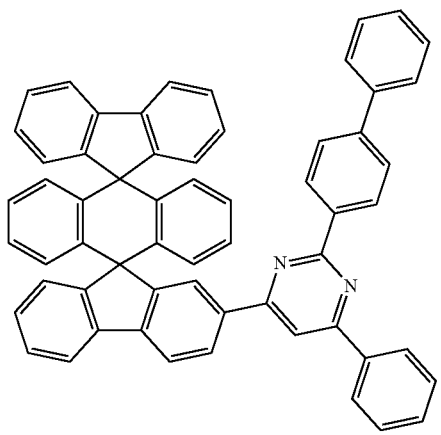
3-4-15(3-14)
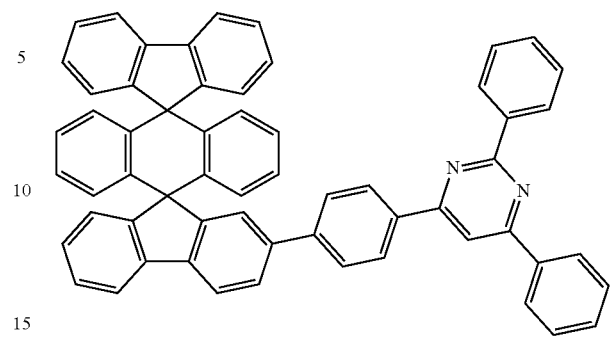
3-4-6(3-14)
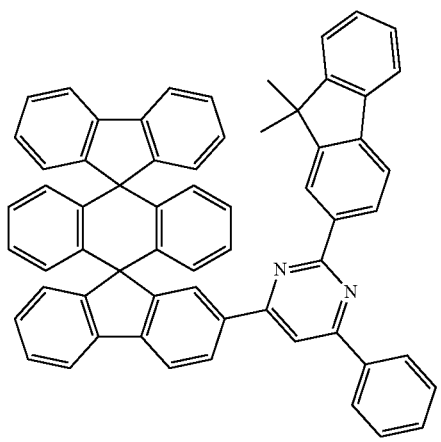
3-4-16(3-14)
3-4-9(3-14)
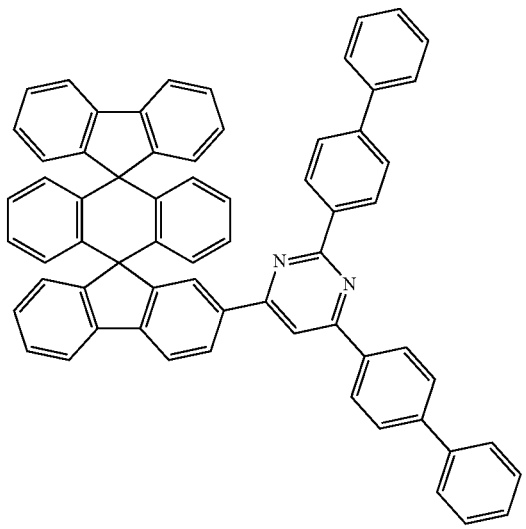
3-4-18(3-14)

3-4-20(3-14)

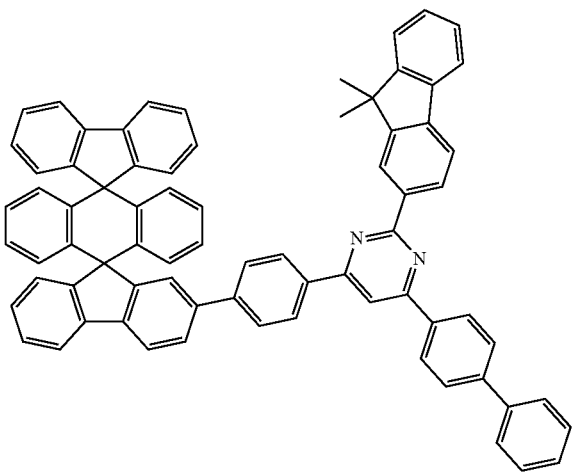

Preparation Example 3-1

Preparation of Compound 4-4-1 (4-5)

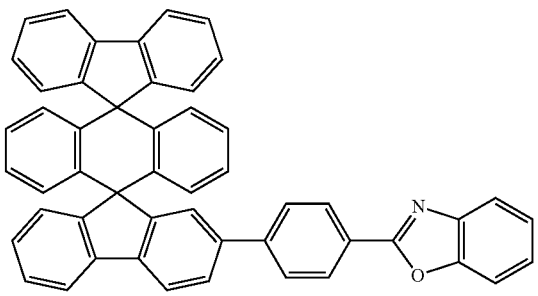 [SMILES: c1ccc2c(c1)-c1ccccc1C21c2ccccc2C2(c3ccccc3-c3ccc(-c4ccc(-c5nc6ccccc6o5)cc4)cc32)c2ccccc21]

Compound 4-4-1 (4-5) was prepared in the same manner as in Preparation Example 1-1 preparing Compound 2-1-1 (2-1) except that 4'-(benzo[d]oxazol-2-yl)biphenyl-4-ylboronic acid was used instead of (4-(diphenylamino)phenyl)boronic acid.

MS[M+H]$^+$=674

Preparation Example 3-2

Preparation of Compound 4-4-2 (4-5)

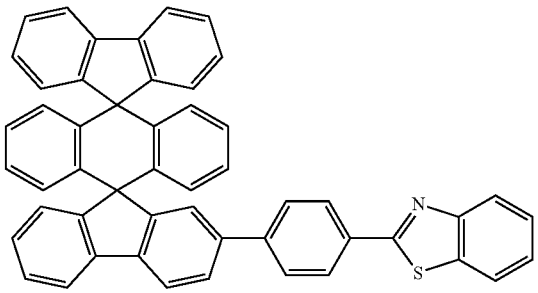 [SMILES: c1ccc2c(c1)-c1ccccc1C21c2ccccc2C2(c3ccccc3-c3ccc(-c4ccc(-c5nc6ccccc6s5)cc4)cc32)c2ccccc21]

Compound 4-4-2 (4-5) was prepared in the same manner as in Preparation Example 1-1 preparing Compound 2-1-1 (2-1) except that 4'-(benzo[d]thiazol-2-yl)biphenyl-4-ylboronic acid was used instead of (4-(diphenylamino)phenyl) boronic acid.

MS[M+H]$^+$=690

Comparative Example 1

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a hole injection layer was formed by thermal vacuum depositing hexanitrile hexaazatriphenylene (HAT) of the following chemical formula to a thickness of 500 Å.

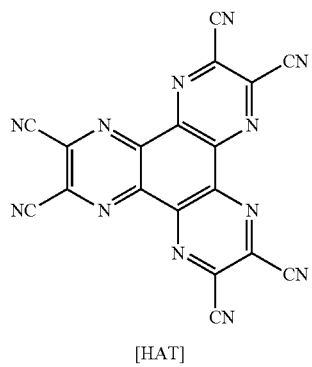

[HAT]

A hole transfer layer was formed on the hole injection layer by vacuum depositing the following compound 4-4'-bis[N-(1-naphthyl)-N-phenylamino]biphenyl (NPB) (300 Å), a material transferring holes.

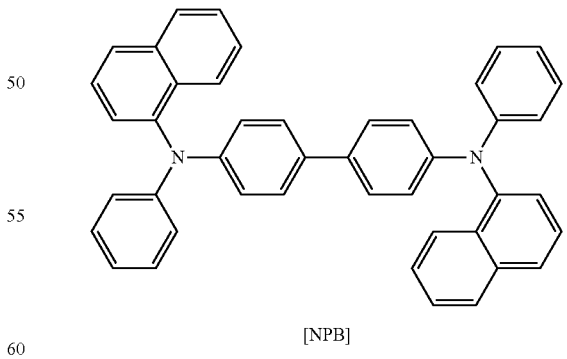

[NPB]

Subsequently, an electron blocking layer was formed on the hole transfer layer to a film thickness of 100 Å by vacuum depositing the following compound N-([1,1'-biphenyl]-4-yl)-N-(4-(11-([1,1'-biphenyl]-4-yl)-11H-benzo[a]carbazol-5-yl)phenyl)-[1,1'-biphenyl]-4-amine (EB1)(100 Å).

[EB1]

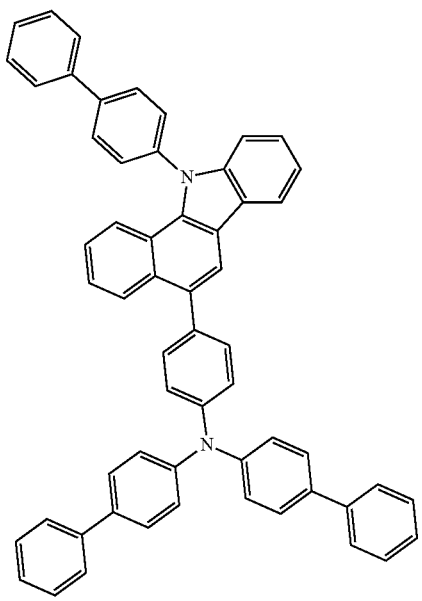

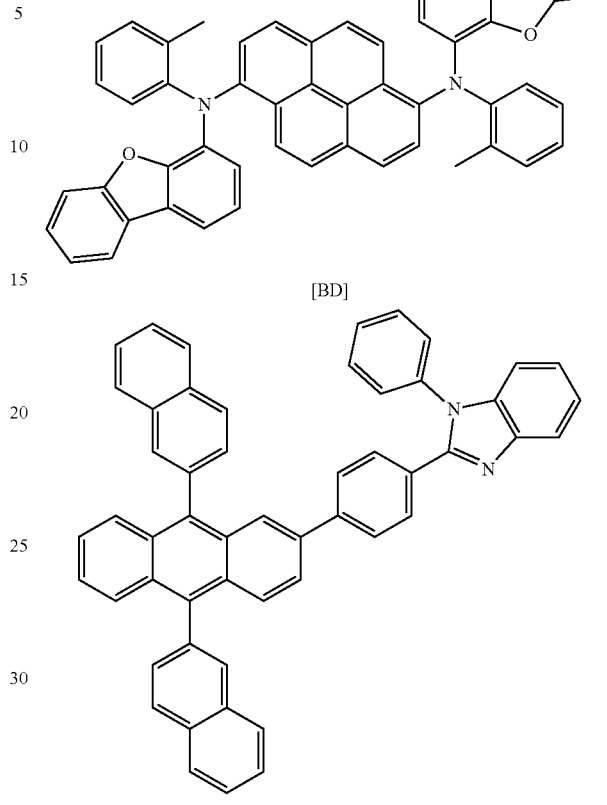

[BD]

[ET1]

[LiQ]

Next, a light emitting layer was formed on the electron blocking layer to a film thickness of 300 Å by vacuum depositing BH and BD shown below in a weight ratio of 25:1.

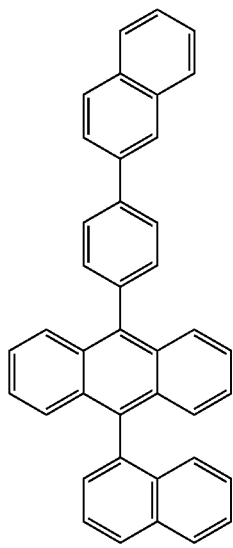

[BH]

An electron injection and transfer layer was formed on the light emitting layer to a thickness of 300 Å by vacuum depositing the compound ET1 and the compound lithium quinolate (LiQ) in a weight ratio of 1:1. A cathode was formed on the electron injection and transfer layer by depositing lithium fluoride (LiF) to a thickness of 12 Å and aluminum to a thickness of 2,000 Å in consecutive order.

An organic light emitting device was manufactured by maintaining, in the above-mentioned processes, the deposition rates of the organic materials at 0.4 Å/sec to 0.7 Å/sec, the deposition rates of the lithium fluoride and the aluminum of the cathode at 0.3 Å/sec and 2 Å/sec, respectively, and the degree of vacuum during the deposition at $2 \times 10^{-7}$ torr to $5 \times 10^{-6}$ torr.

Example 1-1

An organic light emitting device was manufactured in the same manner as in Comparative Example 1 except that Compound 2-1-1 (2-1) was used instead of EB1.

Example 1-2

An organic light emitting device was manufactured in the same manner as in Comparative Example 1 except that Compound 2-1-6 (2-1) was used instead of EB1.

Example 1-3

An organic light emitting device was manufactured in the same manner as in Comparative Example 1 except that Compound 2-1-7 (2-1) was used instead of Compound EB1.

Example 1-4

An organic light emitting device was manufactured in the same manner as in Comparative Example 1 except that Compound 2-1-10 (2-1) was used instead of Compound EB1.

Example 1-5

An organic light emitting device was manufactured in the same manner as in Comparative Example 1 except that Compound 2-1-15 (2-1) was used instead of Compound EB1.

Example 1-6

An organic light emitting device was manufactured in the same manner as in Comparative Example 1 except that Compound 2-1-20 (2-1) was used instead of Compound EB1.

Example 1-7

An organic light emitting device was manufactured in the same manner as in Comparative Example 1 except that Compound 2-1-25 (2-1) was used instead of Compound EB1.

Example 1-8

An organic light emitting device was manufactured in the same manner as in Comparative Example 1 except that Compound 2-1-26 (2-1) was used instead of EB1.

Example 1-9

An organic light emitting device was manufactured in the same manner as in Comparative Example 1 except that Compound 2-1-40 (2-1) was used instead of Compound EB1.

Example 1-10

An organic light emitting device was manufactured in the same manner as in Comparative Example 1 except that Compound 2-1-41 (2-1) was used instead of Compound EB1.

Example 1-11

An organic light emitting device was manufactured in the same manner as in Comparative Example 1 except that Compound 2-1-42 (2-1) was used instead of Compound EB1.

Example 1-12

An organic light emitting device was manufactured in the same manner as in Comparative Example 1 except that Compound 2-1-46 (2-1) was used instead of Compound EB1.

Example 1-13

An organic light emitting device was manufactured in the same manner as in Comparative Example 1 except that Compound 2-1-47 (2-1) was used instead of Compound EB1.

Example 1-14

An organic light emitting device was manufactured in the same manner as in Comparative Example 1 except that Compound 2-1-48 (2-1) was used instead of Compound EB1.

Example 1-15

An organic light emitting device was manufactured in the same manner as in Comparative Example 1 except that Compound 2-1-52 (2-1) was used instead of Compound EB1.

Example 1-16

An organic light emitting device was manufactured in the same manner as in Comparative Example 1 except that Compound 2-1-54 (2-1) was used instead of Compound EB1.

Example 1-17

An organic light emitting device was manufactured in the same manner as in Comparative Example 1 except that Compound 2-1-64 (2-1) was used instead of Compound EB1.

Example 1-18

An organic light emitting device was manufactured in the same manner as in Comparative Example 1 except that Compound 2-1-65 (2-1) was used instead of Compound EB1.

Example 1-19

An organic light emitting device was manufactured in the same manner as in Comparative Example 1 except that Compound 2-1-66 (2-1) was used instead of Compound EB1.

Example 1-20

An organic light emitting device was manufactured in the same manner as in Comparative Example 1 except that Compound 2-1-67 (2-1) was used instead of Compound EB1.

Example 1-21

An organic light emitting device was manufactured in the same manner as in Comparative Example 1 except that Compound 2-1-69 (2-1) was used instead of Compound EB1.

Example 1-22

An organic light emitting device was manufactured in the same manner as in Comparative Example 1 except that Compound 2-1-75 (2-1) was used instead of Compound EB1.

Example 1-23

An organic light emitting device was manufactured in the same manner as in Comparative Example 1 except that Compound 2-1-77 (2-1) was used instead of Compound EB1.

Example 1-24

An organic light emitting device was manufactured in the same manner as in Comparative Example 1 except that Compound 2-1-81 (2-1) was used instead of Compound EB1.

Example 1-25

An organic light emitting device was manufactured in the same manner as in Comparative Example 1 except that Compound 2-1-241 (2-1) was used instead of Compound EB1.

Example 1-26

An organic light emitting device was manufactured in the same manner as in Comparative Example 1 except that Compound 2-1-242 (2-1) was used instead of Compound EB1.

Example 1-27

An organic light emitting device was manufactured in the same manner as in Comparative Example 1 except that Compound 2-1-246 (2-1) was used instead of Compound EB1.

Example 1-28

An organic light emitting device was manufactured in the same manner as in Comparative Example 1 except that Compound 2-1-315 (2-1) was used instead of Compound EB1.

Example 1-29

An organic light emitting device was manufactured in the same manner as in Comparative Example 1 except that Compound 2-1-316 (2-1) was used instead of Compound EB1.

Example 1-30

An organic light emitting device was manufactured in the same manner as in Comparative Example 1 except that Compound 2-1-311 (2-1) was used instead of Compound EB1.

Example 1-31

An organic light emitting device was manufactured in the same manner as in Comparative Example 1 except that Compound 2-1-318 (2-1) was used instead of Compound EB1.

Example 1-32

An organic light emitting device was manufactured in the same manner as in Comparative Example 1 except that Compound 2-1-320 (2-1) was used instead of Compound EB1.

Comparative Example 1-1

An organic light emitting device was manufactured in the same manner as in Comparative Example 1 except that a compound of the following HT1 was used instead of Compound EB1.

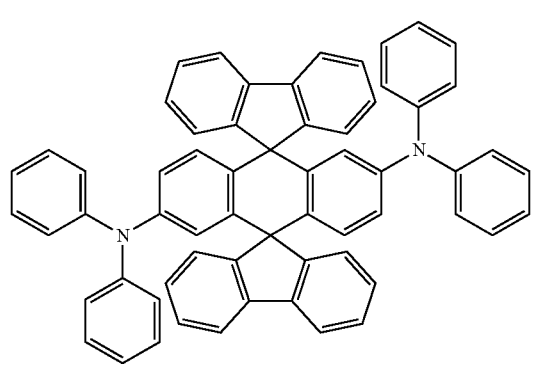

[HT1]

Comparative Example 1-2

An organic light emitting device was manufactured in the same manner as in Comparative Example 1 except that a compound of the following HT2 was used instead of Compound EB1.

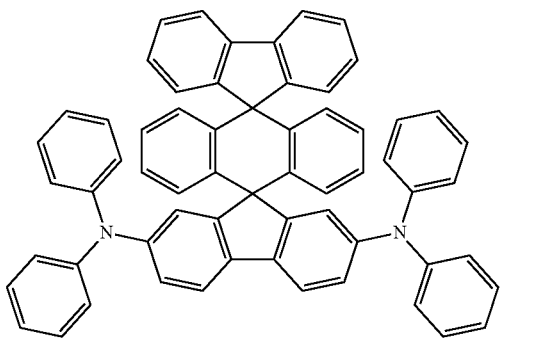

[HT2]

Comparative Example 1-3

An organic light emitting device was manufactured in the same manner as in Comparative Example 1 except that a compound of the following HT3 was used instead of Compound EB1.

[HT3]

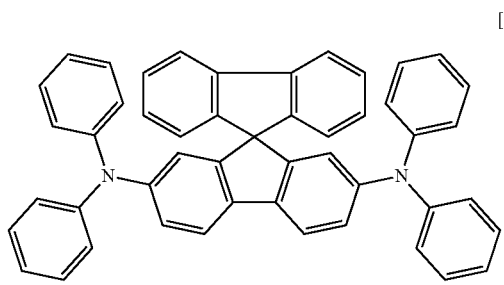

Comparative Example 1-4

An organic light emitting device was manufactured in the same manner as in Comparative Example 1 except that a compound of the following HT4 was used instead of Compound EB1.

[HT4]

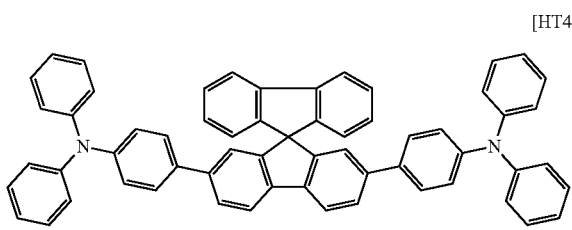 [SMILES: c1ccc(N(c2ccccc2)c2ccc(-c3ccc4c(c3)C3(c5ccccc5-c5ccccc53)c3cc(-c5ccc(N(c6ccccc6)c6ccccc6)cc5)ccc3-4)cc2)cc1]

When a current was applied to the organic light emitting devices manufactured in Comparative Example 1, Examples 1-1 to 1-32 and Comparative Examples 1-1 to 1-4, results of Table 7 were obtained.

TABLE 7

| | Compound (Electron Blocking Layer) | Voltage (V@10 mA/cm$^2$) | Efficiency (cd/A@10 mA/cm$^2$) | Color Coordinate (x, y) |
|---|---|---|---|---|
| Comparative Example 1 | EB1 | 4.11 | 5.33 | (0.138, 0.127) |
| Example 1-1 | Compound 2-1-1 (2-1) | 3.94 | 5.35 | (0.139, 0.122) |
| Example 1-2 | Compound 2-1-6 (2-1) | 3.86 | 5.36 | (0.138, 0.126) |
| Example 1-3 | Compound 2-1-7 (2-1) | 3.85 | 5.51 | (0.138, 0.127) |
| Example 1-4 | Compound 2-1-10 (2-1) | 4.03 | 5.42 | (0.137, 0.125) |
| Example 1-5 | Compound 2-1-15 (2-1) | 3.83 | 5.56 | (0.136, 0.125) |
| Example 1-6 | Compound 2-1-20 (2-1) | 4.03 | 5.54 | (0.136, 0.127) |
| Example 1-7 | Compound 2-1-25 (2-1) | 3.94 | 5.35 | (0.136, 0.125) |
| Example 1-8 | Compound 2-1-26 (2-1) | 3.86 | 5.36 | (0.137, 0.125) |
| Example 1-9 | Compound 2-1-40 (2-1) | 3.85 | 5.51 | (0.138, 0.125) |
| Example 1-10 | Compound 2-1-41 (2-1) | 4.00 | 5.42 | (0.136, 0.125) |
| Example 1-11 | Compound 2-1-42 (2-1) | 3.84 | 5.46 | (0.137, 0.125) |
| Example 1-12 | Compound 2-1-46 (2-1) | 3.88 | 5.42 | (0.136, 0.125) |
| Example 1-13 | Compound 2-1-47 (2-1) | 3.89 | 5.36 | (0.138, 0.126) |
| Example 1-14 | Compound 2-1-48 (2-1) | 3.81 | 5.34 | (0.137, 0.125) |
| Example 1-15 | Compound 2-1-52 (2-1) | 3.80 | 5.50 | (0.136, 0.127) |
| Example 1-16 | Compound 2-1-54 (2-1) | 4.01 | 5.42 | (0.135, 0.127) |
| Example 1-17 | Compound 2-1-64 (2-1) | 3.84 | 5.52 | (0.138, 0.127) |
| Example 1-18 | Compound 2-1-65 (2-1) | 4.05 | 5.58 | (0.137, 0.125) |
| Example 1-19 | Compound 2-1-66 (2-1) | 3.85 | 5.51 | (0.138, 0.127) |
| Example 1-20 | Compound 2-1-67 (2-1) | 4.03 | 5.42 | (0.137, 0.125) |
| Example 1-21 | Compound 2-1-69 (2-1) | 3.83 | 5.56 | (0.136, 0.125) |
| Example 1-22 | Compound 2-1-75 (2-1) | 4.03 | 5.54 | (0.136, 0.127) |
| Example 1-23 | Compound 2-1-77 (2-1) | 3.94 | 5.35 | (0.136, 0.125) |
| Example 1-24 | Compound 2-1-81 (2-1) | 3.86 | 5.36 | (0.137, 0.125) |
| Example 1-25 | Compound 2-1-241 (2-1) | 3.85 | 5.51 | (0.138, 0.125) |
| Example 1-26 | Compound 2-1-242 (2-1) | 4.00 | 5.42 | (0.136, 0.125) |
| Example 1-27 | Compound 2-1-246 (2-1) | 3.84 | 5.46 | (0.137, 0.125) |
| Example 1-28 | Compound 2-1-315 (2-1) | 3.85 | 5.51 | (0.138, 0.125) |
| Example 1-29 | Compound 2-1-316 (2-1) | 4.03 | 5.42 | (0.137, 0.125) |
| Example 1-30 | Compound 2-1-311 (2-1) | 3.83 | 5.56 | (0.136, 0.125) |
| Example 1-31 | Compound 2-1-318 (2-1) | 4.03 | 5.54 | (0.136, 0.127) |
| Example 1-32 | Compound 2-1-320 (2-1) | 3.94 | 5.35 | (0.136, 0.125) |
| Comparative Example 1-1 | HT1 | 4.53 | 4.68 | (0.136, 0.127) |
| Comparative Example 1-2 | HT2 | 4.63 | 4.82 | (0.136, 0.127) |
| Comparative Example 1-3 | HT3 | 4.35 | 4.85 | (0.135, 0.125) |
| Comparative Example 1-4 | HT4 | 4.37 | 4.89 | (0.135, 0.130) |

In Table 7, the devices of Examples 1-1 to 1-32 using compounds having the double spiro structure compound represented by Chemical Formula 2 as the core had a lower driving voltage and enhanced efficiency compared to the devices of Comparative Example 1-1 to 1-4, and the device of Comparative Example 1 using a material of Compound EB1 as an electron blocking layer.

When comparing the devices of Examples 1-1 to 1-32 and Comparative Examples 1-1 to 1-4, it was seen that the devices of Examples 1-1 to 1-32 had more superior properties compared to the structure in which the core of the double spiro structure compound represented by Chemical Formula 2 was substituted with two arylamine (Comparative Example 1-1 and Comparative Example 1-2) and the structure in which arylamine was linked to the spiro structure compound (Comparative Example 1-3 and Comparative Example 1-4). It was also seen that a lifespan property of the device was enhanced when a phenyl group was linked as the linking group.

As shown in the results of Table 7, it can be seen that amine linking various substituents (dibenzofuran, dibenzothiophene, carbazole derivatives and the like) to the core of the double spiro structure compound represented by Chemical Formula 2 of the present specification is suitable to be used as an electron blocking layer in an organic light emitting device by finely adjusting a LUMO level in the molecule.

Accordingly, it was identified that the double spiro structure compound according to the present specification had an excellent electron blocking ability and was capable of being used in an electron blocking layer of an organic light emitting device.

Examples 2-1 to 2-32

An organic light emitting device was manufactured in the same manner as in Comparative Example 1 except that the compounds of Examples 1-1 to 32 were used instead of NPB as the hole transfer layer.

TABLE 8

| | Compound (Hole Transfer Layer) | Voltage (V@10 mA/cm$^2$) | Efficiency (cd/A@10 mA/cm$^2$) | Color Coordinate (x, y) |
|---|---|---|---|---|
| Comparative Example 1 | NPB | 4.31 | 5.53 | (0.138, 0.127) |
| Example 2-1 | Compound 2-1-1 (2-1) | 3.84 | 5.85 | (0.139, 0.122) |
| Example 2-2 | Compound 2-1-6 (2-1) | 3.76 | 5.96 | (0.138, 0.126) |
| Example 2-3 | Compound 2-1-7 (2-1) | 3.75 | 5.81 | (0.138, 0.127) |
| Example 2-4 | Compound 2-1-10 (2-1) | 3.86 | 5.72 | (0.137, 0.125) |
| Example 2-5 | Compound 2-1-15 (2-1) | 3.73 | 5.86 | (0.136, 0.125) |
| Example 2-6 | Compound 2-1-20 (2-1) | 3.83 | 5.94 | (0.136, 0.127) |
| Example 2-7 | Compound 2-1-25 (2-1) | 3.74 | 5.95 | (0.136, 0.125) |
| Example 2-8 | Compound 2-1-26 (2-1) | 3.76 | 5.84 | (0.137, 0.125) |
| Example 2-9 | Compound 2-1-40 (2-1) | 3.75 | 5.81 | (0.138, 0.125) |
| Example 2-10 | Compound 2-1-41 (2-1) | 3.80 | 5.82 | (0.136, 0.125) |
| Example 2-11 | Compound 2-1-42 (2-1) | 3.74 | 5.96 | (0.137, 0.125) |
| Example 2-12 | Compound 2-1-46 (2-1) | 3.78 | 5.82 | (0.136, 0.125) |
| Example 2-13 | Compound 2-1-47 (2-1) | 3.79 | 5.76 | (0.138, 0.126) |
| Example 2-14 | Compound 2-1-48 (2-1) | 3.71 | 5.94 | (0.137, 0.125) |
| Example 2-15 | Compound 2-1-52 (2-1) | 3.80 | 5.80 | (0.136, 0.127) |
| Example 2-16 | Compound 2-1-54 (2-1) | 3.73 | 5.82 | (0.135, 0.127) |
| Example 2-17 | Compound 2-1-64 (2-1) | 3.83 | 5.82 | (0.138, 0.127) |
| Example 2-18 | Compound 2-1-65 (2-1) | 3.74 | 5.88 | (0.137, 0.125) |
| Example 2-19 | Compound 2-1-66 (2-1) | 3.76 | 5.81 | (0.138, 0.127) |
| Example 2-20 | Compound 2-1-67 (2-1) | 3.75 | 5.82 | (0.137, 0.125) |
| Example 2-21 | Compound 2-1-69 (2-1) | 3.80 | 5.76 | (0.136, 0.125) |

TABLE 8-continued

| | Compound (Hole Transfer Layer) | Voltage (V@10 mA/cm$^2$) | Efficiency (cd/A@10 mA/cm$^2$) | Color Coordinate (x, y) |
|---|---|---|---|---|
| Example 2-22 | Compound 2-1-75 (2-1) | 3.74 | 5.84 | (0.136, 0.127) |
| Example 2-23 | Compound 2-1-77 (2-1) | 3.78 | 5.35 | (0.136, 0.125) |
| Example 2-24 | Compound 2-1-81 (2-1) | 3.86 | 5.36 | (0.137, 0.125) |
| Example 2-25 | Compound 2-1-241 (2-1) | 3.73 | 5.82 | (0.138, 0.125) |
| Example 2-26 | Compound 2-1-242 (2-1) | 3.83 | 5.96 | (0.136, 0.125) |
| Example 2-27 | Compound 2-1-246 (2-1) | 3.74 | 5.82 | (0.137, 0.125) |
| Example 2-28 | Compound 2-1-315 (2-1) | 3.76 | 5.86 | (0.138, 0.125) |
| Example 2-29 | Compound 2-1-316 (2-1) | 3.75 | 5.94 | (0.137, 0.125) |
| Example 2-30 | Compound 2-1-311 (2-1) | 3.80 | 5.80 | (0.136, 0.125) |
| Example 2-31 | Compound 2-1-318 (2-1) | 3.74 | 5.82 | (0.136, 0.127) |
| Example 2-32 | Compound 2-1-320 (2-1) | 3.78 | 5.82 | (0.136, 0.125) |
| Comparative Example 1-1 | HT1 | 4.73 | 4.68 | (0.136, 0.127) |
| Comparative Example 1-2 | HT2 | 4.73 | 4.72 | (0.136, 0.127) |
| Comparative Example 1-3 | HT3 | 4.85 | 4.65 | (0.135, 0.125) |
| Comparative Example 1-4 | HT4 | 4.87 | 4.89 | (0.135, 0.130) |

In Table 8, the devices of Examples 2-1 to 2-32 using compounds having the double spiro structure structure represented by Chemical Formula 2 as the core had a lower driving voltage and enhanced efficiency compared to the devices of Comparative Examples 1-1 to 1-4, and the device of Comparative Example 1 using a material of NPB as the hole transfer layer.

When comparing the devices of Examples 2-1 to 2-32 and Comparative Examples 1-1 to 1-4, it was seen that the devices of Examples 2-1 to 2-32 had more superior properties compared to the structure in which the core of the double spiro structure compound represented by Chemical Formula 2 was substituted with two arylamine (Comparative Example 1-1 and Comparative Example 1-2) and the structure in which arylamine was linked to the spiro structure compound (Comparative Example 1-3 and Comparative Example 1-4). It was also seen that a lifespan property of the device was enhanced when a phenyl group was linked as the linking group.

As shown in the results of Table 8, it can be seen that amine linking various substituents (dibenzofuran, dibenzothiophene, carbazole derivatives and the like) to the core of the double spiro structure compound represented by Chemical Formula 2 of the present specification is suitable to be used as a hole transfer layer in an organic light emitting device by adjusting a HOMO level and also having an influence on the hole mobility.

Accordingly, it was identified that the double spiro structure compound according to the present specification had an excellent hole transfer ability, and was capable of being used as a hole transfer layer in an organic light emitting device.

Comparative Example 2

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner.

In addition, the substrate was cleaned for 5 minutes using oxygen plasma, and then transferred to a vacuum depositor.

On the transparent ITO electrode prepared as above, a light emitting device was formed in order of m-MTDATA (60 nm)/TCTA (80 nm)/CBP+10% Ir(ppy)$_3$ (300 nm)/BCP (10 nm)/Alq$_3$ (30 nm)/LiF (1 nm)/Al (200 nm) using CBP as a host to manufacture an organic light emitting device.

Structures of m-MTDATA, TCTA, Ir(ppy)$_3$, CBP and BCP are as follows, respectively.

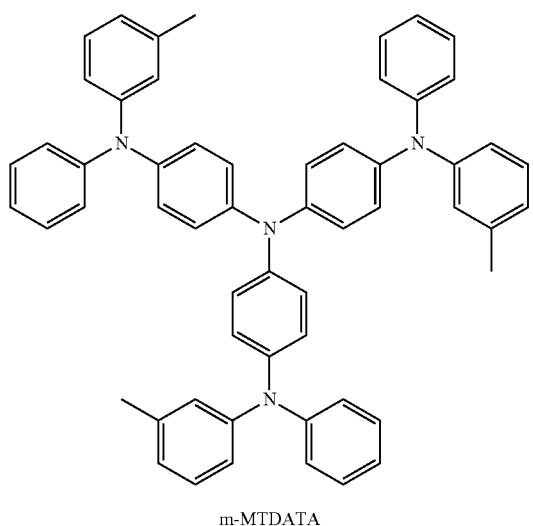

m-MTDATA

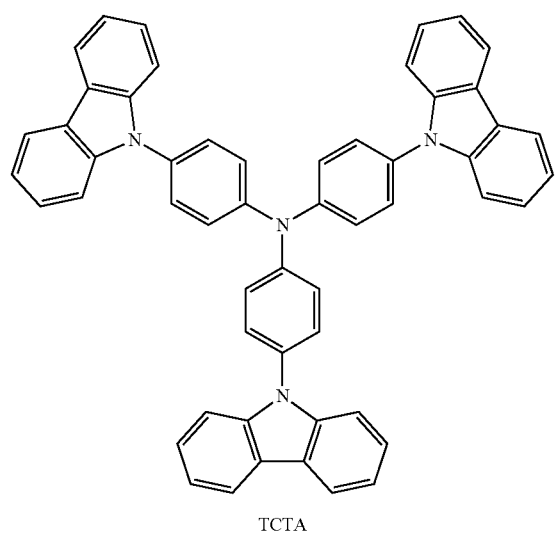

TCTA

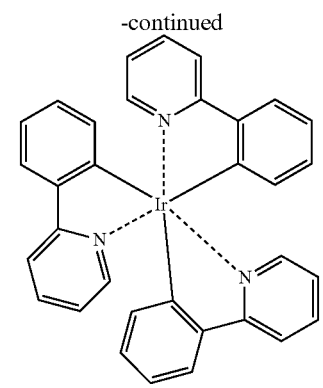

Ir(ppy)$_3$

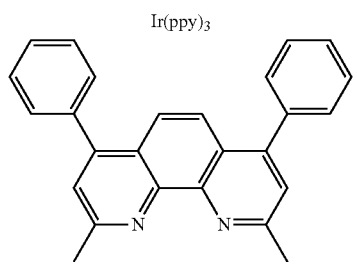

BCP

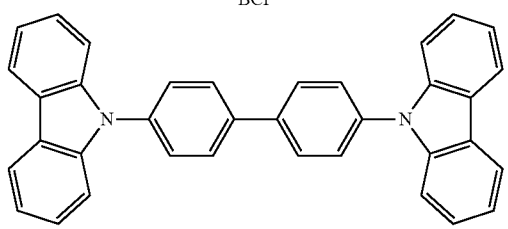

CBP

Example 3-1

An organic light emitting device was manufactured in the same manner as in Comparative Example 2 except that Compound 3-1-1 (3-5) was used instead of CBP.

Example 3-2

An organic light emitting device was manufactured in the same manner as in Comparative Example 2 except that Compound 3-1-2 (3-5) was used instead of CBP.

Example 3-3

An organic light emitting device was manufactured in the same manner as in Comparative Example 2 except that Compound 3-1-6 (3-5) was used instead of Compound CBP.

Example 3-4

An organic light emitting device was manufactured in the same manner as in Comparative Example 2 except that Compound 3-1-9 (3-5) was used instead of Compound CBP.

Example 3-5

An organic light emitting device was manufactured in the same manner as in Comparative Example 2 except that Compound 3-1-15 (3-5) was used instead of Compound CBP.

Example 3-6

An organic light emitting device was manufactured in the same manner as in Comparative Example 2 except that Compound 3-1-16 (3-5) was used instead of Compound CBP.

Example 3-7

An organic light emitting device was manufactured in the same manner as in Comparative Example 2 except that Compound 3-1-18 (3-5) was used instead of Compound CBP.

Example 3-8

An organic light emitting device was manufactured in the same manner as in Comparative Example 2 except that Compound 3-1-20 (3-5) was used instead of CBP.

Example 3-9

An organic light emitting device was manufactured in the same manner as in Comparative Example 2 except that Compound 3-2-1 (3-8) was used instead of CBP.

Example 3-10

An organic light emitting device was manufactured in the same manner as in Comparative Example 2 except that Compound 3-2-2 (3-8) was used instead of CBP.

Example 3-11

An organic light emitting device was manufactured in the same manner as in Comparative Example 2 except that Compound 3-2-6 (3-8) was used instead of Compound CBP.

Example 3-12

An organic light emitting device was manufactured in the same manner as in Comparative Example 2 except that Compound 3-2-9 (3-8) was used instead of Compound CBP.

Example 3-13

An organic light emitting device was manufactured in the same manner as in Comparative Example 2 except that Compound 3-2-15 (3-8) was used instead of Compound CBP.

Example 3-14

An organic light emitting device was manufactured in the same manner as in Comparative Example 2 except that Compound 3-2-16 (3-8) was used instead of Compound CBP.

Example 3-15

An organic light emitting device was manufactured in the same manner as in Comparative Example 2 except that Compound 3-2-18 (3-8) was used instead of Compound CBP.

Example 3-16

An organic light emitting device was manufactured in the same manner as in Comparative Example 2 except that Compound 3-2-20 (3-8) was used instead of CBP.

Example 3-17

An organic light emitting device was manufactured in the same manner as in Comparative Example 2 except that Compound 3-3-1 (3-11) was used instead of CBP.

Example 3-18

An organic light emitting device was manufactured in the same manner as in Comparative Example 2 except that Compound 3-3-2 (3-11) was used instead of CBP.

Example 3-19

An organic light emitting device was manufactured in the same manner as in Comparative Example 2 except that Compound 3-3-6 (3-11) was used instead of Compound CBP.

Example 3-20

An organic light emitting device was manufactured in the same manner as in Comparative Example 2 except that Compound 3-3-9 (3-11) was used instead of Compound CBP.

Example 3-21

An organic light emitting device was manufactured in the same manner as in Comparative Example 2 except that Compound 3-3-15 (3-11) was used instead of Compound CBP.

Example 3-22

An organic light emitting device was manufactured in the same manner as in Comparative Example 2 except that Compound 3-3-16 (3-11) was used instead of Compound CBP.

Example 3-23

An organic light emitting device was manufactured in the same manner as in Comparative Example 2 except that Compound 3-3-18 (3-11) was used instead of Compound CBP.

Example 3-24

An organic light emitting device was manufactured in the same manner as in Comparative Example 2 except that Compound 3-3-20 (3-11) was used instead of CBP.

Example 3-25

An organic light emitting device was manufactured in the same manner as in Comparative Example 2 except that Compound 3-4-1 (3-14) was used instead of CBP.

Example 3-26

An organic light emitting device was manufactured in the same manner as in Comparative Example 2 except that Compound 3-4-2 (3-14) was used instead of CBP.

Example 3-27

An organic light emitting device was manufactured in the same manner as in Comparative Example 2 except that Compound 3-4-6 (3-14) was used instead of Compound CBP.

Example 3-28

An organic light emitting device was manufactured in the same manner as in Comparative Example 2 except that Compound 3-4-9 (3-14) was used instead of Compound CBP.

Example 3-29

An organic light emitting device was manufactured in the same manner as in Comparative Example 2 except that Compound 3-4-15 (3-14) was used instead of Compound CBP.

Example 3-30

An organic light emitting device was manufactured in the same manner as in Comparative Example 2 except that Compound 3-4-16 (3-14) was used instead of Compound CBP.

Example 3-31

An organic light emitting device was manufactured in the same manner as in Comparative Example 2 except that Compound 3-4-18 (3-14) was used instead of Compound CBP.

Example 3-32

An organic light emitting device was manufactured in the same manner as in Comparative Example 2 except that Compound 3-4-20 (3-14) was used instead of CBP.

Comparative Example 2-1

An organic light emitting device was manufactured in the same manner as in Comparative Example 2 except that a compound of the following GH1 was used instead of Compound CBP.

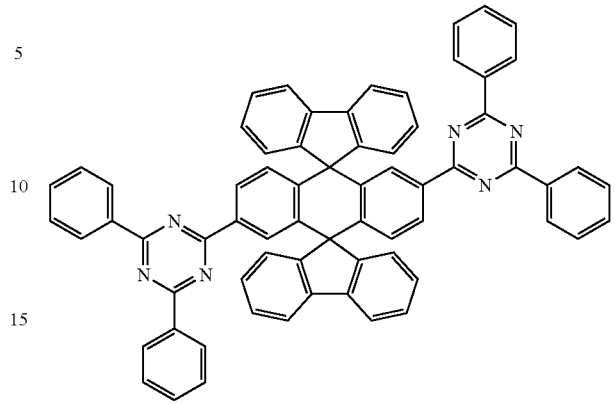

[GH1]

Comparative Example 2-2

An organic light emitting device was manufactured in the same manner as in Comparative Example 2 except that a compound of the following GH2 was used instead of Compound CBP.

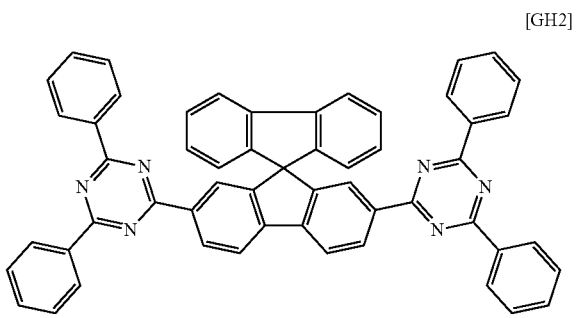 [SMILES: c1ccc(-c2nc(-c3ccccc3)nc(-c3ccc4c(c3)C3(c5ccccc5-c5ccccc53)c3cc(-c5nc(-c6ccccc6)nc(-c6ccccc6)n5)ccc3-4)n2)cc1]

[GH2]

Comparative Example 2-3

An organic light emitting device was manufactured in the same manner as in Comparative Example 2 except that a compound of the following GH3 was used instead of Compound CBP.

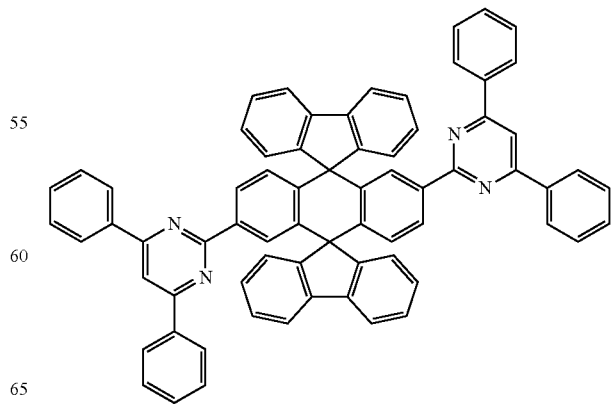

[GH3]

Comparative Example 2-4

An organic light emitting device was manufactured in the same manner as in Comparative Example 2 except that a compound of the following GH4 was used instead of Compound CBP.

[GH4]

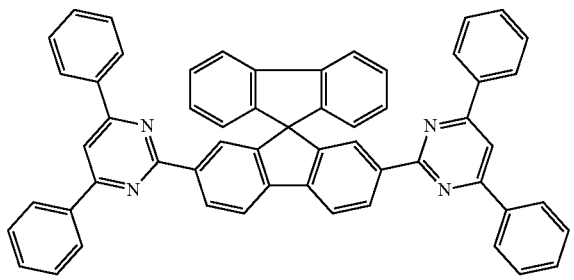

Comparative Example 2-5

An organic light emitting device was manufactured in the same manner as in Comparative Example 2 except that a compound of the following GH5 was used instead of Compound CBP.

[GH5]

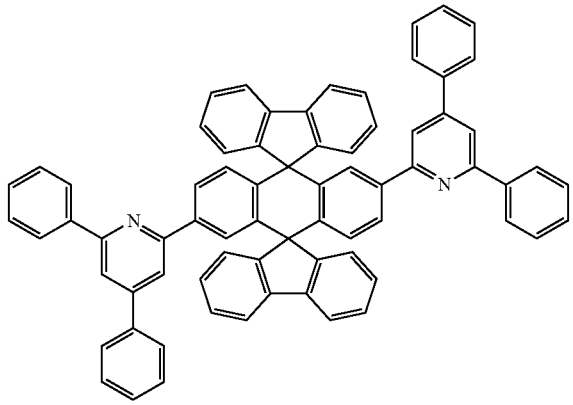

Comparative Example 2-6

An organic light emitting device was manufactured in the same manner as in Comparative Example 2 except that a compound of the following GH6 was used instead of Compound CBP.

[GH6]

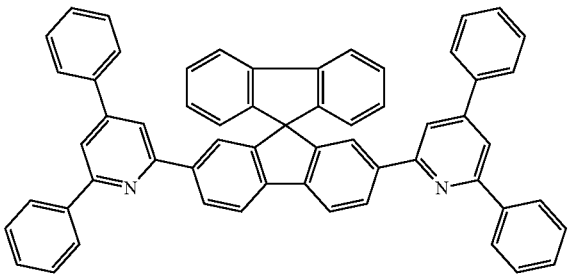

Comparative Example 2-7

An organic light emitting device was manufactured in the same manner as in Comparative Example 2 except that a compound of the following GH7 was used instead of Compound CBP.

[GH7]

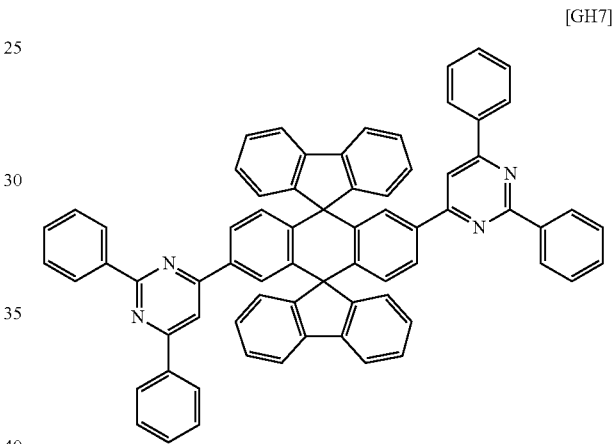

Comparative Example 2-8

An organic light emitting device was manufactured in the same manner as in Comparative Example 2 except that a compound of the following GH8 was used instead of Compound CBP.

[GH8]

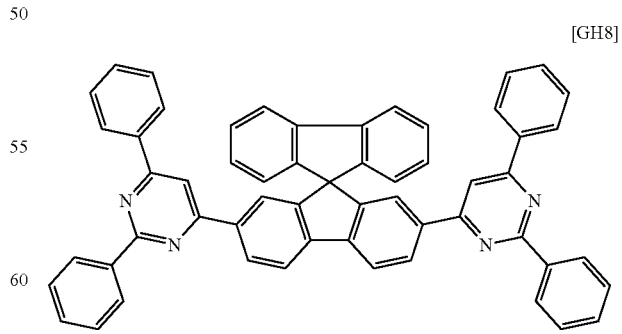

When a current was applied to the organic light emitting devices manufactured in Comparative Example 2, Examples 3-1 to 3-32 and Comparative Examples 2-1 to 2-8, results of Table 9 were obtained.

TABLE 9

| | Compound (Host) | Voltage (V@10 mA/cm²) | Efficiency (cd/A@10 mA/cm²) | EL Peak (nm) |
|---|---|---|---|---|
| Comparative Example 2 | CBP | 6.75 | 45.18 | 516 |
| Example 3-1 | Compound 3-1-1 (3-5) | 6.88 | 44.93 | 517 |
| Example 3-2 | Compound 3-1-2 (3-5) | 6.88 | 44.93 | 517 |
| Example 3-3 | Compound 3-1-6 (3-5) | 6.86 | 45.24 | 516 |
| Example 3-4 | Compound 3-1-9 (3-5) | 6.85 | 44.72 | 518 |
| Example 3-5 | Compound 3-1-15 (3-5) | 6.89 | 44.65 | 517 |
| Example 3-6 | Compound 3-1-16 (3-5) | 6.88 | 44.31 | 515 |
| Example 3-7 | Compound 3-1-18 (3-5) | 6.83 | 44.63 | 516 |
| Example 3-8 | Compound 3-1-20 (3-5) | 6.89 | 44.62 | 516 |
| Example 3-9 | Compound 3-2-1 (3-8) | 6.87 | 44.64 | 517 |
| Example 3-10 | Compound 3-2-2 (3-8) | 6.74 | 45.08 | 518 |
| Example 3-11 | Compound 3-2-6 (3-8) | 6.96 | 44.72 | 517 |
| Example 3-12 | Compound 3-2-9 (3-8) | 6.83 | 44.63 | 516 |
| Example 3-13 | Compound 3-2-15 (3-8) | 6.89 | 44.62 | 516 |
| Example 3-14 | Compound 3-2-16 (3-8) | 6.87 | 44.64 | 517 |
| Example 3-15 | Compound 3-2-18 (3-8) | 6.74 | 45.08 | 518 |
| Example 3-16 | Compound 3-2-20 (3-8) | 6.96 | 44.72 | 517 |
| Example 3-17 | Compound 3-3-1 (3-11) | 6.87 | 44.64 | 517 |
| Example 3-18 | Compound 3-3-2 (3-11) | 6.74 | 45.08 | 518 |
| Example 3-19 | Compound 3-3-6 (3-11) | 6.96 | 44.72 | 517 |
| Example 3-20 | Compound 3-3-9 (3-11) | 6.83 | 44.63 | 516 |
| Example 3-21 | Compound 3-3-15 (3-11) | 6.89 | 44.62 | 516 |
| Example 3-22 | Compound 3-3-16 (3-11) | 6.87 | 44.64 | 517 |
| Example 3-23 | Compound 3-3-18 (3-11) | 6.74 | 45.08 | 518 |
| Example 3-24 | Compound 3-3-20 (3-11) | 6.96 | 44.72 | 517 |
| Example 3-25 | Compound 3-4-1 (3-14) | 6.87 | 44.64 | 517 |
| Example 3-26 | Compound 3-4-2 (3-14) | 6.74 | 45.08 | 518 |
| Example 3-27 | Compound 3-4-6 (3-14) | 6.96 | 44.72 | 517 |
| Example 3-28 | Compound 3-4-9 (3-14) | 6.83 | 44.63 | 516 |
| Example 3-29 | Compound 3-4-15 (3-14) | 6.89 | 44.62 | 516 |
| Example 3-30 | Compound 3-4-16 (3-14) | 6.87 | 44.64 | 517 |
| Example 3-31 | Compound 3-4-18 (3-14) | 6.74 | 45.08 | 518 |
| Example 3-32 | Compound 3-4-20 (3-14) | 6.96 | 44.72 | 517 |
| Comparative Example 2-1 | GH1 | 7.28 | 43.69 | 517 |
| Comparative Example 2-2 | GH2 | 7.35 | 41.70 | 518 |
| Comparative Example 2-3 | GH3 | 7.48 | 43.69 | 517 |
| Comparative Example 2-4 | GH4 | 7.45 | 42.71 | 518 |
| Comparative Example 2-5 | GH5 | 7.58 | 43.69 | 517 |
| Comparative Example 2-6 | GH6 | 7.38 | 42.70 | 518 |
| Comparative Example 2-7 | GH7 | 7.58 | 43.69 | 517 |
| Comparative Example 2-8 | GH8 | 7.65 | 40.70 | 518 |

In Table 9, it was identified that the green organic light emitting devices of Examples 3-1 to 3-32 manufactured using the double spiro structure compound according to the present specification exhibited excellent properties in terms of current efficiency and a driving voltage compared to the green organic light emitting devices of Comparative Example 2 and Comparative Examples 2-1 to 2-8 using existing CBP.

Examples 4-1 to 4-34

An organic light emitting device was manufactured in the same manner as in Comparative Example 1 except that compounds of Examples 4-1 to 4-34 were used as in the following Table 10 instead of ET1 as the electron transfer layer.

TABLE 10

| | Compound (Electron Transfer Layer) | Voltage (V@10 mA/cm²) | Efficiency (cd/A@10 mA/cm²) | Color Coordinate (x, y) |
|---|---|---|---|---|
| Comparative Example 1 | ET1 | 4.21 | 4.51 | (0.138, 0.127) |
| Example 4-1 | Compound 3-1-1 (3-5) | 3.95 | 5.15 | (0.139, 0.122) |
| Example 4-2 | Compound 3-1-2 (3-5) | 3.86 | 5.04 | (0.138, 0.126) |
| Example 4-3 | Compound 3-1-6 (3-5) | 3.85 | 4.72 | (0.138, 0.127) |
| Example 4-4 | Compound 3-1-9 (3-5) | 3.89 | 4.65 | (0.137, 0.129) |
| Example 4-5 | Compound 3-1-15 (3-5) | 3.95 | 4.64 | (0.138, 0.128) |
| Example 4-6 | Compound 3-1-16 (3-5) | 3.90 | 4.62 | (0.138, 0.129) |
| Example 4-7 | Compound 3-1-18 (3-5) | 3.96 | 4.55 | (0.136, 0.128) |
| Example 4-8 | Compound 3-1-20 (3-5) | 3.98 | 4.52 | (0.137, 0.127) |
| Example 4-9 | Compound 3-2-1 (3-8) | 3.85 | 5.15 | (0.138, 0.127) |
| Example 4-10 | Compound 3-2-2 (3-8) | 3.86 | 5.04 | (0.139, 0.122) |
| Example 4-11 | Compound 3-2-6 (3-8) | 3.85 | 4.82 | (0.138, 0.126) |
| Example 4-12 | Compound 3-2-9 (3-8) | 3.89 | 4.95 | (0.138, 0.127) |
| Example 4-13 | Compound 3-2-15 (3-8) | 3.95 | 4.84 | (0.137, 0.129) |
| Example 4-14 | Compound 3-2-16 (3-8) | 3.90 | 4.82 | (0.138, 0.128) |

TABLE 10-continued

| Compound (Electron Transfer Layer) | | Voltage (V@10 mA/cm²) | Efficiency (cd/A@10 mA/cm²) | Color Coordinate (x, y) |
|---|---|---|---|---|
| Example 4-15 | Compound 3-2-18 (3-8) | 3.75 | 5.15 | (0.138, 0.127) |
| Example 4-16 | Compound 3-2-20 (3-8) | 3.86 | 5.04 | (0.139, 0.122) |
| Example 4-17 | Compound 3-3-1 (3-11) | 3.85 | 4.72 | (0.138, 0.126) |
| Example 4-18 | Compound 3-3-2 (3-11) | 3.89 | 4.65 | (0.138, 0.127) |
| Example 4-19 | Compound 3-3-6 (3-11) | 3.95 | 4.64 | (0.137, 0.129) |
| Example 4-20 | Compound 3-3-9 (3-11) | 3.90 | 4.62 | (0.138, 0.128) |
| Example 4-21 | Compound 3-3-15 (3-11) | 3.96 | 4.75 | (0.138, 0.127) |
| Example 4-22 | Compound 3-3-16 (3-11) | 3.98 | 4.52 | (0.136, 0.128) |
| Example 4-23 | Compound 3-3-18 (3-11) | 3.96 | 4.75 | (0.138, 0.127) |
| Example 4-24 | Compound 3-3-20 (3-11) | 3.98 | 4.62 | (0.138, 0.128) |
| Example 4-25 | Compound 3-4-1 (3-14) | 3.85 | 5.25 | (0.138, 0.127) |
| Example 4-26 | Compound 3-4-2 (3-14) | 3.86 | 5.04 | (0.139, 0.122) |
| Example 4-27 | Compound 3-4-6 (3-14) | 3.85 | 4.82 | (0.138, 0.126) |
| Example 4-28 | Compound 3-4-9 (3-14) | 3.89 | 4.65 | (0.138, 0.127) |
| Example 4-29 | Compound 3-4-15 (3-14) | 3.85 | 5.15 | (0.138, 0.128) |
| Example 4-30 | Compound 3-4-16 (3-14) | 3.86 | 5.04 | (0.138, 0.127) |
| Example 4-31 | Compound 3-4-18 (3-14) | 3.85 | 4.72 | (0.139, 0.122) |
| Example 4-32 | Compound 3-4-20 (3-14) | 3.89 | 4.65 | (0.138, 0.126) |
| Example 4-33 | Compound 4-4-1 (4-5) | 3.95 | 4.94 | (0.138, 0.127) |
| Example 4-34 | Compound 4-4-2 (4-5) | 3.90 | 4.72 | (0.137, 0.129) |

In Table 10, it was identified that the double spiro structure compound represented by Chemical Formula 3 or Chemical Formula 4 according to the present specification had an excellent electron transfer ability and was capable of being used in an organic light emitting device.

Hereinbefore, preferred embodiments (electron blocking layer, hole transfer layer, green light emitting layer and electron transfer layer) of the present specification have been described, however, the present specification is not limited thereto, and may be modified in various other forms within the scope of the claims and the scope of the detailed descriptions of the present invention, and these modifications also fall into the scope of the present specification.

REFERENCE NUMERAL

10, 11: Organic Light Emitting Device
20: Substrate
30: Anode
40: Light Emitting Layer
50: Cathode
60: Hole Injection Layer
70: Hole Transfer Layer
80: Electron Transfer Layer
90: Electron Injection Layer

The invention claimed is:

1. A double Spiro structure compound represented by the following Chemical Formula 1:

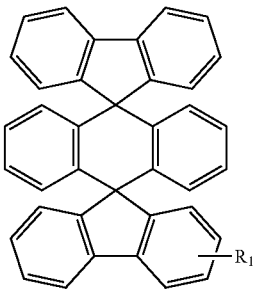

[Chemical Formula 1]

wherein, in Chemical Formula 1,
$R_1$ is represented by the following Chemical Formula B,

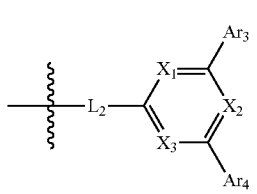

[Chemical Formula B]

wherein, in Chemical Formula B,
$X_1$ to $X_3$ are the same as or different from each other, and each independently CH or N;
at least one of $X_1$ to $X_3$ is N;
$L_2$ is selected from the group consisting of a direct bond and a monocyclic or multicyclic arylene group having 6 to 30 carbon atoms; and
$Ar_3$ and $Ar_4$ are the same as or different from each other, and each independently selected from the group consisting of any one of the following structural formula:

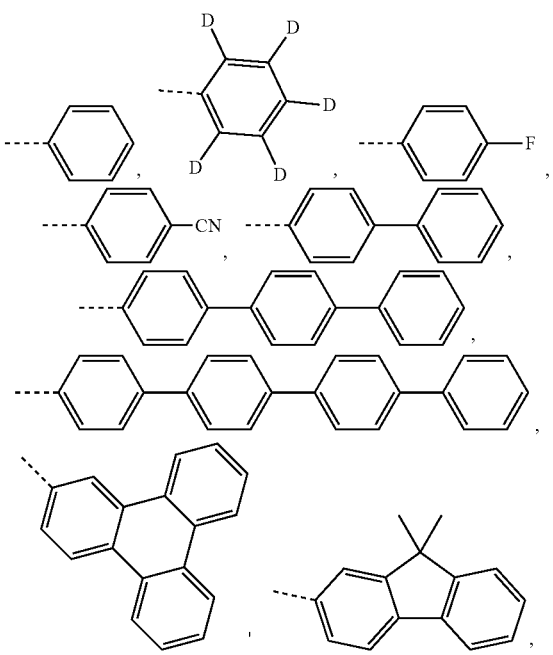

301
-continued
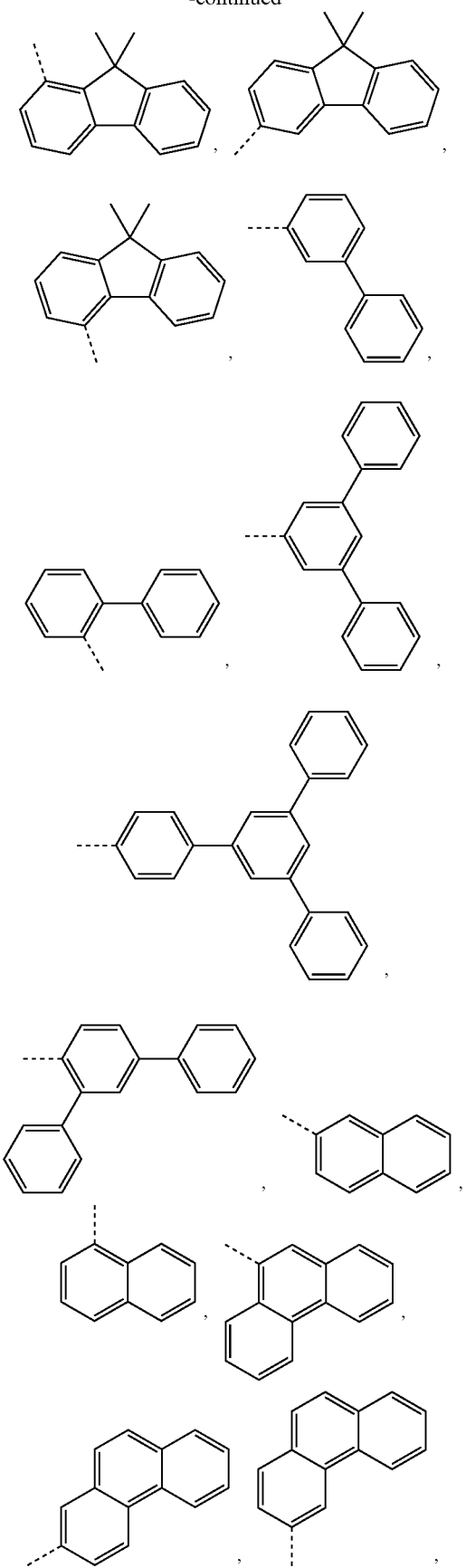
302
-continued
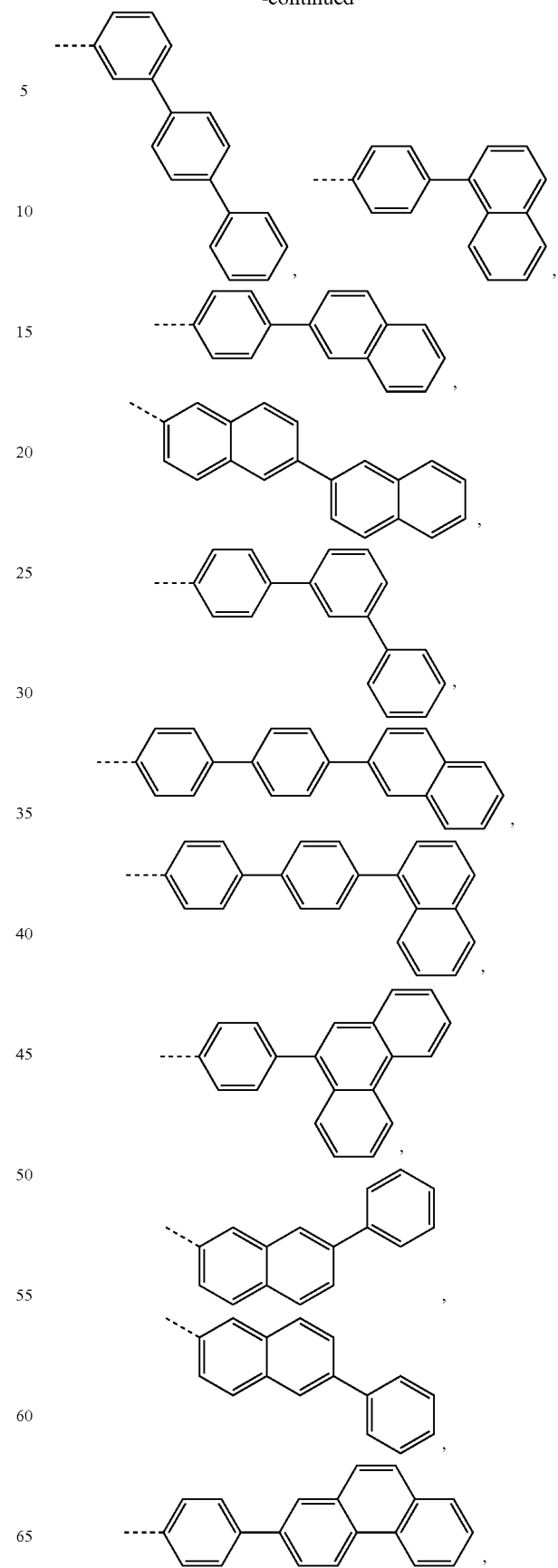

303
-continued
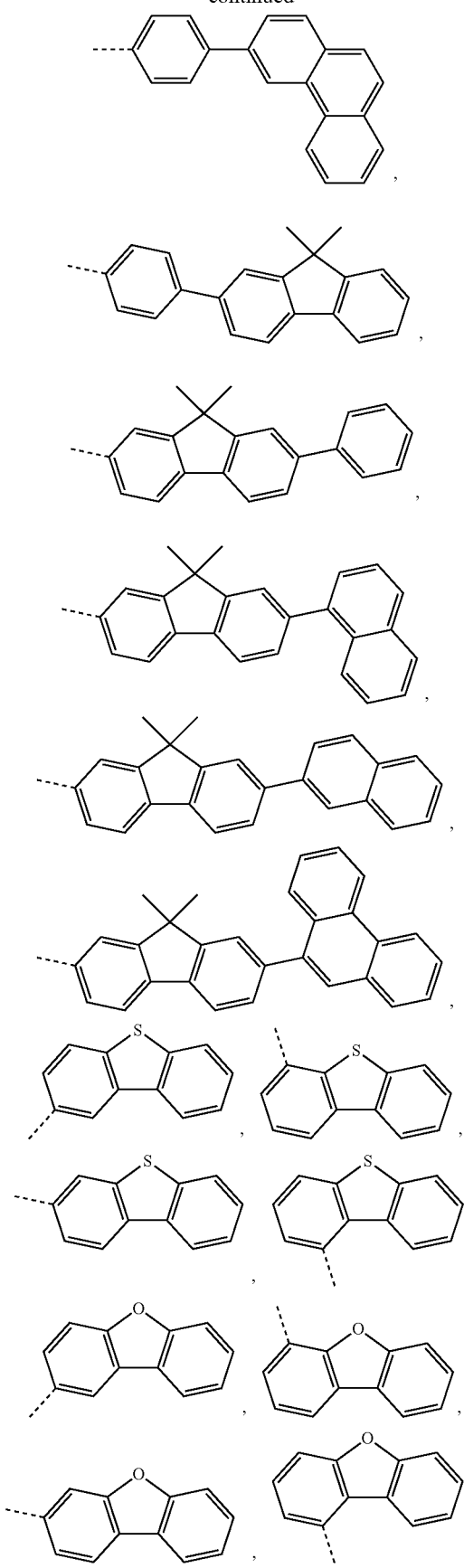
304
-continued
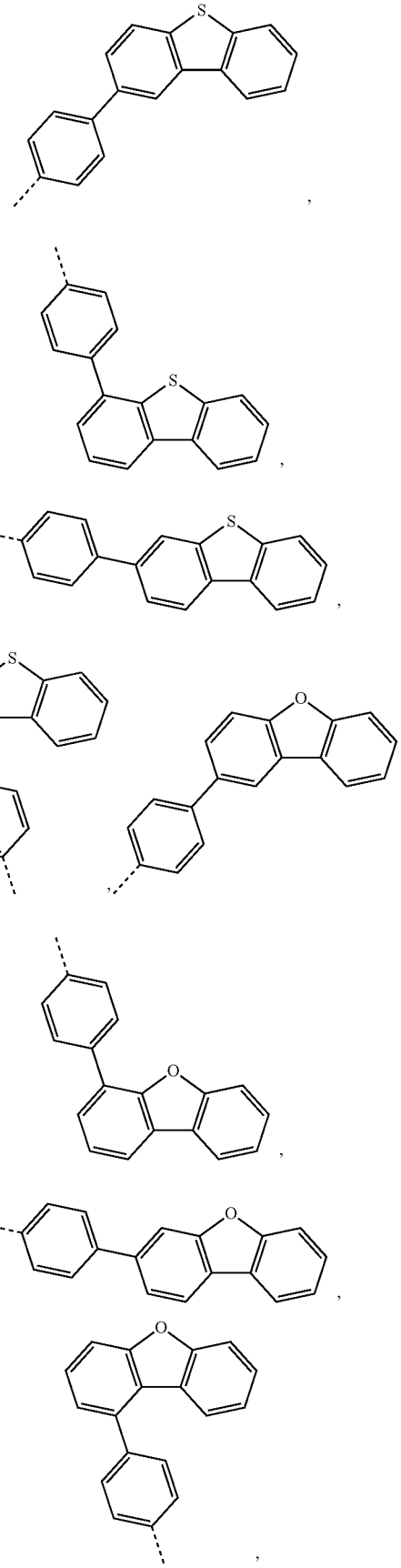

305
-continued
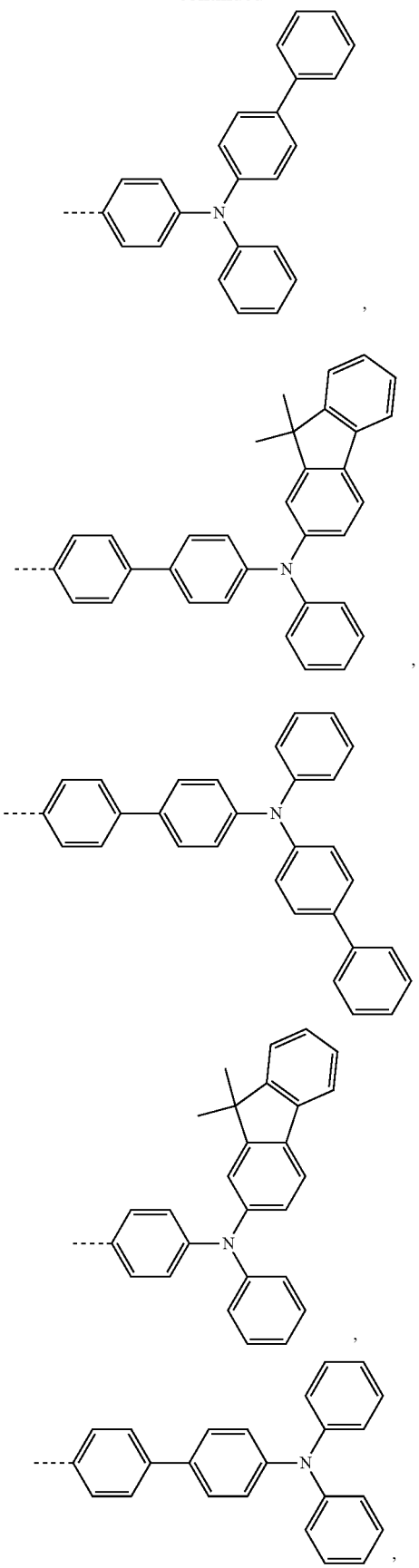
306
-continued
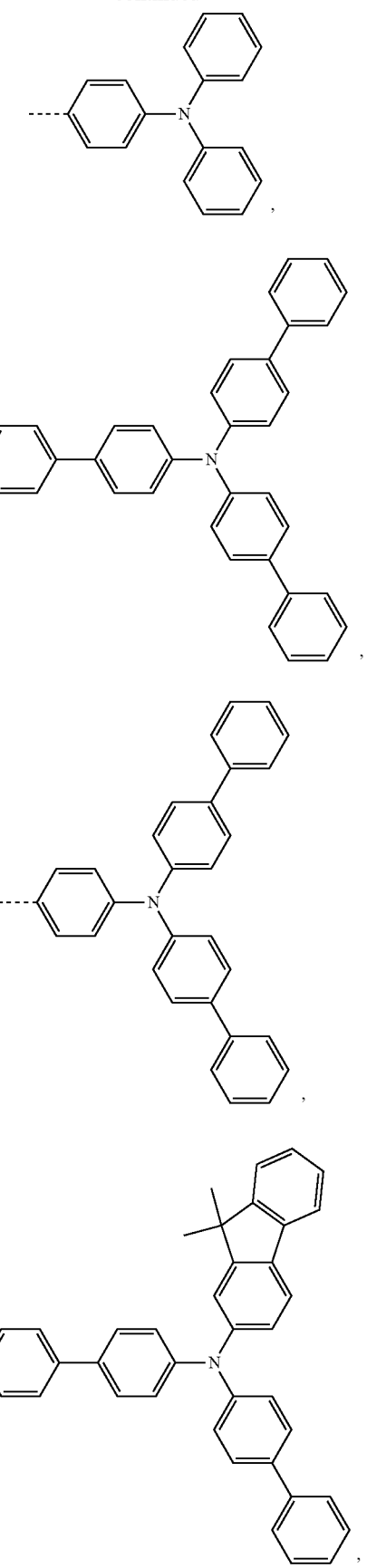

-continued

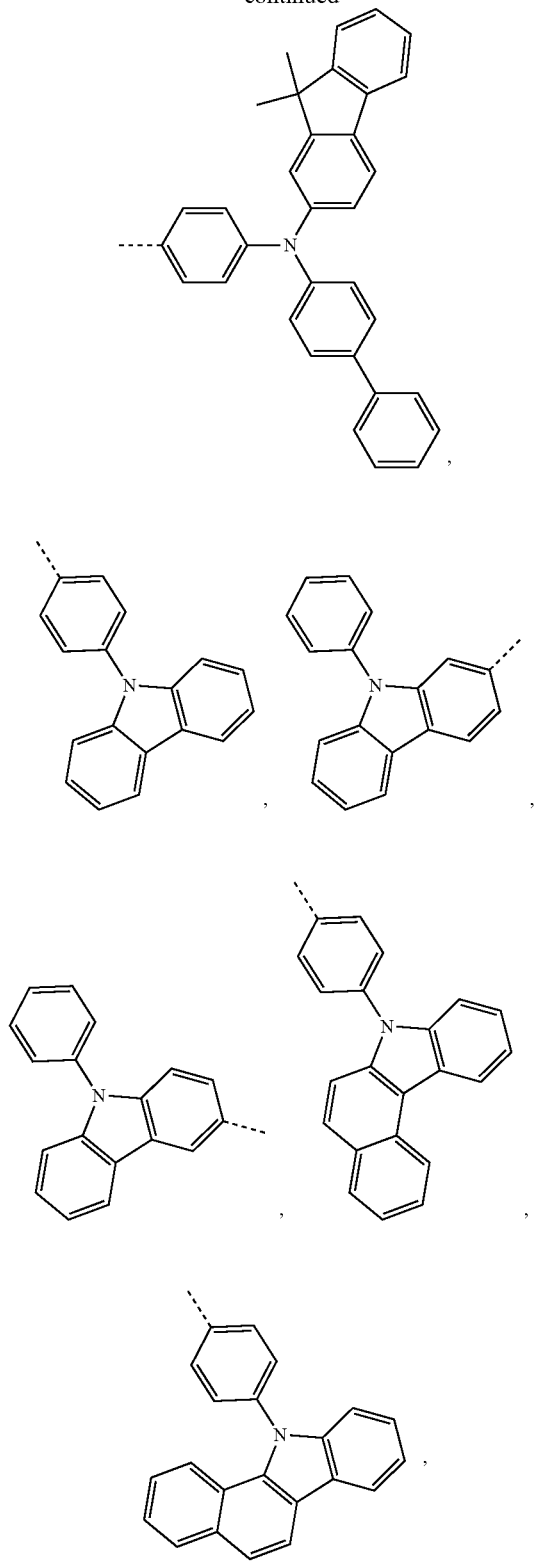

wherein ---- is a linker between substituents.

2. The double spiro structure compound of claim 1, wherein the double spiro structure compound represented by Chemical Formula 1 is represented by any one of the following Chemical Formulae 1-1 to 1-3:

[Chemical Formula 1-1]

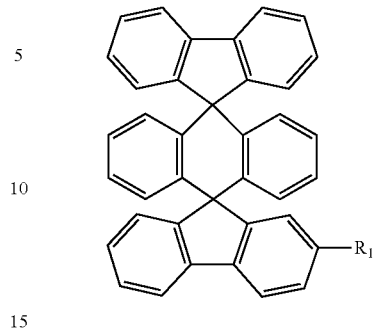

[Chemical Formula 1-2]

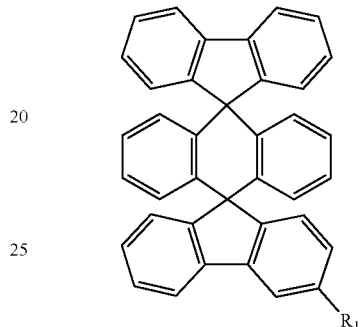

[Chemical Formula 1-3]

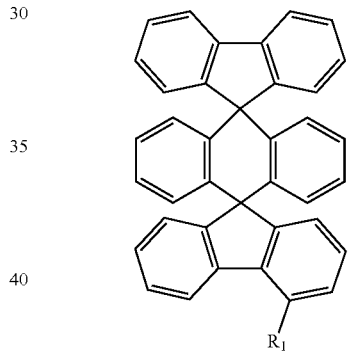

wherein, in Chemical Formula 1-1 to Chemical Formula 1-3, a definition of $R_1$ is the same as in Chemical Formula 1.

3. The double Spiro structure compound of claim 1, wherein $L_2$ is selected from the group consisting of a direct bond; a phenylene group; and a biphenylylene group.

4. An organic light emitting device comprising:
an anode;
a cathode provided opposite to the anode; and
a light emitting layer and one or more organic material layers provided between the anode and the cathode,
wherein the light emitting layer or one or more layers of the organic material layers comprise the double spiro structure compound of claim 1.

5. The organic light emitting device of claim 4, wherein the organic material layer comprises a hole injection layer or a hole transfer layer, and the hole injection layer or the hole transfer layer comprises the double Spiro structure compound.

6. The organic light emitting device of claim 4, wherein the organic material layer comprises an electron blocking layer, and the electron blocking layer comprises the double Spiro structure compound.

7. The organic light emitting device of claim 4, wherein the light emitting layer comprises the double spiro structure compound.

8. The organic light emitting device of claim 4, wherein the organic material layer comprises an electron transfer layer, an electron injection layer or a layer carrying out electron transfer and electron injection at the same time, and the electron transfer layer, the electron injection layer or the layer carrying out electron transfer and electron injection at the same time comprises the double spiro structure compound.

9. A double spiro structure compound represented by Chemical Formula 1:

[Chemical Formula 1]

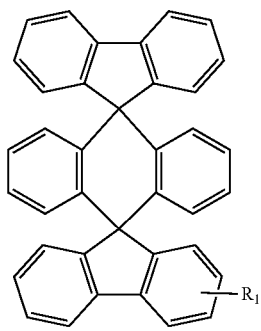

wherein in Chemical Formula 1,
R₁ is a moiety selected from the group consisting of:

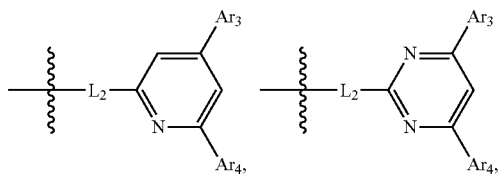

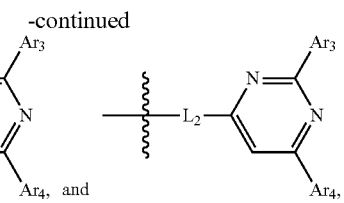

wherein L₂ is selected from the group consisting of a direct bond; a substituted or unsubstituted monocyclic or multicyclic arylene group having 6 to 30 carbon atoms; and a substituted or unsubstituted heteroarylene group having 2 to 30 carbon atoms; and wherein Ar₃ and Ar₄ are the same as or different from each other, and each independently selected from the group consisting of a substituted or unsubstituted arylamine group; a substituted or unsubstituted monocyclic or multicyclic aryl group having 6 to 30 carbon atoms; and a substituted or unsubstituted heteroaryl group having 2 to 30 carbon atoms.

10. The double spiro structure compound of claim 9, wherein the double spiro structure compound represented by Chemical Formula 1 is represented by the following Chemical Formula 3-1, and in the following Chemical Formula 3-1, L₂, Ar₃ and Ar₄ are any one selected from among 3-1-1 to 3-1-104 of the following Table 2:

[Chemical Formula 3-1]

TABLE 2

| | ----L₂--- | ----Ar₃ | ----Ar₄ |
|---|---|---|---|
| 3-1-1 | Direct bond | phenyl | phenyl |
| 3-1-2 | Direct bond | biphenyl | phenyl |
| 3-1-3 | Direct bond | biphenyl | naphthyl |

TABLE 2-continued
| | ----L₂--- | ----Ar₃--- | ----Ar₄--- |
|---|---|---|---|
| 3-1-4 | Direct bond | 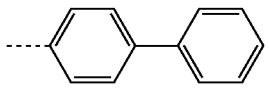 | 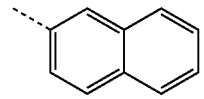 |
| 3-1-5 | Direct bond | 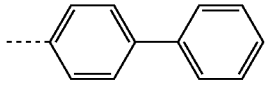 | 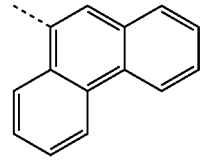 |
| 3-1-6 | Direct bond | 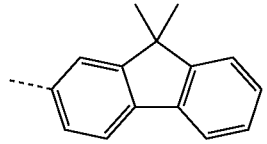 | 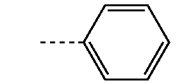 |
| 3-1-7 | Direct bond | 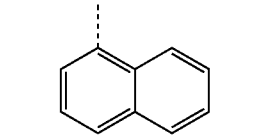 | 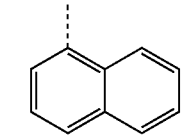 |
| 3-1-8 | Direct bond | 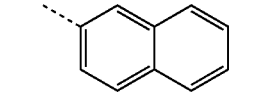 | 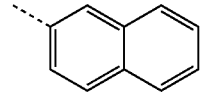 |
| 3-1-9 | Direct bond | 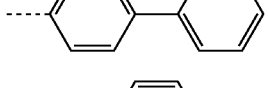 | 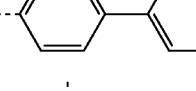 |
| 3-1-10 | Direct bond | 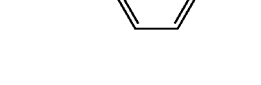 | 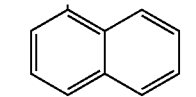 |
| 3-1-11 | Direct bond | 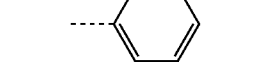 | 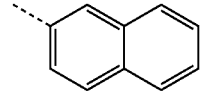 |
| 3-1-12 | 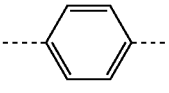 | 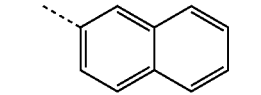 | 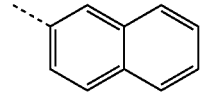 |
| 3-1-13 | 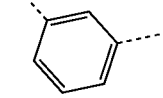 | 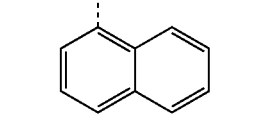 | 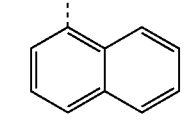 |
| 3-1-14 | 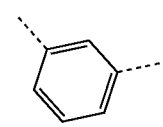 | 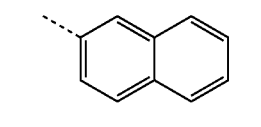 | 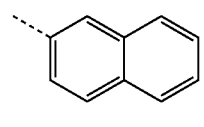 |
| 3-1-15 | 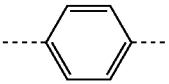 | 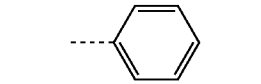 | 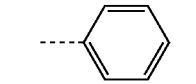 |

US 11,208,368 B2
313 314
TABLE 2-continued
| | ----L$_2$---- | ----Ar$_3$---- | ----Ar$_4$---- |
|---|---|---|---|
| 3-1-16 | 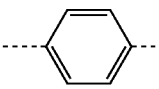 | 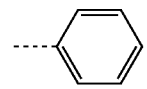 | 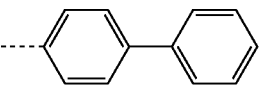 |
| 3-1-17 | 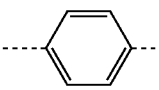 | 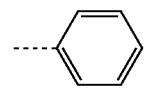 | 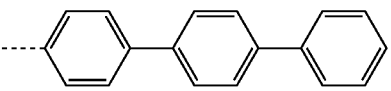 |
| 3-1-18 | 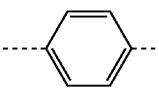 | 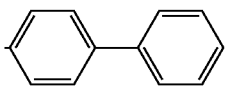 | 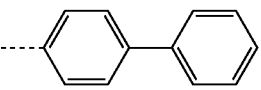 |
| 3-1-19 | 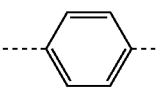 | 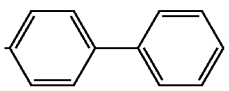 | 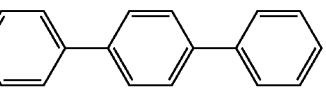 |
| 3-1-20 | 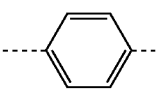 | 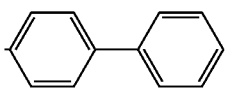 | 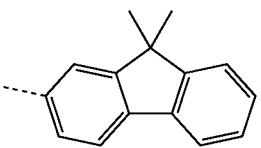 |
| 3-1-21 | 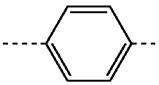 | 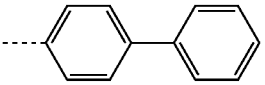 | 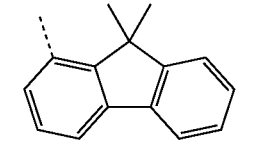 |
| 3-1-22 | 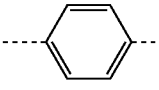 | 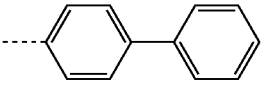 | 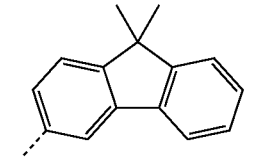 |
| 3-1-23 | 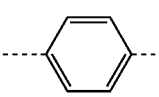 | 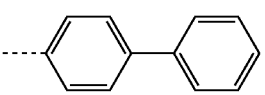 | 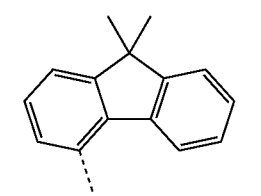 |
| 3-1-24 | 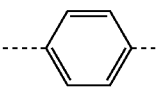 | 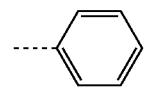 | 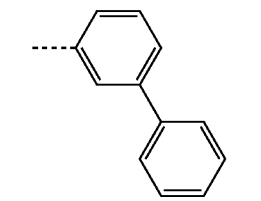 |
| 3-1-25 | 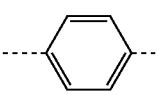 | 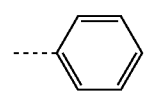 | 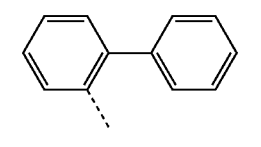 |
| 3-1-26 | 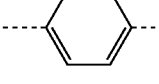 | 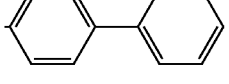 | 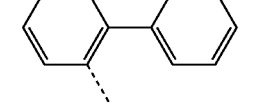 |

TABLE 2-continued
| | ----L$_2$---- | ----Ar$_3$---- | ----Ar$_4$---- |
|---|---|---|---|
| 3-1-27 |  | 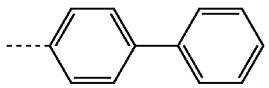 | 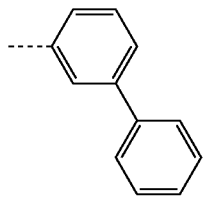 |
| 3-1-28 |  | 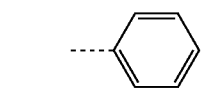 | 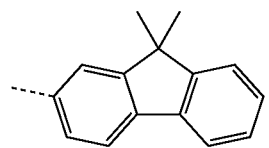 |
| 3-1-29 | 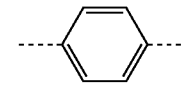 | 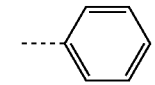 | 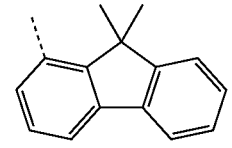 |
| 3-1-30 | 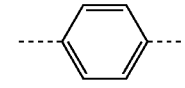 | 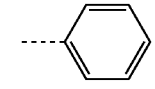 | 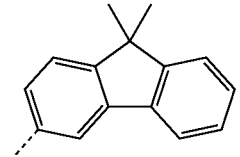 |
| 3-1-31 | 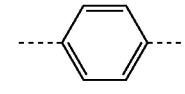 | 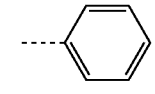 | 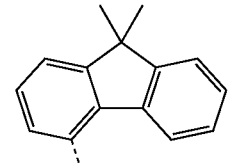 |
| 3-1-32 | 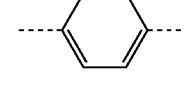 | 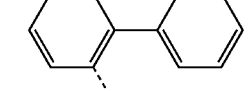 | 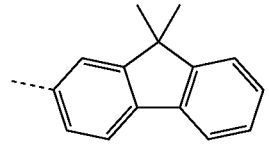 |
| 3-1-33 | 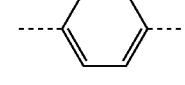 | 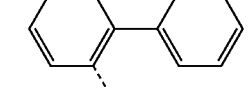 | 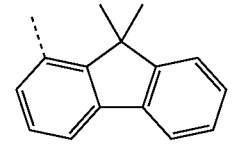 |
| 3-1-34 | 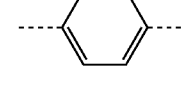 | 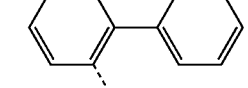 | 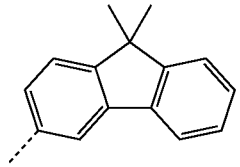 |
| 3-1-35 | 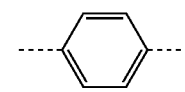 | 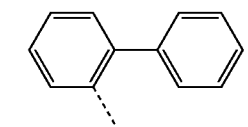 | 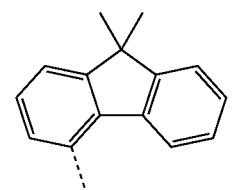 |

TABLE 2-continued
| | ----L$_2$--- | ----Ar$_3$ | ----Ar$_4$ |
|---|---|---|---|
| 3-1-36 | 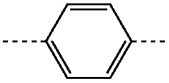 | 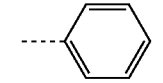 | 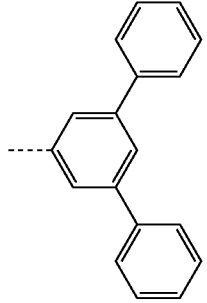 |
| 3-1-37 | 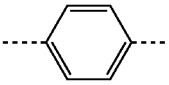 | 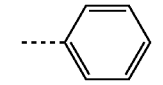 | 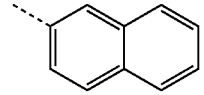 |
| 3-1-38 | 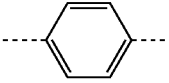 | 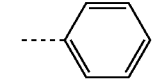 | 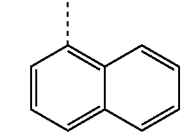 |
| 3-1-39 | 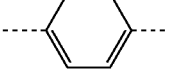 | 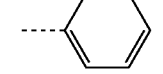 | 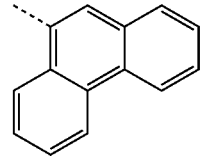 |
| 3-1-40 |  | 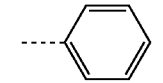 | 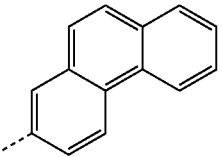 |
| 3-1-41 | 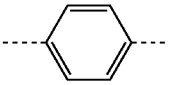 | 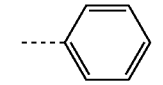 | 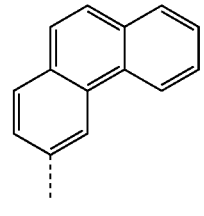 |
| 3-1-42 |  | 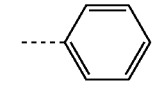 | 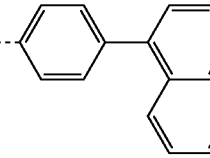 |
| 3-1-43 | 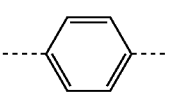 | 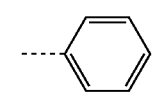 | 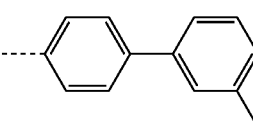 |

TABLE 2-continued
| | ----L₂---- | ----Ar₃ | ----Ar₄ |
|---|---|---|---|
| 3-1-44 | 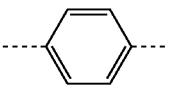 | 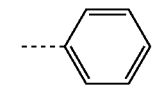 | 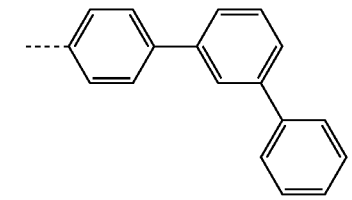 |
| 3-1-45 | 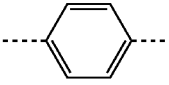 | 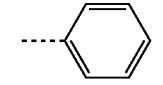 | 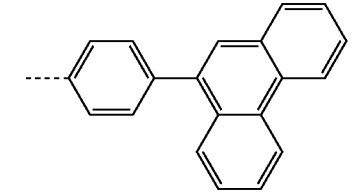 |
| 3-1-46 | 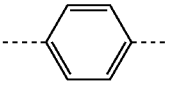 | 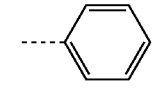 | 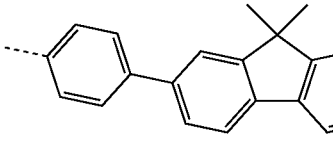 |
| 3-1-47 | 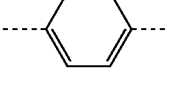 | 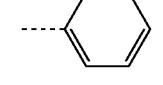 | 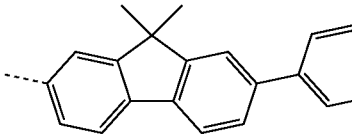 |
| 3-1-48 | 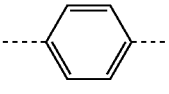 | 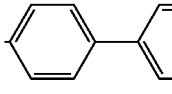 | 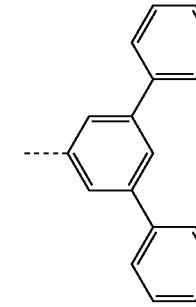 |
| 3-1-49 | 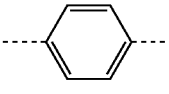 | 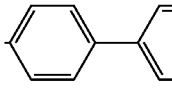 | 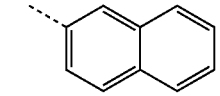 |
| 3-1-50 | 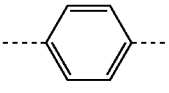 | 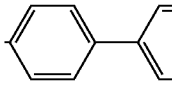 | 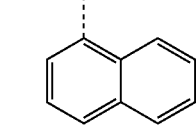 |
| 3-1-51 | 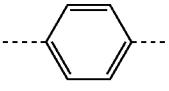 | 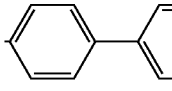 | 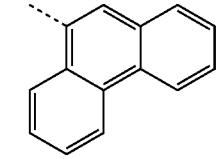 |

TABLE 2-continued

| | ----L₂---- | ----Ar₃ | ----Ar₄ |
|---|---|---|---|
| 3-1-52 | | | |
| 3-1-53 | | | |
| 3-1-54 | | | |
| 3-1-55 | | | |
| 3-1-56 | | | |
| 3-1-57 | | | |
| 3-1-58 | | | |
| 3-1-59 | | | |
| 3-1-60 | | | |

TABLE 2-continued

| | ----L₂---- | ----Ar₃ | ----Ar₄ |
|---|---|---|---|
| 3-1-61 | phenylene | phenyl | biphenyl |
| 3-1-62 | phenylene | phenyl | terphenyl |
| 3-1-63 | phenylene | biphenyl | biphenyl |
| 3-1-64 | phenylene | biphenyl | terphenyl |
| 3-1-65 | phenylene | biphenyl | 9,9-dimethylfluoren-2-yl |
| 3-1-66 | phenylene | biphenyl | 9,9-dimethylfluoren-1-yl |
| 3-1-67 | phenylene | biphenyl | 9,9-dimethylfluoren-3-yl |
| 3-1-68 | phenylene | biphenyl | 9,9-dimethylfluoren-4-yl |
| 3-1-69 | phenylene | phenyl | biphenyl (meta) |
| 3-1-70 | phenylene | phenyl | biphenyl (ortho) |

TABLE 2-continued

| | ----L₂---- | ----Ar₃---- | ----Ar₄---- |
|---|---|---|---|
| 3-1-71 | phenylene | 4-biphenyl | 2-biphenyl |
| 3-1-72 | phenylene | 4-biphenyl | 3-biphenyl |
| 3-1-73 | phenylene | phenyl | 9,9-dimethylfluoren-2-yl |
| 3-1-74 | phenylene | phenyl | 9,9-dimethylfluoren-1-yl |
| 3-1-75 | phenylene | phenyl | 9,9-dimethylfluoren-3-yl |
| 3-1-76 | phenylene | phenyl | 9,9-dimethylfluoren-4-yl |
| 3-1-77 | phenylene | 2-biphenyl | 9,9-dimethylfluoren-2-yl |
| 3-1-78 | phenylene | 2-biphenyl | 9,9-dimethylfluoren-1-yl |
| 3-1-79 | phenylene | 2-biphenyl | 9,9-dimethylfluoren-3-yl |

TABLE 2-continued
| | ----L$_2$---- | ----Ar$_3$---- | ----Ar$_4$---- |
|---|---|---|---|
| 3-1-80 | 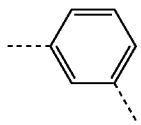 | 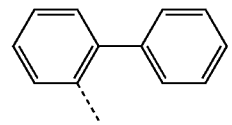 | 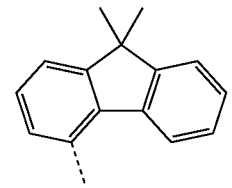 |
| 3-1-81 | 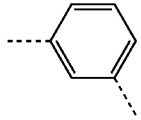 | 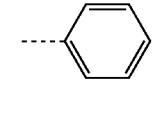 | 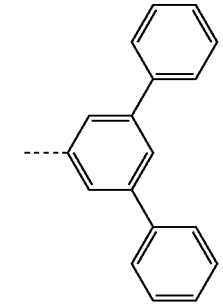 |
| 3-1-82 | 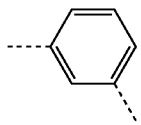 | 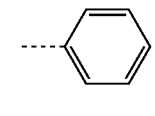 | 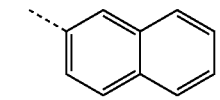 |
| 3-1-83 | 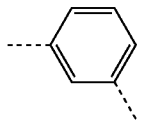 | 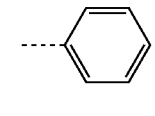 | 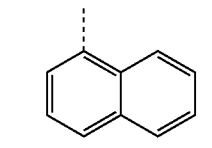 |
| 3-1-84 | 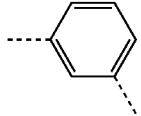 | 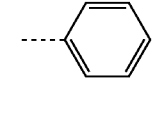 | 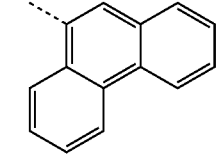 |
| 3-1-85 | 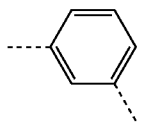 | 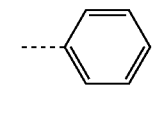 | 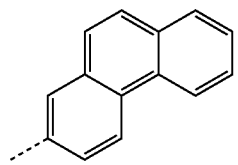 |
| 3-1-86 | 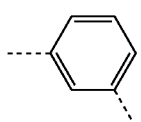 | 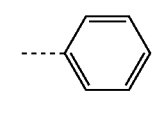 | 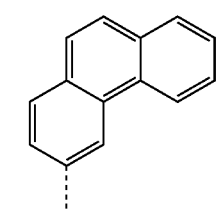 |
| 3-1-87 | 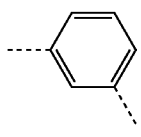 | 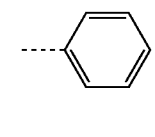 | 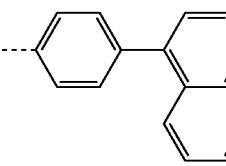 |

TABLE 2-continued

| | ----L₂---- | ----Ar₃---- | ----Ar₄---- |
|---|---|---|---|
| 3-1-88 | (1,3-phenylene) | (phenyl) | (4-(2-naphthyl)phenyl) |
| 3-1-89 | (1,3-phenylene) | (phenyl) | (3-biphenyl via 4-phenylene) |
| 3-1-90 | (1,3-phenylene) | (phenyl) | (9-phenanthrenyl-phenyl) |
| 3-1-91 | (1,3-phenylene) | (phenyl) | (9,9-dimethylfluoren-2-yl-phenyl) |
| 3-1-92 | (1,3-phenylene) | (phenyl) | (7-phenyl-9,9-dimethylfluoren-2-yl) |
| 3-1-93 | (1,3-phenylene) | (4-biphenyl) | (3,5-diphenylphenyl) |
| 3-1-94 | (1,3-phenylene) | (4-biphenyl) | (2-naphthyl) |
| 3-1-95 | (1,3-phenylene) | (4-biphenyl) | (1-naphthyl) |

TABLE 2-continued

| | ----L₂---- | ----Ar₃---- | ----Ar₄---- |
|---|---|---|---|
| 3-1-96 | | | |
| 3-1-97 | | | |
| 3-1-98 | | | |
| 3-1-99 | | | |
| 3-1-100 | | | |
| 3-1-101 | | | |
| 3-1-102 | | | |
| 3-1-103 | | | |

TABLE 2-continued

| | ----L₂--- | ----Ar₃ | ----Ar₄ |
|---|---|---|---|
| 3-1-104 | ![phenyl] | ![biphenyl] | ![9,9-dimethyl-fluorene-phenyl] |

11. The double spiro structure compound of claim 9, wherein the double spiro structure compound represented by Chemical Formula 1 is represented by the following Chemical Formula 3-2, and in the following Chemical Formula 3-2, $L_2$, $Ar_3$ and $Ar_4$ are any one selected from among 3-2-1 to 3-2-104 of the following Table 3:

[Chemical Formula 3-2]

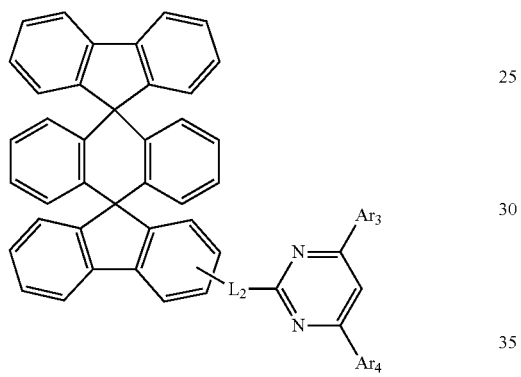

TABLE 3

| | ----L₂--- | ----Ar₃ | ----Ar₄ |
|---|---|---|---|
| 3-2-1 | Direct bond | ![phenyl] | ![phenyl] |
| 3-2-2 | Direct bond | ![biphenyl] | ![phenyl] |
| 3-2-3 | Direct bond | ![biphenyl] | ![naphthyl] |
| 3-2-4 | Direct bond | ![biphenyl] | ![naphthyl] |

TABLE 3-continued

| | ----L₂---- | ----Ar₃ | ----Ar₄ |
|---|---|---|---|
| 3-2-5 | Direct bond | biphenyl | phenanthrene |
| 3-2-6 | Direct bond | 9,9-dimethylfluorene | phenyl |
| 3-2-7 | Direct bond | 1-naphthyl | 1-naphthyl |
| 3-2-8 | Direct bond | 2-naphthyl | 2-naphthyl |
| 3-2-9 | Direct bond | biphenyl | biphenyl |
| 3-2-10 | Direct bond | phenyl | 1-naphthyl |
| 3-2-11 | Direct bond | phenyl | 2-naphthyl |
| 3-2-12 | 1,4-phenylene | 2-naphthyl | 2-naphthyl |
| 3-2-13 | 1,3-phenylene | 1-naphthyl | 1-naphthyl |
| 3-2-14 | 1,3-phenylene | 2-naphthyl | 2-naphthyl |
| 3-2-15 | 1,4-phenylene | phenyl | phenyl |
| 3-2-16 | 1,4-phenylene | phenyl | biphenyl |

TABLE 3-continued
| | ----L₂---- | ----Ar₃---- | ----Ar₄---- |
|---|---|---|---|
| 3-2-17 | 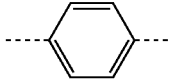 | 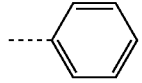 | 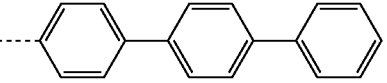 |
| 3-2-18 | 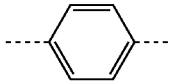 | 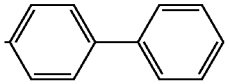 | 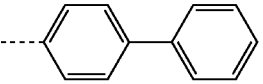 |
| 3-2-19 | 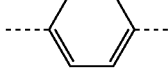 | 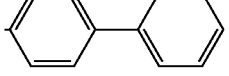 | 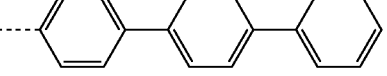 |
| 3-2-20 | 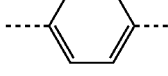 | 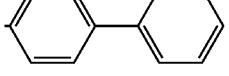 | 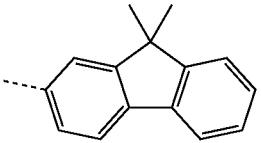 |
| 3-2-21 |  | 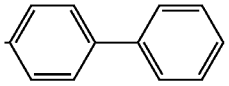 | 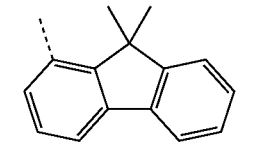 |
| 3-2-22 | 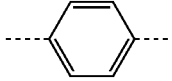 | 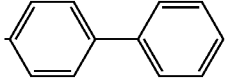 | 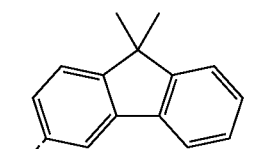 |
| 3-2-23 | 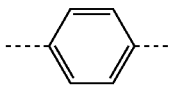 | 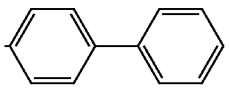 | 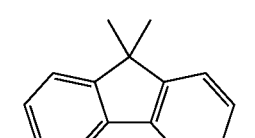 |
| 3-2-24 | 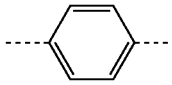 | 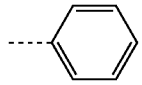 | 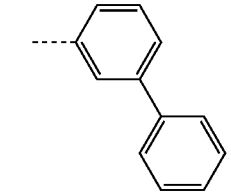 |
| 3-2-25 |  | 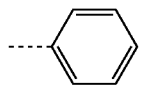 | 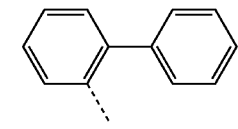 |
| 3-2-26 | 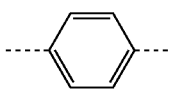 | 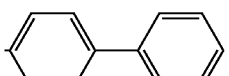 | 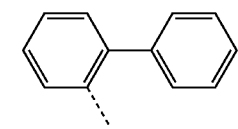 |

TABLE 3-continued

| | ----L₂--- | ----Ar₃ | ----Ar₄ |
|---|---|---|---|
| 3-2-27 | (1,4-phenylene) | (4-biphenylyl) | (3-biphenylyl) |
| 3-2-28 | (1,4-phenylene) | (phenyl) | (9,9-dimethylfluoren-2-yl) |
| 3-2-29 | (1,4-phenylene) | (phenyl) | (9,9-dimethylfluoren-1-yl) |
| 3-2-30 | (1,4-phenylene) | (phenyl) | (9,9-dimethylfluoren-3-yl) |
| 3-2-31 | (1,4-phenylene) | (phenyl) | (9,9-dimethylfluoren-4-yl) |
| 3-2-32 | (1,4-phenylene) | (2-biphenylyl) | (9,9-dimethylfluoren-2-yl) |
| 3-2-33 | (1,4-phenylene) | (2-biphenylyl) | (9,9-dimethylfluoren-1-yl) |
| 3-2-34 | (1,4-phenylene) | (2-biphenylyl) | (9,9-dimethylfluoren-3-yl) |
| 3-2-35 | (1,4-phenylene) | (2-biphenylyl) | (9,9-dimethylfluoren-4-yl) |

TABLE 3-continued
| | ----L₂---- | ----Ar₃ | ----Ar₄ |
|---|---|---|---|
| 3-2-36 |  | 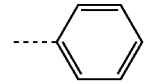 | 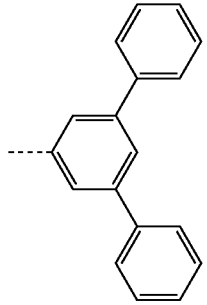 |
| 3-2-37 |  | 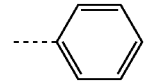 | 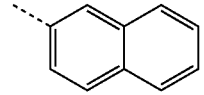 |
| 3-2-38 |  | 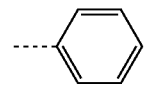 | 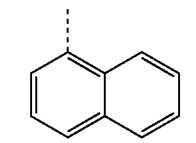 |
| 3-2-39 |  | 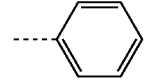 | 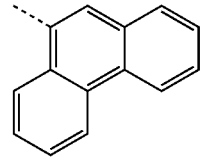 |
| 3-2-40 |  | 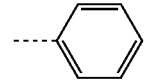 | 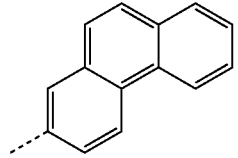 |
| 3-2-41 |  | 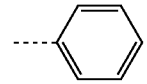 | 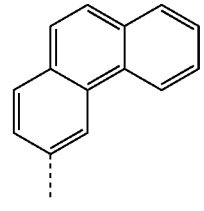 |
| 3-2-42 |  | 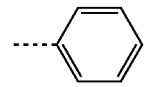 | 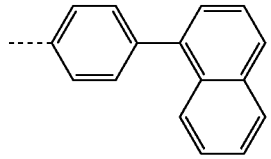 |
| 3-2-43 |  | 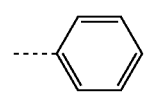 | 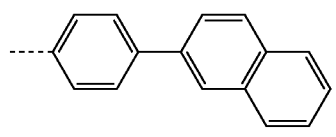 |

TABLE 3-continued
| | ----L₂---- | ----Ar₃ | ----Ar₄ |
|---|---|---|---|
| 3-2-44 | 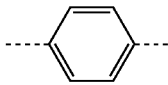 | 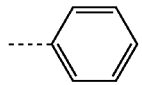 | 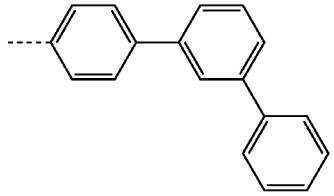 |
| 3-2-45 | 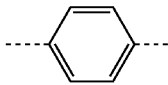 | 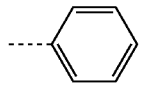 | 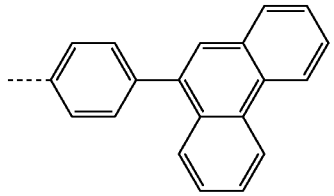 |
| 3-2-46 | 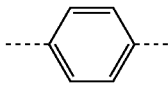 | 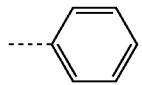 | 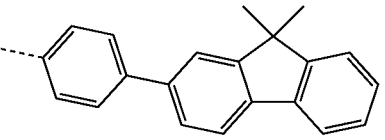 |
| 3-2-47 | 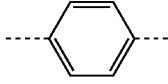 | 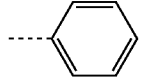 | 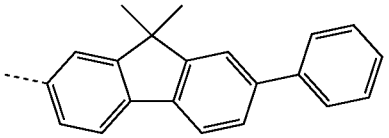 |
| 3-2-48 | 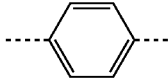 | 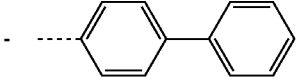 | 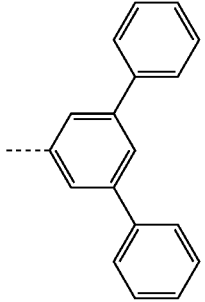 |
| 3-2-49 | 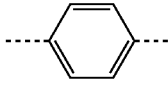 | 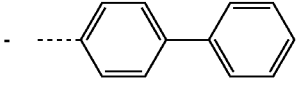 | 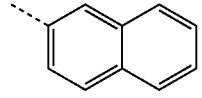 |
| 3-2-50 | 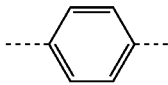 | 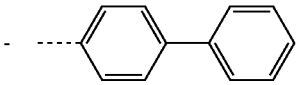 | 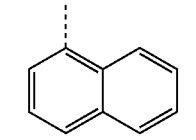 |
| 3-2-51 | 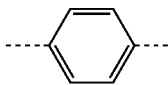 | 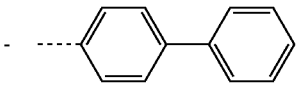 | 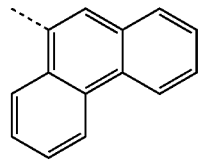 |

TABLE 3-continued

| | ----L₂---- | ----Ar₃ | ----Ar₄ |
|---|---|---|---|
| 3-2-52 | phenylene | biphenyl | chrysenyl |
| 3-2-53 | phenylene | biphenyl | phenanthrenyl |
| 3-2-54 | phenylene | biphenyl | phenyl-1-naphthyl |
| 3-2-55 | phenylene | biphenyl | phenyl-2-naphthyl |
| 3-2-56 | phenylene | biphenyl | m-terphenyl |
| 3-2-57 | phenylene | biphenyl | phenyl-phenanthrenyl |
| 3-2-58 | phenylene | biphenyl | 9,9-dimethylfluorenyl-phenyl |
| 3-2-59 | phenylene | biphenyl | 9,9-dimethyl-phenylfluorenyl |
| 3-2-60 | m-phenylene | phenyl | phenyl |

TABLE 3-continued

| | ----L₂---- | ----Ar₃ | ----Ar₄ |
|---|---|---|---|
| 3-2-61 | phenylene | phenyl | biphenyl |
| 3-2-62 | phenylene | phenyl | terphenyl |
| 3-2-63 | phenylene | biphenyl | biphenyl |
| 3-2-64 | phenylene | biphenyl | terphenyl |
| 3-2-65 | phenylene | biphenyl | 9,9-dimethylfluoren-2-yl |
| 3-2-66 | phenylene | biphenyl | 9,9-dimethylfluoren-1-yl |
| 3-2-67 | phenylene | biphenyl | 9,9-dimethylfluoren-3-yl |
| 3-2-68 | phenylene | biphenyl | 9,9-dimethylfluoren-4-yl |
| 3-2-69 | phenylene | phenyl | 3-biphenyl |
| 3-2-70 | phenylene | phenyl | 2-biphenyl |

TABLE 3-continued
| | ----L₂---- | ----Ar₃ | ----Ar₄ |
|---|---|---|---|
| 3-2-71 | 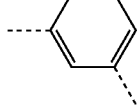 | 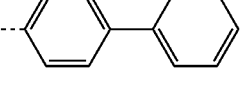 | 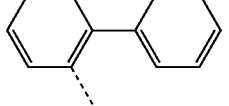 |
| 3-2-72 | 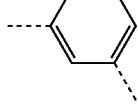 | 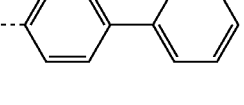 | 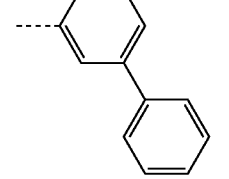 |
| 3-2-73 | 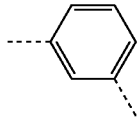 | 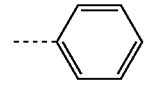 | 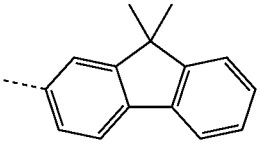 |
| 3-2-74 | 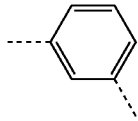 | 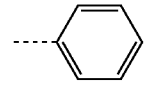 | 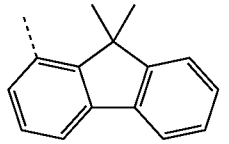 |
| 3-2-75 | 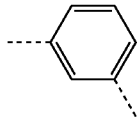 | 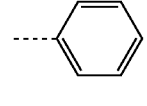 | 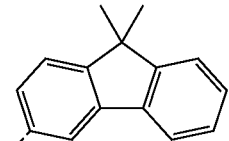 |
| 3-2-76 | 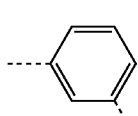 | 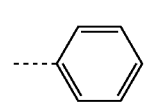 | 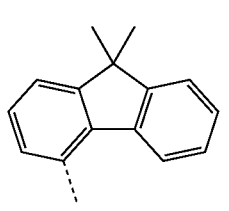 |
| 3-2-77 | 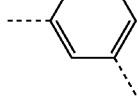 | 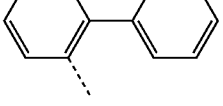 | 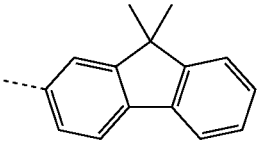 |
| 3-2-78 | 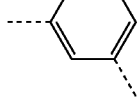 | 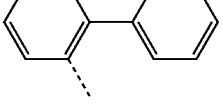 | 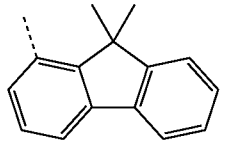 |
| 3-2-79 | 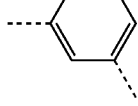 | 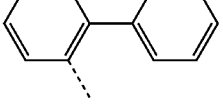 | 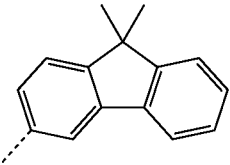 |

TABLE 3-continued
| | ----L₂---- | ----Ar₃---- | ----Ar₄---- |
|---|---|---|---|
| 3-2-80 | 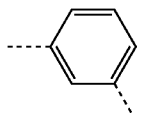 | 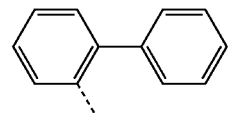 | 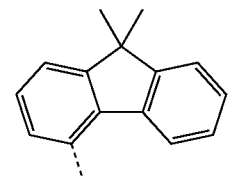 |
| 3-2-81 | 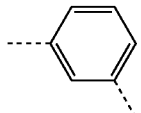 | 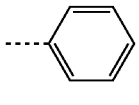 | 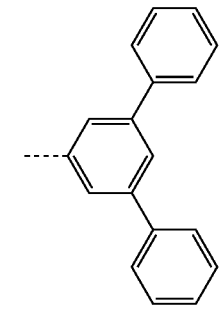 |
| 3-2-82 | 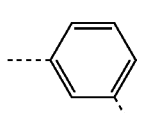 | 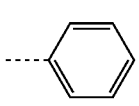 | 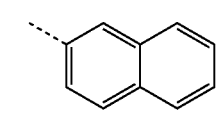 |
| 3-2-83 | 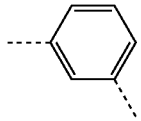 | 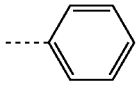 | 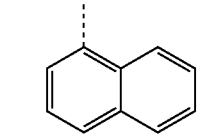 |
| 3-2-84 | 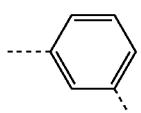 | 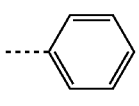 | 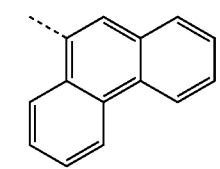 |
| 3-2-85 | 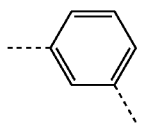 | 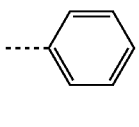 | 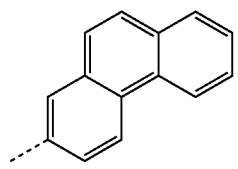 |
| 3-2-86 | 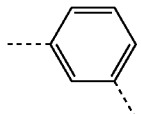 | 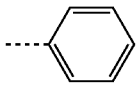 | 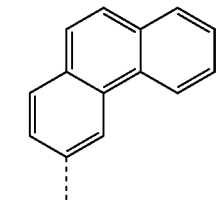 |
| 3-2-87 | 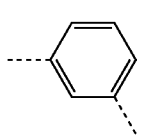 | 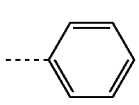 | 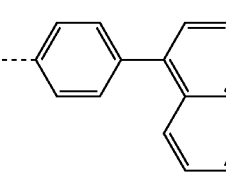 |

TABLE 3-continued

| | ----L₂---- | ----Ar₃ | ----Ar₄ |
|---|---|---|---|
| 3-2-88 | | | |
| 3-2-89 | | | |
| 3-2-90 | | | |
| 3-2-91 | | | |
| 3-2-92 | | | |
| 3-2-93 | | | |
| 3-2-94 | | | |
| 3-2-95 | | | |

TABLE 3-continued

| | ----L₂---- | ----Ar₃---- | ----Ar₄---- |
|---|---|---|---|
| 3-2-96 | phenylene | biphenyl | phenanthrene |
| 3-2-97 | phenylene | biphenyl | phenanthrene |
| 3-2-98 | phenylene | biphenyl | phenanthrene |
| 3-2-99 | phenylene | biphenyl | phenyl-naphthalene |
| 3-2-100 | phenylene | biphenyl | phenyl-naphthalene |
| 3-2-101 | phenylene | biphenyl | terphenyl |
| 3-2-102 | phenylene | biphenyl | phenyl-anthracene |
| 3-2-103 | phenylene | biphenyl | phenyl-9,9-dimethylfluorene |
| 3-2-104 | phenylene | biphenyl | 9,9-dimethyl-phenylfluorene |

12. The double spiro structure compound of claim 9, wherein in the double spiro structure compound represented by Chemical Formula 1 is represented by the following Chemical Formula 3-3, and in the following Chemical Formula 3-3, $L_2$, $Ar_3$ and $Ar_4$ are any one selected from among 3-3-1 to 3-3-104 of the following Table 4:

[Chemical Formula 3-3]

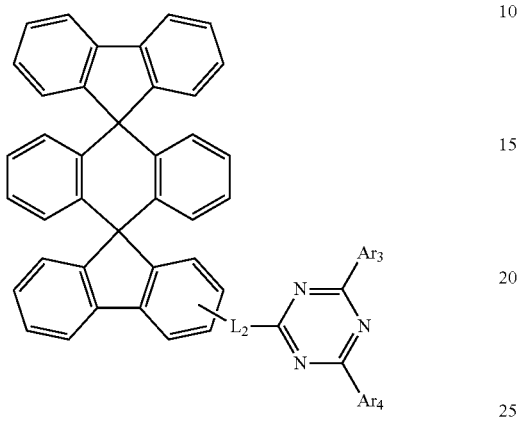

TABLE 4

| | ---$L_2$--- | ---$Ar_3$--- | ---$Ar_4$--- |
|---|---|---|---|
| 3-3-1 | Direct bond | phenyl | phenyl |
| 3-3-2 | Direct bond | biphenyl | phenyl |
| 3-3-3 | Direct bond | biphenyl | 1-naphthyl |
| 3-3-4 | Direct bond | biphenyl | 2-naphthyl |
| 3-3-5 | Direct bond | biphenyl | phenanthrenyl |
| 3-3-6 | Direct bond | 9,9-dimethylfluorenyl | phenyl |

TABLE 4-continued
| | ---L$_2$--- | ---Ar$_3$ | ---Ar$_4$ |
|---|---|---|---|
| 3-3-7 | Direct bond | 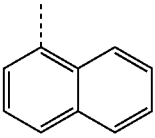 | 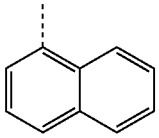 |
| 3-3-8 | Direct bond | 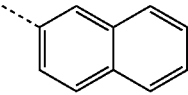 | 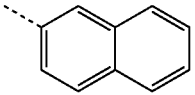 |
| 3-3-9 | Direct bond | 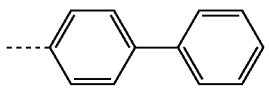 | 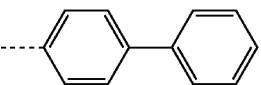 |
| 3-3-10 | Direct bond | 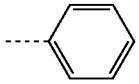 | 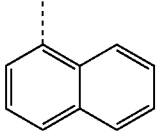 |
| 3-3-11 | Direct bond | 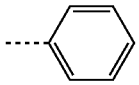 | 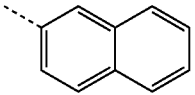 |
| 3-3-12 |  | 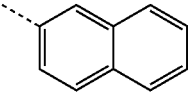 | 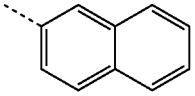 |
| 3-3-13 | 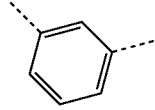 | 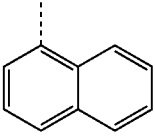 | 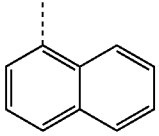 |
| 3-3-14 | 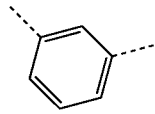 | 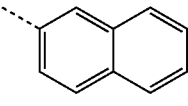 | 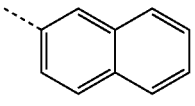 |
| 3-3-15 | 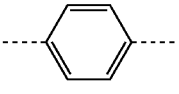 | 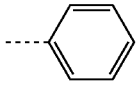 | 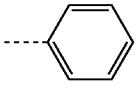 |
| 3-3-16 | 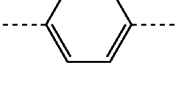 | 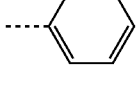 | 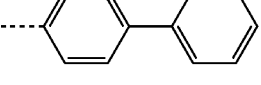 |
| 3-3-17 | 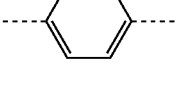 | 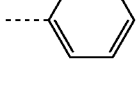 | 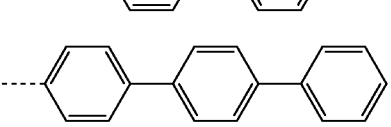 |
| 3-3-18 | 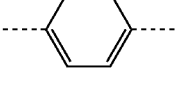 | 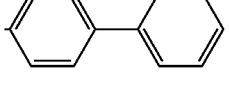 | 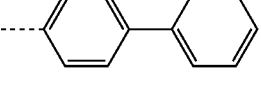 |
| 3-3-19 | 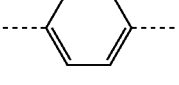 | 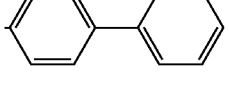 | 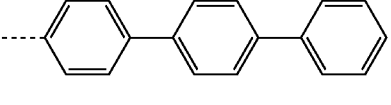 |

TABLE 4-continued

| | ---L$_2$--- | ---Ar$_3$--- | ---Ar$_4$ |
|---|---|---|---|
| 3-3-20 | phenylene | biphenyl | 9,9-dimethylfluoren-2-yl |
| 3-3-21 | phenylene | biphenyl | 9,9-dimethylfluoren-1-yl |
| 3-3-22 | phenylene | biphenyl | 9,9-dimethylfluoren-3-yl |
| 3-3-23 | phenylene | biphenyl | 9,9-dimethylfluoren-4-yl |
| 3-3-24 | phenylene | phenyl | biphenyl-3-yl |
| 3-3-25 | phenylene | phenyl | biphenyl-2-yl |
| 3-3-26 | phenylene | biphenyl | biphenyl-2-yl |
| 3-3-27 | phenylene | biphenyl | biphenyl-3-yl |
| 3-3-28 | phenylene | phenyl | 9,9-dimethylfluoren-2-yl |

TABLE 4-continued
| | ---L$_2$--- | ---Ar$_3$--- | ---Ar$_4$--- |
|---|---|---|---|
| 3-3-29 | 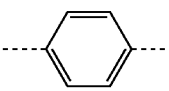 | 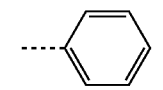 | 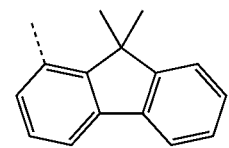 |
| 3-3-30 | 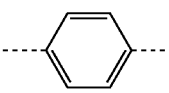 | 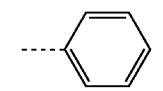 | 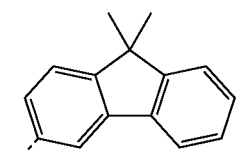 |
| 3-3-31 | 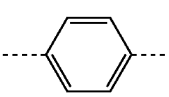 | 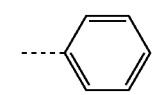 | 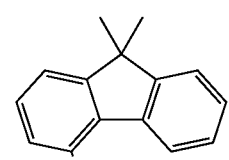 |
| 3-3-32 | 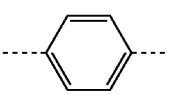 | 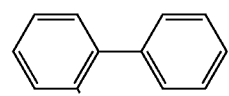 | 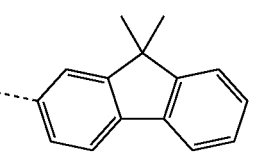 |
| 3-3-33 | 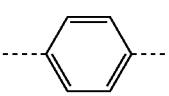 | 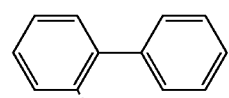 | 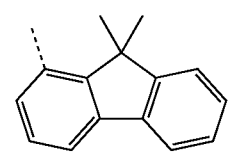 |
| 3-3-34 | 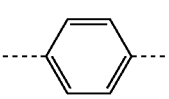 | 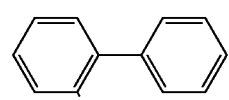 | 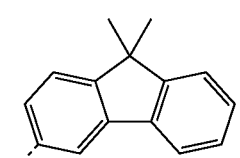 |
| 3-3-35 | 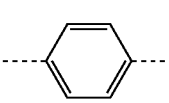 | 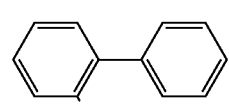 | 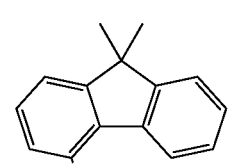 |
| 3-3-36 | 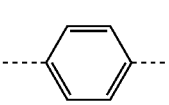 | 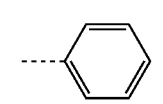 | 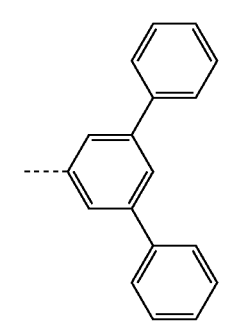 |

TABLE 4-continued
| | ---L₂--- | ---Ar₃ | ---Ar₄ |
|---|---|---|---|
| 3-3-37 | 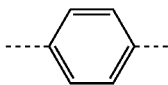 | 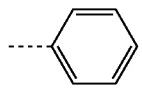 | 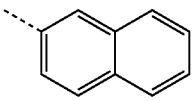 |
| 3-3-38 | 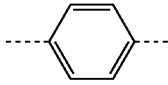 | 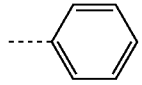 | 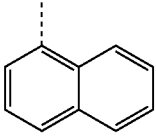 |
| 3-3-39 | 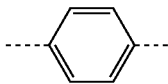 | 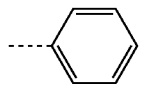 | 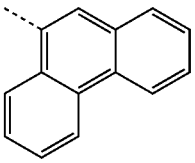 |
| 3-3-40 | 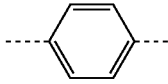 | 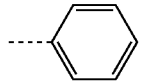 | 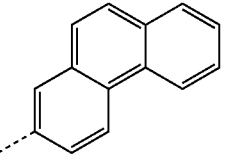 |
| 3-3-41 | 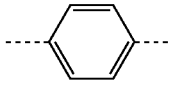 | 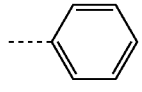 | 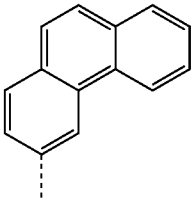 |
| 3-3-42 | 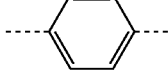 | 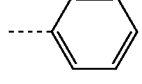 | 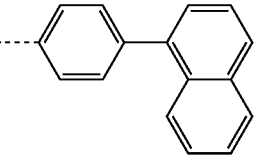 |
| 3-3-43 | 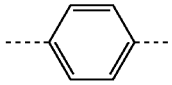 | 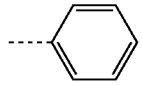 | 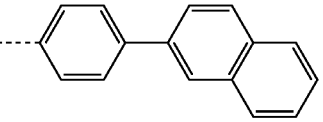 |
| 3-3-44 | 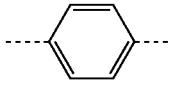 | 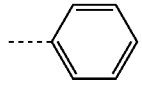 | 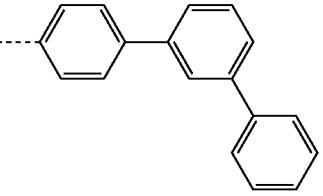 |
| 3-3-45 | 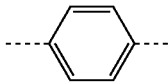 | 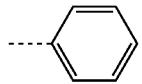 | 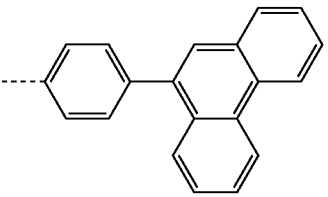 |

TABLE 4-continued
| | ---L$_2$--- | ---Ar$_3$--- | ---Ar$_4$ |
|---|---|---|---|
| 3-3-46 | 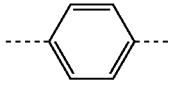 | 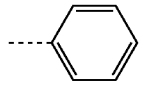 | 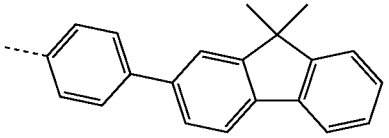 |
| 3-3-47 | 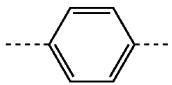 | 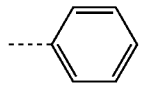 | 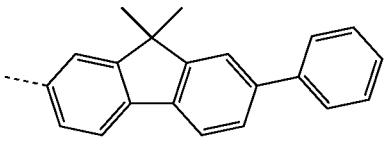 |
| 3-3-48 | 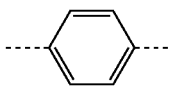 | 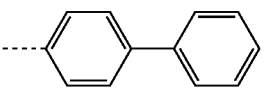 | 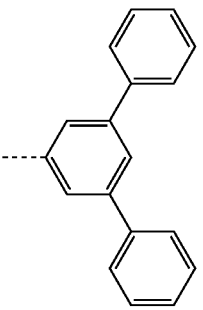 |
| 3-3-49 | 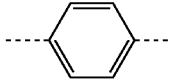 | 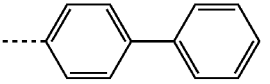 | 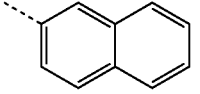 |
| 3-3-50 | 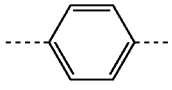 | 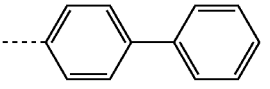 | 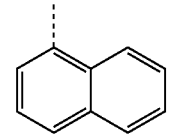 |
| 3-3-51 | 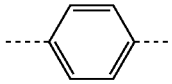 | 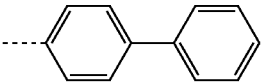 | 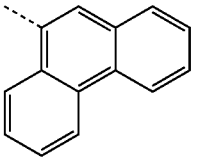 |
| 3-3-52 | 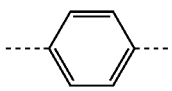 | 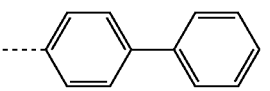 | 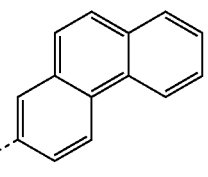 |
| 3-3-53 | 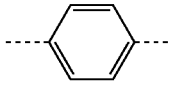 | 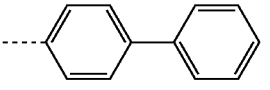 | 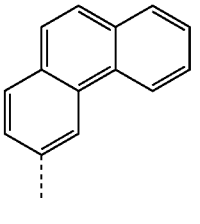 |
| 3-3-54 | 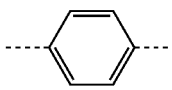 | 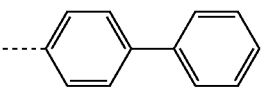 | 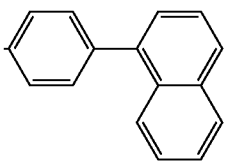 |

TABLE 4-continued
| | ---L₂--- | ---Ar₃ | ---Ar₄ |
|---|---|---|---|
| 3-3-55 |  | 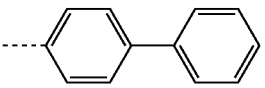 | 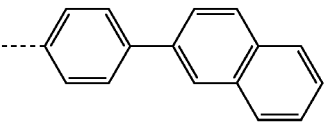 |
| 3-3-56 | 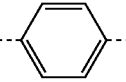 | 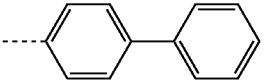 | 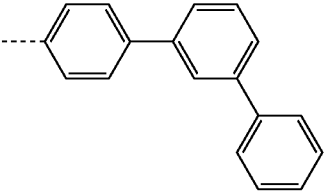 |
| 3-3-57 |  | 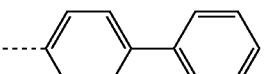 | 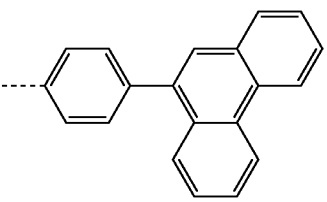 |
| 3-3-58 |  | 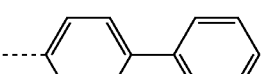 | 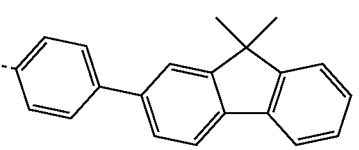 |
| 3-3-59 | 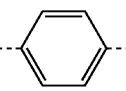 | 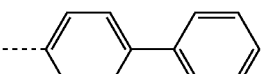 | 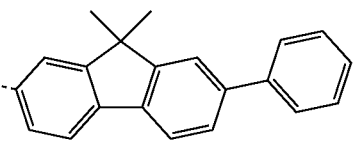 |
| 3-3-60 | 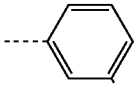 | 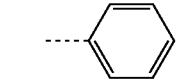 | 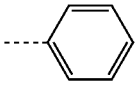 |
| 3-3-61 | 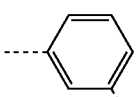 | 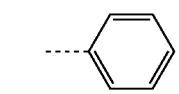 | 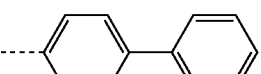 |
| 3-3-62 | 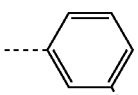 | 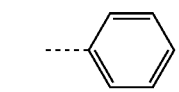 | 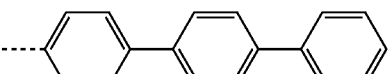 |
| 3-3-63 | 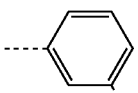 | 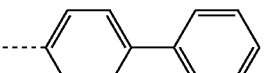 | 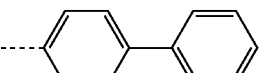 |
| 3-3-64 | 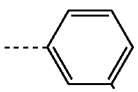 | 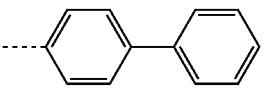 | 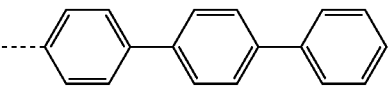 |

TABLE 4-continued

| | ---L₂--- | ---Ar₃ | ---Ar₄ |
|---|---|---|---|
| 3-3-65 | | | |
| 3-3-66 | | | |
| 3-3-67 | | | |
| 3-3-68 | | | |
| 3-3-69 | | | |
| 3-3-70 | | | |
| 3-3-71 | | | |
| 3-3-72 | | | |
| 3-3-73 | | | |

TABLE 4-continued

| | ---L₂--- | ---Ar₃ | ---Ar₄ |
|---|---|---|---|
| 3-3-74 | | | |
| 3-3-75 | | | |
| 3-3-76 | | | |
| 3-3-77 | | | |
| 3-3-78 | | | |
| 3-3-79 | | | |
| 3-3-80 | | | |
| 3-3-81 | | | |

TABLE 4-continued

| | ---L₂--- | ---Ar₃ | ---Ar₄ |
|---|---|---|---|
| 3-3-82 | phenylene | phenyl | 2-naphthyl |
| 3-3-83 | phenylene | phenyl | 1-naphthyl |
| 3-3-84 | phenylene | phenyl | phenanthrenyl |
| 3-3-85 | phenylene | phenyl | phenanthrenyl |
| 3-3-86 | phenylene | phenyl | phenanthrenyl |
| 3-3-87 | phenylene | phenyl | 4-(1-naphthyl)phenyl |
| 3-3-88 | phenylene | phenyl | 4-(2-naphthyl)phenyl |
| 3-3-89 | phenylene | phenyl | m-terphenyl |
| 3-3-90 | phenylene | phenyl | 4-(9-phenanthrenyl)phenyl |

TABLE 4-continued

| | ---L$_2$--- | ---Ar$_3$--- | ---Ar$_4$--- |
|---|---|---|---|
| 3-3-91 | phenylene (meta) | phenyl | 4-(9,9-dimethylfluoren-2-yl)phenyl |
| 3-3-92 | phenylene (meta) | phenyl | 7-phenyl-9,9-dimethylfluoren-2-yl |
| 3-3-93 | phenylene (meta) | 4-biphenyl | 3,5-diphenylphenyl |
| 3-3-94 | phenylene (meta) | 4-biphenyl | naphthalen-2-yl |
| 3-3-95 | phenylene (meta) | 4-biphenyl | naphthalen-1-yl |
| 3-3-96 | phenylene (meta) | 4-biphenyl | phenanthren-9-yl |
| 3-3-97 | phenylene (meta) | 4-biphenyl | phenanthren-2-yl |
| 3-3-98 | phenylene (meta) | 4-biphenyl | phenanthren-3-yl |

TABLE 4-continued

| | ---L$_2$--- | ---Ar$_3$ | ---Ar$_4$ |
|---|---|---|---|
| 3-3-99 | | | |
| 3-3-100 | | | |
| 3-3-101 | | | |
| 3-3-102 | | | |
| 3-3-103 | | | |
| 3-3-104 | | | |

13. The double spiro structure compound of claim 9, wherein the double spiro structure compound represented by Chemical Formula 1 is represented by the following Chemical Formula 3-4, and in the following Chemical Formula 3-4, L$_2$, Ar$_3$ and Ar$_4$ are any one selected from among 3-4-1 to 3-4-104 of the following Table 5:

[Chemical Formula 3-4]
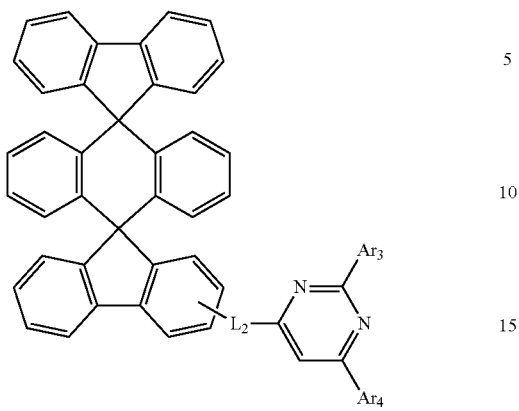
TABLE 5
| | ---L$_2$--- | ---Ar$_3$--- | ---Ar$_4$--- |
|---|---|---|---|
| 3-4-1 | Direct bond | phenyl | phenyl |
| 3-4-2 | Direct bond | biphenyl | phenyl |
| 3-4-3 | Direct bond | biphenyl | naphthyl |
| 3-4-4 | Direct bond | biphenyl | naphthyl |
| 3-4-5 | Direct bond | biphenyl | phenanthryl |
| 3-4-6 | Direct bond | 9,9-dimethylfluorenyl | phenyl |
| 3-4-7 | Direct bond | naphthyl | naphthyl |
| 3-4-8 | Direct bond | naphthyl | naphthyl |

TABLE 5-continued
| | ---L$_2$--- | ---Ar$_3$ | ---Ar$_4$ |
|---|---|---|---|
| 3-4-9 | Direct bond | 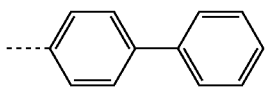 | 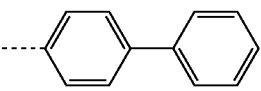 |
| 3-4-10 | Direct bond | 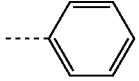 | 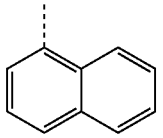 |
| 3-4-11 | Direct bond | 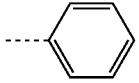 | 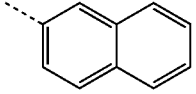 |
| 3-4-12 |  | 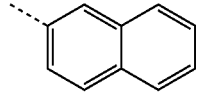 | 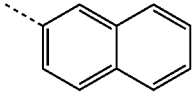 |
| 3-4-13 | 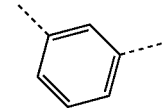 | 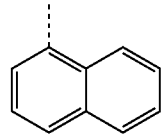 | 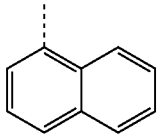 |
| 3-4-14 | 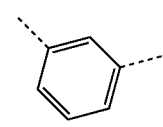 | 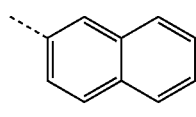 | 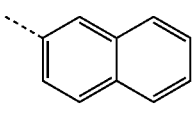 |
| 3-4-15 | 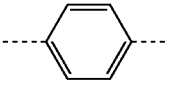 | 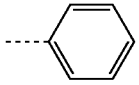 | 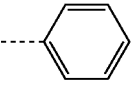 |
| 3-4-16 | 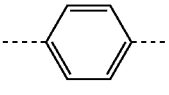 | 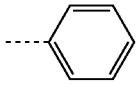 | 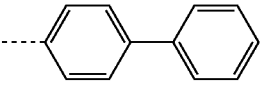 |
| 3-4-17 | 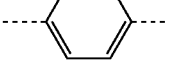 | 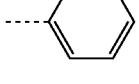 | 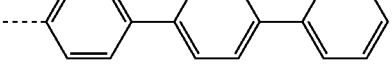 |
| 3-4-18 | 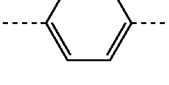 | 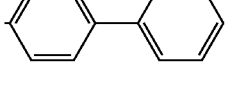 | 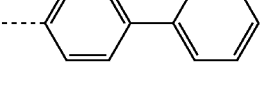 |
| 3-4-19 | 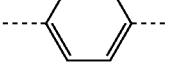 | 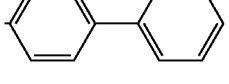 | 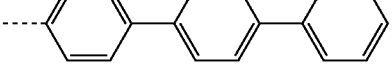 |
| 3-4-20 | 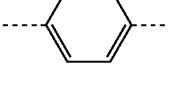 | 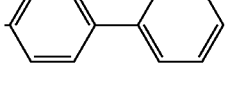 | 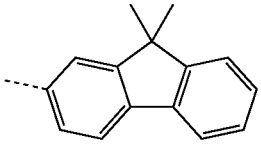 |
| 3-4-21 | 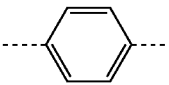 | 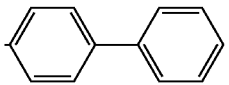 | 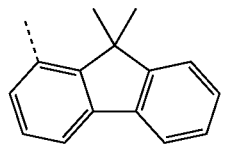 |

TABLE 5-continued
| | ---L$_2$--- | ---Ar$_3$ | ---Ar$_4$ |
|---|---|---|---|
| 3-4-22 | 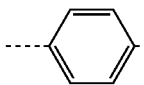 | 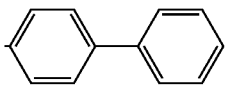 | 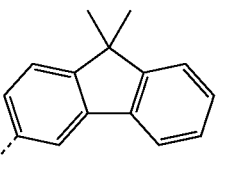 |
| 3-4-23 | 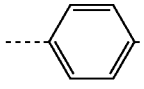 | 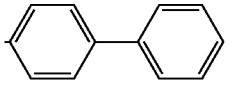 | 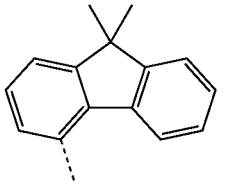 |
| 3-4-24 | 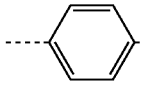 | 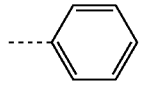 | 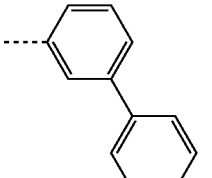 |
| 3-4-25 | 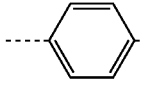 | 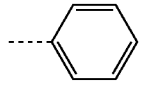 | 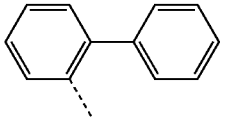 |
| 3-4-26 | 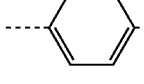 | 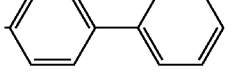 | 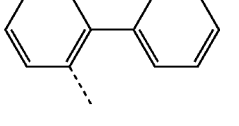 |
| 3-4-27 | 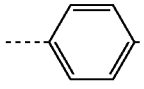 | 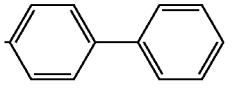 | 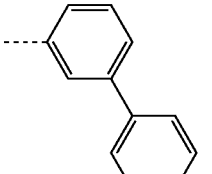 |
| 3-4-28 | 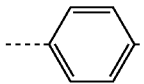 | 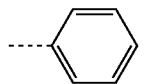 | 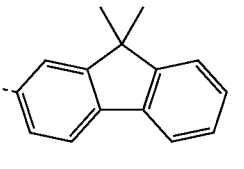 |
| 3-4-29 | 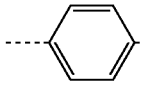 | 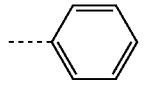 | 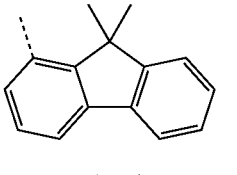 |
| 3-4-30 | 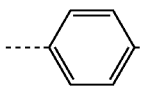 | 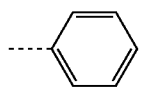 | 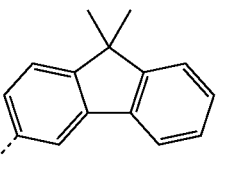 |

TABLE 5-continued
| | ---L$_2$--- | ---Ar$_3$--- | ---Ar$_4$--- |
|---|---|---|---|
| 3-4-31 | 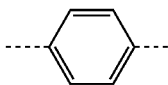 | 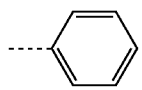 | 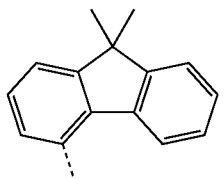 |
| 3-4-32 | 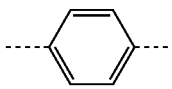 | 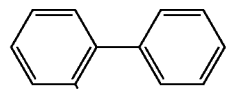 | 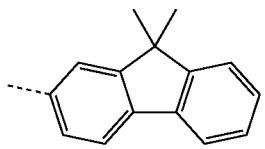 |
| 3-4-33 | 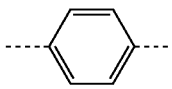 | 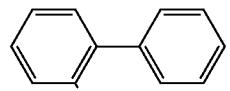 | 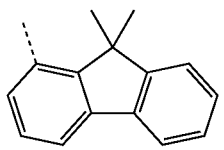 |
| 3-4-34 | 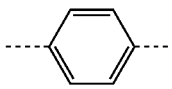 | 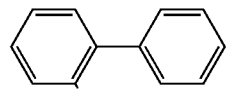 | 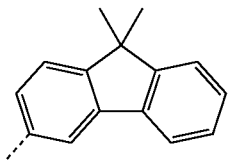 |
| 3-4-35 | 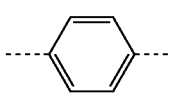 | 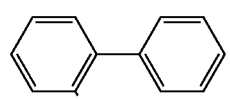 | 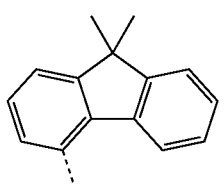 |
| 3-4-36 | 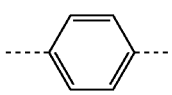 | 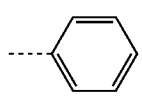 | 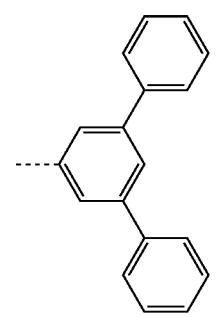 |
| 3-4-37 | 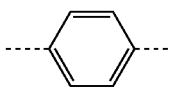 | 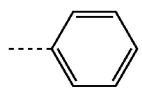 | 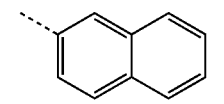 |
| 3-4-38 | 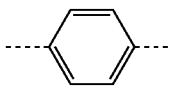 | 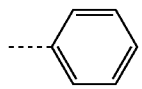 | 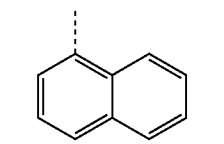 |

TABLE 5-continued
| | ---L$_2$--- | ---Ar$_3$--- | ---Ar$_4$ |
|---|---|---|---|
| 3-4-39 | 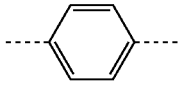 | 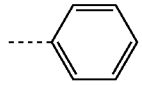 | 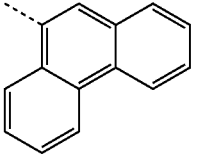 |
| 3-4-40 | 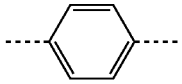 | 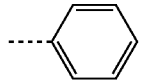 | 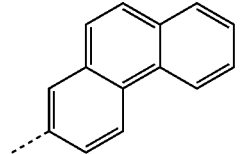 |
| 3-4-41 | 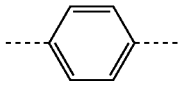 | 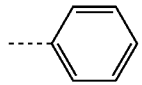 | 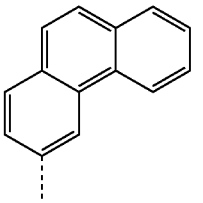 |
| 3-4-42 | 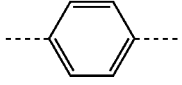 | 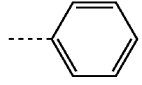 | 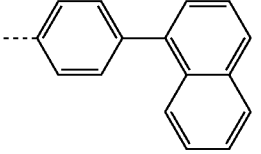 |
| 3-4-43 | 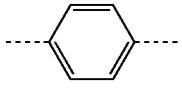 | 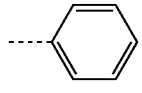 | 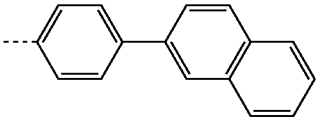 |
| 3-4-44 | 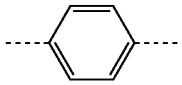 | 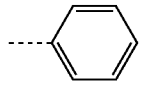 | 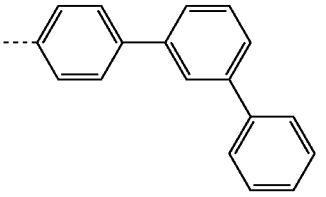 |
| 3-4-45 | 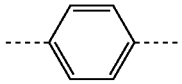 | 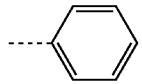 | 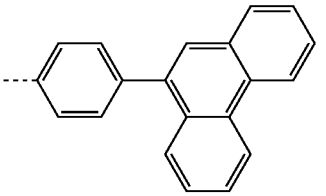 |
| 3-4-46 | 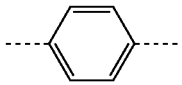 | 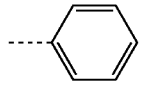 | 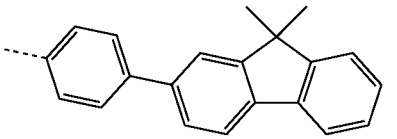 |
| 3-4-47 | 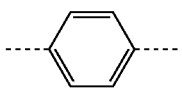 | 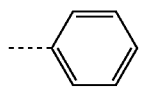 | 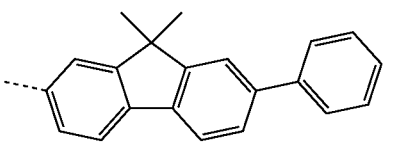 |

TABLE 5-continued

| | ---L₂--- | ---Ar₃ | ---Ar₄ |
|---|---|---|---|
| 3-4-48 | phenylene | biphenyl | 1,3-diphenylphenyl |
| 3-4-49 | phenylene | biphenyl | naphthalen-2-yl |
| 3-4-50 | phenylene | biphenyl | naphthalen-1-yl |
| 3-4-51 | phenylene | biphenyl | phenanthren-9-yl |
| 3-4-52 | phenylene | biphenyl | phenanthren-2-yl |
| 3-4-53 | phenylene | biphenyl | phenanthren-3-yl |
| 3-4-54 | phenylene | biphenyl | 4-(naphthalen-1-yl)phenyl |
| 3-4-55 | phenylene | biphenyl | 4-(naphthalen-2-yl)phenyl |

TABLE 5-continued
| | ---L₂--- | ---Ar₃--- | ---Ar₄--- |
|---|---|---|---|
| 3-4-56 | 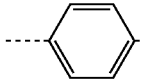 | 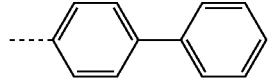 | 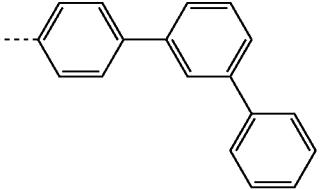 |
| 3-4-57 | 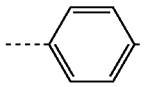 | 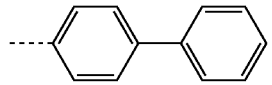 | 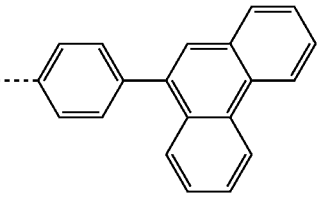 |
| 3-4-58 | 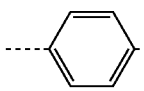 | 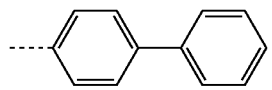 | 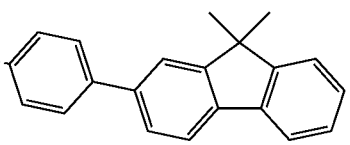 |
| 3-4-59 | 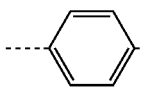 | 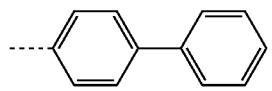 | 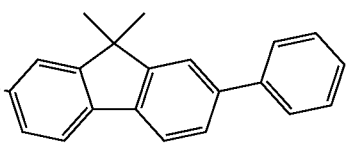 |
| 3-4-60 | 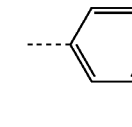 | 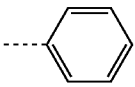 | 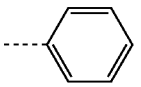 |
| 3-4-61 | 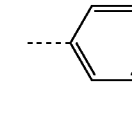 | 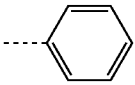 | 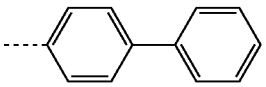 |
| 3-4-62 | 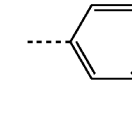 | 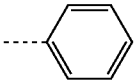 | 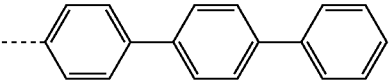 |
| 3-4-63 | 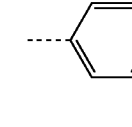 | 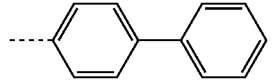 | 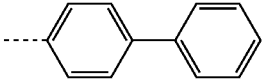 |
| 3-4-64 | 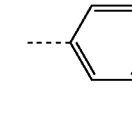 | 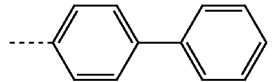 | 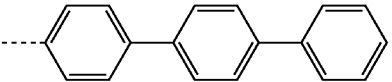 |
| 3-4-65 | 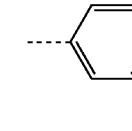 | 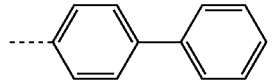 | 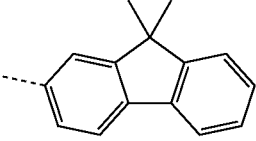 |

TABLE 5-continued

| | ---L₂--- | ---Ar₃ | ---Ar₄ |
|---|---|---|---|
| 3-4-66 | | | |
| 3-4-67 | | | |
| 3-4-68 | | | |
| 3-4-69 | | | |
| 3-4-70 | | | |
| 3-4-71 | | | |
| 3-4-72 | | | |
| 3-4-73 | | | |
| 3-4-74 | | | |

TABLE 5-continued

| | ---L₂--- | ---Ar₃ | ---Ar₄ |
|---|---|---|---|
| 3-4-75 | | | |
| 3-4-76 | | | |
| 3-4-77 | | | |
| 3-4-78 | | | |
| 3-4-79 | | | |
| 3-4-80 | | | |
| 3-4-81 | | | |
| 3-4-82 | | | |

TABLE 5-continued

| | ---L₂--- | ---Ar₃ | ---Ar₄ |
|---|---|---|---|
| 3-4-83 | phenylene | phenyl | 1-naphthyl |
| 3-4-84 | phenylene | phenyl | phenanthrenyl |
| 3-4-85 | phenylene | phenyl | chrysenyl |
| 3-4-86 | phenylene | phenyl | phenanthrenyl |
| 3-4-87 | phenylene | phenyl | 4-(1-naphthyl)phenyl |
| 3-4-88 | phenylene | phenyl | 4-(2-naphthyl)phenyl |
| 3-4-89 | phenylene | phenyl | m-terphenyl |
| 3-4-90 | phenylene | phenyl | 4-(phenanthren-9-yl)phenyl |
| 3-4-91 | phenylene | phenyl | 4-(9,9-dimethylfluoren-2-yl)phenyl |

TABLE 5-continued

| | ---L$_2$--- | ---Ar$_3$--- | ---Ar$_4$ |
|---|---|---|---|
| 3-4-92 | phenylene | phenyl | 9,9-dimethyl-2-phenylfluorenyl |
| 3-4-93 | phenylene | biphenyl | 3,5-diphenylphenyl |
| 3-4-94 | phenylene | biphenyl | 2-naphthyl |
| 3-4-95 | phenylene | biphenyl | 1-naphthyl |
| 3-4-96 | phenylene | biphenyl | phenanthrenyl |
| 3-4-97 | phenylene | biphenyl | phenanthrenyl |
| 3-4-98 | phenylene | biphenyl | phenanthrenyl |
| 3-4-99 | phenylene | biphenyl | 4-(1-naphthyl)phenyl |

TABLE 5-continued

| | ---L$_2$--- | ---Ar$_3$--- | ---Ar$_4$--- |
|---|---|---|---|
| 3-4-100 | | | |
| 3-4-101 | | | |
| 3-4-102 | | | |
| 3-4-103 | | | |
| 3-4-104 | | | |

14. An organic light emitting device comprising:
    an anode;
    a cathode provided opposite to the anode; and
    a light emitting layer and one or more organic material layers provided between the cathode and the light emitting layer;
    wherein the light emitting layer or the one or more organic material layers comprises the double spiro structure compound of claim 9.

15. An organic light emitting device comprising:
    an anode;
    a cathode provided opposite to the anode; and
    a light emitting layer and one or more organic material layers provided between the anode and the cathode,
    wherein the light emitting layer or the one or more organic material layers comprises the double spiro compound of claim 9.

* * * * *